US012709751B2

(12) United States Patent
Mcininch et al.

(10) Patent No.: US 12,709,751 B2
(45) Date of Patent: Aug. 18, 2026

(54) MANNAN BINDING LECTIN SERINE PEPTIDASE 2 (MASP2) IRNA COMPOSITIONS AND METHODS OF USE THEREOF

(71) Applicant: ALNYLAM PHARMACEUTICALS, INC., Cambridge, MA (US)

(72) Inventors: James D. Mcininch, Burlington, MA (US); Anna Borodovsky, Melrose, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 932 days.

(21) Appl. No.: 17/800,471

(22) PCT Filed: Feb. 18, 2021

(86) PCT No.: PCT/US2021/018624
§ 371 (c)(1),
(2) Date: Aug. 17, 2022

(87) PCT Pub. No.: WO2021/168148
PCT Pub. Date: Aug. 26, 2021

(65) Prior Publication Data

US 2023/0125933 A1 Apr. 27, 2023

Related U.S. Application Data

(60) Provisional application No. 62/978,788, filed on Feb. 19, 2020.

(51) Int. Cl.
*C12N 15/113* (2010.01)

(52) U.S. Cl.
CPC .. *C12N 15/1137* (2013.01); *C12Y 304/21104* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2320/30* (2013.01)

(58) Field of Classification Search
None
See application file for complete search history.

(56) References Cited

U.S. PATENT DOCUMENTS 3,687,808 A 8/1972 Merigan, Jr. et al.
4,426,330 A 1/1984 Sears
4,469,863 A 9/1984 Ts'o et al.
4,476,301 A 10/1984 Imbach et al.
4,534,899 A 8/1985 Sears
4,587,044 A 5/1986 Miller et al.
4,605,735 A 8/1986 Miyoshi et al.
4,667,025 A 5/1987 Miyoshi et al.
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,837,028 A 6/1989 Allen
4,845,205 A 7/1989 Huynh Dinh et al.
4,876,335 A 10/1989 Yamane et al.
4,904,582 A 2/1990 Tullis
4,948,882 A 8/1990 Ruth
4,958,013 A 9/1990 Letsinger
4,981,957 A 1/1991 Lebleu et al.
5,013,556 A 5/1991 Woodle et al.
5,023,243 A 6/1991 Tullis
5,032,401 A 7/1991 Jamas et al.
5,034,506 A 7/1991 Summerton et al.
5,082,830 A 1/1992 Brakel et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spielvogel et al.
5,134,066 A 7/1992 Rogers et al.
5,138,045 A 8/1992 Cook et al.
5,139,941 A 8/1992 Muzyczka et al.
5,166,315 A 11/1992 Summerton et al.
5,175,273 A 12/1992 Bischofberger et al.
5,177,195 A 1/1993 Gregory et al.
5,185,444 A 2/1993 Summerton et al.
5,188,897 A 2/1993 Suhadolnik et al.
5,213,804 A 5/1993 Martin et al.
5,214,134 A 5/1993 Weis et al.
5,214,136 A 5/1993 Lin et al.
5,216,141 A 6/1993 Benner
5,218,105 A 6/1993 Cook et al.
5,225,212 A 7/1993 Martin et al.
5,235,033 A 8/1993 Summerton et al.
5,245,022 A 9/1993 Weis et al.
5,252,479 A 10/1993 Srivastava
5,254,469 A 10/1993 Warren, III et al.
(Continued)

FOREIGN PATENT DOCUMENTS

EP 0445131 4/1994
EP 0496813 12/1994
(Continued)

OTHER PUBLICATIONS

Aigner, "Delivery Systems for the Direct Application of siRNAs to Induce RNA Interference (RNAi) In Vivo," J. Biomed. Biotechnol., 2006, 2006:71659, 15 pp.
(Continued)

*Primary Examiner* — Tracy Vivlemore
(74) *Attorney, Agent, or Firm* — Womble Bond Dickinson (US) LLP

(57) ABSTRACT

The present invention relates to RNAi agents, e.g., double stranded RNA (dsRNA) agents, targeting the mannan binding lectin serine peptidase 2 gene (MASP2). The invention also relates to methods of using such RNAi agents to inhibit expression of a MASP2 gene and to methods of preventing and treating a MASP2-associated disorders, e.g., arthritis, IgA nephropathy, thrombotic microangiopathy, diabetic nephropathy and membranous nephropathy.

20 Claims, No Drawings

Specification includes a Sequence Listing.

(56) References Cited

U.S. PATENT DOCUMENTS 5,258,506 A 11/1993 Urdea et al.
5,262,536 A 11/1993 Hobbs, Jr.
5,264,221 A 11/1993 Tagawa et al.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,319,080 A 6/1994 Leumann
5,321,131 A 6/1994 Agrawal et al.
5,356,633 A 10/1994 Woodle et al.
5,359,044 A 10/1994 Cook et al.
5,367,066 A 11/1994 Urdea et al.
5,371,241 A 12/1994 Brush
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,436,146 A 7/1995 Shenk et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,540,935 A 7/1996 Miyazaki et al.
5,541,307 A 7/1996 Cook et al.
5,541,313 A 7/1996 Ruth
5,541,316 A 7/1996 Engelskirchen et al.
5,543,152 A 8/1996 Webb et al.
5,545,730 A 8/1996 Urdea et al.
5,550,111 A 8/1996 Suhadolnik et al.
5,552,538 A 9/1996 Urdea et al.
5,552,540 A 9/1996 Haralambidis
5,556,948 A 9/1996 Tagawa et al.
5,561,225 A 10/1996 Maddry et al.
5,563,253 A 10/1996 Agrawal et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 De Mesmaeker et al.
5,607,677 A 3/1997 Jamas et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,646,265 A 7/1997 McGee
5,658,873 A 8/1997 Bertsch-Frank et al.
5,663,312 A 9/1997 Chaturvedula
5,665,557 A 9/1997 Murray et al.
5,665,710 A 9/1997 Rahman et al.
5,670,633 A 9/1997 Cook et al.
5,677,437 A 10/1997 Teng et al.
5,677,439 A 10/1997 Weis et al.
5,681,941 A 10/1997 Cook et al.
5,688,941 A 11/1997 Cook et al.
5,700,920 A 12/1997 Altmann et al.
5,705,188 A 1/1998 Junichi et al.
5,714,331 A 2/1998 Buchardt et al.
5,719,262 A 2/1998 Buchardt et al.
5,750,692 A 5/1998 Cook et al.
5,976,567 A 11/1999 Wheeler et al.
5,981,276 A 11/1999 Sodroski et al.
5,981,501 A 11/1999 Wheeler et al.
6,015,886 A 1/2000 Dale et al.
6,028,188 A 2/2000 Arnold, Jr. et al.
6,054,299 A 4/2000 Conrad
6,124,445 A 9/2000 Imbach et al.
6,143,520 A 11/2000 Marasco et al.
6,147,200 A 11/2000 Manoharan et al.
6,160,109 A 12/2000 Just et al.
6,166,197 A 12/2000 Cook et al.
6,169,170 B1 1/2001 Gryaznov et al.
6,172,209 B1 1/2001 Manoharan et al.
6,191,105 B1 2/2001 Ekwuribe et al.
6,222,025 B1 4/2001 Cook et al.
6,235,887 B1 5/2001 Froehler et al.
6,239,265 B1 5/2001 Cook
6,268,490 B1 7/2001 Imanishi et al.
6,277,603 B1 8/2001 Cook
6,294,664 B1 9/2001 Ravikumar et al.
6,320,017 B1 11/2001 Ansell
6,326,199 B1 12/2001 Cook et al.
6,346,614 B1 2/2002 Metelev et al.
6,355,245 B1 3/2002 Evans et al.
6,380,368 B1 4/2002 Froehler et al.
6,444,423 B1 9/2002 Meade et al.
6,525,191 B1 2/2003 Ramasamy
6,528,640 B1 3/2003 Beigelman et al.
6,531,590 B1 3/2003 Manoharan et al.
6,534,484 B1 3/2003 Wheeler et al.
6,534,639 B1 3/2003 Manoharan et al.
6,576,752 B1 6/2003 Manoharan et al.
6,586,410 B1 7/2003 Wheeler et al.
6,608,035 B1 8/2003 Agrawal et al.
6,617,438 B1 9/2003 Beigelman et al.
6,639,062 B2 10/2003 Manoharan et al.
6,670,461 B1 12/2003 Wengel et al.
6,683,167 B2 1/2004 Metelev et al.
6,747,014 B2 6/2004 Teng et al.
6,770,748 B2 8/2004 Imanishi et al.

(56) References Cited

U.S. PATENT DOCUMENTS 6,783,931 B1 8/2004 Cook et al.
6,794,499 B2 9/2004 Wengel et al.
6,815,432 B2 11/2004 Wheeler et al.
6,858,225 B2 2/2005 Semple et al.
6,858,715 B2 2/2005 Ravikumar et al.
6,867,294 B1 3/2005 Sanghvi et al.
6,878,805 B2 4/2005 Manoharan et al.
6,887,906 B1 5/2005 Teng et al.
6,900,297 B1 5/2005 Cook et al.
6,998,484 B2 2/2006 Koch et al.
7,015,315 B1 3/2006 Cook et al.
7,034,133 B2 4/2006 Wengel et al.
7,037,646 B1 5/2006 Cook et al.
7,041,816 B2 5/2006 Ravikumar et al.
7,045,610 B2 5/2006 Dempcy et al.
7,053,207 B2 5/2006 Wengel
7,063,860 B2 6/2006 Chancellor et al.
7,070,802 B1 7/2006 Bhalani et al.
7,084,125 B2 8/2006 Wengel
RE39,464 E 1/2007 Cook et al.
7,157,099 B2 1/2007 Autuori et al.
7,273,933 B1 9/2007 Krotz et al.
7,321,029 B2 1/2008 Gryaznov et al.
7,399,845 B2 7/2008 Seth et al.
7,427,605 B2 9/2008 Davis et al.
7,427,672 B2 9/2008 Imanishi et al.
7,495,088 B1 2/2009 Brakel et al.
7,569,686 B1 8/2009 Bhat et al.
7,741,457 B2 6/2010 Seth et al.
7,858,769 B2 12/2010 Jadhav et al.
8,022,193 B2 9/2011 Seth et al.
8,030,467 B2 10/2011 Seth et al.
8,058,069 B2 11/2011 Yaworski et al.
8,101,348 B2 1/2012 Tuschl et al.
8,106,022 B2 1/2012 Manoharan et al.
8,158,601 B2 4/2012 Chen et al.
8,278,283 B2 10/2012 Seth et al.
8,278,425 B2 10/2012 Prakash et al.
8,278,426 B2 10/2012 Seth et al.
8,314,227 B2 11/2012 Wengel
8,883,202 B2 11/2014 Manoharan et al.
9,249,415 B2 2/2016 Fitzgerald et al.
2003/0027780 A1 2/2003 Hardee et al.
2004/0171570 A1 9/2004 Allerson et al.
2005/0226848 A1 10/2005 Kuwabara et al.
2005/0281781 A1 12/2005 Ostroff
2006/0240093 A1 10/2006 Maclachlan et al.
2007/0111963 A1 5/2007 Corey et al.
2007/0135372 A1 6/2007 Maclachlan et al.
2008/0039618 A1 2/2008 Allerson et al.
2009/0012281 A1 1/2009 Swayze et al.
2009/0023673 A1 1/2009 Manoharan et al.
2011/0313020 A1 12/2011 Templin et al.
2012/0101148 A1 4/2012 Aking et al.
2012/0157511 A1 6/2012 Manoharan et al.
2013/0011922 A1 1/2013 Quay et al.
2013/0096289 A1 4/2013 Wengel
2013/0190383 A1 7/2013 Vaish et al.
2019/0292272 A1 9/2019 Demopulos et al.
2020/0032270 A1 1/2020 Masuda et al.

FOREIGN PATENT DOCUMENTS

WO WO 1988/04924 7/1988
WO WO 1990/04384 5/1990
WO WO 1991/05545 5/1991
WO WO 1993/24641 12/1993
WO WO 1994/02595 2/1994
WO WO 1994/12649 6/1994
WO WO 1994/13788 6/1994
WO WO 1994/20073 9/1994
WO WO 1996/10391 4/1996
WO WO 1996/40062 12/1996
WO WO 1996/40964 12/1996
WO WO 1997/04787 2/1997
WO WO 1997/13499 4/1997
WO WO 1997/30731 8/1997
WO WO 1999/14226 3/1999
WO WO 2000/22114 4/2000
WO WO 2000/66604 11/2000
WO WO 2007/091269 8/2007
WO WO 2007/117686 10/2007
WO WO 2008/042973 4/2008
WO WO 2009/014887 1/2009
WO WO 2009/082817 7/2009
WO WO 2009/127060 10/2009
WO WO 2010/011895 1/2010
WO WO 2010/048536 4/2010
WO WO 2010/054406 5/2010
WO WO 2010/088537 8/2010
WO WO 2010/129709 11/2010
WO WO 2010/141511 12/2010
WO WO 2010/144740 12/2010
WO WO 2011/005861 1/2011
WO WO 2011/031520 3/2011
WO WO 2011/133876 10/2011
WO WO 2013/036868 3/2013
WO WO 2013/075035 5/2013
WO WO 2014/179620 11/2014
WO WO 2014/179627 11/2014
WO WO-2018164186 A1 * 9/2018 ......... C12N 15/1137
WO WO 2000/22113 4/2022

OTHER PUBLICATIONS

Akaneya et al., "RNAi-Induced Gene Silencing by Local Electroporation in Targeting Brain Region," J. Neurophysiol., 2005, 93:594-602.

Akhtar et al., "Cellular uptake and intracellular fate of antisense oligonucleotides," Trends Cell. Biol., 1992, 2(5):139-144.

Allen et al., "Large unilamellar liposomes with low uptake into the reticuloendothelial system," FEBS Letters, 1987, 223(1):42-46.

Aoki et al., "Potential tumor-targeting peptide vector of histidylated oligolysine conjugated to a tumor-homing RGD motif," Cancer Gene Therapy, 2001, 8(10):783-787.

Arnold et al., "Specific beta1-adrenergic receptor silencing with small interfering RNA lowers high blood pressure and improves cardiac function in myocardial ischemia," J. Hypertens., 2007, 25(1):197-205.

Bernstein et al., "Role for a bidentate ribonuclease in the initiation step of RNA interference," Nature, 2001, 409:363-366.

Bessis et al., "Use of Hollow Fibers Filled with Cells Engineered to Secrete IL-4 or IL-13 for Treatment of Experimental Arthritis, " Arthr. Rheum., 1996, 39(S9): S308.

Bitko et al., "Inhibition of respiratory viruses by nasally administered siRNA," Nat. Med., 2005, 11:50-55.

Blume et al., "Liposomes for the sustained drug release in vivo," Biochimica et Biophysica Acta, 1990, 1029:91-97.

Boesen et al., "Circumvention of chemotherapy-induced myelosuppression by transfer of the mdr1 gene," Biotherapy, 1994, 6:291-302.

Bonnet et al., "Systemic Delivery of DNA or siRNA Mediated by Linear Polyethylenimine (L-PEI) Does Not Induce an Inflammatory Response," Pharm. Res., 2008, 25(12):2972-2982.

Bout et al., "Lung Gene Therapy: In Vivo Adenovirus-Mediated Gene Transfer to Rhesus Monkey Airway Epithelium," Hum. Gene Ther., 1994, 5:3-10.

Bruncko et al., "Studies Leading to Potent, Dual Inhibitors of Bcl-2 and Bcl-xL," J. Med. Chem., 2007, 50:641-662.

Buur et al., "Penetration of 5-Fluorouracil and Prodrugs Across the Intestine of the Albino Rabbit: Evidence for Shift in Absorption Site from the Upper to the Lower Region of the Gastrointestinal Tract by Prodrugs," J. Control Rel., 1990, 14:43-51.

Chien et al., "Novel cationic cardiolipin analogue-based liposome for efficient DNA and small interfering RNA delivery in vitro and in vivo," Cancer Gene Ther., 2005, 12:321-328.

Chikanza et al., "Treatment of Patients with Rheumatoid Arthritis with RP73401 Phosphodiesterase Type IV Inhibitor," Arthr. Rheum., 1996, 39(S9):S282(1).

(56) References Cited

OTHER PUBLICATIONS

Chu et al., "Potent RNAi by short RNA triggers," RNA, 2008 14:1714-1719.
Clowes et al., "Long-Term Biological Response of Injured Rat Carotid Artery Seeded with Smooth Muscle Cells Expressing Retrovirally Introduced Human Genes," J. Clin. Invest., 1994, 93:644-651.
Constantinides et al., "Formulation and Intestinal Absorption Enhancement Evaluation of Water-in-Oil Microemulsions Incorporating Medium-Chain Glycerides," Pharmaceutical Research, 1994, 11(10): 1385-1390.
Couture et al., "Anti-gene therapy: the use of ribozymes to inhibit gene function," Trends in Genetics, 1996, 12(12):510-515.
Crooke et al., "Pharmacokinetic Properties of Several Novel Oligonucleotide Analogs in mice," J. Pharmacol. Exp. Ther., 1996, 277:923-937.
Deluca et al., "Marine and Botanical Lipids as Immunomodulatory and Therapeutic Agents in the Treatment of Rheumatoid Arthritis," Rheum. Dis. Clin. N. Am., 1995, 21(3):759-777.
Dias et al., "Antisense Oligonucleotides: Basic Concepts and Mechanisms," Mol Cancer Ther, 2002, 1:347-355.
Docherty et al., "Nutrient regulation of insulin gene expression," FASEB J., 1994, 8:20-27.
Dorn et al., "siRNA relieves chronic neuropathic pain," Nucleic Acids, 2004, 32:e49, 6 pp.
Du Plessis et al., "Topical delivery of liposomally encapsulated gamma-interferon," Antiviral Research, 1992, 18:259-265.
Ehrich et al., "Efficacy of MK-966, A Highly Selective Inhibitor of COX-2, in the Treatment of Postoperative Dental Pain," Arthr. Rheum., 1996, 39(S9):S81.
Elbashir et al., "Functional anatomy of siRNAs for mediating efficient RNAi in *Drosophila melanogaster* embryo lysate," EMBO J., 2001, 20(23):6877-6888.
Elbashir et al., "RNA interference is mediated by 21- and 22-nucleotide RNAs," Genes Dev., 2001, 15:188-200.
El-Hariri et al., "The Mitigating Effects of Phosphatidylcholines on Bile Salt- and Lysophosphatidylcholine- induced Membrane Damage," J. Pharm. Pharmacol., 1992, 44:651-654.
Elmén et al., "Locked nucleic acid (LNA) mediated improvements in siRNA stability and functionality," Nucleic Acids Research, 2005, 33(1):439-447.
Evans et al., "Efficacy of Tumor Necrosis Factor Binding Protein (TNF-bp) in the Streptococcal Cell Wall-Induced Reactivation Model of Arthritis," Arthr. Rheum., 1996, 39(S9):S284(1).
Farr et al., "Sulphasalazine (SASP) in Rheumatoid Arthritis (RA): A 5 Year Prospective Study," Arthr. Rheum., 1996, 39(S9):S281(1).
Fiebich et al., "Effects of NSAIDs on IL-1β-induced IL-6 mRNA and protein synthesis in human astrocytoma cells," 1996, Neuro. Report, 1996, 7(6):1209-1213.
Finnegan et al., "Leflunomide Inhibits Immunoglobulin Production by Two Separate Mechanisms," Arthr. Rheum., 1996, 39(S9):S131.
Fisher et al., "Transduction with Recombinant Adeno-Associated Virus for Gene Therapy Is Limited by Leading- Strand Synthesis," J. Virol., 1996, 70(1):520-532.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5:838-843.
Gabizon et al., "Liposome formulations with prolonged circulation time in blood and enhanced uptake by tumors," Proc. Natl. Acad. Sci. USA, 1988, 85:6949-6953.
Gassmann et al., "Maintenance of an extrachromosomal plasmid vector in mouse embryonic stem cells," Proc. Natl. Acad. Sci. USA, 1995, 92:1292-1296.
GenBank NCBI Reference Sequence: NM_172043.1, "Rattus norvegicus MBL associated serine protease 2 (Masp2), mRNA," Dec. 21, 2022.
GenBank: AJ542538.1, "Rattus norvegicus partial masp2 gene for mannose binding lectin-associated serine protease-2, truncated variant MAp19," Jul. 24, 2016.
GenBank NCBI Reference Sequence: NM_001003893.2, "Mus musculus mannan-binding lectin serine peptidase 2 (Masp2), transcript variant 1, mRNA," Dec. 20, 2022.
GenBank NCBI Reference Sequence: NM_006610.3, "*Homo sapiens* mannan binding lectin serine peptidase 2 (MASP2), transcript variant 1, mRNA," May 4, 2019.
GenBank NCBI Reference Sequence: NM_006610.4, "*Homo sapiens* MBL associated serine protease 2 (MASP2), transcript variant 1, mRNA," Mar. 1, 2023.
GenBank NCBI Reference Sequence: NM_010767.3, "Mus musculus mannan-binding lectin serine peptidase 2 (Masp2), transcript variant 2, mRNA," Dec. 20, 2022.
GenBank NCBI Reference Sequence: NM_139208.2, "*Homo sapiens* mannan binding lectin serine peptidase 2 (MASP2), transcript variant 2, mRNA," Feb. 23, 2019.
GenBank NCBI Reference Sequence: XM_005544812.2, "PREDICTED: Macaca fascicularis mannan-binding lectin serine peptidase 2 (MASP2), transcript variant X1, mRNA," Jan. 25, 2016.
GenBank NCBI Reference Sequence: XR_001487411.1, "PREDICTED: Macaca fascicularis mannan-binding lectin serine peptidase 2 (MASP2), transcript variant X2, misc_RNA," Jan. 25, 2016.
Grossman et al., "Retroviruses: delivery vehicle to the liver," Curr. Opin. in Genetics and Devel., 1993, 3:110-114.
Grünweller et al., "Comparison of different antisense strategies in mammalian cells using locked nucleic acids, 2'-O-methyl RNA, phosphorothioates and small interfering RNA," Nucleic Acids Research, 2003, 31(12):3185-3193.
Gultadauria, "Tenidap in Rheumatoid Arthritis Collaborative International Study (TRACIS): A 6-Month Interim Analysis," Arthr. Rheum., 1996, 39(S9):S280.
Hara et al., "Therapeutic Effect of T-614, a New Anti-Arthritic Agent, on Rheumatoid Arthritis, " Arthr. Rheum., 1996, 39(S9):S282(3).
Haubner et al., "Glycosylated RGD-Containing Peptides: Tracer for Tumor Targeting and Angiogenesis Imaging with Improved Biokinetics," J Nucl Med, 2001, 42:326-336.
Hickey et al., "The Rheumatoid Arthritis Azathloprine Registry (RAAR)—Interim Analysis of Malignancy and Mortality," Arthr. Rheum., 1996, 39(S9):S281(2).
Ho et al., "Preparation of Microemulsions Using Polyglycerol Fatty Acid Esters as Surfactant for the Delivery of Protein Drugs," J. Pharm. Sci., 1996, 85(2):138-143.
Howard et al., "RNA Interference in Vitro and in Vivo Using a Chitosan/siRNA Nanoparticle System," Mol. Ther., 2006, 14(4):476-484.
Hu et al., "Topical delivery of cyclosporin A from non-ionic liposomal systems : an in vivo/in vitro correlation study using hairless mouse skin," S.T.P. Pharma. Sci., 1994, 4(6):466-469.
Illum et al., "The organ uptake of intravenously administered colloidal particles can be altered using a non-ionic surfactant (Poloxamer 338)," FEBS Lett., 1984, 167(1):79-82.
Jackson et al., "Expression profiling reveals off-target gene regulation by RNAi," Nat. Biot., 2003, 21(6):635-637.
Jensen et al., "Unlocked nucleic acid (UNA) and UNA derivatives: Thermal denaturation studies," Nuc. Acids Symp. Series, 2008, 52(1):133-134.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259(2):327-330.
Karzai et al., "Hemodynamic effects of dopamine, norepinephrine, and fluids in a dog model of sepsis," Amer. J. Physiol—Heart and Circ. Physiol., 1995, 268(2):H692-H702.
Keith, Jr., et al., "Recombinant Human Interleukin Eleven Decreases Arthritis in HLA-B27 Transgenic Rats," Arthr. Rheum. 1996, 39(S9):S296.
Kiem et al., "Retrovirus-Mediated Gene Transduction Into Canine Peripheral Blood Repopulating Cells," Blood, 1994, 83(6):1467-1473.
Kim et al., "Synthetic dsRNA Dicer substrates enhance RNAi potency and efficacy," Nat Biotech, 2005, 23(2):222-226.
Kim et al., "Cholesteryl Oligoarginine Delivering Vascular Endothelial Growth Factor siRNA Effectively Inhibits Tumor Growth in Colon Adenocarcinoma," Mol. Ther., 2006, 14(3):343-350.

(56) References Cited

OTHER PUBLICATIONS

Kim et al., "Local and systemic delivery of VEGF siRNA using polyelectrolyte complex micelles for effective treatment of cancer," Journal of Controlled Release, 2008, 129:107-116.
Klibanov et al., "Amphipathic polyethyleneglycols effectively prolong the circulation time of liposomes," FEBS Lett., 1990, 268(1):235-237.
Kozarsky et al., "Gene therapy: adenovirus vectors," Current Opinion in Genetics and Development, 1993, 3:499-503.
Kubo et al., "Chemically modified symmetric and asymmetric duplex RNAs: an enhanced stability to nuclease degradation and gene silencing effect," Biochem. Biophys. Res. Comm., 2007, 365:54-61.
Lam et al., "A new type of synthetic peptide library for identifying ligand-binding activity," Nature, 1991, 354:82-84.
Lee et al., "Mucosal Penetration Enhancers For Facilitation of Peptide and Protein Drug Absorption," Critical Reviews in Therapeutic Drug Carrier Systems, 1991, 8(2):91-192.
Lee et al., "Treatment of Rheumatoid Arthritis (RA) with Thalidomide," Arthr. Rheum., 1996, 39(S9):S282(2).
Letsinger et al., "Cholesteryl-conjugated oligonucleotides: Synthesis, properties, and activity as inhibitors of replication of human immunodeficiency virus in cell culture," Proc. Natl. Acid. Sci. USA, 1989, 86:6553-6556.
Li et al., "Small dsRNAs induce transcriptional activation in human cells," Proc. Natl. Acad. Sci., U.S.A., 2006, 103(46):17337-17342.
Li et al., "Polyethylenimine-complexed Plasmid Particles Targeting Focal Adhesion Kinase Function as Melanoma Tumor Therapeutics," Mol. Ther., 2007, 15(3):515-523.
Lima et al., "Single-Stranded siRNAs Activate RNAi in Animals," Cell, 2012, 150:883-894.
Lin et al., "A Cytosine Analogue Capable of Clamp-Like Binding to a Guanine in Helical Nucleic Acids," J. Am. Chem. Soc., 1998, 120:8531-8532.
Lin et al., "siRNA-mediated off-target gene silencing triggered by a 7 nt complementation," Nucleic Acids Res., 2005, 33(14):4527-4535.
Liu, "Radiolabeled Multimeric Cyclic RGD Peptides as Integrin $\alpha v\beta 3$ Targeted Radiotracers for Tumor Imaging," Mol. Pharm., 2006, 3(5):472-487.
Lotz et al., "IL-17 Promotes Cartilage Degradation," Arthr. Rheum., 1996, 39(S9):S120.
Makimura et al., "Reducing hypothalamic AGRP by RNA interference increases metabolic rate and decreases body weight without influencing food intake," BMC Neurosci., 2002, 3:18, 6 pp.
Manoharan et al., "Chemical Modifications to Improve Uptake and Bioavailability of Antisense Oligonucleotides," Ann. N.Y. Acad. Sci., 1992, 660:306-309.
Manoharan et al., "Introduction of a Lipophilic Thioether Tether in the Minor Groove of Nucleic Acids for Antisense Applications," Biorg. Med. Chem. Let., 1993, 3(12):2765-2770.
Manoharan et al., "Cholic Acid-Oligonucleotide Conjugates for Antisense Applications," Biorg. Med. Chem. Let., 1994, 4(8):1053-1060.
Manoharan et al., "Lipidic Nucleic Acids," Tetrahedron Lett., 1995, 36(21):3651-3654.
Manoharan et al., "Oligonucleotide Conjugates: Alteration of the Pharmacokinetic Properties of Antisense Agents," Nucleosides & Nucleotides, 1995, 14(3-5):969-973.
Martin et al., "A New Access to 2'-O-alkylated Ribonucleosides and Properties of 2'-O-Alkylated Oligoribonucleotides," Helv. Chim. Acta, 1995, 78:486-504 (including machine translation).
Mastrangeli et al., "Diversity of Airway Epithelial Cell Targets for In Vivo Recombinant Adenovirus-mediated Gene Transfer," J. Clin. Invest., 1993, 91:225-234.
Mcnamara et al., "Cell type-specific delivery of siRNAs with aptamer-siRNA chimeras," Nat. Biotechnol., 2006, 24(8):1005-1015.
Mikhailov et al., "Synthesis of a New Class of Acyclic 2',5'- and 3',5'-Oligonucleotide Analogs Based on 9-[1,5-dihydroxy-4(S)-hydroxymethyl-3-oxapent-2(R)-yl]-adenine," Tetrahedron Letters, 1985, 26(17):2059-2062.
Miller et al., "Use of Retroviral Vectors for Gene Transfer and Expression," Meth. Enzymol., 1993, 217:581-599.
Mishra et al., "Improved leishmanicidal effect of phosphorotioate antisense oligonucleotides by LDL-mediated delivery," Biochim. Biophys. Acta, 1995, 1264:229-237.
Miyao et al., "Stability and Pharmacokinetic Characteristics of Oligonucleotides Modified at Terminal Linkages in Mice," Antisense Res Dev, 1995, 5:115-121.
Mook et al., "Evaluation of locked nucleic acid-modified small interfering RNA in vitro and in vivo," Mol Canc Ther, 2007, 6(3):833-843.
Moriuchi et al., "Treatment of Established Collagen-Induced Arthritis with PGE1 Incorporated in Lipid Microspheres," Arthr. Rheum., 1996, 39(S9):S282(4).
Muranishi, "Absorption Enhancers," Critical Reviews in Therapeutic Drug Carrier Systems, 1990, 7(1):1-33.
Nielsen et al., "Sequence-Selective Recognition of DNA by Strand Displacement with a Thymine-Substituted Polyamide," Science, 1991, 254(5037):1497-1500.
Nykänen et al., "ATP Requirements and Small Interfering RNA Structure in the RNA Interference Pathway," Cell, 2001, 107(3):309-321.
Oberhauser et al., "Effective incorporation of 2'-O-methyl-oligoribonucleotides into liposomes and enhanced cell association through modification with thiocholesterol," Nucl. Acids Res., 1992, 20(3):533-538.
Pal et al., "Systemic delivery of RafsiRNA using cationic cardiolipin liposomes silences Raf-1 expression and inhibits tumor growth in xenograft model of human prostate cancer," Int J. Oncol., 2005, 26:1087-1091.
Papahadjopoulos et al., "Targeting of Liposomes to Tumor Cells in Vivo," Ann. N.Y. Acad. Sci., 1987, 507(1):64-74.
Pillé et al., "Anti-RhoA and Anti-RhoC siRNAs Inhibit the Proliferation and Invasiveness of MDA-MB-231 Breast Cancer Cells in Vitro and in Vivo," Mol. Ther., 2005, 11(2):267-274.
Rabinowitz et al., "Cross-Packaging of a Single Adeno-Associated Virus (AAV) Type 2 Vector Genome into Multiple AAV Serotypes Enables Transduction with Broad Specificity," J Virol, 2002, 76(2):791-801.
Reich et al., "Small interfering RNA (siRNA) targeting VEGF effectively inhibits ocular neovascularization in a mouse model," Mol. Vis., 2003, 9:210-216.
Ritschel, "Microemulsions for Improved Peptide Absorption from the Gastrointestinal Tract," Meth. Find. Exp. Clin. Pharmacol., 1991, 13(3):205-220.
Ronday et al., "Tranexamic Acid (TEA), an Inhibitor of Plasminogen Activation, Reduces Collagen Crosslink Excretion in Arthritis," Arthr. Rheum., 1996, 39(S9):S284(2).
Rosenfeld et al., "Adenovirus-Mediated Transfer of a Recombinant $\alpha 1$-Antitrypsin Gene to the Lung Epithelium in Vivo," Science, 1991, 252(5004):431-434.
Rosenfeld et al., "In Vivo Transfer of the Human Cystic Fibrosis Transmembrane Conductance Regulator Gene to the Airway Epithelium," Cell, 1992, 68:143-155.
Saison-Behmoaras et al., "Short modified antisense oligonucleotides directed against Ha-ras point mutation induce selective cleavage of the mRNA and inhibit T24 cells proliferation," EMBO J, 1991, 10(5):1111-1118.
Salmons et al., "Targeting of Retroviral Vectors for Gene Therapy," Human Gene Therapy, 1993, 4:129-141.
Samulski et al., "A Recombinant Plasmid from Which an Infectious Adeno-Associated Virus Genome Can Be Excised In Vitro and Its Use to Study Viral Replication," J. Virol., 1987, 61(10):3096-3101.
Samulski et al., "Helper-Free Stocks of Recombinant Adeno-Associated Viruses: Normal Integration Does Not Require Viral Gene Expression," J. Virol., 1989, 63(9):3822-3826.
Scholz, "Inhibition of the production and effect of TNF-alpha by Iloprost: possible impact for treatment of rheumatoid arthritis," Arthr. Rheum., 1996, 39(S9):S82.

(56) References Cited

OTHER PUBLICATIONS

Sewell et al., "$DAB_{486}$IL-2 Fusion Toxin in Refractory Rheumatoid Arthritis," Arthr. Rheum., 1993, 36(9):1223-1233.
Sharp, "RNA interference—2001," Genes Dev., 2001, 15:485-490.
Shea et al., "Synthesis, hybridization properties and antiviral activity of lipid-oligodeoxynucleotide conjugates," Nucl. Acids Res., 1990, 18(13):3777-3783.
Shishkina et al., "Attenuation of α2A-Adrenergic Receptor Expression in Neonatal Rat Brain by RNA Interference or Antisense Oligonucleotide Reduced Anxiety in Adulthood," Neuroscience, 2004, 129:521-528.
Simeoni et al., "Insight into the mechanism of the peptide-based gene delivery system MPG: implications for delivery of siRNA into mammalian cells," Nucl. Acids Res., 2003, 31(11):2717-2724.
Sorensen et al., "Gene Silencing by Systemic Delivery of Synthetic siRNAs in Adult Mice," J. Mol. Biol., 2003, 327:761-766.
Soutschek et al., "Therapeutic silencing of an endogenous gene by systemic administration of modified siRNAs," Nature, 2004, 432:173-178.
Sunamoto et al., "Liposomal Membranes. V. Interaction of Zinc(II) Ion with Egg Phosphatidylcholine Liposomes," Bull. Chem. Soc. Jpn., 1980, 53(10):2778-2781.
Svinarchuk et al., "Inhibition of HIV proliferation in MT-4 cells by antisense oligonucleotide conjugated to lipophilic groups," Biochimie, 1993, 75:49-54.
Takahashi et al., "The Use of a Perfluorochemical Emulsion as a Vascular Perfusate in Drug Absorption," J. Pharm. Pharmacol., 1988, 40:252-257.
Takakura et al., "Uptake Characteristics of Oligonucleotides in the Isolated Rat Liver Perfusion System," Antisense Nucleic Acid Drug Dev., 1996, 6:177-183.
Tan et al., "Gene knockdown with intrathecal siRNA of NMDA receptor NR2B subunit reduces formalin-induced nociception in the rat," Gene Ther., 2005, 12:59-66.
Thakker et al., "Neurochemical and behavioral consequences of widespread gene knockdown in the adult mouse brain by using nonviral RNA interference," Proc. Natl. Acad. Sci. U.S.A., 2004, 101(49):17270-17275.
Thoss et al., "Immunomodulation of rat antigen-induced arthritis by leflunomide alone and in combination with cyclosporin A," 1996, Inflamm. Res., 45:103-107.
Tolentino et al., "Intravitreal Injection of Vascular Endothelial Growth Factor Small Interfering RNA Inhibits Growth and Leakage in a Nonhuman Primate, Laser-Induced Model of Choroidal Neovascularization," Retina, 2004, 24(1):132-138.
Tomalia et al., "Dendrimers as multi-purpose nanodevices for oncology drug delivery and diagnostic imaging," Biochem. Soc. Trans., 2007, 35(1):61-67.
Verma et al., "Small Interfering RNAs Directed against—Catenin Inhibit the in Vitro and in Vivo Growth of Colon Cancer Cells," Clin. Cancer Res., 2003, 9:1291-1300.
Walsh et al., "Gene Therapy for Human Hemoglobinopathies," Proc. Soc. Exp. Biol. Med., 1993, 204(3):289-300.
Wang et al., "Plasmid DNA Adsorbed to pH-sensitive Liposomes Efficiently Transforms the Target Cells," Biochem. Biophys. Res. Commun., 1987, 147(3):980-985.
Wang et al., "A packaging cell line for propagation of recombinant adenovirus vectors containing two lethal gene- region deletions," Gene Therapy, 1995, 2:775-783.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122:8595-8602.
Weiner et al., "Liposomes: A Novel Topical Delivery System for Pharmaceutical and Cosmetic Applications," Journal of Drug Targeting, 1992, 2:405-410.
Wu et al., "Increased Microvascular Permeability Contributes to Preferential Accumulation of Stealth Liposomes in Tumor Tissue," Cancer Research, 1993, 53:3765-3770.
Xia et al., "siRNA-mediated gene silencing in vitro and in vivo," Nat. Biotech., 2002, 20:1006-1010.
Yamamoto et al., "A Mechanistic Study on Enhancement of Rectal Permeability to Insulin in the Albino Rabbit," J. Pharm. Exp. Ther., 1992, 263(1):25-31.
Yamashita et al., "Effects of diclofenac sodium and disodium ethylenediaminetetraacetate on electrical parameters of the mucosal membrane and their relation to the permeability enhancing effects in the rat jejunum," J. Pharm. Pharmacol., 1987, 39:621-626.
Yamashita et al., "Effect of Adjuvants on Charge-Selective Permeability and Electrical Resistance of Rat Jejunal Membrane," J. Pharm. Sci., 1990, 79(7):579-583.
Yoo et al., "PAMAM Dendrimers as Delivery Agents for Antisense Oligonucleotides," Pharm. Res., 1999, 16:1799-1804.
Zhang et al., "Small Interfering RNA Targeting Heme Oxygenase-1 Enhances Ischemia-Reperfusion-induced Lung Apoptosis," J. Biol. Chem., 2004, 279(11):10677-10684.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties," J. Org. Chem., 2009, 74:118-134.
Zhou et al., "Targeted delivery of DNA by liposomes and polymers," Journal of Controlled Release, 1992, 19:269-274.
Zimmermann et al., "RNAi-mediated gene silencing in non-human primates," Nature, 2006, 441:111-114.
Zitzmann et al., "Arginine-glycine-aspartic acid (RGD)-peptide binds to both tumor and tumor endothelial cells in vivo.," Cancer Res., 2002, 62:5139-5143.
Holers et al., "Key Components of the Complement Lectin Pathway Are Not Only Required for the Development of Inflammatory Arthritis but Also Regulate the Transcription of Factor D," Front. Immunol., Feb. 2020, 11(201):1-18.
Partial supplementary search report and provisional opinion issued Jan. 28, 2025, in European patent application No. 21756268.5.
Extended European search report issued Apr. 22, 2025, in European patent application No. 21756268.5.
International Search Report and Written Opinion issued Jun. 30, 2021 in PCT/US2021/018624.

* cited by examiner

MANNAN BINDING LECTIN SERINE PEPTIDASE 2 (MASP2) IRNA COMPOSITIONS AND METHODS OF USE THEREOF

CROSS-REFERENCE TO RELATED APPLICATIONS

This application claims the benefit of priority to U.S. Provisional Application No. 62/978,788, filed on Feb. 19, 2020. The entire contents of the foregoing application is hereby incorporated herein by reference.

SEQUENCE LISTING

The instant application contains a Sequence Listing which has been submitted electronically in ASCII format and is hereby incorporated by reference in its entirety. The ASCII copy, created on Feb. 12, 2021, is named A108868_1020 WO_SL.txt and is 356,834 bytes in size.

BACKGROUND OF THE INVENTION

The complement system consists of more than 30 proteins that are either present as soluble proteins in the blood or are present as membrane-associated proteins. Activation of complement leads to a sequential cascade of enzymatic reactions, known as complement activation pathways that elicit a plethora of physiological responses that range from chemoattraction to apoptosis. Initially, complement was thought to play a major role in innate immunity where a robust and rapid response is mounted against invading pathogens. However, recently it is becoming increasingly evident that complement also plays an important role in adaptive immunity involving T and B cells that help in elimination of pathogens, in maintaining immunologic memory preventing pathogenic re-invasion, and is involved in numerous human pathological states.

Complement activation is known to occur through three different pathways: alternate, classical and lectin involving proteins that mostly exist as inactive zymogens that are then sequentially cleaved and activated.

The mannan binding lectin serine peptidase 2 (MASP2) gene, encoding the protein MASP2, is involved in the lectin pathway of the complement system. The MASP2 gene is located on chromosome 1p36.23-31 and belongs to the peptidase 51 family of serine proteases. Two gene products are encoded by the MASP2 gene, a 76 kDa serine protease, MASP2 (long isoform), which is highly expressed in the liver, and a 19 kDa alternative splice product, Map19 (short isoform), which is present in plasma. MASP2 cleaves complement components C2 and C4 to form the C3 convertase in the lectin complement activation pathway. MASP2 is also involved in the coagulation cascade by cleaving prothrombin to generate thrombin.

Inappropriate activation of components of the complement system, including MASP2, is responsible for propagating and/or initiating pathology in many different diseases, including, for example, arthritis, IgA nephropathy, thrombotic microangiopathy, diabetic nephropathy and membranous nephropathy. Accordingly, there is a need for agents that can selectively and efficiently inhibit expression of the MASP2 gene such that subjects having a MASP2-associated disorder can be effectively treated.

BRIEF SUMMARY OF THE INVENTION

The present invention provides iRNA compositions which affect the RNA-induced silencing complex (RISC)-mediated cleavage of RNA transcripts of a gene encoding mannan binding lectin serine peptidase 2 (MASP2). The MASP2 may be within a cell, e.g., a cell within a subject, such as a human subject.

In an aspect, the invention provides a double stranded ribonucleic acid (dsRNA) agent for inhibiting expression of MASP2 in a cell, wherein the dsRNA agent comprises a sense strand and an antisense strand forming a double stranded region, wherein the sense strand comprises at least 15 contiguous nucleotides differing by no more than 0, 1, 2, or 3 nucleotides from the nucleotide sequence of SEQ ID NOs:1, 3 or 5 and the antisense strand comprises at least 15 contiguous nucleotides differing by no more than 1, 2, or 3 nucleotides from the nucleotide sequence of SEQ ID NOs:2, 4 or 6.

In another aspect, the present invention provides a double stranded ribonucleic acid (dsRNA) for inhibiting expression of MASP2 in a cell, wherein said dsRNA comprises a sense strand and an antisense strand forming a double stranded region, wherein the antisense strand comprises a region of complementarity to an mRNA encoding MASP2, and wherein the region of complementarity comprises at least 15 contiguous nucleotides differing by no more than 0, 1, 2, or 3 nucleotides from any one of the antisense nucleotide sequences in any one of Tables 2-7.

In one aspect, the present invention provides a double stranded ribonucleic acid (dsRNA) for inhibiting expression of MASP2 in a cell, wherein said dsRNA comprises a sense strand and an antisense strand forming a double stranded region, wherein the sense strand comprises (a) at least 15 contiguous nucleotides differing by no more than three nucleotides from any one of the nucleotide sequence of nucleotides 3-23, 21-41, 39-59, 57-77, 76-96, 94-114, 112-132, 130-150, 148-168, 166-186, 184-204, 203-223, 221-241, 239-259, 257-277, 275-295, 293-313, 312-332, 330-350, 348-368, 366-386, 384-404, 402-422, 420-440, 439-459, 457-477, 475-495, 493-513, 511-531, 529-549, 547-567, 566-586, 584-604, 602-622, 620-640, 638-658, 656-676, 675-695, 693-713, 711-731, 729-749, 747-767, 765-785, 783-803, 802-822, 820-840, 838-858, 856-876, 874-894, 892-912, 910-930, 929-949, 947-967, 965-985, 983-1003, 1001-1021, 1019-1039, 1038-1058, 1056-1076, 1074-1094, 1092-1112, 1110-1130, 1128-1148, 1146-1166, 1165-1185, 1183-1203, 1201-1221, 1219-1239, 1237-1257, 1255-1275, 1273-1293, 1292-1312, 1310-1330, 1328-1348, 1346-1366, 1364-1384, 1382-1402, 1400-1420, 1419-1439, 1437-1457, 1455-1475, 1473-1493, 1491-1511, 1509-1529, 1528-1548, 1546-1566, 1564-1584, 1582-1602, 1600-1620, 1618-1638, 1636-1656, 1655-1675, 1673-1693, 1691-1711, 1709-1729, 1727-1747, 1745-1765, 1763-1783, 1782-1802, 1800-1820, 1818-1838, 1836-1856, 1854-1874, 1872-1892, 1891-1911, 1909-1929, 1927-1947, 1945-1965, 1963-1983, 1981-2001, 1999-2019, 2018-2038, 2036-2056, 2054-2074, 2072-2092, 2090-2110, 2108-2128, 2126-2146, 2145-2165, 2163-2183, 2181-2201, 2199-2219, 2217-2237, 2235-2255, 2254-2274, 2272-2292, 2290-2310, 2308-2328, 2326-2346, 2344-2364, 2362-2382, 2381-2401, 2399-2419, 2417-2437 or 2435-2455 of the nucleotide sequence of SEQ ID NO:1, and the antisense strand comprises at least 19 contiguous nucleotides from the corresponding nucleotide sequence of SEQ ID NO:2; (b) at least 15 contiguous nucleotides differing by no more than three nucleotides from any one of the nucleotide sequence of nucleotides 1263-1283, 1190-1210, 1191-1211, 1078-1098, 1270-

1290, 885-905, 761-781, 1255-1275, 1279-1299, 1197-1217, 1021-1041, 704-724, 1968-1988, 1277-1297, 1204-1224, 1193-1213, 1201-1221, 1390-1410, 1272-1292, 1282-1302, 959-979, 1199-1219, 1620-1640, 1806-1826, 1783-1803, 1623-1643, 1397-1417, 1782-1802, 1777-1797, 1490-1510, 1712-1732, 1676-1696, 1353-1373, 2189-2209, 1438-1458, 1820-1840, 1664-1684, 1386-1406, 1665-1685, 1282-1302, 1864-1884, 1785-1805, 2333-2353, 1779-1799, 1351-1371, 1350-1370, 1031-1051, 2046-2066, 1616-1636, 2372-2392, 1667-1687, 1675-1695, 1780-1800, 1541-1561, 1551-1571, 1399-1419, 1701-1721, 1715-1735, 1700-1720, 1668-1688, 1366-1386, 2191-2211, 2374-2394, 1400-1420, 1314-1334, 1821-1841, 1807-1827, 1652-1672, 2129-2149, 1778-1798, 1702-1722, 1404-1424, 1593-1613, 1773-1793, 2373-2393, 1545-1565, 1812-1832, 1677-1697, 1359-1379, 1663-1683, 1365-1385, 2194-2214, 1393-1413, 1621-1641, 1673-1693, 1594-1614, 1387-1407, 1542-1562, 1972-1992, 1550-1570, 1323-1343, 1357-1377, 1360-1380, 1711-1731, 1830-1850, 1781-1801, 1405-1425, 2122-2142, 1437-1457, 1973-1993, 2379-2399, 1398-1418, 1669-1689, 1355-1375, 2196-2216, 1320-1340, 1407-1427, 1862-1882, 1666-1686, 1354-1374, 1974-1994, 1662-1682 or 1653-1673 of the nucleotide sequence of SEQ ID NO:3, and the antisense strand comprises at least 19 contiguous nucleotides from the corresponding nucleotide sequence of SEQ ID NO:4; or (c) at least 15 contiguous nucleotides differing by no more than three nucleotides from any one of the nucleotide sequence of nucleotides 363-383, 543-563, 437-457, 93-113, 243-263, 144-164, 85-105, 257-277, 435-455, 358-378, 26-46 or 344-364 of the nucleotide sequence of SEQ ID NO:5, and the antisense strand comprises at least 19 contiguous nucleotides from the corresponding nucleotide sequence of SEQ ID NO:6.

In one embodiment, the antisense strand comprises at least 15 contiguous nucleotides differing by nor more than 0, 1, 2, or 3 nucleotides from any one of the antisense strand nucleotide sequences of a duplex selected from the group consisting of AD-1143337, AD-1143348, AD-155520, AD-1143374, AD-1144836, AD-1143386, AD-1144837, AD-1144838, AD-1143406, AD-1143416, AD-1144839, AD-155599, AD-1143442, AD-155635, AD-1143470, AD-1144840, AD-1143479, AD-1143498, AD-1144841, AD-1143511, AD-1143523, AD-1143538, AD-1144842, AD-1143554, AD-1143570, AD-1144843, AD-1144844, AD-1143594, AD-155809, AD-1143619, AD-1143635, AD-1143649, AD-1143662, AD-1144845, AD-1143677, AD-1143691, AD-155927, AD-1144846, AD-155946, AD-1143731, AD-1143748, AD-155999, AD-1143774, AD-1143789, AD-1143802, AD-1144847, AD-1143816, AD-1143828, AD-1143845, AD-1143860, AD-156136, AD-1143891, AD-1143904, AD-1143919, AD-156208, AD-1143945, AD-1143957, AD-1144848, AD-156260, AD-1143982, AD-1144849, AD-156308, AD-1144019, AD-1144035, AD-1144050, AD-1144065, AD-1144077, AD-1144092, AD-1144105, AD-1144117, AD-156460, AD-156477, AD-156495, AD-1144173, AD-156531, AD-1144205, AD-1144217, AD-156584, AD-1144246, AD-1144257, AD-156639, AD-1144284, AD-1144299, AD-1144313, AD-156712, AD-1144343, AD-156748, AD-1144365, AD-1144376, AD-1144391, AD-1144850, AD-156832, AD-1144424, AD-1144440, AD-1144453, AD-1144466, AD-1144851, AD-1144852, AD-1144481, AD-1144494, AD-156962, AD-1144522, AD-1144853, AD-1144534, AD-1144854, AD-1144548, AD-1144855, AD-1144565, AD-1144578, AD-1144856, AD-1144857, AD-1144591, AD-1144604, AD-1144614, AD-1144858, AD-1144631, AD-1144640, AD-1144654, AD-1144669, AD-1144682, AD-157219, AD-1144859, AD-1144708, AD-1144718, AD-157273, AD-1144860, AD-1144745, AD-1144758, AD-1144771, AD-1144781, AD-1144793, AD-1144803, AD-157398, AD-157416, AD-1144861, AD-156804.1, AD-156950.1, AD-156927.1, AD-156807.1, AD-156581.1, AD-156926.1, AD-156921.1, AD-156674.1, AD-156889.1, AD-156853.1, AD-156538.1, AD-157227.1, AD-156622.1, AD-156964.1, AD-156841.1, AD-156571.1, AD-156842.1, AD-68457.2, AD-156990.1, AD-156929.1, AD-157334.1, AD-156923.1, AD-156536.1, AD-156535.1, AD-156255.1, AD-157093.1, AD-156800.1, AD-157371.1, AD-156844.1, AD-156852.1, AD-156924.1, AD-156725.1, AD-156735.1, AD-156583.1, AD-156878.1, AD-156892.1, AD-156877.1, AD-156845.1, AD-156551.1, AD-157229.1, AD-157373.1, AD-156584.1, AD-156499.1, AD-156965.1, AD-156951.1, AD-156829.1, AD-157167.1, AD-156922.1, AD-156879.1, AD-156588.1, AD-156777.1, AD-156917.1, AD-157372.1, AD-156729.1, AD-156956.1, AD-156854.1, AD-156544.1, AD-156840.1, AD-156550.1, AD-157232.1, AD-156577.1, AD-156805.1, AD-156850.1, AD-156778.1, AD-156572.1, AD-156726.1, AD-157059.1, AD-156734.1, AD-156508.1, AD-156542.1, AD-156545.1, AD-156888.1, AD-156974.1, AD-156925.1, AD-156589.1, AD-157160.1, AD-156621.1, AD-157060.1, AD-157378.1, AD-156582.1, AD-156846.1, AD-156540.1, AD-157234.1, AD-156505.1, AD-156591.1, AD-156988.1, AD-156843.1, AD-156539.1, AD-157061.1, AD-156839.1, AD-156830.1, AD-68438.1, AD-68439.1, AD-68440.1, AD-68441.1, AD-68442.1, AD-68443.1, AD-68444.1, AD-68445.1, AD-68446.1, AD-68447.1, AD-68448.1, AD-68449.1, AD-68450.1, AD-68451.1, AD-68452.1, AD-68453.1, AD-68454.1, AD-68455.1, AD-68456.1, AD-68457.1, AD-68458.1, AD-68459.1, AD-68460.1, AD-68461.1, AD-68462.1, AD-68463.1, AD-68464.1, AD-68465.1, AD-68466.1, AD-68467.1, AD-68468.1, AD-68469.1, AD-68470.1 and AD-68471.1.

In one embodiment, the dsRNA agent comprises at least one modified nucleotide.

In one embodiment, substantially all of the nucleotides of the sense strand; substantially all of the nucleotides of the antisense strand comprise a modification; or substantially all of the nucleotides of the sense strand and substantially all of the nucleotides of the antisense strand comprise a modification.

In one embodiment, all of the nucleotides of the sense strand comprise a modification; all of the nucleotides of the antisense strand comprise a modification; or all of the nucleotides of the sense strand and all of the nucleotides of the antisense strand comprise a modification.

In one embodiment, at least one of the modified nucleotides is selected from the group consisting of a deoxynucleotide, a 3'-terminal deoxythimidine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide; and combinations thereof.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and glycol; and combinations thereof.

In one embodiment, at least one of the modified nucleotides is selected from the group consisting of a deoxynucleotide, a 2'-O-methyl modified nucleotide, a 2'-fluoro modified nucleotide, a 2'-deoxy-modified nucleotide, a glycol modified nucleotide (GNA), e.g., Ggn, Cgn, Tgn, or Agn, and, a vinyl-phosphonate nucleotide; and combinations thereof.

In another embodiment, at least one of the modifications on the nucleotides is a thermally destabilizing nucleotide modification.

In one embodiment, the thermally destabilizing nucleotide modification is selected from the group consisting of an abasic modification; a mismatch with the opposing nucleotide in the duplex; and destabilizing sugar modification, a 2'-deoxy modification, an acyclic nucleotide, an unlocked nucleic acids (UNA), and a glycerol nucleic acid (GNA)

The double stranded region may be 19-30 nucleotide pairs in length; 19-25 nucleotide pairs in length; 19-23 nucleotide pairs in length; 23-27 nucleotide pairs in length; or 21-23 nucleotide pairs in length.

In one embodiment, each strand is independently no more than 30 nucleotides in length.

In one embodiment, the sense strand is 21 nucleotides in length and the antisense strand is 23 nucleotides in length.

The region of complementarity may be at least 17 nucleotides in length; between 19 and 23 nucleotides in length; or 19 nucleotides in length.

In one embodiment, at least one strand comprises a 3' overhang of at least 1 nucleotide. In another embodiment, at least one strand comprises a 3' overhang of at least 2 nucleotides.

In one embodiment, the dsRNA agent further comprises a ligand.

In one embodiment, the ligand is conjugated to the 3' end of the sense strand of the dsRNA agent.

In one embodiment, the ligand is an N-acetylgalactosamine (GalNAc) derivative.

In one embodiment, the ligand is one or more GalNAc derivatives attached through a monovalent, bivalent, or trivalent branched linker.

In one embodiment, the ligand is

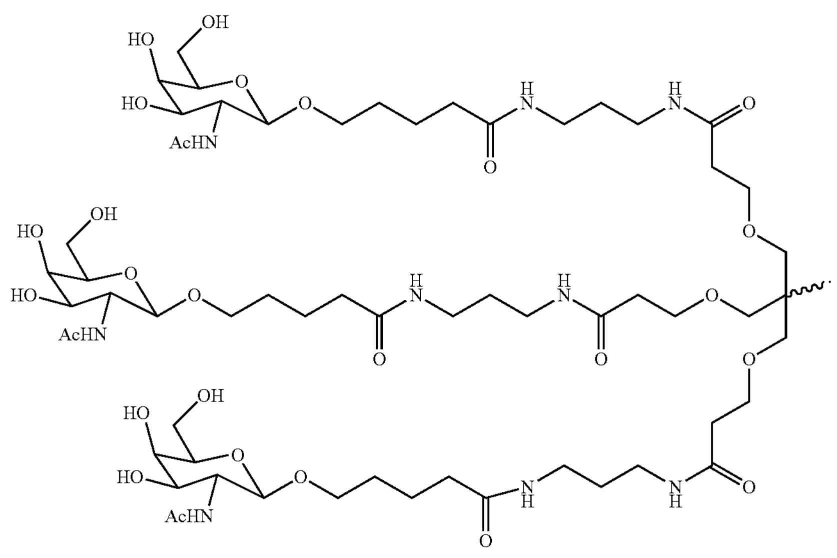 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

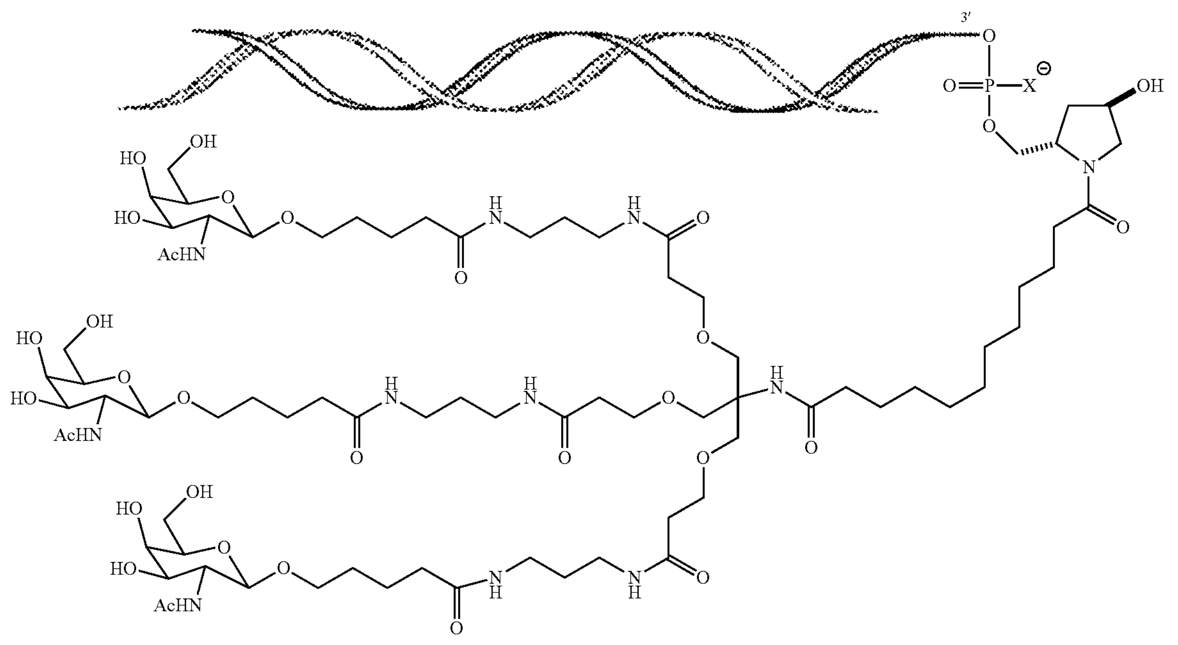

and, wherein X is O or S.

In one embodiment, the X is O.

In one embodiment, the dsRNA agent further comprises at least one phosphorothioate or methylphosphonate internucleotide linkage.

In one embodiment, the phosphorothioate or methylphosphonate internucleotide linkage is at the 3'-terminus of one strand, e.g., the antisense strand or the sense strand.

In another embodiment, the phosphorothioate or methylphosphonate internucleotide linkage is at the 5'-terminus of one strand, e.g., the antisense strand or the sense strand.

In one embodiment, the phosphorothioate or methylphosphonate internucleotide linkage is at the both the 5'- and 3'-terminus of one strand. In one embodiment, the strand is the antisense strand.

In one embodiment, the base pair at the 1 position of the 5'-end of the antisense strand of the duplex is an AU base pair.

The present invention also provides cells containing any of the dsRNA agents of the invention and pharmaceutical compositions comprising any of the dsRNA agents of the invention.

The pharmaceutical composition of the invention may include dsRNA agent in an unbuffered solution, e.g., saline or water, or the pharmaceutical composition of the invention may include the dsRNA agent is in a buffer solution, e.g., a buffer solution comprising acetate, citrate, prolamine, carbonate, or phosphate or any combination thereof; or phosphate buffered saline (PBS).

In one aspect, the present invention provides a method of inhibiting expression of a MASP2 gene in a cell. The method includes contacting the cell with any of the dsRNAs of the invention or any of the pharmaceutical compositions of the invention, thereby inhibiting expression of the MASP2 gene in the cell.

In one embodiment, the cell is within a subject, e.g., a human subject, e.g., a subject having a MASP2-associated disorder, such as a MASP2-associated disorder selected from the group consisting of arthritis, IgA nephropathy, thrombotic microangiopathy, diabetic nephropathy and membranous nephropathy.

In one embodiment, contacting the cell with the dsRNA agent inhibits the expression of MASP2 by at least 50%, 60%, 70%, 80%, 90%, or 95%.

In one embodiment, inhibiting expression of MASP2 decreases MASP2 protein level in serum of the subject by at least 50%, 60%, 70%, 80%, 90%, or 95%.

In one aspect, the present invention provides a method of treating a subject having a disorder that would benefit from reduction in MASP2 expression. The method includes administering to the subject a therapeutically effective amount of any of the dsRNAs of the invention or any of the pharmaceutical compositions of the invention, thereby treating the subject having the disorder that would benefit from reduction in MASP2 expression.

In another aspect, the present invention provides a method of preventing at least one symptom in a subject having a disorder that would benefit from reduction in MASP2 expression. The method includes administering to the subject a prophylactically effective amount of any of the dsRNAs of the invention or any of the pharmaceutical compositions of the invention, thereby preventing at least one symptom in the subject having the disorder that would benefit from reduction in MASP2 expression.

In one embodiment, the disorder is a MASP2-associated disorder, e.g., a MASP2-associated disorder is selected from the group consisting of arthritis, IgA nephropathy, thrombotic microangiopathy, diabetic nephropathy and membranous nephropathy.

In one embodiment, the MASP2-associated disorder is IgA nephropathy.

In one embodiment, the subject is human.

In one embodiment, the administration of the agent to the subject causes a decrease in inflammation and/or a decrease in MASP2 protein accumulation.

In one embodiment, the dsRNA agent is administered to the subject at a dose of about 0.01 mg/kg to about 50 mg/kg.

In one embodiment, the dsRNA agent is administered to the subject subcutaneously.

In one embodiment, the methods of the invention include further determining the level of MASP2 in a sample(s) from the subject.

In one embodiment, the level of MASP2 in the subject sample(s) is a MASP2 protein level in a blood or serum sample(s).

In one embodiment, the methods of the invention further include administering to the subject an additional therapeutic agent for treatment of inflammation.

The present invention also provides kits comprising any of the dsRNAs of the invention or any of the pharmaceutical compositions of the invention, and optionally, instructions for use.

DETAILED DESCRIPTION OF THE INVENTION

The present invention provides iRNA compositions which effect the RNA-induced silencing complex (RISC)-mediated cleavage of RNA transcripts of a MASP2 gene. The gene may be within a cell, e.g., a cell within a subject, such as a human. The use of these iRNAs enables the targeted degradation of mRNAs of the corresponding gene (MASP2 gene) in mammals.

The iRNAs of the invention have been designed to target the human MASP2 gene, including portions of the gene that are conserved in the MASP2 orthologs of other mammalian species. Without intending to be limited by theory, it is believed that a combination or sub-combination of the foregoing properties and the specific target sites or the specific modifications in these iRNAs confer to the iRNAs of the invention improved efficacy, stability, potency, durability, and safety.

Accordingly, the present invention provides methods for treating and preventing a MASP2-associated disorder, e.g., arthritis, IgA nephropathy, thrombotic microangiopathy, diabetic nephropathy and membranous nephropathy, using iRNA compositions which effect the RNA-induced silencing complex (RISC)-mediated cleavage of RNA transcripts of a MASP2 gene.

The iRNAs of the invention include an RNA strand (the antisense strand) having a region which is up to about 30 nucleotides or less in length, e.g., 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a MASP2 gene.

In certain embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of a MASP2 gene. In some embodiments, such iRNA agents having longer length antisense strands may include a second RNA strand (the sense strand) of 20-60 nucleotides in length wherein the sense and antisense strands form a duplex of 18-30 contiguous nucleotides.

The use of iRNAs of the invention enables the targeted degradation of mRNAs of the corresponding gene (MASP2 gene) in mammals. Using in vitro and in vivo assays, the present inventors have demonstrated that iRNAs targeting a MASP2 gene can potently mediate RNAi, resulting in significant inhibition of expression of a MASP2 gene. Thus, methods and compositions including these iRNAs are useful for treating a subject having a MASP2-associated disorder, e.g., arthritis, IgA nephropathy, thrombotic microangiopathy, diabetic nephropathy and membranous nephropathy.

Accordingly, the present invention provides methods and combination therapies for treating a subject having a disorder that would benefit from inhibiting or reducing the expression of a MASP2 gene, e.g., a MASP2-associated disease, such as arthritis, IgA nephropathy, thrombotic microangiopathy, diabetic nephropathy and membranous nephropathy, using iRNA compositions which effect the RNA-induced silencing complex (RISC)-mediated cleavage of RNA transcripts of a MASP2 gene.

The present invention also provides methods for preventing at least one symptom in a subject having a disorder that would benefit from inhibiting or reducing the expression of a MASP2 gene, e.g., arthritis, IgA nephropathy, thrombotic microangiopathy, diabetic nephropathy and membranous nephropathy.

For example, in a subject having arthritis, the methods of the present invention may prevent at least one symptom in the subject including, e.g., pain, edema and stiffness in one or more joints, MAC deposition and tissue damage, and inflammation (e.g., chronic inflammation); in a subject having IgA nephropathy, the methods of the present invention may prevent at least one symptom in the subject including, e.g., hematuria, proteinuria, hypertension, inflammation (e.g., chronic inflammation), pain, high blood pressure, and edema in hands and/or feet; in a subject having thrombotic microangiopathy, the methods of the present invention may prevent at least one symptom in the subject including, e.g., hemolysis, thrombocytopenia, inflammation (e.g., chronic inflammation), renal failure, hypertension, fever, fatigue, and seizures; in a subject having diabetic nephropathy, the methods of the present invention may prevent at least one symptom in the subject including, e.g., inflammation (e.g., chronic inflammation), proteinuria, edema, hypertension, fatigue, itching, nausea or vomiting, and renal failure; and in a subject having membranous nephropathy, the methods of the present invention may prevent at least one symptom in the subject including, e.g., proteinuria, renal failure, edema, fatigue, hematuria, hypertension, and inflammation (e.g., chronic inflammation).

The following detailed description discloses how to make and use compositions containing iRNAs to inhibit the expression of a MASP2 gene as well as compositions, uses, and methods for treating subjects that would benefit from inhibition and/or reduction of the expression of a MASP2 gene, e.g., subjects susceptible to or diagnosed with a MASP2-associated disorder.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means ±10%. In certain embodiments, about means ±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 19 nucleotides of a 21 nucleotide nucleic acid molecule" means that 19, 20, or 21 nucleotides have the indicated property. When at least is present before a series of numbers or a range, it is understood that "at least" can modify each of the numbers in the series or range.

As used herein, "no more than" or "or less" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

In the event of a conflict between a sequence and its indicated site on a transcript or other sequence, the nucleotide sequence recited in the specification takes precedence.

As used herein, the term "mannan binding lectin serine peptidase 2," used interchangeably with the term "MASP2," refers to the well-known gene and polypeptide, also known in the art as mannan binding lectin serine protease 2, MBL-associated serine protease 2, mannose-binding protein-associated serine protease 2, MBL-associated plasma protein of 19 KDa (Map19) and MASP1P1.

Exemplary nucleotide and amino acid sequences of MASP2 can be found, for example, at GenBank Accession No. NM_006610.4 (SEQ ID NO: 1; reverse complement SEQ ID NO: 2) and NM-006610.3 (SEQ ID NO: 3; reverse complement SEQ ID NO: 4) for *Homo sapiens* MASP2 long isoform; GenBank Accession No. NM_139208.2 (SEQ ID NO: 5; reverse complement SEQ ID NO: 6) for *Homo sapiens* MASP2 short isoform; GenBank Accession No. NM_001003893.2 (SEQ ID NO: 7; reverse complement SEQ ID NO: 8) for *Mus musculus* MASP2 long isoform; GenBank Accession No. NM_010767.3 (SEQ ID NO: 9; reverse complement SEQ ID NO: 10) for *Mus musculus* MASP2 short isoform; GenBank Accession No. XM_005544812.2 (SEQ ID NO: 11; reverse complement SEQ ID NO: 12) for *Macaca fascicularis* MASP2 long isoform; GenBank Accession No. XR_001487411.1 (SEQ ID NO: 13; reverse complement SEQ ID NO: 14) for *Macaca fascicularis* MASP2 short isoform; GenBank Accession No. NM_172043.1 (SEQ ID NO: 15; reverse complement SEQ ID NO: 16) for *Rattus norvegicus* MASP2 long isoform; and GenBank Accession No. AJ542538.1 (SEQ ID NO: 17; reverse complement SEQ ID NO: 18) for *Rattus norvegicus* MASP2 short isoform.

Additional examples of MASP2 mRNA sequences are readily available using, e.g., GenBank, UniProt, OMIM, and the *Macaca* genome project web site.

Further information on MASP2 is provided, for example in the NCBI Gene database at http://www.ncbi.nlm.nih.gov/gene/10747.

The entire contents of each of the foregoing GenBank Accession numbers and the Gene database numbers are incorporated herein by reference as of the date of filing this application.

The terms "mannan binding lectin serine peptidase 2" and "MASP2," as used herein, also refers to naturally occurring DNA sequence variations of the MASP2 gene. Numerous sequence variations within the MASP2 gene have been identified and may be found at, for example, NCBI dbSNP and UniProt (see, e.g., http://www.ncbi.nlm.nih.gov/snp?LinkName=gene_snp&from_uid=10747, the entire contents of which is incorporated herein by reference as of the date of filing this application.

As used herein, "target sequence" refers to a contiguous portion of the nucleotide sequence of an mRNA molecule formed during the transcription of a MASP2 gene, including mRNA that is a product of RNA processing of a primary transcription product. The target portion of the sequence will be at least long enough to serve as a substrate for iRNA-directed cleavage at or near that portion of the nucleotide sequence of an mRNA molecule formed during the transcription of a MASP2 gene. In one embodiment, the target sequence is within the protein coding region of MASP2.

The target sequence may be from about 19-36 nucleotides in length, e.g., about 19-30 nucleotides in length. For example, the target sequence can be about 19-30 nucleotides, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of a MASP2 gene in a cell, e.g., a cell within a subject, such as a mammalian subject.

In one embodiment, an RNAi agent of the invention includes a single stranded RNA that interacts with a target RNA sequence, e.g., a MASP2 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a MASP2 gene. Accordingly, the term "siRNA" is also used herein to refer to an iRNA as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In certain embodiments, an "iRNA" for use in the compositions, uses, and methods of the invention is a double stranded RNA and is referred to herein as a "double stranded RNA agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a MASP2 gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide or a modified nucleotide. In addition, as used in this specification, an "iRNA" may include ribonucleotides with chemical modifications; an iRNA may include substantial modifications at multiple nucleotides. As used herein, the term "modified nucleotide" refers to a nucleotide having, independently, a modified sugar moiety, a modified internucleotide linkage, or modified nucleobase, or any combination thereof. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "iRNA" or "RNAi agent" for the purposes of this specification and claims.

The duplex region may be of any length that permits specific degradation of a desired target RNA through a RISC pathway, and may range from about 19 to 36 base pairs in length, e.g., about 19-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and they may be connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, 3, 4, 5, 6, 7, 8, 9, 10, 20, 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In certain embodiments, an iRNA agent of the invention is a dsRNA, each strand of which comprises 19-23 nucleotides, that interacts with a target RNA sequence, e.g., a MASP2 gene, to direct cleavage of the target RNA.

In some embodiments, an iRNA of the invention is a dsRNA of 24-30 nucleotides that interacts with a target RNA sequence, e.g., a MASP2 target mRNA sequence, to direct the cleavage of the target RNA.

As used herein, the term "nucleotide overhang" refers to at least one unpaired nucleotide that protrudes from the duplex structure of a double stranded iRNA. For example, when a 3'-end of one strand of a dsRNA extends beyond the 5'-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of either an antisense or sense strand of a dsRNA.

In certain embodiments, the antisense strand of a dsRNA has a 1-10 nucleotides, e.g., a 1, 2, 3, 4, 5, 6, 7, 8, 9, or 10 nucleotide, overhang at the 3'-end or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, 10-25 nucleotides, 10-20 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the extended overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNA agent, i.e., no nucleotide overhang. A "blunt ended" double stranded RNA agent is double stranded over its entire length, i.e., no nucleotide overhang at either end of the molecule. The RNAi agents of the invention include RNAi agents with no nucleotide overhang at one end (i.e., agents with one overhang and one blunt end) or with no nucleotide overhangs at either end. Most often such a molecule will be double-stranded over its entire length.

The term "antisense strand" or "guide strand" refers to the strand of an iRNA, e.g., a dsRNA, which includes a region that is substantially complementary to a target sequence, e.g., a MASP2 mRNA.

As used herein, the term "region of complementarity" refers to the region on the antisense strand that is substantially complementary to a sequence, for example a target sequence, e.g., a MASP2 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, or 3 nucleotides of the 5'- or 3'-end of the iRNA. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, a RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, when the antisense strand of the RNAi agent contains mismatches to the target sequence, then the mismatch can optionally be restricted to be within the last 5 nucleotides from either the 5'- or 3'-end of the region of complementarity. For example, in such embodiments, for a 23 nucleotide RNAi agent, the strand which is complementary to a region of a MASP2 gene, generally does not contain any mismatch within the central 13 nucleotides. The methods described herein or methods known in the art can be used to determine whether an RNAi agent containing a mismatch to a target sequence is effective in inhibiting the expression of a MASP2 gene. For example, Jackson et al. (*Nat. Biotechnol.* 2003; 21: 635-637) described an expression profile study where the expression of a small set of genes with sequence identity to the MAPK14 siRNA only at 12-18 nt of the sense strand, was down-regulated with similar kinetics to MAPK14. Similarly, Lin et al., (*Nucleic Acids Res.* 2005; 33(14): 4527-4535) using qPCR and reporter assays, showed that a 7 nt complementation between a siRNA and a target is sufficient to cause mRNA degradation of the target. Consideration of the efficacy of RNAi agents with mismatches in inhibiting expression of a MASP2 gene is important, especially if the particular region of complementarity in a MASP2 gene is known to have polymorphic sequence variation within the population.

The term "sense strand" or "passenger strand" as used herein, refers to the strand of an iRNA that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can be, for example, "stringent conditions", including but not limited to, 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). As used herein, "stringent conditions" or "stringent hybridization conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs. In some embodiments, the "substantially complementary" sequences disclosed herein comprise a contiguous nucleotide sequence which is at least about 80% complementary over its entire length to the equivalent region of the target MASP2 sequence, such as about 85%, about 90%, about 91%, about 92%, about 93%, about 94%, about 95%, about 96%, about 97%, about 98%, or about 99% complementary. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogsteen base pairing.

The terms "complementary," "fully complementary" and "substantially complementary" herein can be used with respect to the base matching between two oligonucleotides or polynucleotides, such as the sense strand and the antisense strand of a dsRNA, or between the antisense strand of a double stranded RNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a MASP2 gene). For example, a polynucleotide is complementary to at least a part of a MASP2 mRNA if the sequence is substantially complementary to a non-interrupted portion of an mRNA encoding a MASP2 gene.

Accordingly, in some embodiments, the antisense polynucleotides disclosed herein are fully complementary to the target MASP2 sequence. In other embodiments, the antisense polynucleotides disclosed herein are substantially complementary to the target MASP2 sequence and comprise a contiguous nucleotide sequence which is at least 80% complementary over its entire length to the equivalent region of the nucleotide sequence of any one of SEQ ID NOs:1, 3, 5, 7, 9, 11, 13, 15 or 17, or a fragment of any one of SEQ ID NOs: 1, 3, 5, 7, 9, 11, 13, 15 or 17, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target MASP2 sequence and comprise a contiguous nucleotide sequence which is at least 80% complementary over its entire length to a fragment of SEQ ID NO: 1 selected from the group of nucleotides 3-23, 21-41, 39-59, 57-77, 76-96, 94-114, 112-132, 130-150, 148-168, 166-186, 184-204, 203-223, 221-241, 239-259, 257-277, 275-295, 293-313, 312-332, 330-350, 348-368, 366-386, 384-404, 402-422, 420-440, 439-459, 457-477, 475-495, 493-513, 511-531, 529-549, 547-567, 566-586, 584-604, 602-622, 620-640, 638-658, 656-676, 675-695, 693-713, 711-731, 729-749, 747-767, 765-785, 783-803, 802-822, 820-840, 838-858, 856-876, 874-894, 892-912, 910-930, 929-949, 947-967, 965-985, 983-1003, 1001-1021, 1019-1039, 1038-1058, 1056-1076, 1074-1094, 1092-1112, 1110-1130, 1128-1148, 1146-1166, 1165-1185, 1183-1203, 1201-1221, 1219-1239, 1237-1257, 1255-1275, 1273-1293, 1292-1312, 1310-1330, 1328-1348, 1346-1366, 1364-1384, 1382-1402, 1400-1420, 1419-1439, 1437-1457, 1455-1475, 1473-1493, 1491-1511, 1509-1529, 1528-1548, 1546-1566, 1564-1584, 1582-1602, 1600-1620, 1618-1638, 1636-1656, 1655-1675, 1673-1693, 1691-1711, 1709-1729, 1727-1747, 1745-1765, 1763-1783, 1782-1802, 1800-1820, 1818-1838, 1836-1856, 1854-1874, 1872-1892, 1891-1911, 1909-1929, 1927-1947, 1945-1965, 1963-1983, 1981-2001, 1999-2019, 2018-2038, 2036-2056, 2054-2074, 2072-2092, 2090-2110, 2108-2128, 2126-2146, 2145-2165, 2163-2183, 2181-2201, 2199-2219, 2217-2237, 2235-2255, 2254-2274, 2272-2292, 2290-2310, 2308-2328, 2326-2346, 2344-2364, 2362-2382, 2381-2401, 2399-2419, 2417-2437 or 2435-2455 of SEQ ID NO: 1, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target MASP2 sequence and comprise a contiguous nucleotide sequence which is at least 80% complementary over its entire length to a fragment of SEQ ID NO: 3 selected from the group of nucleotides 1263-1283, 1190-1210, 1191-

1211, 1078-1098, 1270-1290, 885-905, 761-781, 1255-1275, 1279-1299, 1197-1217, 1021-1041, 704-724, 1968-1988, 1277-1297, 1204-1224, 1193-1213, 1201-1221, 1390-1410, 1272-1292, 1282-1302, 959-979, 1199-1219, 1620-1640, 1806-1826, 1783-1803, 1623-1643, 1397-1417, 1782-1802, 1777-1797, 1490-1510, 1712-1732, 1676-1696, 1353-1373, 2189-2209, 1438-1458, 1820-1840, 1664-1684, 1386-1406, 1665-1685, 1282-1302, 1864-1884, 1785-1805, 2333-2353, 1779-1799, 1351-1371, 1350-1370, 1031-1051, 2046-2066, 1616-1636, 2372-2392, 1667-1687, 1675-1695, 1780-1800, 1541-1561, 1551-1571, 1399-1419, 1701-1721, 1715-1735, 1700-1720, 1668-1688, 1366-1386, 2191-2211, 2374-2394, 1400-1420, 1314-1334, 1821-1841, 1807-1827, 1652-1672, 2129-2149, 1778-1798, 1702-1722, 1404-1424, 1593-1613, 1773-1793, 2373-2393, 1545-1565, 1812-1832, 1677-1697, 1359-1379, 1663-1683, 1365-1385, 2194-2214, 1393-1413, 1621-1641, 1673-1693, 1594-1614, 1387-1407, 1542-1562, 1972-1992, 1550-1570, 1323-1343, 1357-1377, 1360-1380, 1711-1731, 1830-1850, 1781-1801, 1405-1425, 2122-2142, 1437-1457, 1973-1993, 2379-2399, 1398-1418, 1669-1689, 1355-1375, 2196-2216, 1320-1340, 1407-1427, 1862-1882, 1666-1686, 1354-1374, 1974-1994, 1662-1682 or 1653-16 of SEQ ID NO: 3, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target MASP2 sequence and comprise a contiguous nucleotide sequence which is at least 80% complementary over its entire length to a fragment of SEQ ID NO: 5 selected from the group of nucleotides 363-383, 543-563, 437-457, 93-113, 243-263, 144-164, 85-105, 257-277, 435-455, 358-378, 26-46 or 344-364 of SEQ ID NO: 5, such as about 85%, about 90%, about 91%, about 92%, about 93%, about 94%, about 95%, about 96%, about 97%, about 98%, or about 99% complementary.

In other embodiments, the antisense polynucleotides disclosed herein are substantially complementary to the target MASP2 sequence and comprise a contiguous nucleotide sequence which is at least about 80% complementary over its entire length to any one of the sense strand nucleotide sequences in any one of any one of Tables 2-7, or a fragment of any one of the sense strand nucleotide sequences in any one of Tables 2-7, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target MASP2 sequence, and wherein the sense strand polynucleotide comprises a contiguous nucleotide sequence which is at least about 80% complementary over its entire length to the equivalent region of the nucleotide sequence of SEQ ID NOs: 2, 4, 6, 8, 10, 12, 14, 16 or 18, or a fragment of any one of SEQ ID NOs: 2, 4, 6, 8, 10, 12, 14, 16 or 18, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target MASP2 sequence, and wherein the sense strand polynucleotide comprises a contiguous nucleotide sequence which is at least about 80% complementary over its entire length to any one of the antisense strand nucleotide sequences in any one of any one of Tables 2-7, or a fragment of any one of the antisense strand nucleotide sequences in any one of Tables 2-7, such as about 85%, about 90%, about 91%, about 92%, about 93%, about 94%, about 95%, about 96%, about 97%, about 98%, about 99%, or 100% complementary.

In certain embodiments, the sense and antisense strands are selected from any one of duplexes AD-1143337, AD-1143348, AD-155520, AD-1143374, AD-1144836, AD-1143386, AD-1144837, AD-1144838, AD-1143406, AD-1143416, AD-1144839, AD-155599, AD-1143442, AD-155635, AD-1143470, AD-1144840, AD-1143479, AD-1143498, AD-1144841, AD-1143511, AD-1143523, AD-1143538, AD-1144842, AD-1143554, AD-1143570, AD-1144843, AD-1144844, AD-1143594, AD-155809, AD-1143619, AD-1143635, AD-1143649, AD-1143662, AD-1144845, AD-1143677, AD-1143691, AD-155927, AD-1144846, AD-155946, AD-1143731, AD-1143748, AD-155999, AD-1143774, AD-1143789, AD-1143802, AD-1144847, AD-1143816, AD-1143828, AD-1143845, AD-1143860, AD-156136, AD-1143891, AD-1143904, AD-1143919, AD-156208, AD-1143945, AD-1143957, AD-1144848, AD-156260, AD-1143982, AD-1144849, AD-156308, AD-1144019, AD-1144035, AD-1144050, AD-1144065, AD-1144077, AD-1144092, AD-1144105, AD-1144117, AD-156460, AD-156477, AD-156495, AD-1144173, AD-156531, AD-1144205, AD-1144217, AD-156584, AD-1144246, AD-1144257, AD-156639, AD-1144284, AD-1144299, AD-1144313, AD-156712, AD-1144343, AD-156748, AD-1144365, AD-1144376, AD-1144391, AD-1144850, AD-156832, AD-1144424, AD-1144440, AD-1144453, AD-1144466, AD-1144851, AD-1144852, AD-1144481, AD-1144494, AD-156962, AD-1144522, AD-1144853, AD-1144534, AD-1144854, AD-1144548, AD-1144855, AD-1144565, AD-1144578, AD-1144856, AD-1144857, AD-1144591, AD-1144604, AD-1144614, AD-1144858, AD-1144631, AD-1144640, AD-1144654, AD-1144669, AD-1144682, AD-157219, AD-1144859, AD-1144708, AD-1144718, AD-157273, AD-1144860, AD-1144745, AD-1144758, AD-1144771, AD-1144781, AD-1144793, AD-1144803, AD-157398, AD-157416, AD-1144861, AD-156804.1, AD-156950.1, AD-156927.1, AD-156807.1, AD-156581.1, AD-156926.1, AD-156921.1, AD-156674.1, AD-156889.1, AD-156853.1, AD-156538.1, AD-157227.1, AD-156622.1, AD-156964.1, AD-156841.1, AD-156571.1, AD-156842.1, AD-68457.2, AD-156990.1, AD-156929.1, AD-157334.1, AD-156923.1, AD-156536.1, AD-156535.1, AD-156255.1, AD-157093.1, AD-156800.1, AD-157371.1, AD-156844.1, AD-156852.1, AD-156924.1, AD-156725.1, AD-156735.1, AD-156583.1, AD-156878.1, AD-156892.1, AD-156877.1, AD-156845.1, AD-156551.1, AD-157229.1, AD-157373.1, AD-156584.1, AD-156499.1, AD-156965.1, AD-156951.1, AD-156829.1, AD-157167.1, AD-156922.1, AD-156879.1, AD-156588.1, AD-156777.1, AD-156917.1, AD-157372.1, AD-156729.1, AD-156956.1, AD-156854.1, AD-156544.1, AD-156840.1, AD-156550.1, AD-157232.1, AD-156577.1, AD-156805.1, AD-156850.1, AD-156778.1, AD-156572.1, AD-156726.1, AD-157059.1, AD-156734.1, AD-156508.1, AD-156542.1, AD-156545.1, AD-156888.1, AD-156974.1, AD-156925.1, AD-156589.1, AD-157160.1, AD-156621.1, AD-157060.1, AD-157378.1, AD-156582.1, AD-156846.1, AD-156540.1, AD-157234.1, AD-156505.1, AD-156591.1, AD-156988.1, AD-156843.1, AD-156539.1, AD-157061.1, AD-156839.1, AD-156830.1, AD-68438.1, AD-68439.1, AD-68440.1, AD-68441.1, AD-68442.1, AD-68443.1, AD-68444.1, AD-68445.1, AD-68446.1, AD-68447.1, AD-68448.1, AD-68449.1, AD-68450.1, AD-68451.1, AD-68452.1, AD-68453.1, AD-68454.1, AD-68455.1, AD-68456.1, AD-68457.1, AD-68458.1, AD-68459.1, AD-68460.1, AD-68461.1, AD-68462.1, AD-68463.1, AD-68464.1, AD-68465.1, AD-68466.1, AD-68467.1, AD-68468.1, AD-68469.1, AD-68470.1 or AD-68471.1.

In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims.

In an aspect of the invention, an agent for use in the methods and compositions of the invention is a single-stranded antisense oligonucleotide molecule that inhibits a target mRNA via an antisense inhibition mechanism. The single-stranded antisense oligonucleotide molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense oligonucleotide molecule may be about 14 to about 30 nucleotides in length and have a sequence that is complementary to a target sequence. For example, the single-stranded antisense oligonucleotide molecule may comprise a sequence that is at least about 14, 15, 16, 17, 18, 19, 20, or more contiguous nucleotides from any one of the antisense sequences described herein.

The phrase "contacting a cell with an iRNA," such as a dsRNA, as used herein, includes contacting a cell by any possible means. Contacting a cell with an iRNA includes contacting a cell in vitro with the iRNA or contacting a cell in vivo with the iRNA. The contacting may be done directly or indirectly. Thus, for example, the iRNA may be put into physical contact with the cell by the individual performing the method, or alternatively, the iRNA may be put into a situation that will permit or cause it to subsequently come into contact with the cell.

Contacting a cell in vitro may be done, for example, by incubating the cell with the iRNA. Contacting a cell in vivo may be done, for example, by injecting the iRNA into or near the tissue where the cell is located, or by injecting the iRNA into another area, e.g., the bloodstream (i.e., intravenous) or the subcutaneous space, such that the agent will subsequently reach the tissue where the cell to be contacted is located. For example, the iRNA may contain or be coupled to a ligand, e.g., GalNAc, that directs the iRNA to a site of interest, e.g., the liver. Combinations of in vitro and in vivo methods of contacting are also possible. For example, a cell may also be contacted in vitro with an iRNA and subsequently transplanted into a subject.

In certain embodiments, contacting a cell with an iRNA includes "introducing" or "delivering the iRNA into the cell" by facilitating or effecting uptake or absorption into the cell. Absorption or uptake of an iRNA can occur through unaided diffusion or active cellular processes, or by auxiliary agents or devices. Introducing an iRNA into a cell may be in vitro or in vivo. For example, for in vivo introduction, iRNA can be injected into a tissue site or administered systemically. In vitro introduction into a cell includes methods known in the art such as electroporation and lipofection. Further approaches are described herein below or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a horse, a goat, a rabbit, a sheep, a hamster, a guinea pig, a cat, a dog, a rat, or a mouse), or a bird that expresses the target gene, either endogenously or heterologously. In an embodiment, the subject is a human, such as a human being treated or assessed for a disease or disorder that would benefit from reduction in MASP2 expression; a human at risk for a disease or disorder that would benefit from reduction in MASP2 expression; a human having a disease or disorder that would benefit from reduction in MASP2 expression; or human being treated for a disease or disorder that would benefit from reduction in MASP2 expression as described herein. In some embodiments, the subject is a female human. In other embodiments, the subject is a male human. In one embodiment, the subject is an adult subject. In another embodiment, the subject is a pediatric subject.

As used herein, the terms "treating" or "treatment" refer to a beneficial or desired result, such as reducing at least one sign or symptom of a MASP2-associated disorder, e.g., inflammation in a subject. Treatment also includes a reduction of one or more sign or symptoms associated with unwanted MASP2 expression, e.g., inflammation; diminishing the extent of unwanted MASP2 activation or stabilization; amelioration or palliation of unwanted MASP2 activation or stabilization. "Treatment" can also mean prolonging survival as compared to expected survival in the absence of treatment.

The term "lower" in the context of the level of MASP2 gene expression or MASP2 protein production in a subject, or a disease marker or symptom refers to a statistically significant decrease in such level. The decrease can be, for example, at least 50%, 55%, 60%, 65%, 70%, 75%, 80%, 85%, 90%, or 95%, or below the level of detection for the detection method in a relevant cell or tissue, e.g., a liver cell, or other subject sample, e.g., blood or serum derived therefrom, urine.

As used herein, "prevention" or "preventing," when used in reference to a disease or disorder, that would benefit from a reduction in expression of a MASP2 gene or production of MASP2 protein, e.g., in a subject susceptible to a MASP2-associated disorder due to, e.g., aging, genetic factors, hormone changes, diet, and a sedentary lifestyle. In certain embodiments, the disease or disorder is e.g., a symptom of unwanted MASP2 activation or stabilization, such as inflammation. The likelihood of developing, e.g., inflammation, is reduced, for example, when an individual having one or more risk factors for inflammation either fails to develop inflammation or develops inflammation with less severity relative to a population having the same risk factors and not receiving treatment as described herein. The failure to develop a MASP2-associated disorder, e.g., inflammation, or a delay in the time to develop inflammation by months or years is considered effective prevention. Prevention may require administration of more than one dose if the iRNA agent.

As used herein, the term "mannan binding lectin serine peptidase 2-associated disease" or "MASP2-associated disease," is a disease or disorder that would benefit from reduction in MASP2 expression. Non-limiting examples of MASP2-associated diseases include, arthritis, IgA nephropathy, thrombotic microangiopathy, diabetic nephropathy and membranous nephropathy.

A "therapeutically-effective amount" or "prophylactically effective amount" also includes an amount of an RNAi agent that produces some desired effect at a reasonable benefit/risk ratio applicable to any treatment. The iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Such carriers are known in the art. Pharmaceutically acceptable carriers include carriers for administration by injection.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to urine obtained from the subject. A "sample derived from a subject" can refer to blood or blood derived serum or plasma from the subject.

The term "substituted" refers to the replacement of one or more hydrogen radicals in a given structure with the radical of a specified substituent including, but not limited to: alkyl, alkenyl, alkynyl, aryl, heterocyclyl, halo, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, "(C1-C6) alkyl" means a radical having from 1 6 carbon atoms in a linear or branched arrangement. "(C1-C6) alkyl" includes, for example, methyl, ethyl, propyl, iso-propyl, n-butyl, tert-butyl, pentyl and hexyl. In certain embodiments, a lipophilic moiety of the instant disclosure can include a C6-C18 alkyl hydrocarbon chain.

The term "alkylene" refers to an optionally substituted saturated aliphatic branched or straight chain divalent hydrocarbon radical having the specified number of carbon atoms. For example, "(C1-C6) alkylene" means a divalent saturated aliphatic radical having from 1-6 carbon atoms in a linear arrangement, e.g., $[(CH_2)_n]$, where n is an integer from 1 to 6. "(C1-C6) alkylene" includes methylene, ethylene, propylene, butylene, pentylene and hexylene. Alternatively, "(C1-C6) alkylene" means a divalent saturated radical having from 1-6 carbon atoms in a branched arrangement, for example: $[(CH_2CH_2CH_2CH_2CH(CH_3)]$, $[(CH_2CH_2CH_2CH_2C(CH_3)_2]$, $[(CH_2C(CH_3)_2CH(CH_3))]$, and the like. The term "alkylenedioxo" refers to a divalent species of the structure —O—R—O—, in which R represents an alkylene.

The term "mercapto" refers to an —SH radical. The term "thioalkoxy" refers to an —S-alkyl radical.

The term "halo" refers to any radical of fluorine, chlorine, bromine or iodine. "Halogen" and "halo" are used interchangeably herein.

As used herein, the term "cycloalkyl" means a saturated or unsaturated nonaromatic hydrocarbon ring group having from 3 to 14 carbon atoms, unless otherwise specified. For example, "(C3-C10) cycloalkyl" means a hydrocarbon radical of a (3-10)-membered saturated aliphatic cyclic hydrocarbon ring. Examples of cycloalkyl groups include, but are not limited to, cyclopropyl, methyl-cyclopropyl, 2,2-dimethyl-cyclobutyl, 2-ethyl-cyclopentyl, cyclohexyl, etc. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight or branched, containing at least one carbon-carbon double bond, and having from 2 to 10 carbon atoms unless otherwise specified. Up to five carbon-carbon double bonds may be present in such groups. For example, "C2-C6" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "C2-C6 alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may contain triple bonds as permitted by normal valency, and may be optionally mono-, di-, tri-, tetra-, or penta-substituted on any position as permitted by normal valency.

As used herein, "alkoxyl" or "alkoxy" refers to an alkyl group as defined above with the indicated number of carbon atoms attached through an oxygen bridge. For example, "(C1-C3)alkoxy" includes methoxy, ethoxy and propoxy. For example, "(C1-C6)alkoxy", is intended to include C1, C2, C3, C4, C5, and C6 alkoxy groups. For example, "(C1-C8)alkoxy", is intended to include C1, C2, C3, C4, C5, C6, C7, and C8 alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy. "Alkylthio" means an alkyl radical attached through a sulfur linking atom. The terms "alkylamino" or "aminoalkyl", means an alkyl radical attached through an NH linkage. "Dialkylamino" means two alkyl radical attached through a nitrogen linking atom. The amino groups may be unsubstituted, monosubstituted, or di-substituted. In some embodiments, the two alkyl radicals are the same (e.g., N,N-dimethylamino) In some embodiments, the two alkyl radicals are different (e.g., N-ethyl-N-methylamino).

As used herein, "aryl" or "aromatic" means any stable monocyclic or polycyclic carbon ring of up to 7 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency. The term "arylalkyl" or the term "aralkyl" refers to alkyl substituted with an aryl. The term "arylalkoxy" refers to an alkoxy substituted with aryl.

"Hetero" refers to the replacement of at least one carbon atom in a ring system with at least one heteroatom selected from N, S and O. "Hetero" also refers to the replacement of at least one carbon atom in an acyclic system. A hetero ring system or a hetero acyclic system may have, for example, 1, 2 or 3 carbon atoms replaced by a heteroatom.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

"Heterocycloalkyl" refers to a cycloalkyl residue in which one to four of the carbons is replaced by a heteroatom such as oxygen, nitrogen or sulfur. Examples of heterocycles whose radicals are heterocyclyl groups include tetrahydropyran, morpholine, pyrrolidine, piperidine, thiazolidine, oxazole, oxazoline, isoxazole, dioxane, tetrahydrofuran and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "acyl" refers to an alkylcarbonyl, cycloalkylcarbonyl, arylcarbonyl, heterocyclylcarbonyl, or heteroarylcarbonyl substituent, any of which may be further substituted by substituents.

As used herein, "keto" refers to any alkyl, alkenyl, alkynyl, cycloalkyl, cycloalkenyl, heterocyclyl, heteroaryl, or aryl group as defined herein attached through a carbonyl bridge.

Examples of keto groups include, but are not limited to, alkanoyl (e.g., acetyl, propionyl, butanoyl, pentanoyl, hexanoyl), alkenoyl (e.g., acryloyl) alkynoyl (e.g., ethynoyl, propynoyl, butynoyl, pentynoyl, hexynoyl), aryloyl (e.g., benzoyl), heteroaryloyl (e.g., pyrroloyl, imidazoloyl, quinolinoyl, pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

The term "oxo" refers to an oxygen atom, which forms a carbonyl when attached to carbon, an N-oxide when attached to nitrogen, and a sulfoxide or sulfone when attached to sulfur.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

II. iRNAs of the Invention

The present invention provides iRNAs that inhibit the expression of a MASP2 gene. In certain embodiments, the iRNA includes double stranded ribonucleic acid (dsRNA) molecules for inhibiting the expression of a MASP2 gene in a cell, such as a cell within a subject, e.g., a mammal, such as a human susceptible to developing a MASP2-associated disorder, e.g., inflammation. The dsRNAi agent includes an antisense strand having a region of complementarity which is complementary to at least a part of an mRNA formed in the expression of a MASP2 gene. The region of complementarity is about 19-30 nucleotides in length (e.g., about 30, 29, 28, 27, 26, 25, 24, 23, 22, 21, 20, or 19 nucleotides in length). Upon contact with a cell expressing the MASP2 gene, the iRNA inhibits the expression of the MASP2 gene (e.g., a human, a primate, a non-primate, or a rat MASP2 gene) by at least about 50% as compared to a similar cell not contacted with the RNAi agent or an RNAi agent not complimentary to the MASP2 gene. Expression of the gene may be assayed by, for example, a PCR or branched DNA (bDNA)-based method, or by a protein-based method, such as by immunofluorescence analysis, using, for example, western blotting or flow cytometric techniques. In some embodiments, inhibition of expression is determined by the qPCR method provided in the examples, especially in Example 2 with the siRNA at a 10 nM concentration in an appropriate organism cell line provided therein. In some embodiments, inhibition of expression in vivo is determined by knockdown of the human gene in a rodent expressing the human gene, e.g., a mouse or an AAV-infected mouse expressing the human target gene, e.g., when administered as single dose, e.g., at 3 mg/kg at the nadir of RNA expression. RNA expression in liver is determined using the PCR methods provided in Example 2.

A dsRNA includes two RNA strands that are complementary and hybridize to form a duplex structure under conditions in which the dsRNA will be used. One strand of a dsRNA (the antisense strand) includes a region of complementarity that is substantially complementary, or fully complementary, to a target sequence. The target sequence can be derived from the sequence of an mRNA formed during the expression of a MASP2 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 19 to 30 base pairs in length. Similarly, the region of complementarity to the target sequence is 19 to 30 nucleotides in length.

In some embodiments, the dsRNA is about 19 to about 23 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19 to about 30 base pairs, e.g., about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target MASP2 gene expression is not generated in the target cell by cleavage of a larger dsRNA.

A dsRNA as described herein can further include one or more single-stranded nucleotide overhangs e.g., 1-4, 2-4, 1-3, 2-3, 1, 2, 3, or 4 nucleotides. dsRNAs having at least one nucleotide overhang can have superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the dsRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In an aspect, a dsRNA of the invention includes at least two nucleotide sequences, a sense sequence and an antisense sequence. The sense strand is selected from the group of sequences provided in any one of Tables 2-7, and the corresponding antisense strand of the sense strand is selected from the group of sequences of any one of Tables 2-7. In this aspect, one of the two sequences is complementary to the other of the two sequences, with one of the sequences being substantially complementary to a sequence of an mRNA generated in the expression of a MASP2 gene. As such, in this aspect, a dsRNA will include two oligonucleotides, where one oligonucleotide is described as the sense strand in any one of Tables 2-7, and the second oligonucleotide is described as the corresponding antisense strand of the sense strand in any one of Tables 2-7. In certain embodiments, the substantially complementary sequences of the dsRNA are contained on separate oligonucleotides. In other embodiments, the substantially complementary sequences of the dsRNA are contained on a single oligonucleotide. In certain embodiments, the sense or antisense strand is selected from the sense or antisense strand of any one of duplexes AD-565541.2, AD-569272.2, AD-569765.2, AD-564730.2, AD-564745.2, AD-571715.2, AD-572041.2, AD-572039.2, AD-568586.2, AD-566837.2, AD-566444.2, AD-567700.2, AD-567814.2, AD-568003.2, AD-569164.2, AD-569763.2, AD-565281.2, AD-571539.2, AD-572389.2, AD-567315.2, AD-571752.2, AD-568026.2, AD-572110.2, AD-572062.2, AD-572388.2, AD-572040.2, AD-567713.2, AD-567521.2, or AD-567066.2.

It will be understood that, although the sequences in Tables 2, 4, and 6 are not described as modified or conjugated sequences, the RNA of the iRNA of the invention e.g., a dsRNA of the invention, may comprise any one of the sequences set forth in any one of Tables 2-7 that is unmodified, un-conjugated, or modified or conjugated differently than described therein. In other words, the invention encompasses dsRNA of Tables 2-7 which are un-modified, un-conjugated, modified, or conjugated, as described herein.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 2-7, dsRNAs described herein can include at least one strand of a length of minimally 21 nucleotides. It can be reasonably expected that shorter duplexes having any one of the sequences in any one of Tables 2-7 minus only a few nucleotides on one or both ends can be similarly effective as compared to the dsRNAs described above. Hence, dsRNAs having a sequence of at least 19, 20, or more contiguous nucleotides derived from any one of the sequences of any one of Tables 2-7, and differing in their ability to inhibit the expression of a MASP2 gene by not more than about 5, 10, 15, 20, 25, or 30% inhibition from a dsRNA comprising the full sequence, are contemplated to be within the scope of the present invention.

In addition, the RNA agents provided in Tables 2-7 identify a site(s) in a MASP2 mRNA transcript that is susceptible to RISC-mediated cleavage. As such, the present invention further features iRNAs that target within one of these sites. As used herein, an iRNA is said to "target within" a particular site of an mRNA transcript if the iRNA promotes cleavage of the mRNA transcript anywhere within that particular site. Such an iRNA will generally include at least about 19 contiguous nucleotides from any one of the sequences provided in any one of Tables 2-7 coupled to additional nucleotide sequences taken from the region contiguous to the selected sequence in a MASP2 gene.

III. Modified iRNAs of the Invention

In certain embodiments, the RNA of the iRNA of the invention e.g., a dsRNA, is un-modified, and does not comprise modified nucleotides, e.g., chemical modifications or conjugations known in the art and described herein. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA or substantially all of the nucleotides of an iRNA are modified, i.e., not more than 5, 4, 3, 2, or 1 unmodified nucleotides are present in a strand of the iRNA.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothiotate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothiotate groups present in the agent.

Representative U.S. Patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and RE39,464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Suitable RNA mimetics are contemplated for use in iRNAs provided herein, in which both the sugar and the internucleoside linkage, i.e., the backbone, of the nucleotide units are replaced with alternate groups. The nucleobase units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular $—CH_2—NH—CH_2—$, $—CH_2—N(CH_3—O—CH_2$-[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$ of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506. The native phosphodiester backbone can be represented as $—O—P(O)(OH)—OCH_2—$.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ alkyl, substituted alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxythimidine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further modified nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these modified nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In some embodiments, the RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-$(CH_2)$—O-2' (LNA); 4'-$(CH_2)$—S-2'; 4'-$(CH_2)_2$—O-2' (ENA); 4'-$CH(CH_3)$—O-2' (also referred to as "constrained ethyl" or "cEt") and 4'-$CH(CH_2OCH_3)$—O-2' (and analogs thereof; see, e.g., U.S. Pat. No. 7,399,845); 4'-$C(CH_3)(CH_3)$—O-2' (and analogs thereof; see e.g., U.S. Pat. No. 8,278,283); 4'-$CH_2$—N$(OCH_3)$-2' (and analogs thereof; see e.g., U.S. Pat. No. 8,278,425); 4'-$CH_2$—O—N$(CH_3)$-2' (see, e.g., U.S. Patent Publication No. 2004/0171570); 4'-$CH_2$—N(R)—O-2', wherein R is H, $C_1$-$C_{12}$ alkyl, or a protecting group (see, e.g., U.S. Pat. No. 7,427,672); 4'-$CH_2$—C(H)$(CH_3)$-2' (see, e.g., Chattopadhyaya et al., *J. Org. Chem.*, 2009, 74, 118-134); and 4'-$CH_2$—C$(H_2)$-2' (and analogs thereof; see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-$CH(CH_3)$—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3' and —C5' carbons of ribose.

CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

An RNAi agent of the disclosure may also include one or more "cyclohexene nucleic acids" or ("CeNA"). CeNA are nucleotide analogs with a replacement of the furanose moiety of DNA by a cyclohexene ring. Incorporation of cylcohexenyl nucleosides in a DNA chain increases the stability of a DNA/RNA hybrid. CeNA is stable against degradation in serum and a CeNA/RNA hybrid is able to activate *E. Coli* RNase H, resulting in cleavage of the RNA strand. (see Wang et al., *Am. Chem. Soc.* 2000, 122, 36, 8595-8602, hereby incorporated by reference).

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified iRNAs Comprising Motifs of the Invention

In certain aspects of the invention, the double stranded RNA agents of the invention include agents with chemical modifications as disclosed, for example, in WO2013/075035, the entire contents of each of which are incorporated herein by reference. WO2013/075035 provides motifs of three identical modifications on three consecutive nucleotides into a sense strand or antisense strand of a dsRNAi agent, particularly at or near the cleavage site. In some embodiments, the sense strand and antisense strand of the dsRNAi agent may otherwise be completely modified. The introduction of these motifs interrupts the modification pattern, if present, of the sense or antisense strand. The dsRNAi agent may be optionally conjugated with a GalNAc derivative ligand, for instance on the sense strand.

More specifically, when the sense strand and antisense strand of the double stranded RNA agent are completely modified to have one or more motifs of three identical modifications on three consecutive nucleotides at or near the cleavage site of at least one strand of a dsRNAi agent, the gene silencing activity of the dsRNAi agent was observed.

Accordingly, the invention provides double stranded RNA agents capable of inhibiting the expression of a target gene (i.e., MASP2 gene) in vivo. The RNAi agent comprises a sense strand and an antisense strand. Each strand of the RNAi agent may be, for example, 17-30 nucleotides in length, 25-30 nucleotides in length, 27-30 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as "dsRNAi agent." The duplex region of a dsRNAi agent may be, for example, the duplex region can be 27-30 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 19, 20, 21, 22, 23, 24, 25, 26, and 27 nucleotides in length.

In certain embodiments, the dsRNAi agent may contain one or more overhang regions or capping groups at the 3'-end, 5'-end, or both ends of one or both strands. The overhang can be, independently, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In certain embodiments, the overhang regions can include extended overhang regions as provided above. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In certain embodiments, the nucleotides in the overhang region of the dsRNAi agent can each independently be a modified or unmodified nucleotide including, but no limited to 2'-sugar modified, such as, 2'-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the dsRNAi agent may be phosphorylated. In some embodiments, the overhang region(s) contains two nucleotides having a phosphorothioate between the two nucleotides, where the two nucleotides can be the same or different. In some embodiments, the overhang is present at the 3'-end of the sense strand, antisense strand, or both strands. In some embodiments, this 3'-overhang is present in the antisense strand. In some embodiments, this 3'-overhang is present in the sense strand.

The dsRNAi agent may contain only a single overhang, which can strengthen the interference activity of the RNAi, without affecting its overall stability. For example, the single-stranded overhang may be located at the 3'-end of the sense strand or, alternatively, at the 3'-end of the antisense strand. The RNAi may also have a blunt end, located at the 5'-end of the antisense strand (i.e., the 3'-end of the sense strand) or vice versa. Generally, the antisense strand of the dsRNAi agent has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In certain embodiments, the dsRNAi agent is a double blunt-ended of 19 nucleotides in length, wherein the sense strand contains at least one motif of three 2'-F modifications on three consecutive nucleotides at positions 7, 8, and 9 from the 5'end. The antisense strand contains at least one motif of three 2'-O-methyl modifications on three consecutive nucleotides at positions 11, 12, and 13 from the 5'end.

In other embodiments, the dsRNAi agent is a double blunt-ended of 20 nucleotides in length, wherein the sense strand contains at least one motif of three 2'-F modifications on three consecutive nucleotides at positions 8, 9, and 10 from the 5'end. The antisense strand contains at least one motif of three 2'-O-methyl modifications on three consecutive nucleotides at positions 11, 12, and 13 from the 5'end.

In yet other embodiments, the dsRNAi agent is a double blunt-ended of 21 nucleotides in length, wherein the sense strand contains at least one motif of three 2'-F modifications on three consecutive nucleotides at positions 9, 10, and 11 from the 5' end. The antisense strand contains at least one motif of three 2'-O-methyl modifications on three consecutive nucleotides at positions 11, 12, and 13 from the 5'end.

In certain embodiments, the dsRNAi agent comprises a 21 nucleotide sense strand and a 23 nucleotide antisense strand, wherein the sense strand contains at least one motif of three 2'-F modifications on three consecutive nucleotides at positions 9, 10, and 11 from the 5'end; the antisense strand contains at least one motif of three 2'-O-methyl modifications on three consecutive nucleotides at positions 11, 12, and 13 from the 5' end, wherein one end of the RNAi agent is blunt, while the other end comprises a 2 nucleotide overhang. The 2 nucleotide overhang can be at the 3'-end of the antisense strand.

When the 2 nucleotide overhang is at the 3'-end of the antisense strand, there may be two phosphorothioate internucleotide linkages between the terminal three 3'-nucleotides of the antisense strand, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In certain embodiments, every nucleotide in the sense strand and the antisense strand of the dsRNAi agent, including the nucleotides that are part of the motifs are modified nucleotides. In certain embodiments each residue is independently modified with a 2'-O-methyl or 2'-fluoro, e.g., in an alternating motif. Optionally, the dsRNAi agent further comprises a ligand (such as, $GalNAc_3$).

In certain embodiments, the dsRNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3 ‘ terminal nucleotide of antisense strand is unpaired with sense strand, and up to 6 consecutive 3’ terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In certain embodiments, the dsRNAi agent comprises sense and antisense strands, wherein the dsRNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, and 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein Dicer cleavage of the dsRNAi agent preferentially results in an siRNA comprising the 3'-end of the second strand, thereby reducing expression of the target gene in the mammal Optionally, the dsRNAi agent further comprises a ligand.

In certain embodiments, the sense strand of the dsRNAi agent contains at least one motif of three identical modifications on three consecutive nucleotides, where one of the motifs occurs at the cleavage site in the sense strand.

In certain embodiments, the antisense strand of the dsRNAi agent can also contain at least one motif of three identical modifications on three consecutive nucleotides, where one of the motifs occurs at or near the cleavage site in the antisense strand.

For a dsRNAi agent having a duplex region of 19-23 nucleotides in length, the cleavage site of the antisense strand is typically around the 10, 11, and 12 positions from the 5'-end. Thus the motifs of three identical modifications may occur at the 9, 10, and 11 positions; the 10, 11, and 12 positions; the 11, 12, and 13 positions; the 12, 13, and 14 positions; or the 13, 14, and 15 positions of the antisense strand, the count starting from the first nucleotide from the 5'-end of the antisense strand, or, the count starting from the first paired nucleotide within the duplex region from the 5'-end of the antisense strand. The cleavage site in the antisense strand may also change according to the length of the duplex region of the dsRNAi agent from the 5'-end.

The sense strand of the dsRNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In some embodiments, the sense strand of the dsRNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistries of the motifs are distinct from each other, and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the dsRNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In some embodiments, the wing modification on the sense strand or antisense strand of the dsRNAi agent typically does not include the first one or two terminal nucleotides at the 3'-end, 5'-end, or both ends of the strand.

In other embodiments, the wing modification on the sense strand or antisense strand of the dsRNAi agent typically does not include the first one or two paired nucleotides within the duplex region at the 3'-end, 5'-end, or both ends of the strand.

When the sense strand and the antisense strand of the dsRNAi agent each contain at least one wing modification, the wing modifications may fall on the same end of the duplex region, and have an overlap of one, two, or three nucleotides.

When the sense strand and the antisense strand of the dsRNAi agent each contain at least two wing modifications, the sense strand and the antisense strand can be so aligned that two modifications each from one strand fall on one end of the duplex region, having an overlap of one, two, or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In some embodiments, every nucleotide in the sense strand and antisense strand of the dsRNAi agent, including the nucleotides that are part of the motifs, may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2'-hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking 0 of a phosphate moiety. In some cases, the modification will occur at all of the subject positions in the nucleic acid but in many cases it will not. By way of example, a modification may only occur at a 3'- or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking 0 position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5'-end or ends can be phosphorylated.

It may be possible, e.g., to enhance stability, to include particular bases in overhangs, or to include modified nucleotides or nucleotide surrogates, in single strand overhangs, e.g., in a 5'- or 3'-overhang, or in both. For example, it can be desirable to include purine nucleotides in overhangs. In some embodiments all or some of the bases in a 3'- or 5'-overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In certain embodiments, the $N_a$ or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAA- BAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5' to 3' of the strand and the alternating motif in the antisense strand may start with "BABABA" from 5' to 3' of the strand within the duplex region. As another example, the alternating motif in the sense strand may start with "AABBAABB" from 5' to 3' of the strand and the alternating motif in the antisense strand may start with "BBAABBAA" from 5' to 3' of the strand within the duplex region, so that there is a complete or partial shift of the modification patterns between the sense strand and the antisense strand.

In some embodiments, the dsRNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand or antisense strand interrupts the initial modification pattern present in the sense strand or antisense strand. This interruption of the modification pattern of the sense or antisense strand by introducing one or more motifs of three identical modifications on three consecutive nucleotides to the sense or antisense strand may enhance the gene silencing activity against the target gene.

In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YY$N_b$ . . . ," where "Y" represents the modification of the motif of three identical modifications on three consecutive nucleotides, and "$N_a$" and "$N_b$" represent a modification to the nucleotide next to the motif "YYY" that is different than the modification of Y, and where $N_a$ and $N_b$ can be the same or different modifications. Alternatively, $N_a$ or $N_b$ may be present or absent when there is a wing modification present.

The iRNA may further comprise at least one phosphorothioate or methylphosphonate internucleotide linkage. The phosphorothioate or methylphosphonate internucleotide linkage modification may occur on any nucleotide of the sense strand, antisense strand, or both strands in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In some embodiments, the antisense strand comprises two phosphorothioate internucleotide linkages at the 5'-end and two phosphorothioate internucleotide linkages at the 3'-end, and the sense strand comprises at least two phosphorothioate internucleotide linkages at either the 5'-end or the 3'-end.

In some embodiments, the dsRNAi agent comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, or the 5'end of the antisense strand.

In some embodiments, the 2-nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the dsRNAi agent may additionally have two phosphorothioate internucleotide linkages between the terminal three nucleotides at both the 5'-end of the sense strand and at the 5'-end of the antisense strand.

In one embodiment, the dsRNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In certain embodiments, the dsRNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In certain embodiments, the nucleotide at the 1 position within the duplex region from the 5'-end in the antisense strand is selected from A, dA, dU, U, and dT. Alternatively, at least one of the first 1, 2, or 3 base pair within the duplex region from the 5'-end of the antisense strand is an AU base pair. For example, the first base pair within the duplex region from the 5'-end of the antisense strand is an AU base pair.

In other embodiments, the nucleotide at the 3'-end of the sense strand is deoxythimidine (dT) or the nucleotide at the 3'-end of the antisense strand is deoxythimidine (dT). For example, there is a short sequence of deoxythimidine nucleotides, for example, two dT nucleotides on the 3'-end of the sense, antisense strand, or both strands.

In certain embodiments, the sense strand sequence may be represented by formula (I):

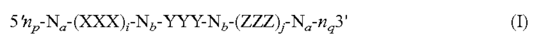

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein $N_b$ and Y do not have the same modification; and

XXX, YYY, and ZZZ each independently represent one motif of three identical modifications on three consecutive nucleotides. In one embodiment, YYY is all 2'-F modified nucleotides.

In some embodiments, the $N_a$ or $N_b$ comprises modifications of alternating pattern.

In some embodiments, the YYY motif occurs at or near the cleavage site of the sense strand. For example, when the dsRNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12; or 11, 12, 13) of the sense strand, the count starting from the first nucleotide, from the 5'-end; or optionally, the count starting at the first paired nucleotide within the duplex region, from the 5'-end.

In one embodiment, i is 1 and j is 0, or i is 0 and j is 1, or both i and j are 1. The sense strand can therefore be represented by the following formulas:

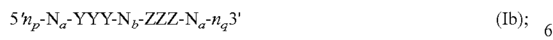

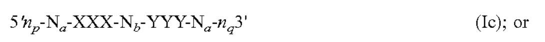

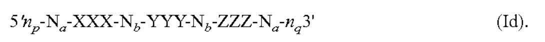

When the sense strand is represented by formula (Ib), $N_b$ represents an oligonucleotide sequence comprising 0-10, 0-7, 0-5, 0-4, 0-2, or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2, or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2, or 0 modified nucleotides. In certain embodiments, $N_b$ is 0, 1, 2, 3, 4, 5, or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

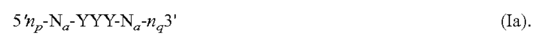

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

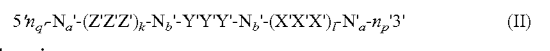

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y', and Z'Z'Z' each independently represent one motif of three identical modifications on three consecutive nucleotides.

In some embodiments, the $N_a'$ or $N_b'$ comprises modifications of alternating pattern.

The Y'Y'Y' motif occurs at or near the cleavage site of the antisense strand. For example, when the dsRNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the first nucleotide, from the 5'-end; or optionally, the count starting at the first paired nucleotide within the duplex region, from the 5'-end. In certain embodiments, the Y'Y'Y' motif occurs at positions 11, 12, 13.

In certain embodiments, Y'Y'Y' motif is all 2'-OMe modified nucleotides.

In certain embodiments, k is 1 and 1 is 0, or k is 0 and 1 is 1, or both k and 1 are 1.

The antisense strand can therefore be represented by the following formulas:

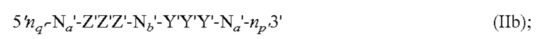

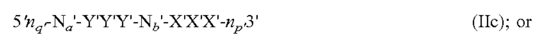

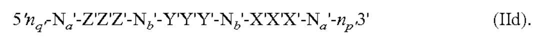

When the antisense strand is represented by formula (IIb), $N_b'$ represents an oligonucleotide sequence comprising 0-10, 0-7, 0-10, 0-7, 0-5, 0-4, 0-2, or 0 modified nucleotides. Each $N_a$' independently represents an oligonucleotide sequence comprising 2-20, 2-15, or 2-10 modified nucleotides.

When the antisense strand is represented as formula (IIC), $N_b$' represents an oligonucleotide sequence comprising 0-10, 0-7, 0-10, 0-7, 0-5, 0-4, 0-2, or 0 modified nucleotides. Each $N_a$' independently represents an oligonucleotide sequence comprising 2-20, 2-15, or 2-10 modified nucleotides.

When the antisense strand is represented as formula (IId), each $N_b$' independently represents an oligonucleotide sequence comprising 0-10, 0-7, 0-10, 0-7, 0-5, 0-4, 0-2, or 0 modified nucleotides. Each $N_a$' independently represents an oligonucleotide sequence comprising 2-20, 2-15, or 2-10 modified nucleotides. In certain embodiments, $N_b$ is 0, 1, 2, 3, 4, 5, or 6.

In other embodiments, k is 0 and 1 is 0 and the antisense strand may be represented by the formula:

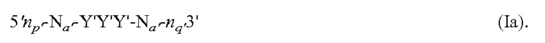

(Ia).

When the antisense strand is represented as formula (IIa), each $N_a$' independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y', and Z', in particular, may represent a 2'-O-methyl modification or a 2'-fluoro modification.

In some embodiments, the sense strand of the dsRNAi agent may contain YYY motif occurring at 9, 10, and 11 positions of the strand when the duplex region is 21 nt, the count starting from the first nucleotide from the 5'-end, or optionally, the count starting at the first paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In some embodiments the antisense strand may contain Y'Y'Y' motif occurring at positions 11, 12, 13 of the strand, the count starting from the first nucleotide from the 5'-end, or optionally, the count starting at the first paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with an antisense strand being represented by any one of formulas (Ha), (IIb), (IIc), and (IId), respectively.

Accordingly, the dsRNAi agents for use in the methods of the invention may comprise a sense strand and an antisense strand, each strand having 14 to 30 nucleotides, the iRNA duplex represented by formula (III):

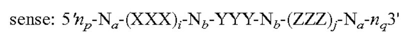

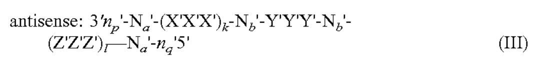

(III)

wherein:

j, k, and l are each independently 0 or 1;

p, p', q, and q' are each independently 0-6;

each $N_a$ and $N_a$' independently represents an oligonucleotide sequence comprising 0-25 modified nucleotides, each sequence comprising at least two differently modified nucleotides;

each $N_b$ and $N_b$' independently represents an oligonucleotide sequence comprising 0-10 modified nucleotides;

wherein each $n_p$', $n_p$, $n_q$', and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming an iRNA duplex include the formulas below:

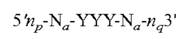

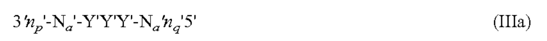

(IIIa)

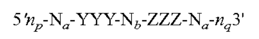

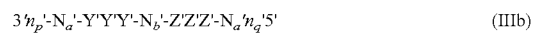

(IIIb)

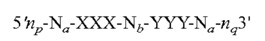

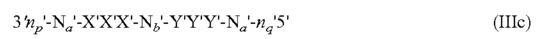

(IIIc)

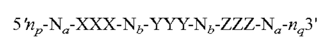

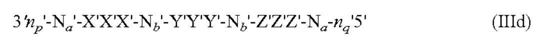

(IIId)

When the dsRNAi agent is represented by formula (IIIa), each $N_a$ independently represents an oligonucleotide sequence comprising 2-20, 2-15, or 2-10 modified nucleotides.

When the dsRNAi agent is represented by formula (Mb), each $N_b$ independently represents an oligonucleotide sequence comprising 1-10, 1-7, 1-5, or 1-4 modified nucleotides. Each $N_a$ independently represents an oligonucleotide sequence comprising 2-20, 2-15, or 2-10 modified nucleotides.

When the dsRNAi agent is represented as formula (IIIc), each $N_b$, $N_b$' independently represents an oligonucleotide sequence comprising 0-10, 0-7, 0-10, 0-7, 0-5, 0-4, 0-2, or 0 modified nucleotides. Each $N_a$ independently represents an oligonucleotide sequence comprising 2-20, 2-15, or 2-10 modified nucleotides.

When the dsRNAi agent is represented as formula (IIId), each $N_b$, $N_b$' independently represents an oligonucleotide sequence comprising 0-10, 0-7, 0-10, 0-7, 0-5, 0-4, 0-2, or 0 modified nucleotides. Each $N_a$, $N_a$' independently represents an oligonucleotide sequence comprising 2-20, 2-15, or 2-10 modified nucleotides. Each of $N_a$, $N_a$', $N_b$, and $N_b$' independently comprises modifications of alternating pattern.

Each of X, Y, and Z in formulas (III), (IIIa), (IIIb), (IIIc), and (IIId) may be the same or different from each other.

When the dsRNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In certain embodiments, the modification on the Y nucleotide is different than the modification on the Y' nucleotide, the modification on the Z nucleotide is different than the modification on the Z' nucleotide, or the modification on the X nucleotide is different than the modification on the X' nucleotide.

In certain embodiments, when the dsRNAi agent is represented by formula (IIId), the $N_a$ modifications are 2'-O-methyl or 2'-fluoro modifications. In other embodiments, when the RNAi agent is represented by formula (IIId), the $N_a$ modifications are 2'-O-methyl or 2'-fluoro modifications and $n_p$'>0 and at least one $n_p$' is linked to a neighboring nucleotide a via phosphorothioate linkage. In yet other embodiments, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, and the sense strand is conjugated to one or more GalNAc derivatives attached through a bivalent or trivalent branched linker (described below). In other embodiments, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, when the dsRNAi agent is represented by formula (IIIa), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, the dsRNAi agent is a multimer containing at least two duplexes represented by formula (III), (IIIa), (Mb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In some embodiments, the dsRNAi agent is a multimer containing three, four, five, six, or more duplexes represented by formula (III), (IIIa), (Mb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two dsRNAi agents represented by at least one of formulas (III), (IIIa), (Mb), (IIIc), and (IIId) are linked to each other at the 5' end, and one or both of the 3' ends, and are optionally conjugated to a ligand. Each of the agents can target the same gene or two different genes; or each of the agents can target same gene at two different target sites.

In certain embodiments, an RNAi agent of the invention may contain a low number of nucleotides containing a 2'-fluoro modification, e.g., 10 or fewer nucleotides with 2'-fluoro modification. For example, the RNAi agent may contain 10, 9, 8, 7, 6, 5, 4, 3, 2, 1 or 0 nucleotides with a 2'-fluoro modification. In a specific embodiment, the RNAi agent of the invention contains 10 nucleotides with a 2'-fluoro modification, e.g., 4 nucleotides with a 2'-fluoro modification in the sense strand and 6 nucleotides with a 2'-fluoro modification in the antisense strand. In another specific embodiment, the RNAi agent of the invention contains 6 nucleotides with a 2'-fluoro modification, e.g., 4 nucleotides with a 2'-fluoro modification in the sense strand and 2 nucleotides with a 2'-fluoro modification in the antisense strand.

In other embodiments, an RNAi agent of the invention may contain an ultra low number of nucleotides containing a 2'-fluoro modification, e.g., 2 or fewer nucleotides containing a 2'-fluoro modification. For example, the RNAi agent may contain 2, 1 of 0 nucleotides with a 2'-fluoro modification. In a specific embodiment, the RNAi agent may contain 2 nucleotides with a 2'-fluoro modification, e.g., 0 nucleotides with a 2-fluoro modification in the sense strand and 2 nucleotides with a 2'-fluoro modification in the antisense strand.

Various publications describe multimeric iRNAs that can be used in the methods of the invention. Such publications include WO2007/091269, U.S. Pat. No. 7,858,769, WO2010/141511, WO2007/117686, WO2009/014887, and WO2011/031520 the entire contents of each of which are hereby incorporated herein by reference.

As described in more detail below, the iRNA that contains conjugations of one or more carbohydrate moieties to an iRNA may improve one or more properties of the iRNA. In many cases, the carbohydrate moiety will be attached to a modified subunit of the iRNA. For example, the ribose sugar of one or more ribonucleotide subunits of a iRNA can be replaced with another moiety, e.g., a non-carbohydrate (e.g., cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," such as two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide, or polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The iRNA may be conjugated to a ligand via a carrier, wherein the carrier can be cyclic group or acyclic group. The cyclic group can be selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalinyl. The acyclic group can be a serinol backbone or diethanolamine backbone.

In another embodiment of the invention, an iRNA agent comprises a sense strand and an antisense strand, each strand having 14 to 40 nucleotides. The RNAi agent may be represented by formula (L):

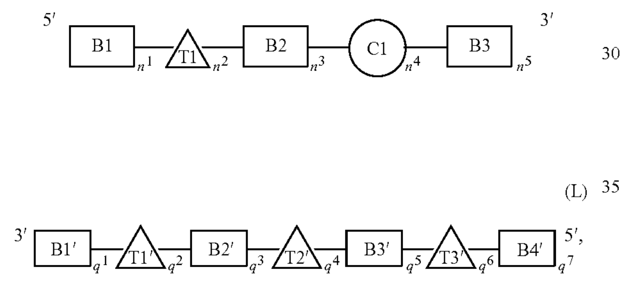

(L)

In formula (L), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

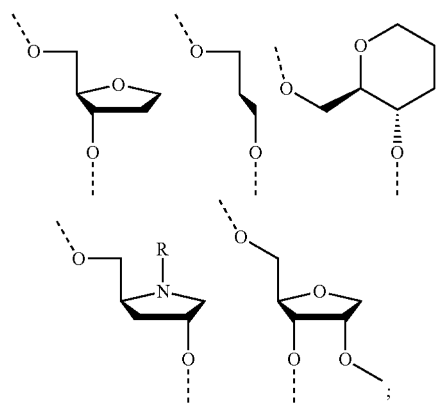

;

and iii) sugar modification selected from the group consisting of:

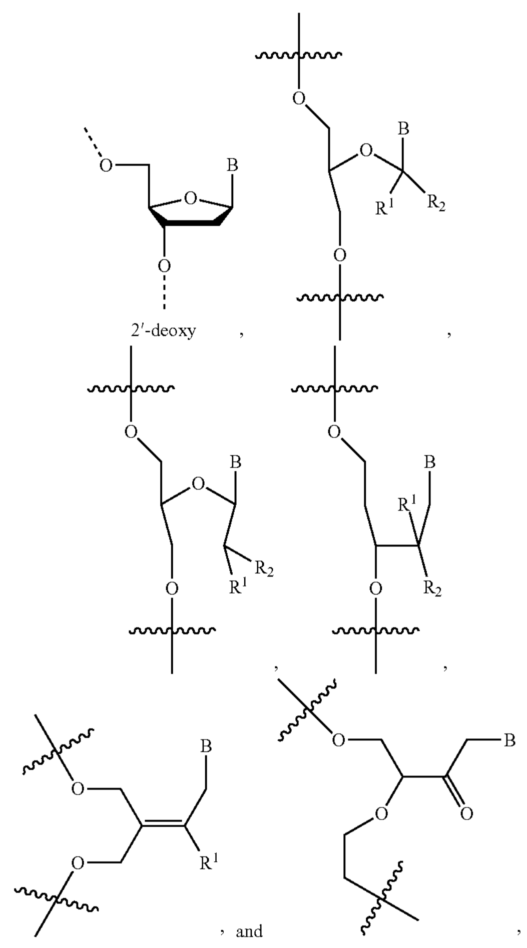

, , , , and , wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

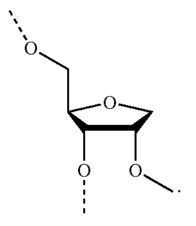

- T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.
- $n^1$, $n^3$, and $q^1$ are independently 4 to 15 nucleotides in length.
- $n^5$, $q^3$, and $q^7$ are independently 1-6 nucleotide(s) in length.
- $n^4$, $q^2$, and $q^6$ are independently 1-3 nucleotide(s) in length; alternatively, $n^4$ is 0.
- $q^5$ is independently 0-10 nucleotide(s) in length.
- $n^2$ and $q^4$ are independently 0-3 nucleotide(s) in length.
- Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, $q^4$, and $q^6$ are each 1.

In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1.

In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose.

In one embodiment, T2' starts at position 8 from the 5' end of the antisense strand. In one example, T2' starts at position 8 from the 5' end of the antisense strand, and $q^4$ is 2.

In one embodiment, T2' starts at position 9 from the 5' end of the antisense strand. In one example, T2' is at position 9 from the 5' end of the antisense strand, and $q^4$ is 1.

In one embodiment, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, q' is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The RNAi agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-$PS_2$), 5'-end vinylphosphonate (5'-VP), 5'-end methylphosphonate (MePhos), or 5'-deoxy-5'-C-malonyl

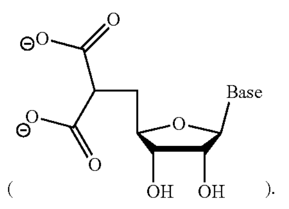

When the 5'-end phosphorus-containing group is 5'-end vinylphosphonate (5'-VP), the 5'-VP can be either 5'-E-VP isomer (i.e., trans-vinylphosphate,

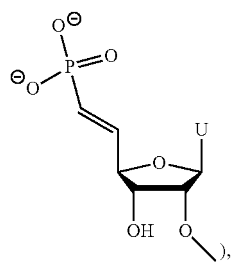

5'-Z-VP isomer (i.e., cis-vinylphosphate,

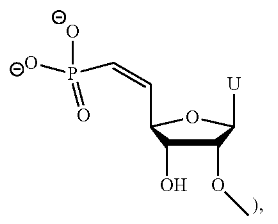

or mixtures thereof.

In one embodiment, the RNAi agent comprises a phosphorus-containing group at the 5'-end of the sense strand. In one embodiment, the RNAi agent comprises a phosphorus-containing group at the 5'-end of the antisense strand.

In one embodiment, the RNAi agent comprises a 5'-P. In one embodiment, the RNAi agent comprises a 5'-P in the antisense strand.

In one embodiment, the RNAi agent comprises a 5'-PS. In one embodiment, the RNAi agent comprises a 5'-PS in the antisense strand.

In one embodiment, the RNAi agent comprises a 5'-VP. In one embodiment, the RNAi agent comprises a 5'-VP in the antisense strand. In one embodiment, the RNAi agent comprises a 5'-E-VP in the antisense strand. In one embodiment, the RNAi agent comprises a 5'-Z-VP in the antisense strand.

In one embodiment, the RNAi agent comprises a 5'-$PS_2$. In one embodiment, the RNAi agent comprises a 5'-$PS_2$ in the antisense strand.

In one embodiment, the RNAi agent comprises a 5'-$PS_2$. In one embodiment, the RNAi agent comprises a 5'-deoxy-5'-C-malonyl in the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, q' is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-VP. The 5'-VP may be 5'-E-VP, 5'-Z-VP, or combination thereof. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNAi RNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z-VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof), and a targeting ligand.

In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, BF is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z-VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, an RNAi agent of the present invention comprises:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 1, 3, 5, 7, 9 to 11, 13, 17, 19, and 21, and 2'-OMe modifications at positions 2, 4, 6, 8, 12, 14 to 16, 18, and 20 (counting from the 5' end);

and (b) an antisense strand having:
  (i) a length of 23 nucleotides;
  (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
  (iii) phosphorothioate internucleotide linkages between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, an RNAi agent of the present invention comprises:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
  (iv) phosphorothioate internucleotide linkages between nucleotide positions 1 and 2, and between nucleotide positions 2 and 3 (counting from the 5' end);

and (b) an antisense strand having:
  (i) a length of 23 nucleotides;
  (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, and 12 to 21, 2'-F modifications at positions 7, and 9, and a deoxy-nucleotide (e.g. dT) at position 11 (counting from the 5' end); and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, 12, 14, and 16 to 21, and 2'-F modifications at positions 7, 9, 11, 13, and 15; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 9, and 12 to 21, and 2'-F modifications at positions 10, and 11; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 1, 3, 5, 7, 9 to 11, and 13, and 2'-OMe modifications at positions 2, 4, 6, 8, 12, and 14 to 21; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
(iv) phosphorothioate internucleotide linkages between nucleotide positions 1 and 2, and between nucleotide positions 2 and 3 (counting from the 5' end);

and (b) an antisense strand having:

(i) a length of 25 nucleotides;

(ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxy-nucleotides (e.g. dT) at positions 24 and 25 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a four nucleotide overhang at the 3'-end of the antisense strand, and a blunt end at the 5'-end of the antisense strand.

In another particular embodiment, a RNAi agent of the present invention comprises:

(a) a sense strand having:

(i) a length of 21 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 6, 8, and 12 to 21, and 2'-F modifications at positions 7, and 9 to 11; and (iv) phosphorothioate internucleotide linkages between nucleotide positions 1 and 2, and between nucleotide positions 2 and 3 (counting from the 5' end);

and (b) an antisense strand having:

(i) a length of 23 nucleotides;

(ii) 2'-OMe modifications at positions 1, 3 to 5, 7, 8, 10 to 13, 15, and 17 to 23, and 2'-F modifications at positions 2, 6, 9, 14, and 16 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:

(i) a length of 21 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 6, 8, and 12 to 21, and 2'-F modifications at positions 7, and 9 to 11; and (iv) phosphorothioate internucleotide linkages between nucleotide positions 1 and 2, and between nucleotide positions 2 and 3 (counting from the 5' end);

and (b) an antisense strand having:

(i) a length of 23 nucleotides;

(ii) 2'-OMe modifications at positions 1, 3 to 5, 7, 10 to 13, 15, and 17 to 23, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:

(i) a length of 19 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 4, 6, and 10 to 19, and 2'-F modifications at positions 5, and 7 to 9; and (iv) phosphorothioate internucleotide linkages between nucleotide positions 1 and 2, and between nucleotide positions 2 and 3 (counting from the 5' end);

and (b) an antisense strand having:

(i) a length of 21 nucleotides;

(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 19 and 20, and between nucleotide positions 20 and 21 (counting from the 5' end);

wherein the RNAi agents have a two nucleotide overhang at the 3'-end of the antisense strand, and a blunt end at the 5'-end of the antisense strand.

In certain embodiments, the iRNA for use in the methods of the invention is an agent selected from agents listed in any one of Tables 2-7. These agents may further comprise a ligand.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acid. Sci. USA,* 1989, 86: 6553-6556). In other embodiments, the ligand is cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In certain embodiments, a ligand alters the distribution, targeting, or lifetime of an iRNA agent into which it is incorporated. In certain embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), mPEG, $[mPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxol, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, polyethylene glycol (PEG), vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule may bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. It may bind HSA with a sufficient affinity such that the conjugate will be distributed to a non-kidney tissue. However, the affinity is typically not so strong that the HSA-ligand binding cannot be reversed.

In other embodiments, the lipid based ligand binds HSA weakly or not at all, such that the conjugate may be distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an alpha-helical agent and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 19). An RFGF analogue (e.g., amino acid sequence AALLPVLLAAP (SEQ ID NO: 20) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 21) and the *Drosophila* Antennapedia protein (RQIKIWFQNRRMKWKK (SEQ ID NO: 22) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidomimetics may include D-amino acids, as well as synthetic RGD mimics. In addition to RGD, one can use other moieties that target the integrin ligand. Certain conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In one embodiment, a carbohydrate conjugate for use in the compositions and methods of the invention is selected from the group consisting of:

Formula II

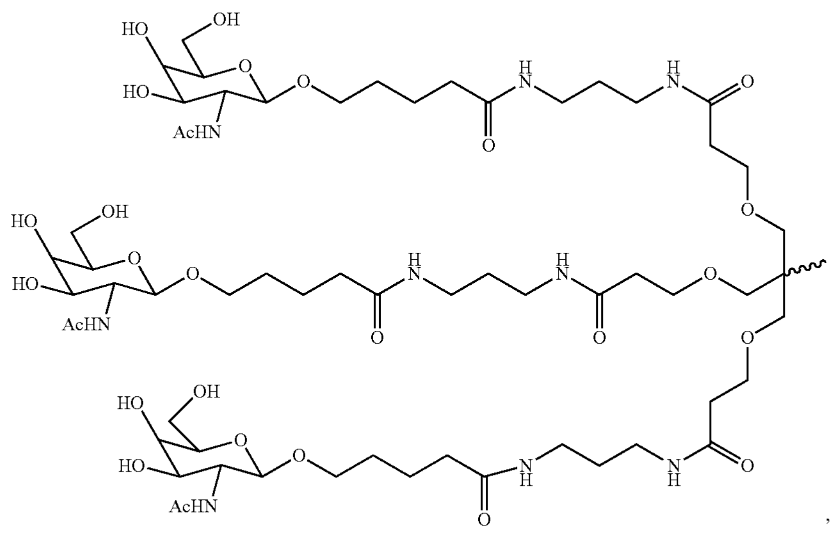

,

Formula III

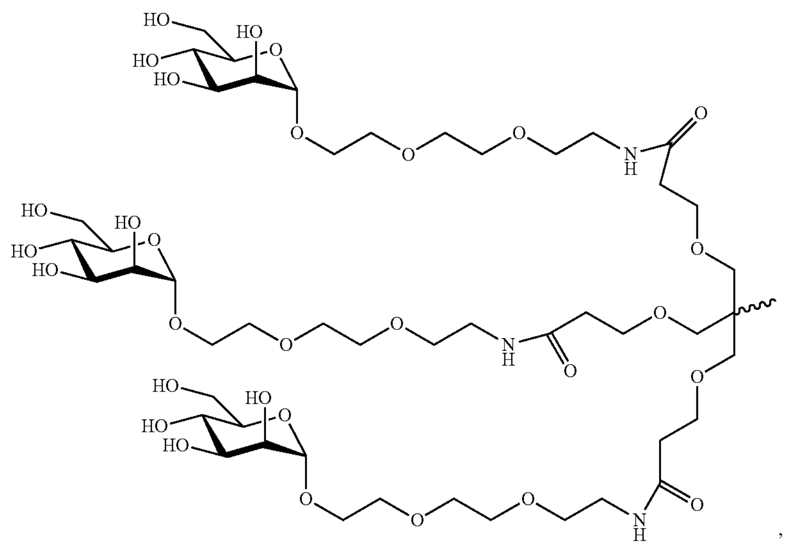

,

-continued
Formula IV
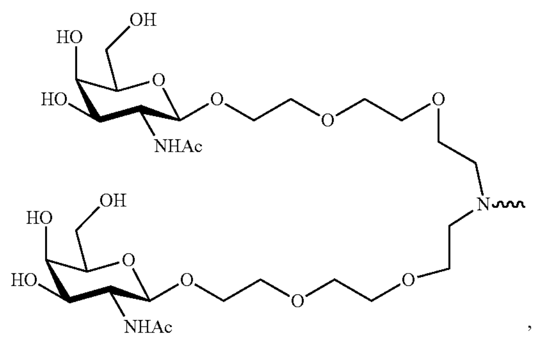
,
Formula V
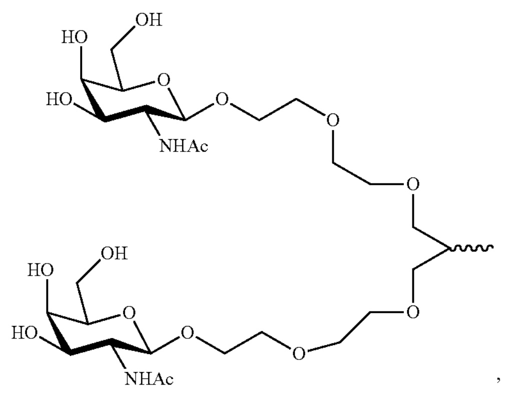
,
Formula VI
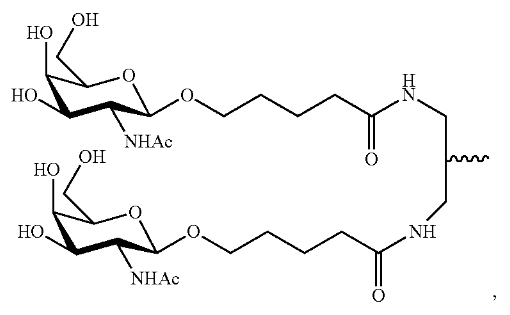
,
Formula VII
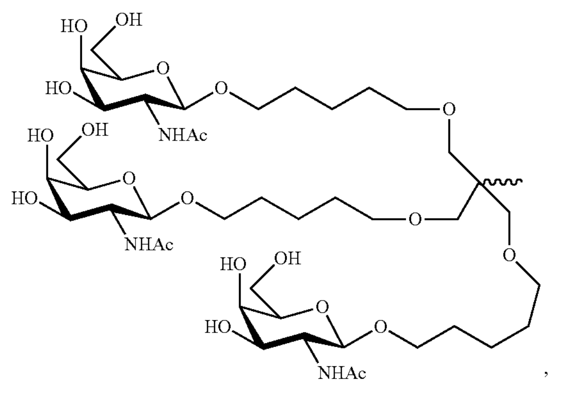
,
Formula VIII
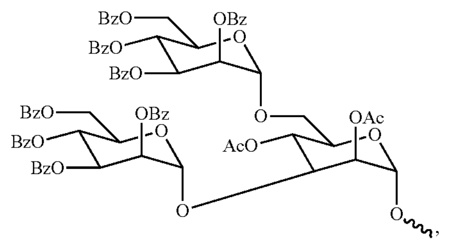
, -continued
Formula IX
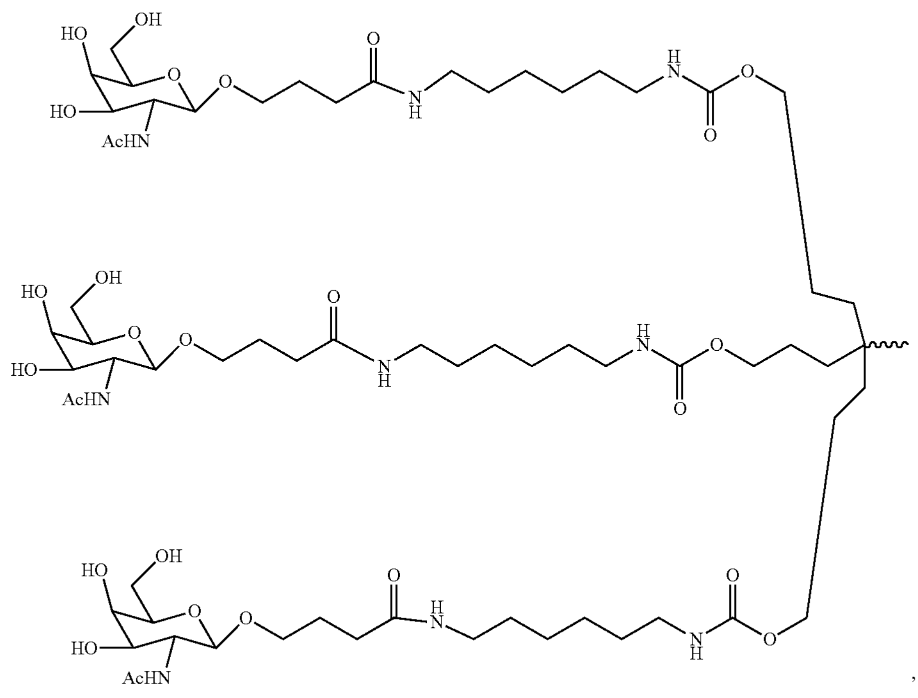
,
Formula X
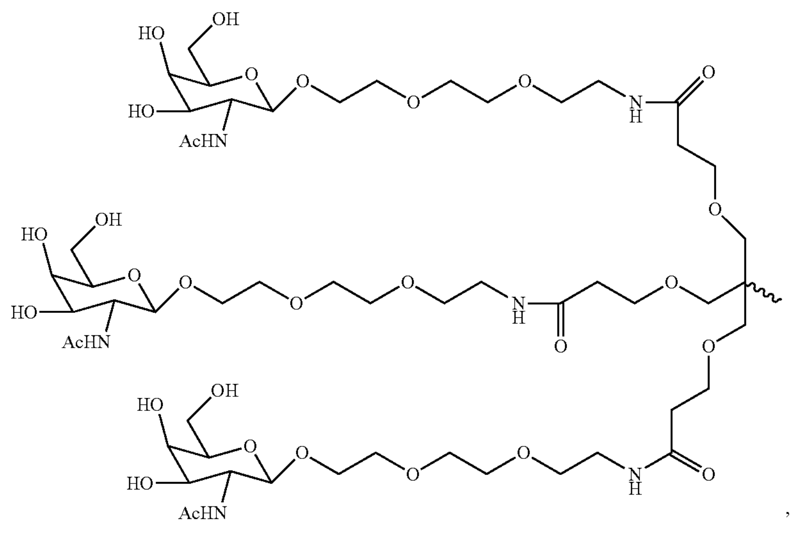
, -continued
Formula XI
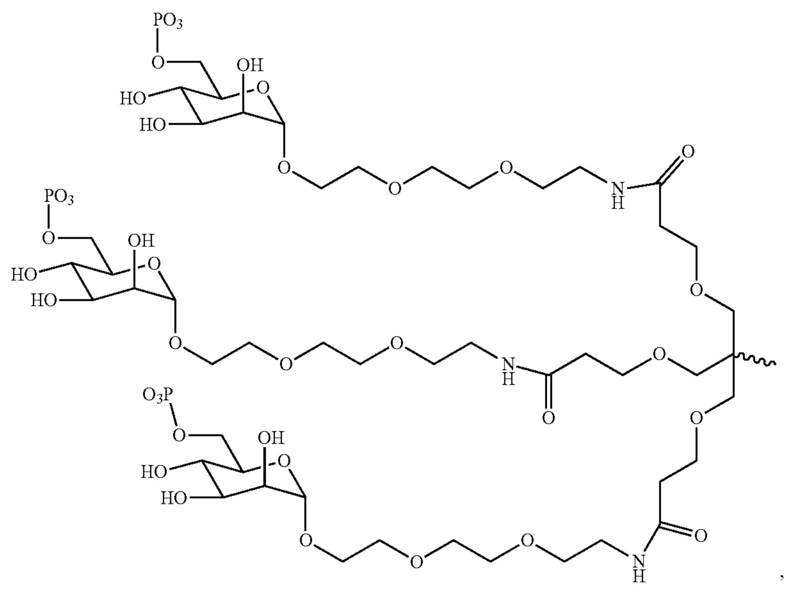
,
Formula XII
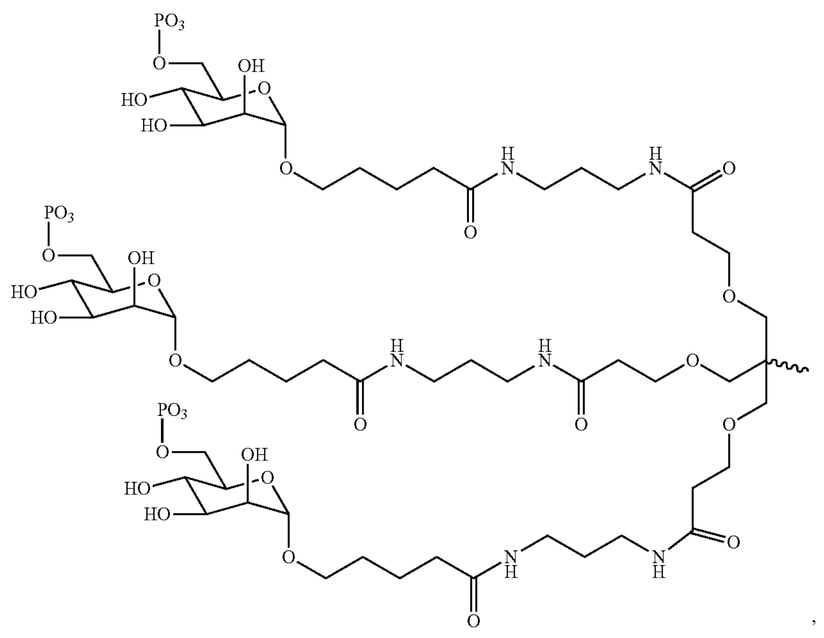
,
Formula XIII
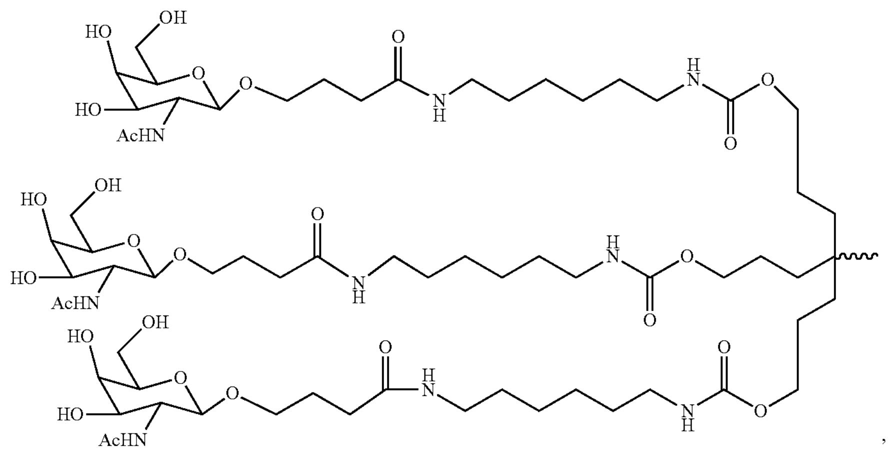
, -continued
Formula XIV
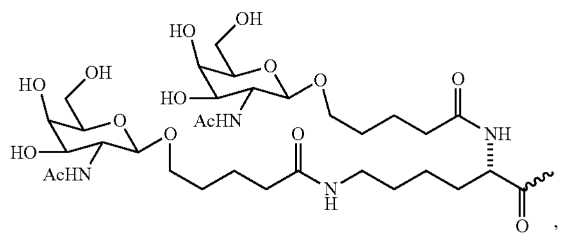
,
Formula XV
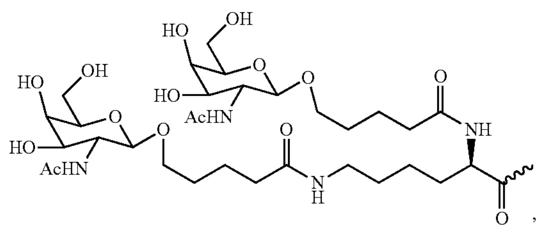
,
Formula XVI
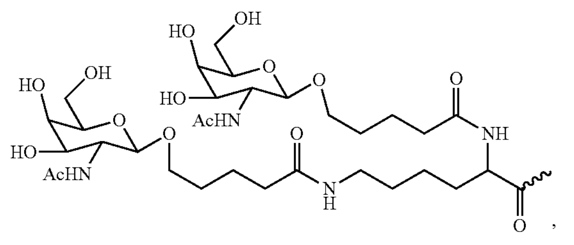
,
Formula XVII
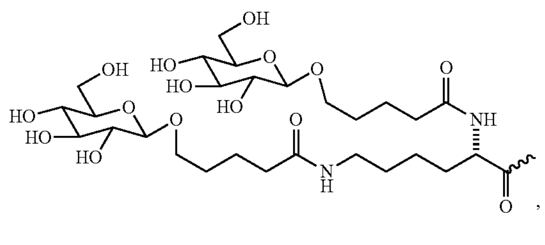
,
Formula XVIII
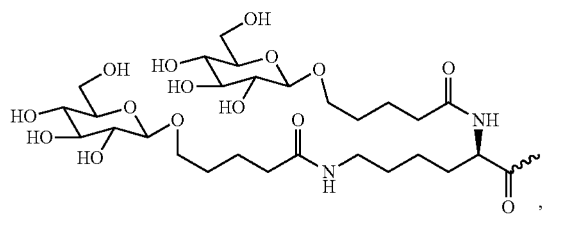
,
Formula XIX
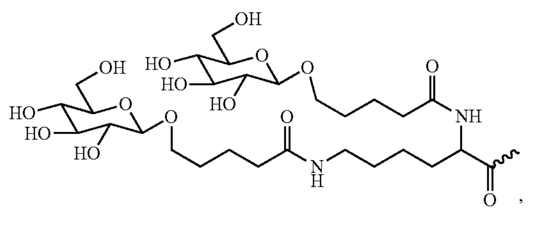
,
Formula XX
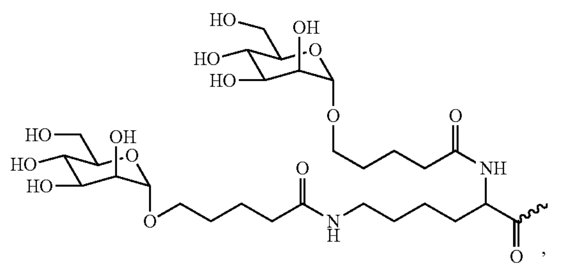
,
Formula XXI
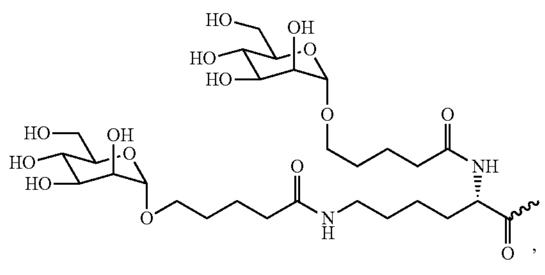
,
Formula XXII
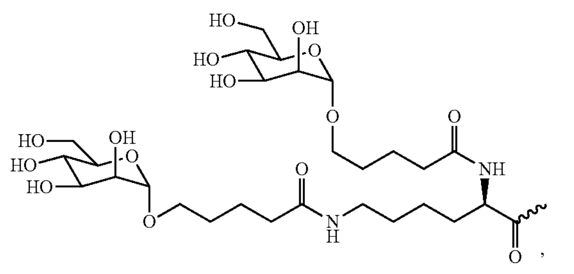
,
Formula XXIII
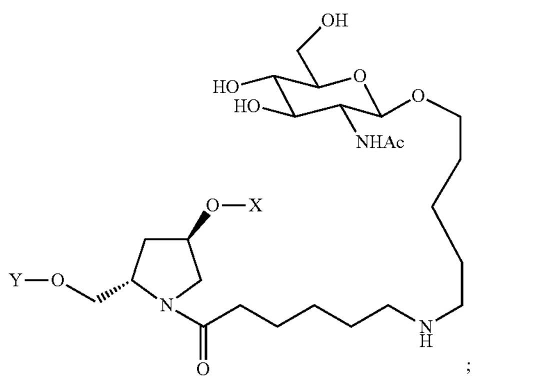
;

-continued
(Formula XXIV)
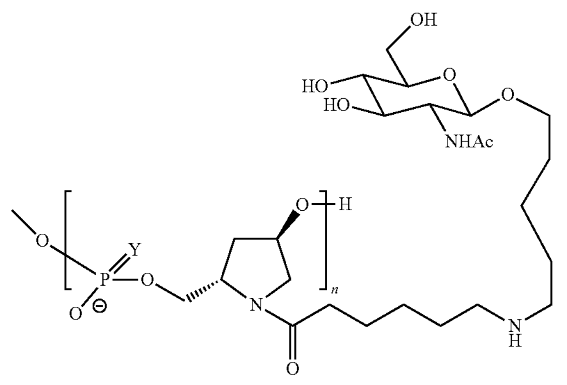
wherein Y is O or S and n is 3 -6
,
(Formula XXV)
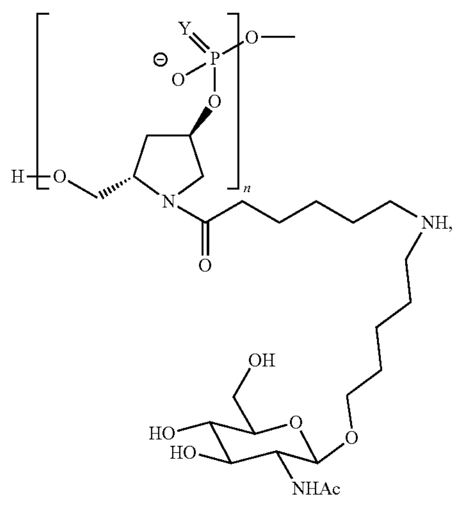
wherein Y is O or S and n is 3-6
Formula XXVI
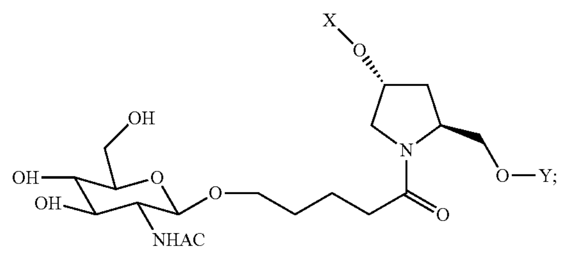
(Formula XXVII)
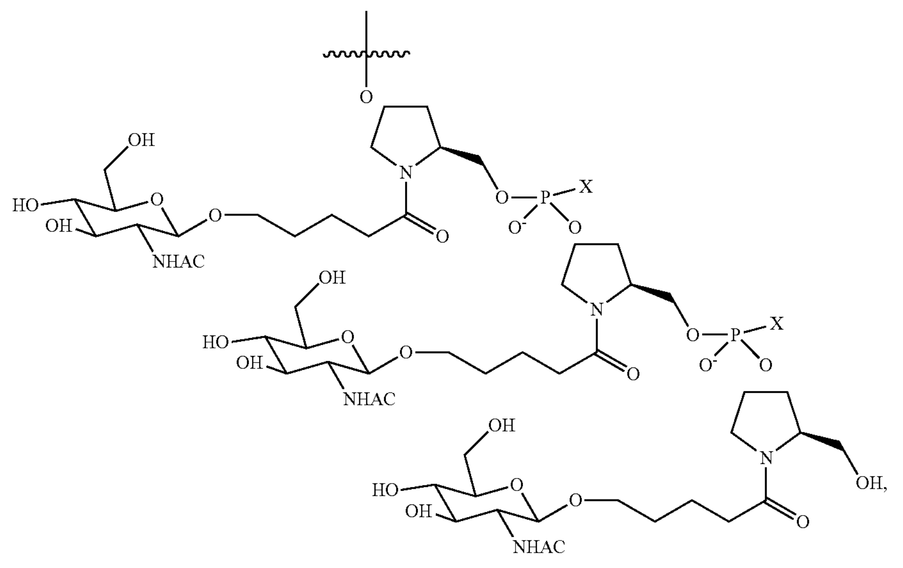
wherein X is O or S -continued
Formula XXVII
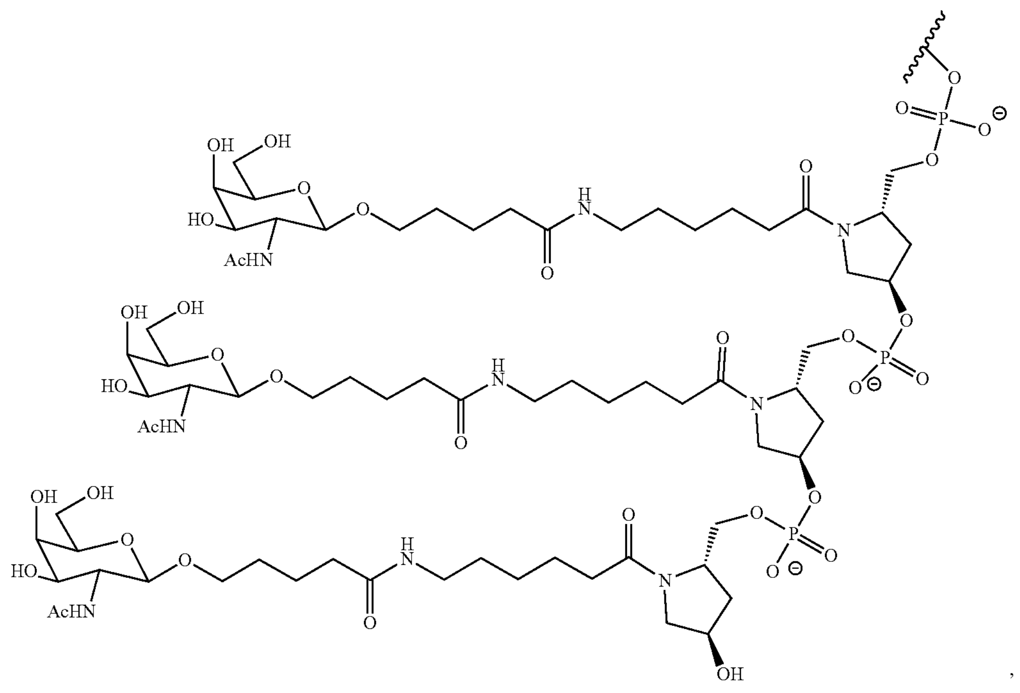
,
Formula XXIX
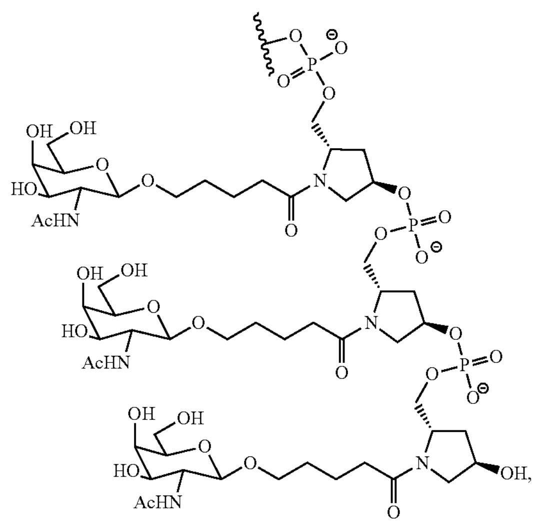
, -continued
Formula XXX
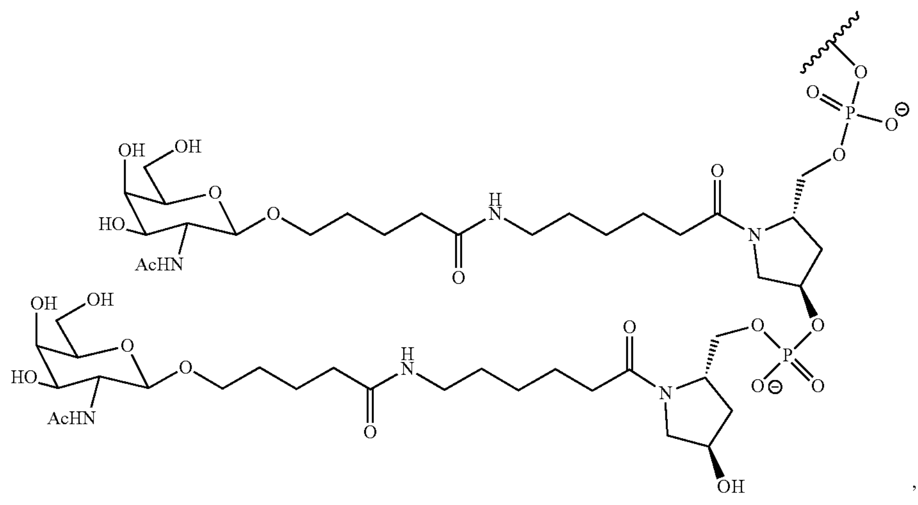
,
Formula XXXI
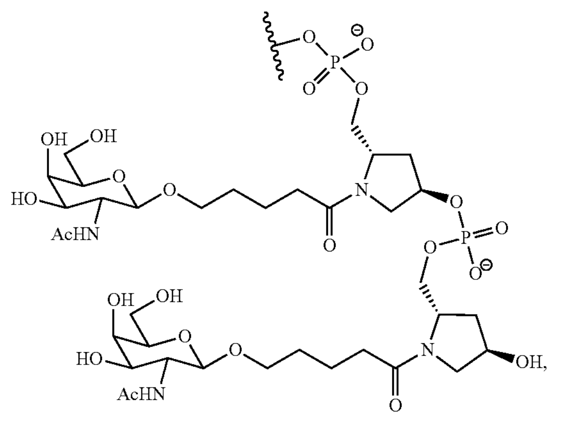
Formula XXXII
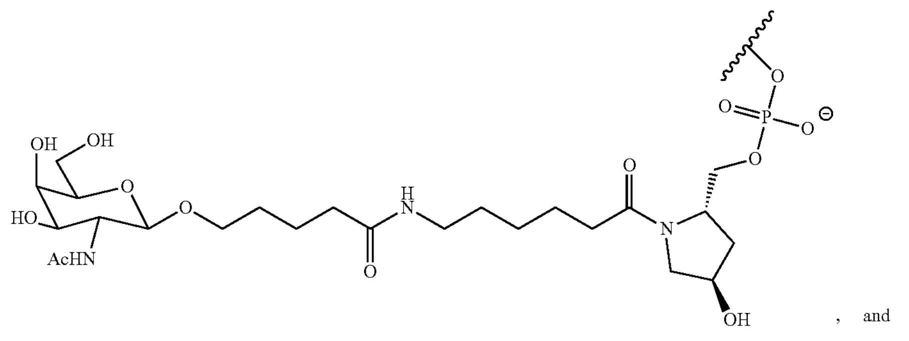
, and
Formula XXXIII
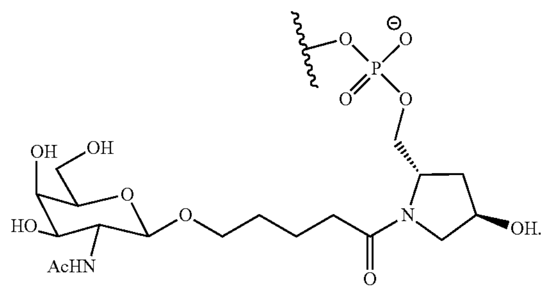

-continued

Formula XXXIV

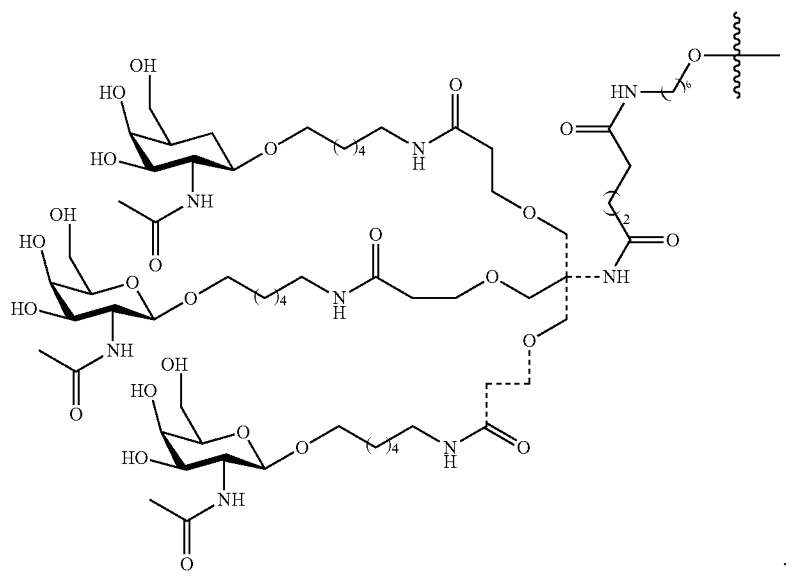

In another embodiment, a carbohydrate conjugate for use in the compositions and methods of the invention is a monosaccharide. In one embodiment, the monosaccharide is an N-acetylgalactosamine, such as Formula II

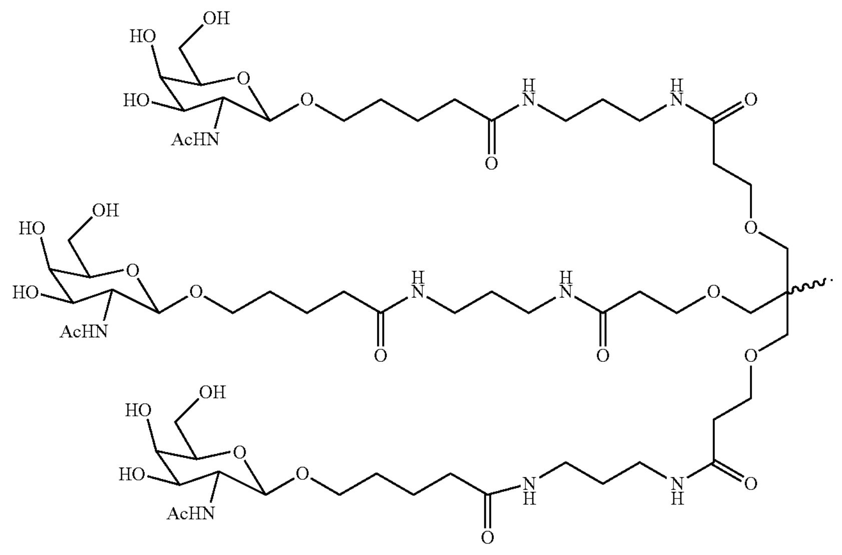 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Another representative carbohydrate conjugate for use in the embodiments described herein includes, but is not limited to, (Formula XXXVI)
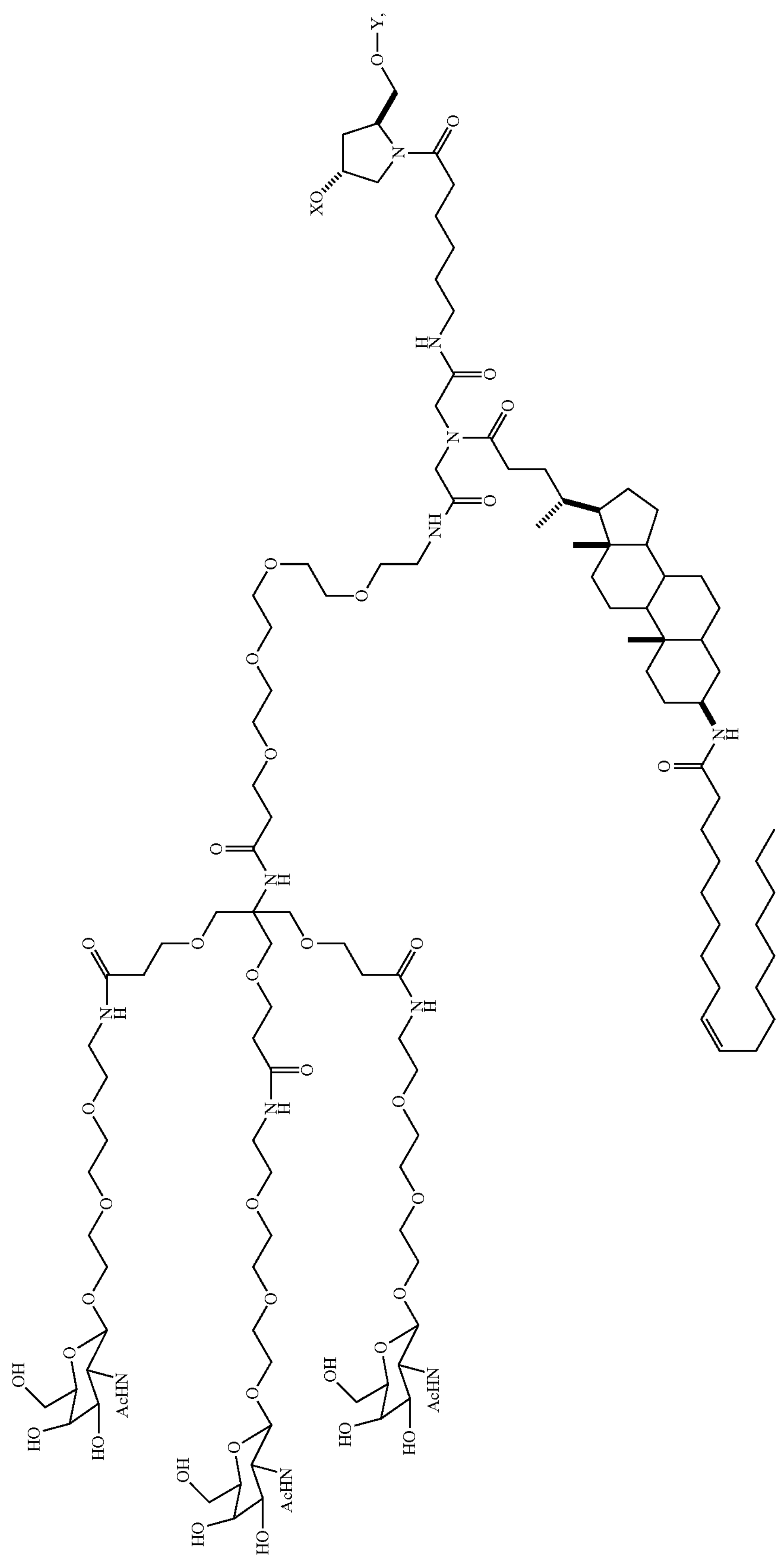

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NRB, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a certain embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a selected pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In certain embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S. Additional embodiments include —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—, wherein Rk at each occurrence can be, independently, C1-C20 alkyl, C1-C20 haloalkyl, C6-C10 aryl, or C7-C12 aralkyl. In certain embodiments a phosphate-based linking group is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In certain embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). One exemplary embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVII)
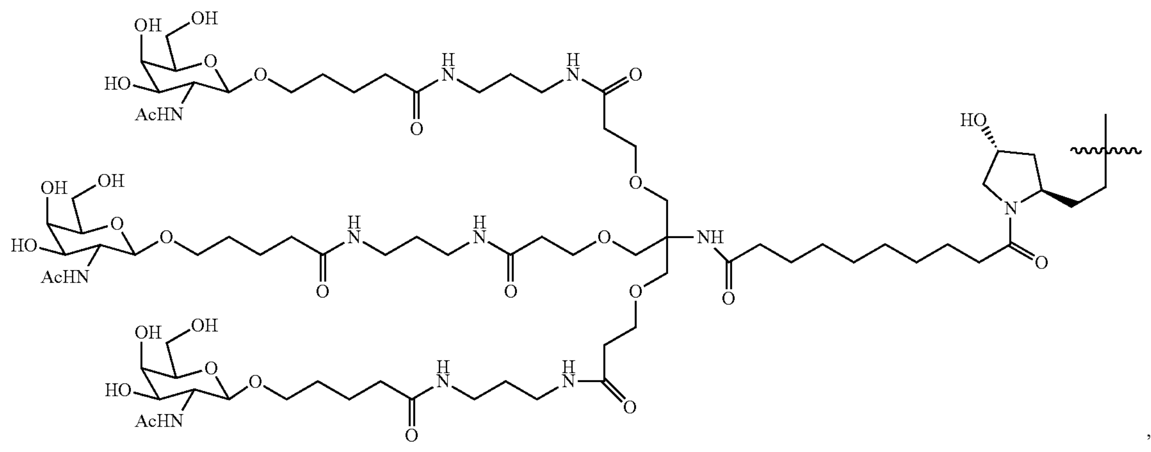
,
(Formula XXXVIII)
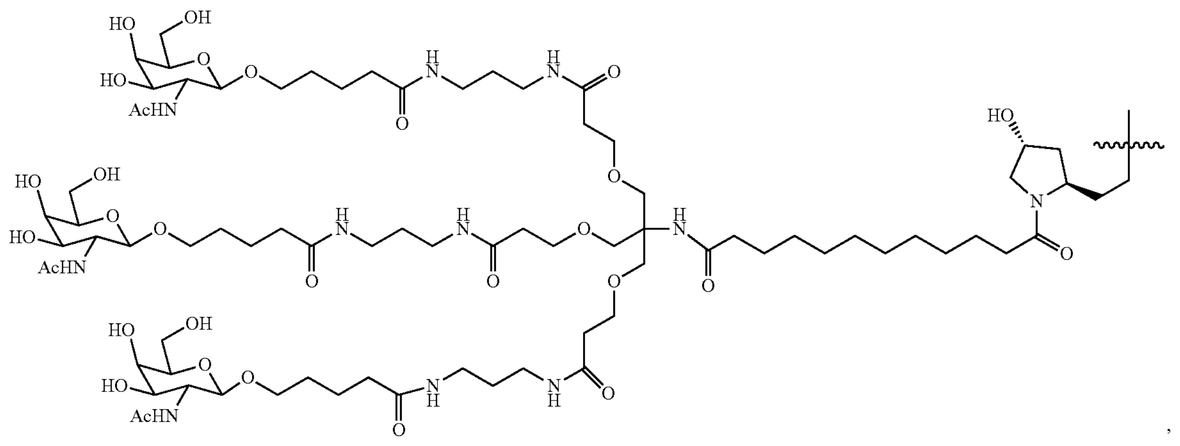
,
(Formula XXXIX)
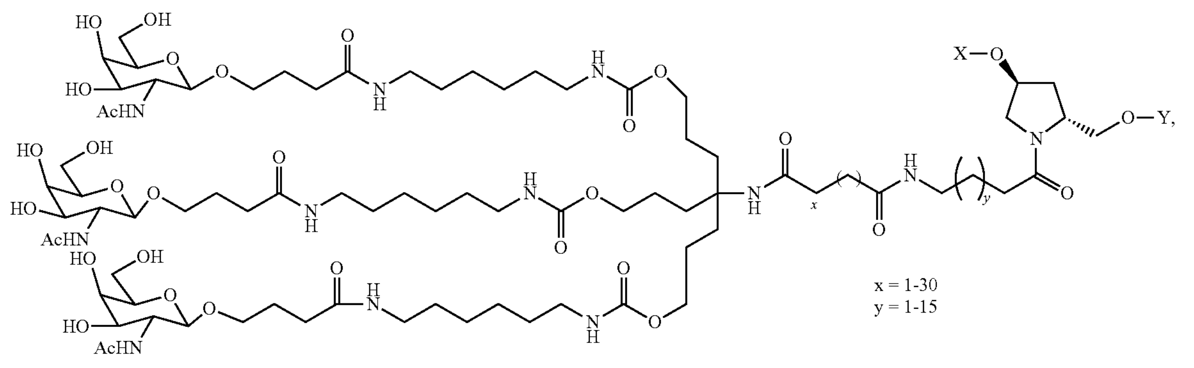
x = 1-30
y = 1-15
(Formula XL)
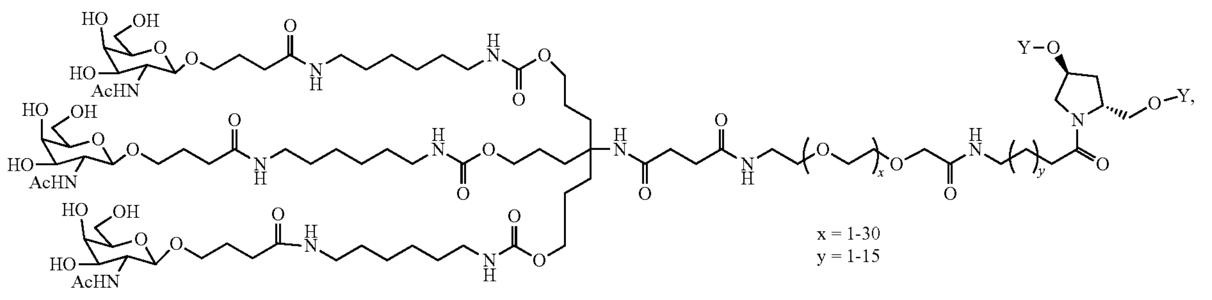
x = 1-30
y = 1-15

-continued
(Formula XLI)
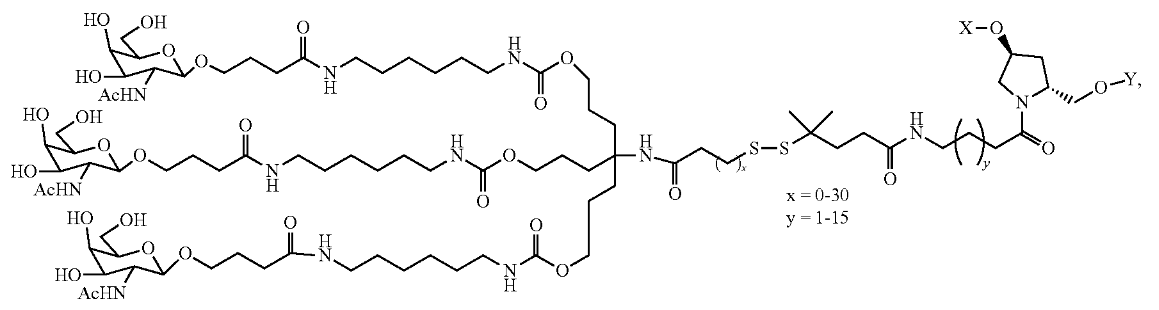
(Formula XLII)
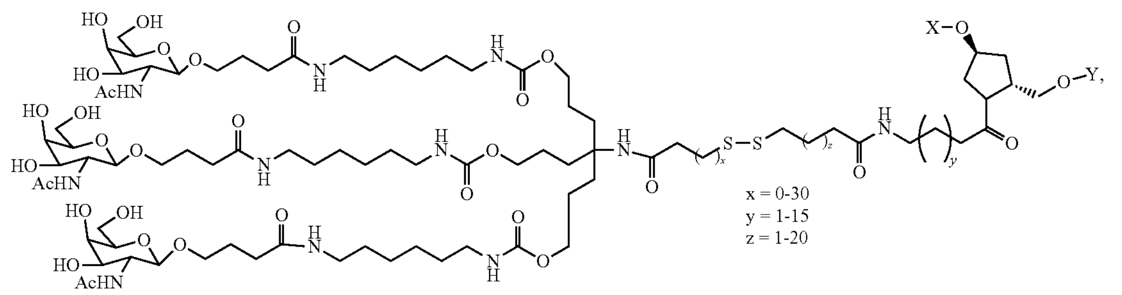
(Formula XLIII)
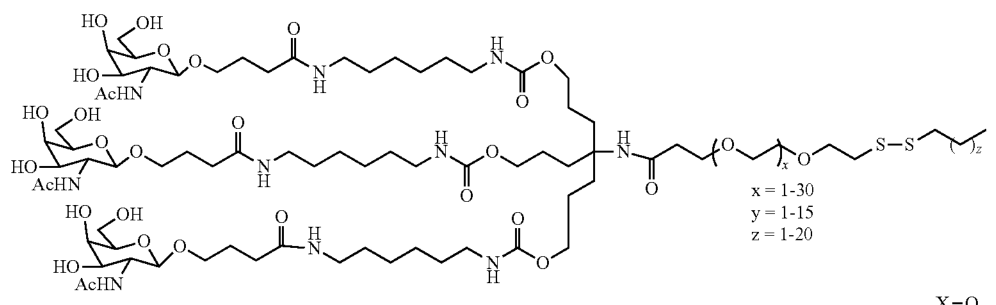
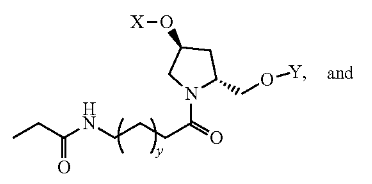
and
(Formula XLIV)
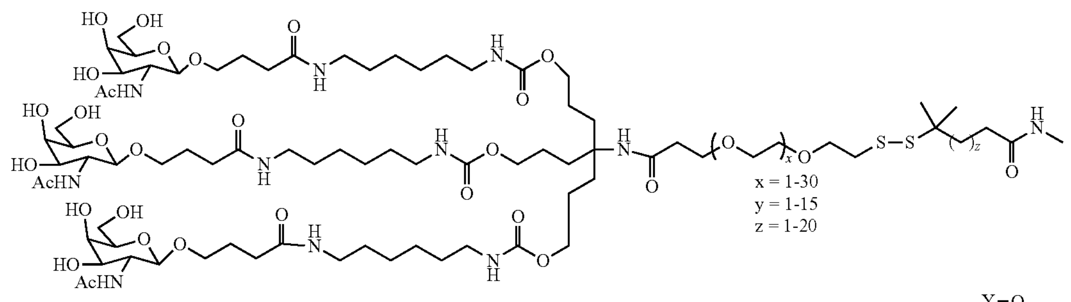
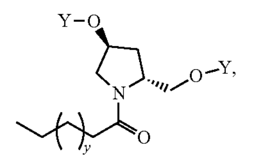
when one of X or Y is an oligonucleotide, the other is a hydrogen.
In certain embodiments of the compositions and methods of the invention, a ligand is one or more "GalNAc"

(N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

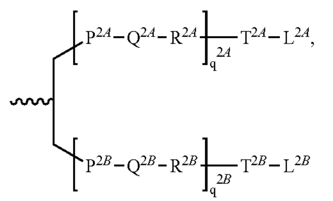

Formula XLVI

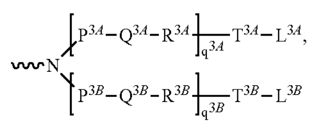

Formula XLVII

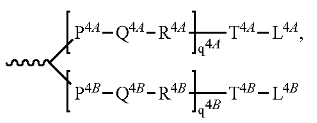

Formula XLVIII

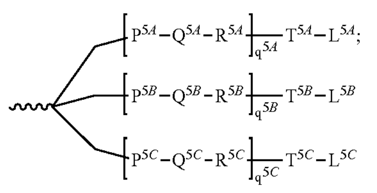

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')═C(R"), CEC or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH═N—O,

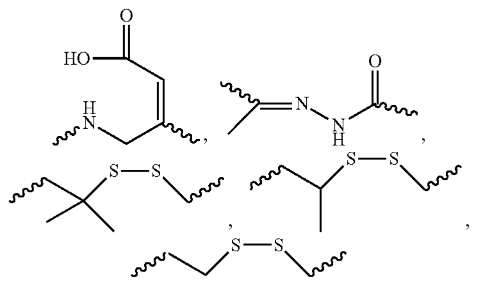

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

Formula (VII

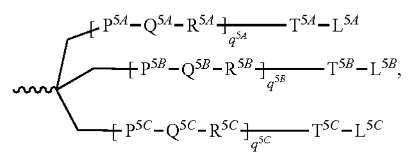

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, such as dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject susceptible to or diagnosed with a MASP2-associated disorder, e.g., inflammation) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602). Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178).

In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), "solid nucleic acid lipid particles" (Zimmermann, T S, et al (2006) *Nature* 441:111-114), cardiolipin (Chien, P Y, et al (2005) *Cancer Gene Ther.* 12:321-328; Pal, A, et al (2005) *Int J. Oncol.* 26:1087-1091), polyethyleneimine (Bonnet M E, et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the MASP2 gene can be expressed from transcription units inserted into DNA or RNA vectors (see, e.g., Couture, A, et al., *TIG.* (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for preventing or treating a MASP2-associated disorder, e.g., inflammation. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. The pharmaceutical compositions of the invention may be administered in dosages sufficient to inhibit expression of a MASP2 gene.

In some embodiments, the pharmaceutical compositions of the invention are sterile. In another embodiment, the pharmaceutical compositions of the invention are pyrogen free.

The pharmaceutical compositions of the invention may be administered in dosages sufficient to inhibit expression of a MASP2 gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, about 0.3 mg/kg and about 3.0 mg/kg. A repeat-dose regimen may include administration of a therapeutic amount of iRNA on a regular basis, such as every month, once every 3-6 months, or once a year. In certain embodiments, the iRNA is administered about once per month to about once per six months.

After an initial treatment regimen, the treatments can be administered on a less frequent basis. Duration of treatment can be determined based on the severity of disease.

In other embodiments, a single dose of the pharmaceutical compositions can be long lasting, such that doses are administered at not more than 1, 2, 3, or 4 month intervals. In some embodiments of the invention, a single dose of the pharmaceutical compositions of the invention is administered about once per month. In other embodiments of the invention, a single dose of the pharmaceutical compositions of the invention is administered quarterly (i.e., about every three months). In other embodiments of the invention, a single dose of the pharmaceutical compositions of the invention is administered twice per year (i.e., about once every six months).

The skilled artisan will appreciate that certain factors can influence the dosage and timing required to effectively treat a subject, including but not limited to mutations present in the subject, previous treatments, the general health or age of the subject, and other diseases present. Moreover, treatment of a subject with a prophylactically or therapeutically effective amount, as appropriate, of a composition can include a single treatment or a series of treatments.

The iRNA can be delivered in a manner to target a particular tissue (e.g., hepatocytes).

Pharmaceutical compositions of the present invention include, but are not limited to, solutions, emulsions, and liposome-containing formulations. These compositions can be generated from a variety of components that include, but are not limited to, preformed liquids, self-emulsifying solids, and self-emulsifying semisolids. Formulations include those that target the liver.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers.

A. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, N.Y., volume 1, p. 285).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

The application of emulsion formulations via dermatological, oral, and parenteral routes, and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

ii. Microemulsions

In one embodiment of the present invention, the compositions of iRNAs and nucleic acids are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers and their use in manufacture of pharmaceutical compositions and delivery of pharmaceutical agents are well known in the art.

v. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Such agents are well known in the art.

vi. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings, or aromatic substances, and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating a MASP2-associated disorder, e.g., inflammation.

Toxicity and prophylactic efficacy of such compounds can be determined by standard pharmaceutical procedures in cell cultures or experimental animals, e.g., for determining the LD50 (the dose lethal to 50% of the population) and the ED50 (the dose prophylactically effective in 50% of the population). The dose ratio between toxic and therapeutic effects is the therapeutic index and it can be expressed as the ratio LD50/ED50. Compounds that exhibit high therapeutic indices are typical.

The data obtained from cell culture assays and animal studies can be used in formulating a range of dosage for use in humans. The dosage of compositions featured herein in the invention lies generally within a range of circulating concentrations that include the ED50, such as an ED80 or ED90, with little or no toxicity. The dosage can vary within this range depending upon the dosage form employed and the route of administration utilized. For any compound used in the methods featured in the invention, the prophylactically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) or higher levels of inhibition as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents used for the prevention or treatment of a MASP2-associated disorder, e.g., inflammation. In any event, the administering physician can adjust the amount and timing of iRNA administration on the basis of results observed using standard measures of efficacy known in the art or described herein.

VI. Methods for Inhibiting MASP2 Expression

The present invention also provides methods of inhibiting expression of a MASP2 gene in a cell. The methods include contacting a cell with an RNAi agent, e.g., double stranded RNA agent, in an amount effective to inhibit expression of MASP2 in the cell, thereby inhibiting expression of MASP2 in the cell.

Contacting of a cell with an iRNA, e.g., a double stranded RNA agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In certain embodiments, the targeting ligand is a carbohydrate moiety, e.g., a $GalNAc_3$ ligand, or any other ligand that directs the RNAi agent to a site of interest.

The term "inhibiting," as used herein, is used interchangeably with "reducing," "silencing," "downregulating", "suppressing", and other similar terms, and includes any level of inhibition.

The phrase "inhibiting expression of a MASP2" is intended to refer to inhibition of expression of any MASP2 gene (such as, e.g., a mouse MASP2 gene, a rat MASP2 gene, a monkey MASP2 gene, or a human MASP2 gene) as well as variants or mutants of a MASP2 gene. Thus, the MASP2 gene may be a wild-type MASP2 gene, a mutant MASP2 gene, or a transgenic MASP2 gene in the context of a genetically manipulated cell, group of cells, or organism.

"Inhibiting expression of a MASP2 gene" includes any level of inhibition of a MASP2 gene, e.g., at least partial suppression of the expression of a MASP2 gene. The expression of the MASP2 gene may be assessed based on the level, or the change in the level, of any variable associated with MASP2 gene expression, e.g., MASP2 mRNA level or MASP2 protein level. This level may be assessed in an individual cell or in a group of cells, including, for example, a sample derived from a subject. It is understood that MASP2 is expressed predominantly in the liver, but also in the brain, gall bladder, heart, and kidney, and is present in circulation.

Inhibition may be assessed by a decrease in an absolute or relative level of one or more variables that are associated with MASP2 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a MASP2 gene is inhibited by at least 50%, 55%, 60%, 65%, 70%, 75%, 80%, 85%, 90%, or 95%, or to below the level of detection of the assay. In certain embodiments, expression of a MASP2 gene is inhibited by at least 70%. It is further understood that inhibition of MASP2 expression in certain tissues, e.g., in liver, without a significant inhibition of expression in other tissues, e.g., brain, may be desirable. In certain embodiments, expression level is determined using the assay method provided in Example 2 with a 10 nM siRNA concentration in the appropriate species matched cell line.

In certain embodiments, inhibition of expression in vivo is determined by knockdown of the human gene in a rodent expressing the human gene, e.g., an AAV-infected mouse expressing the human target gene (i.e., MASP2), e.g., when administered as a single dose, e.g., at 3 mg/kg at the nadir of RNA expression. Knockdown of expression of an endogenous gene in a model animal system can also be determined, e.g., after administration of a single dose at, e.g., 3 mg/kg at the nadir of RNA expression. Such systems are useful when the nucleic acid sequence of the human gene and the model animal gene are sufficiently close such that the human iRNA provides effective knockdown of the model animal gene. RNA expression in liver is determined using the PCR methods provided in Example 2.

Inhibition of the expression of a MASP2 gene may be manifested by a reduction of the amount of mRNA expressed by a first cell or group of cells (such cells may be present, for example, in a sample derived from a subject) in which a MASP2 gene is transcribed and which has or have been treated (e.g., by contacting the cell or cells with an iRNA of the invention, or by administering an iRNA of the invention to a subject in which the cells are or were present) such that the expression of a MASP2 gene is inhibited, as compared to a second cell or group of cells substantially identical to the first cell or group of cells but which has not or have not been so treated (control cell(s) not treated with an iRNA or not treated with an iRNA targeted to the gene of interest). In some embodiments, the inhibition is assessed by the method provided in Example 2 using a 10 nM siRNA concentration in the species matched cell line and expressing the level of mRNA in treated cells as a percentage of the level of mRNA in control cells, using the following formula:

$$\frac{(mRNA\text{ in control cells}) - (mRNA\text{ in treated cells})}{(mRNA\text{ in control cells})} \cdot 100\%$$

In other embodiments, inhibition of the expression of a MASP2 gene may be assessed in terms of a reduction of a parameter that is functionally linked to MASP2 gene expression, e.g., MASP2 protein level in blood or serum from a subject. MASP2 gene silencing may be determined in any cell expressing MASP2, either endogenous or heterologous from an expression construct, and by any assay known in the art.

Inhibition of the expression of a MASP2 protein may be manifested by a reduction in the level of the MASP2 protein that is expressed by a cell or group of cells or in a subject sample (e.g., the level of protein in a blood sample derived from a subject). As explained above, for the assessment of mRNA suppression, the inhibition of protein expression levels in a treated cell or group of cells may similarly be expressed as a percentage of the level of protein in a control cell or group of cells, or the change in the level of protein in a subject sample, e.g., blood or serum derived therefrom.

A control cell, a group of cells, or subject sample that may be used to assess the inhibition of the expression of a MASP2 gene includes a cell, group of cells, or subject sample that has not yet been contacted with an RNAi agent of the invention. For example, the control cell, group of cells, or subject sample may be derived from an individual subject (e.g., a human or animal subject) prior to treatment of the subject with an RNAi agent or an appropriately matched population control.

The level of MASP2 mRNA that is expressed by a cell or group of cells may be determined using any method known in the art for assessing mRNA expression. In one embodiment, the level of expression of MASP2 in a sample is determined by detecting a transcribed polynucleotide, or portion thereof, e.g., mRNA of the MASP2 gene. RNA may be extracted from cells using RNA extraction techniques including, for example, using acid phenol/guanidine isothiocyanate extraction (RNAzol B; Biogenesis), RNeasy™ RNA preparation kits (Qiagen®) or PAXgene™ (PreAnalytix™, Switzerland). Typical assay formats utilizing ribonucleic acid hybridization include nuclear run-on assays, RT-PCR, RNase protection assays, northern blotting, in situ hybridization, and microarray analysis.

In some embodiments, the level of expression of MASP2 is determined using a nucleic acid probe. The term "probe", as used herein, refers to any molecule that is capable of selectively binding to a specific MASP2. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to MASP2 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of MASP2 mRNA.

An alternative method for determining the level of expression of MASP2 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of MASP2 is determined by quantitative fluorogenic RT-PCR (i.e., the TaqMan' System). In certain embodiments, expression level is determined by the method provided in Example 2 using, e.g., a 10 nM siRNA concentration, in the species matched cell line.

The expression levels of MASP2 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of MASP2 expression level may also comprise using nucleic acid probes in solution.

In certain embodiments, the level of mRNA expression is assessed using branched DNA (bDNA) assays or real time PCR (qPCR). The use of these methods is described and exemplified in the Examples presented herein. In certain embodiments, expression level is determined by the method provided in Example 2 using a 10 nM siRNA concentration in the species matched cell line.

The level of MASP2 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention are assessed by a decrease in MASP2 mRNA or protein level (e.g., in a liver biopsy).

In some embodiments of the methods of the invention, the iRNA is administered to a subject such that the iRNA is delivered to a specific site within the subject. The inhibition of expression of MASP2 may be assessed using measurements of the level or change in the level of MASP2 mRNA or MASP2 protein in a sample derived from fluid or tissue from the specific site within the subject (e.g., liver or blood).

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Prophylactic and Treatment Methods of the Invention

The present invention also provides methods of using an iRNA of the invention or a composition containing an iRNA of the invention to inhibit expression of MASP2, thereby preventing or treating a MASP2-associated disorder, e.g., arthritis, IgA nephropathy, thrombotic microangiopathy, diabetic nephropathy and membranous nephropathy.

In the methods of the invention the cell may be contacted with the siRNA in vitro or in vivo, i.e., the cell may be within a subject.

A cell suitable for treatment using the methods of the invention may be any cell that expresses a MASP2 gene, e.g., a liver cell, a kidney cell, or a heart cell. A cell suitable for use in the methods of the invention may be a mammalian cell, e.g., a primate cell (such as a human cell, including human cell in a chimeric non-human animal, or a non-human primate cell, e.g., a monkey cell or a chimpanzee cell), or a non-primate cell. In certain embodiments, the cell is a human cell, e.g., a human liver cell. In the methods of the invention, MASP2 expression is inhibited in the cell by at least 50, 55, 60, 65, 70, 75, 80, 85, 90, or 95, or to a level below the level of detection of the assay.

The in vivo methods of the invention may include administering to a subject a composition containing an iRNA, where the iRNA includes a nucleotide sequence that is complementary to at least a part of an RNA transcript of the MASP2 gene of the mammal to which the RNAi agent is to be administered. The composition can be administered by any means known in the art including, but not limited to oral, intraperitoneal, or parenteral routes, including intracranial (e.g., intraventricular, intraparenchymal, and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intramuscular injection.

In one aspect, the present invention also provides methods for inhibiting the expression of a MASP2 gene in a mammal. The methods include administering to the mammal a composition comprising a dsRNA that targets a MASP2 gene in a cell of the mammal and maintaining the mammal for a time sufficient to obtain degradation of the mRNA transcript of the MASP2 gene, thereby inhibiting expression of the MASP2 gene in the cell. Reduction in gene expression can be assessed by any methods known in the art and by methods, e.g. qRT-PCR, described herein, e.g., in Example 2. Reduction in protein production can be assessed by any methods known it the art, e.g. ELISA. In certain embodiments, a puncture liver biopsy sample serves as the tissue material for monitoring the reduction in the MASP2 gene or protein expression. In other embodiments, a blood sample serves as the subject sample for monitoring the reduction in the MASP2 protein expression.

The present invention further provides methods of treatment in a subject in need thereof, e.g., a subject diagnosed with a MASP2-associated disorder, such as, arthritis, IgA nephropathy, thrombotic microangiopathy, diabetic nephropathy and membranous nephropathy.

The present invention further provides methods of prophylaxis in a subject in need thereof. The treatment methods of the invention include administering an iRNA of the invention to a subject, e.g., a subject that would benefit from a reduction of MASP2 expression, in a prophylactically effective amount of an iRNA targeting a MASP2 gene or a pharmaceutical composition comprising an iRNA targeting a MASP2 gene.

In one embodiment, a MASP2-associated disease is selected from the group consisting of arthritis, IgA nephropathy, thrombotic microangiopathy, diabetic nephropathy and membranous nephropathy.

In one embodiment, a MASP2-associated disease is arthritis. Arthritis is a disorder that affects joints and causes inflammation, joint pain and swelling. There are several types of arthritis, including the most common types osteoarthritis and rheumatoid arthritis. Osteoarthritis is a slow, progressive degenerative joint disease that results from the breakdown of cartilage in the joint. Rheumatoid arthritis is an autoimmune disease causes inflammation in the joints but may also affect other parts of the body, such as the lungs, skin and heart.

In one embodiment, a MASP2-associated disease is IgA nephropathy. IgA nephropathy, also called Berger's disease, is a kidney disease caused by accumulation of IgA antibody in the kidney glomeruli resulting in inflammation or glomerulonephritis. Most patients present with a non-aggressive form of the disease while a small percentage develop aggressive disease. Over time, IgA nephropathy can cause kidney disease and lead to kidney failure.

In one embodiment, a MASP2-associated disease is thrombotic microangiopathy. In thrombotic microangiopathy, thrombosis occurs in the capillaries and arterioles resulting from a vascular endothelial injury. There are several types of thrombotic microangiopathies, including, for example, hemolytic uremic syndrome, thrombotic thrombocytopenic purpura and atypical uremic syndrome. Patients with thrombotic microangiopathies typically present with anemia, thrombocytopenia and kidney failure.

In one embodiment, a MASP2-associated disease is diabetic nephropathy. diabetic nephropathy is a kidney disease caused by diabetes and is the leading cause of chronic kidney disease in the United States. Diabetic nephropathy is characterized by high protein levels in the urine, glomerular lesions and a reduction in glomerular filtration rate.

In one embodiment, a MASP2-associated disease is membranous nephropathy. Membranous nephropathy is characterized by formation of immune complexes in the glomerulus in the kidney. The immune complexes trigger complement activation which causes epithelial and mesenchymal cells to release proteases and other agents that damage capillary walls. Membranous nephropathy typically presents with proteinuria and edema and is a slow progressing disease.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from an inhibition of MASP2 gene expression are subjects susceptible to or diagnosed with a MASP2-associated disorder, such as arthritis, IgA nephropathy, thrombotic microangiopathy, diabetic nephropathy and membranous nephropathy.

In an embodiment, the method includes administering a composition featured herein such that expression of the target MASP2 gene is decreased, such as for about 1, 2, 3, 4, 5, 6, 1-6, 1-3, or 3-6 months per dose. In certain embodiments, the composition is administered once every 3-6 months.

In certain embodiments, the iRNAs useful for the methods and compositions featured herein specifically target RNAs (primary or processed) of the target MASP2 gene. Compositions and methods for inhibiting the expression of these genes using iRNAs can be prepared and performed as described herein.

Administration of the iRNA according to the methods of the invention may result prevention or treatment of a MASP2-associated disorder, e.g., arthritis, IgA nephropathy, thrombotic microangiopathy, diabetic nephropathy and membranous nephropathy.

In certain embodiments, subjects can be administered a therapeutic amount of dsRNA, such as about 0.01 mg/kg to about 200 mg/kg. In other embodiments, subjects can be administered a therapeutic amount of dsRNA, such as about 0.01 mg/kg to about 500 mg/kg. In yet other embodiments, subjects can be administered a therapeutic amount of dsRNA of about 500 mg/kg or more.

The iRNA is typically administered subcutaneously, i.e., by subcutaneous injection. One or more injections may be used to deliver the desired dose of iRNA to a subject. The injections may be repeated over a period of time.

The administration may be repeated on a regular basis. In certain embodiments, after an initial treatment regimen, the treatments can be administered on a less frequent basis. A repeat-dose regimen may include administration of a therapeutic amount of iRNA on a regular basis, such as once per month to once a year. In certain embodiments, the iRNA is administered about once per month to about once every three months, or about once every three months to about once every six months.

The invention further provides methods and uses of an iRNA agent or a pharmaceutical composition thereof for treating a subject that would benefit from reduction and/or inhibition of MASP2 gene expression, e.g., a subject having a MASP2-associated disease, in combination with other pharmaceuticals and/or other therapeutic methods, e.g., with known pharmaceuticals and/or known therapeutic methods, such as, for example, those which are currently employed for treating these disorders.

Accordingly, in some aspects of the invention, the methods which include either a single iRNA agent of the invention, further include administering to the subject one or more additional therapeutic agents.

The iRNA agent and an additional therapeutic agent and/or treatment may be administered at the same time and/or in the same combination, e.g., parenterally, or the additional therapeutic agent can be administered as part of a separate composition or at separate times and/or by another method known in the art or described herein.

For example, additional therapeutics and therapeutic methods suitable for treating a subject that would benefit from reduction in MASP2 expression, e.g., a subject having a MASP2-associated disease, include plasmaphoresis, thrombolytic therapy (e.g., streptokinase), antiplatelet agents, folic acid, corticosteroids; immunosuppressive agents; estrogens, methotrexate, 6-MP, azathioprine sulphasalazine, mesalazine, olsalazine, chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines, such as TNF-$\alpha$ or IL-1 (e.g., IRAK, NIK, IKK, p38 or MAP kinase inhibitors), IL-1$\beta$ converting enzyme inhibitors, TNF$\alpha$ converting enzyme (TACE) inhibitors, T-cell signalling inhibitors, such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, and sIL-6R), anti-inflammatory cytokines (e.g., IL-4, IL-10, IL-11, IL-13 and TGF$\beta$), celecoxib, folic acid, hydroxychloroquine sulfate, rofecoxib, etanercept, infliximonoclonal antibody, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hydrochloride, hydrocodone bitartrate/apap, diclofenac sodium/misoprostol, fentanyl, anakinra, human recombinant, tramadol hydrochloride, salsalate, sulindac, cyanocobalamin/folic acid/pyridoxine, acetaminophen, alendronate sodium, prednisolone, morphine sulfate, lidocaine hydrochloride, indomethacin, glucosamine sulf/chondroitin, amitriptyline hydrochloride, sulfadiazine, oxycodone hydrochloride/acetaminophen, olopatadine hydrochloride, misoprostol, naproxen sodium, omeprazole, cyclophosphamide, rituximonoclonal antibody, IL-1 TRAP, MRA, CTLA4-IG, IL-18 BP, anti-IL-18, Anti-IL15, BIRB-796, SC10-469, VX-702, AMG-548, VX-740, Roflumilast, IC-485, CDC-801, Mesopram, cyclosporine, cytokine suppressive anti-inflammatory drug(s) (CSAIDs); CDP-571/BAY-10-3356 (humanized anti-TNFα antibody; Celltech/Bayer); cA2/infliximonoclonal antibody (chimeric anti-TNFα antibody; Centocor); 75 kdTNFR-IgG/etanercept (75 kD TNF receptor-IgG fusion protein; Immunex; see e.g., (1994) *Arthr. Rheum.* 37: 5295; (1996) *J. Invest. Med.* 44: 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., (1995) *Arthr. Rheum.* 38: S185); DAB 486-IL-2 and/or DAB 389-IL-2 (IL-2 fusion proteins; Seragen; see e.g., (1993) *Arthrit. Rheum.* 36: 1223); Anti-Tac (humanized anti-IL-2R$^{a}$; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., (1996) Arthr. Rheum. 39(9 (supplement)): 5284; (1995) Amer. J. Physiol.—Heart and Circ. Physiol. 268: 37-42); R973401 (phosphodiesterase Type IV inhibitor; see e.g., (1996) Arthr. Rheum. 39(9 (supplement): S282); MK-966 (COX-2 Inhibitor; see e.g., (1996) Arthr. Rheum. 39(9 (supplement): S81); Iloprost (see e.g., (1996) Arthr. Rheum. 39(9 (supplement): S82); methotrexate; thalidomide (see e.g., (1996) Arthr. Rheum. 39(9 (supplement): 5282) and thalidomide-related drugs (e.g., Celgen); leflunomide (anti-inflammatory and cytokine inhibitor; see e.g., (1996) Arthr. Rheum. 39(9 (supplement): 5131; (1996) Inflamm. Res. 45: 103-107); tranexamic acid (inhibitor of plasminogen activation; see e.g., (1996) Arthr. Rheum. 39(9 (supplement): S284); T-614 (cytokine inhibitor; see e.g., (1996) Arthr. Rheum. 39(9 (supplement): S282); prostaglandin E1 (see e.g., (1996) Arthr. Rheum. 39(9 (supplement): S282); Tenidap (non-steroidal anti-inflammatory drug; see e.g., (1996) Arthr. Rheum. 39(9 (supplement): S280); Naproxen (non-steroidal anti-inflammatory drug; see e.g., (1996) Neuro. Report 7: 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., (1996) Arthr. Rheum. 39(9 (supplement): S281); Azathioprine (see e.g., (1996) Arthr. Rheum. 39(9 (supplement): S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., (1996) Arthr. Rheum. 39(9 (supplement): S296); interleukin-13 (see e.g., (1996) Arthr. Rheum. 39(9 (supplement): S308); interleukin-17 inhibitors (see e.g., (1996) Arthr. Rheum. 39(9 (supplement): S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21: 759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; bcl-2 inhibitors (see Bruncko, M. et al. (2007) J. Med. Chem. 50(4): 641-662); antivirals and immune-modulating agents, small molecule inhibitor of KDR, small molecule inhibitor of Tie-2; methotrexate; prednisone; celecoxib; folic acid; hydroxychloroquine sulfate; rofecoxib; etanercept; infliximonoclonal antibody; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hydrochloride; sulfadiazine; oxycodone hcl/acetaminophen; olopatadine hcl; misoprostol; naproxen sodium; omeprazole; mycophenolate mofetil; cyclophosphamide; rituximonoclonal antibody; IL-1 TRAP; MRA; CTLA4-IG; IL-18 BP; IL-12/23; anti-IL 18; anti-IL 15; BIRB-796; SC10-469; VX-702; AMG-548; VX-740; Roflumilast; IC-485; CDC-801; mesopram, albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate, aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

In some aspects, the additional therapeutic agent is an iRNA agent targeting a C5 gene, such as described in U.S. Pat. No. 9,249,415, U.S. Provisional Patent Application Nos. 62/174,933, filed on Jun. 12, 2015, 62/263,066, filed on Dec. 4, 2015, the entire contents of each of which are hereby incorporated herein by reference.

In other aspects, the additional therapeutic agent is an anti-complement component C5 antibody, or antigen-binding fragment thereof (e.g., eculizumab). Eculizumab is a humanized monoclonal IgG2/4, kappa light chain antibody that specifically binds complement component C5 with high affinity and inhibits cleavage of C5 to C5a and C5b, thereby inhibiting the generation of the terminal complement complex C5b-9. Eculizumab is described in U.S. Pat. No. 6,355,245, the entire contents of which are incorporated herein by reference.

In yet other aspects, the additional therapeutic is a MASP2 monoclonal antibody. In one embodiment, the MASP2 monoclonal antibody is Narsoplimab (OMS721), a human antibody.

VIII. Kits

The present invention also provides kits for performing any of the methods of the invention. Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe), or means for measuring the inhibition of MASP2 (e.g., means for measuring the inhibition of MASP2 mRNA, MASP2 protein, and/or MASP2 activity). Such means for measuring the inhibition of MASP2 may comprise a means for obtaining a sample from a subject, such as, e.g., a plasma sample. The kits of the invention may optionally further comprise means for determining the therapeutically effective or prophylactically effective amount.

This invention is further illustrated by the following examples which should not be construed as limiting. The entire contents of all references, patents and published patent applications cited throughout this application, as well as the informal Sequence Listing and Figures, are hereby incorporated herein by reference.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

siRNA Design siRNAs targeting the human MASP2 gene (human NCBI refseqIDs NM_006610.3, NM_006610.4 and NM_139208.2; NCBI GeneID: 10747) were designed using custom R and Python scripts. The human NM_006610.3 REFSEQ mRNA has a length of 2471 bases; NM_006610.4 REFSEQ mRNA, has a length of 2455 bases; and NM_139208.2 REFSEQ mRNA has a length of 749 bases.

siRNAs targeting the mouse MASP2 gene (mouse: NCBI refseqID NM_001003893.2) were designed using custom R and Python scripts. The mouse NM_001003893.2 REFSEQ mRNA, has a length of 3061 bases.

Detailed lists of the unmodified MASP2 sense and antisense strand nucleotide sequences are shown in Tables 2, 4, and 6. Detailed lists of the modified MASP2 sense and antisense strand nucleotide sequences are shown in Tables 3, 5, and 7.

It is to be understood that, throughout the application, a duplex name without a decimal is equivalent to a duplex name with a decimal which merely references the batch number of the duplex. For example, AD-68438 is equivalent to AD-68438.1.

siRNA Synthesis siRNAs were synthesized and annealed using routine methods known in the art.

Briefly, siRNA sequences were synthesized at 1 μmol scale on a Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, WI) and Hongene (China). 2'F 2'-O-Methyl, GNA (glycol nucleic acids), 5'phosphate and other modifications were introduced using the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 minutes employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, MA, USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 μL Aqueous Methylamine reagents at 60° C. for 20 minutes. For sequences containing 2' ribo residues (2'-OH) that are protected with a tert-butyl dimethyl silyl (TBDMS) group, a second step deprotection was performed using TEA·3HF (triethylamine trihydro fluoride) reagent. To the methylamine deprotection solution, 200 μL of dimethyl sulfoxide (DMSO) and 300 μl TEA·3HF reagent was added and the solution was incubated for additional 20 minutes at 60° C. At the end of cleavage and deprotection step, the synthesis plate was allowed to come to room temperature and was precipitated by addition of 1 mL of acetontile: ethanol mixture (9:1). The plates were cooled at −80° C. for 2 hours, supernatant decanted carefully with the aid of a multi-channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples by IEX chromatography to determine purity.

Annealing of single strands was performed on a Tecan liquid handling robot. Equimolar mixture of sense and antisense single strands were combined and annealed in 96-well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 μM in 1×PBS and then submitted for in vitro screening assays.

Example 2. In Vitro Screening Methods

Cell Culture and 384-Well Transfections

Hep3b cells (ATCC, Manassas, VA) were grown to near confluence at 37° C. in an atmosphere of 5% $CO_2$ in Eagle's Minimum Essential Medium (Gibco) supplemented with 10% FBS (ATCC) before being released from the plate by trypsinization. For mouse and cynomolgus monkey cross reactive duplexes, primary mouse hepatocytes (PMH) or primary cynomolgus monkey hepatocytes (PCH) were freshly isolated less than 1 hour prior to transfections and grown in primary hepatocyte media. For Hep3B, PMH and PCH, transfection was carried out by adding 14.8 μL of Opti-MEM plus 0.2 μl of Lipofectamine RNAiMax per well (Invitrogen, Carlsbad Calif. cat #13778-150) to 5 μL of each siRNA duplex to an individual well in a 96-well plate. The mixture was then incubated at room temperature for 15 minutes. Eighty μL of complete growth media without antibiotic containing ~$2\times10^4$ Hep3B cells, PMH or PCH were then added to the siRNA mixture. Cells were incubated for 24 hours prior to RNA purification. Single dose experiments were performed at 10 nM and 0.1 nM final duplex concentration.

Total RNA Isolation Using DYNABEADS mRNA Isolation Kit (Invitrogen™, Part #: 610-12)

Cells were lysed in 75 μL of Lysis/Binding Buffer containing 3 μL of beads per well and mixed for 10 minutes on an electrostatic shaker. The washing steps were automated on a Biotek EL406, using a magnetic plate support. Beads were washed (in 90 L), once in Buffer A, once in Buffer B, and twice in Buffer E, with aspiration steps in between. Following a final aspiration, complete 10 μL RT mixture was added to each well, as described below.

cDNA Synthesis Using ABI High Capacity cDNA Reverse Transcription Kit (Applied Biosystems, Foster City, CA, Cat #4368813)

A master mix of 1 μL 10× Buffer, 0.4 μL 25× dNTPs, 1 μL Random primers, 0.5 μL Reverse Transcriptase, 0.5 μL RNase inhibitor and 6.6 μL of $H_2O$ per reaction were added per well. Plates were sealed, agitated for 10 minutes on an electrostatic shaker, and then incubated at 37° C. for 2 hours. Following this, the plates were agitated at 80° C. for 8 minutes.

Real Time PCR

Two microliter (μL) of cDNA were added to a master mix containing 0.5 μL of human GAPDH TaqMan Probe (4326317E) or 0.5 μL Mouse GAPDH TaqMan Probe (4352339E), 0.5 μL human MASP2 probe (Hs00198244_m1 (long isoform-specific) or Hs00373722_m1 (shared with both long and short isoforms)) or 0.5 μL mouse MASP2 probe (Mm01263692_m1 (long-isoform specific) or Mm00521962_g1 (both isoforms)), 2 μL nuclease-free water and 5 μL Lightcycler 480 probe master mix (Roche Cat #04887301001) per well in a 384 well plates (Roche cat #04887301001). Real time PCR was done in a LightCycler480 Real Time PCR system (Roche). Each duplex was tested at least two times and data were normalized to cells transfected with a non-targeting control siRNA. To calculate relative fold change, real time data were analyzed using the ΔΔCt method and normalized to assays performed with cells transfected with a non-targeting control siRNA.

The results of the screening of the dsRNA agents listed in Tables 2 and 3 in PCH cells are shown in Table 8. The results of the screening of the dsRNA agents listed in Tables 2 and 3 in PMH cells are shown in Table 9. Tables 8 and 9 indicate the cross reactivity of the MASP2 probe with human (h), cynomolgus monkey (c), mouse (m) and rat (r) MASP2. Tables 8 and 9 also indicate whether the MASP2 probe recognizes only the long isoform (long-specific) of MASP2 or recognizes both the long and short MASP2 isoforms (shared). The results of the screening of the dsRNA agents listed in Tables 4 and 5 in Hep3B cells are shown in Table 10.

TABLE 1

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position of the parent nucleotide (i.e., it is a 2'-deoxy-2'-fluoronucleotide).

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |

TABLE 1-continued

Abbreviations of nucleotide monomers used in nucleic acid sequence representation. It will be understood that these monomers, when present in an oligonucleotide, are mutually linked by 5'-3'-phosphodiester bonds; and it is understood that when the nucleotide contains a 2'-fluoro modification, then the fluoro replaces the hydroxy at that position of the parent nucleotide (i.e., it is a 2'-deoxy-2'-fluoronucleotide).

| Abbreviation | Nucleotide(s) |
|---|---|
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amido-dodecanoyl)]-4-hydroxyprolinol [Hyp-(GalNAc-alkyl)3] 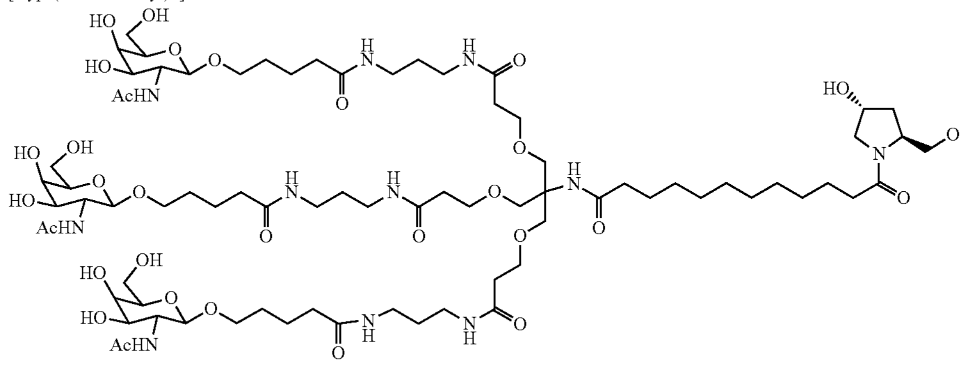 |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |

TABLE 2

| Unmodified Sense and Antisense Strand Sequences of MASP2 dsRNA Agents | | | | | | | |
|---|---|---|---|---|---|---|---|
| Duplex Name | Sense Sequence 5' to 3' | SEQ ID NO: | Source | Range in Source | Antisense Sequence 5' to 3' | SEQ ID NO: | Range in Source |
| AD-68438.1 | GUGUGUGAGGC UGAUGGAUUA | 24 | NM_006610.3 | 1263-1283 | UAAUCCAUCAGC CUCACACACAU | 70 | 1261-1283 |
| AD-68439.1 | CACCUACAAAG CUGUGAUUCA | 25 | NM_006610.3 | 1190-1210 | UGAAUCACAGCU UUGUAGGUGGU | 71 | 1188-1210 |
| AD-68440.1 | ACCUACAAAGC UGUGAUUCAA | 26 | NM_006610.3 | 1191-1211 | UUGAAUCACAGC UUUGUAGGUGG | 72 | 1189-1211 |
| AD-68441.1 | AGAAAGAUGGA UCUUGGGACA | 27 | NM_006610.3 | 1078-1098 | UGUCCCAAGAUC CAUCUUUCUGA | 73 | 1076-1098 |
| AD-68442.1 | AGGCUGAUGGA UUCUGGACGA | 28 | NM_006610.3 | 1270-1290 | UCGUCCAGAAUC CAUCAGCCUCA | 74 | 1268-1290 |
| AD-68443.1 | GACCACACAGG CUGGAAGAUA | 29 | NM_006610.3 | 885-905 | UAUCUUCCAGCC UGUGUGGUCUC | 75 | 883-905 |
| AD-68444.1 | CGACUUUCUCA AGAUUCAAAA | 30 | NM_006610.3 | 761-781 | UUUUGAAUCUUG AGAAAGUCGUA | 76 | 759-781 |
| AD-68445.1 | GUAAAUAUGUG UGUGAGGCUA | 31 | NM_006610.3 | 1255-1275 | UAGCCUCACACA CAUAUUUACCA | 77 | 1253-1275 |
| AD-68446.1 | GAUUCUGGACG AGCUCCAAAA | 32 | NM_006610.3 | 1279-1299 | UUUUGGAGCUCG UCCAGAAUCCA | 78 | 1277-1299 |
| AD-68447.1 | AAAGCUGUGAU UCAGUACAGA | 33 | NM_006610.3 | 1197-1217 | UCUGUACUGAAU CACAGCUUUGU | 79 | 1195-1217 |
| AD-68448.1 | CUGGCUAUGAG CUUCUGCAAA | 34 | NM_006610.3 | 1021-1041 | UUUGCAGAAGCU CAUAGCCAGUC | 80 | 1019-1041 |
| AD-68449.1 | UCUGGACUUUG UGGAGUCCUU | 35 | NM_006610.3 | 704-724 | AAGGACUCCACA AAGUCCAGAAU | 81 | 702-724 |
| AD-68450.1 | AGGUGGUUUGU GGGAGGAAUA | 36 | NM_006610.3 | 1968-1988 | UAUUCCUCCCAC AAACCACCUCU | 82 | 1966-1988 |
| AD-68451.1 | UGGAUUCUGGA CGAGCUCCAA | 37 | NM_006610.3 | 1277-1297 | UUGGAGCUCGUC CAGAAUCCAUC | 83 | 1275-1297 |
| AD-68452.1 | UGAUUCAGUAC AGCUGUGAAA | 38 | NM_006610.3 | 1204-1224 | UUUCACAGCUGU ACUGAAUCACA | 84 | 1202-1224 |
| AD-68453.1 | CUACAAAGCUG UGAUUCAGUA | 39 | NM_006610.3 | 1193-1213 | UACUGAAUCACA GCUUUGUAGGU | 85 | 1191-1213 |
| AD-68454.1 | CUGUGAUUCAG UACAGCUGUA | 40 | NM_006610.3 | 1201-1221 | UACAGCUGUACU GAAUCACAGCU | 86 | 1199-1221 |
| AD-68455.1 | CUGGUGAUUUU CCUUGGCAAA | 41 | NM_006610.3 | 1390-1410 | UUUGCCAAGGAA AAUCACCAGGU | 87 | 1388-1410 |
| AD-68456.1 | GCUGAUGGAUU CUGGACGAGA | 42 | NM_006610.3 | 1272-1292 | UCUCGUCCAGAA UCCAUCAGCCU | 88 | 1270-1292 |
| AD-68457.1 | UCUGGACGAGC UCCAAAGGAA | 43 | NM_006610.3 | 1282-1302 | UUCCUUUGGAGC UCGUCCAGAAU | 89 | 1280-1302 |
| AD-68458.1 | CCACGUUUCAC CUGUGCAAGA | 44 | NM_006610.3 | 959-979 | UCUUGCACAGGU GAAACGUGGCC | 90 | 957-979 |
| AD-68459.1 | AGCUGUGAUUC AGUACAGCUA | 45 | NM_006610.3 | 1199-1219 | UAGCUGUACUGA AUCACAGCUUU | 91 | 1197-1219 |
| AD-68460.1 | UCCAGCCUGGA CAUUACCUUA | 46 | NM_139208.2 | 363-383 | UAAGGUAAUGUC CAGGCUGGAGC | 92 | 361-383 |
| AD-68461.1 | UACGUCCUGCA CCGUAACAAA | 47 | NM_139208.2 | 543-563 | UUUGUUACGGUG CAGGACGUAGC | 93 | 541-563 |
| AD-68462.1 | AGCCGAGGACA UUGACGAGUA | 48 | NM_139208.2 | 437-457 | UACUCGUCAAUG UCCUCGGCUGC | 94 | 435-457 |

TABLE 2-continued

Unmodified Sense and Antisense Strand Sequences of MASP2 dsRNA Agents

| Duplex Name | Sense Sequence 5' to 3' | SEQ ID NO: | Source | Range in Source | Antisense Sequence 5' to 3' | SEQ ID NO: | Range in Source |
|---|---|---|---|---|---|---|---|
| AD-68463.1 | AAGUGGCCUGAACCUGUGUUA | 49 | NM_139208.2 | 93-113 | UAACACAGGUUCAGGCCACUUCG | 95 | 91-113 |
| AD-68464.1 | CUCUGCGAGUACGACUUCGUA | 50 | NM_139208.2 | 243-263 | UACGAAGUCGUACUCGCAGAGGU | 96 | 241-263 |
| AD-68465.1 | GAGUAUGCCAAUGACCAGGAA | 51 | NM_139208.2 | 144-164 | UUCCUGGUCAUUGGCAUACUCCC | 97 | 142-164 |
| AD-68466.1 | UGGGCCCGAAGUGGCCUGAAA | 52 | NM_139208.2 | 85-105 | UUUCAGGCCACUUCGGGCCCAAG | 98 | 83-105 |
| AD-68467.1 | CUUCGUCAAGCUGAGCUCGGA | 53 | NM_139208.2 | 257-277 | UCCGAGCUCAGCUUGACGAAGUC | 99 | 255-277 |
| AD-68468.1 | GCAGCCGAGGACAUUGACGAA | 54 | NM_139208.2 | 435-455 | UUCGUCAAUGUCCUCGGCUGCAU | 100 | 433-455 |
| AD-68469.1 | UGGGCUCCAGCCUGGACAUUA | 55 | NM_139208.2 | 358-378 | UAAUGUCCAGGCUGGAGCCCAGC | 101 | 356-378 |
| AD-68470.1 | GCACACCAUGAGGCUGCUGAA | 56 | NM_139208.2 | 26-46 | UUCAGCAGCCUCAUGGUGUGCCC | 102 | 24-46 |
| AD-68471.1 | CACUUUCUACUCGCUGGGCUA | 57 | NM_139208.2 | 344-364 | UAGCCCAGCGAGUAGAAAGUGUC | 103 | 342-364 |
| AD-68472.1 | GAGUAUGACUUUGUCAAGUUA | 58 | NM_001003893.2 | 259-279 | UAACUUGACAAAGUCAUACUCGC | 104 | 257-279 |
| AD-68473.1 | CAGGGUUUGAGGCCUUCUAUA | 59 | NM_001003893.2 | 425-445 | UAUAGAAGGCCUCAAACCCUGUG | 105 | 423-445 |
| AD-68474.1 | UCCCUUGUGACCAUUAUUGCA | 60 | NM_001003893.2 | 491-511 | UGCAAUAAUGGUCACAAGGGACU | 106 | 489-511 |
| AD-68475.1 | CGCUGCGAGUAUGACUUUGUA | 61 | NM_001003893.2 | 253-273 | UACAAAGUCAUACUCGCAGCGGU | 107 | 251-273 |
| AD-68476.1 | GUAUGACUUUGUCAAGUUGAA | 62 | NM_001003893.2 | 261-281 | UUCAACUUGACAAAGUCAUACUC | 108 | 259-281 |
| AD-68477.1 | UCUGCUGUGGAGUUUGGUGGA | 63 | NM_001003893.2 | 66-86 | UCCACCAAACUCCACAGCAGACC | 109 | 64-86 |
| AD-68478.1 | GCACCUGGCAAUGACACCUUA | 64 | NM_001003893.2 | 340-360 | UAAGGUGUCAUUGCCAGGUGCCU | 110 | 338-360 |
| AD-68479.1 | AGCGGAGGAUGUGGAUGAAUA | 65 | NM_001003893.2 | 447-467 | UAUUCAUCCACAUCCUCCGCUGC | 111 | 445-467 |
| AD-68480.1 | CCCAGCCUAAAGGUCACCUUA | 66 | NM_001003893.2 | 373-393 | UAAGGUGACCUUUAGGCUGGGAC | 112 | 371-393 |
| AD-68481.1 | CACGUGCUCAGCCCUUUGUUA | 67 | NM_001003893.2 | 576-596 | UAACAAAGGGCUGAGCACGUGUG | 113 | 574-596 |
| AD-68482.1 | ACUGAGCAGGCACCUGGCAAU | 68 | NM_001003893.2 | 331-351 | AUUGCCAGGUGCCUGCUCAGUGU | 114 | 329-351 |
| AD-68483.1 | ACCGCUGCGAGUAUGACUUUA | 69 | NM_001003893.2 | 251-271 | UAAAGUCAUACUCGCAGCGGUAA | 115 | 249-271 |

TABLE 3

Modified Sense and Antisense Strand Sequences of MASP2 dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-68438.1 | gsusguguGfaGfGfCfugauggauuaL96 | 116 | usAfsaucCfaUfCfagccUfcAfcacacsasu | 162 | AUGUGUGUGAGGCUGAUGGAUUC | 208 |
| AD-68439.1 | csasccuaCfaAfAfGfcugugauucaL96 | 117 | usGfsaauCfaCfAfgcuuUfgUfaggugsgsu | 163 | ACCACCUACAAAGCUGUGAUUCA | 209 |
| AD-68440.1 | ascscuacAfaAfGfCfugugauucaaL96 | 118 | usUfsgaaUfcAfCfagcuUfuGfuaggusgsg | 164 | CCACCUACAAAGCUGUGAUUCAG | 210 |
| AD-68441.1 | asgsaaagAfuGfGfAfucuugggacaL96 | 119 | usGfsuccCfaAfGfauccAfuCfuuucusgsa | 165 | UCAGAAAGAUGGAUCUUGGGACC | 211 |
| AD-68442.1 | asgsgcugAfuGfGfAfuucuggacgaL96 | 120 | usCfsgucCfaGfAfauccAfuCfagccuscsa | 166 | UGAGGCUGAUGGAUUCUGGACGA | 212 |
| AD-68443.1 | gsasccacAfcAfGfGfcuggaagauaL96 | 121 | usAfsucuUfcCfAfgccuGfuGfuggucsusc | 167 | GAGACCACACAGGCUGGAAGAUC | 213 |
| AD-68444.1 | csgsacuuUfcUfCfAfagauucaaaaL96 | 122 | usUfsuugAfaUfCfuugaGfaAfagucgsusa | 168 | UACGACUUUCUCAAGAUUCAAAC | 214 |
| AD-68445.1 | gsusaaauAfuGfUfGfugugaggcuaL96 | 123 | usAfsgccUfcAfCfacacAfuAfuuuacscsa | 169 | UGGUAAAUAUGUGUGUGAGGCUG | 215 |
| AD-68446.1 | gsasuucuGfgAfCfGfagcuccaaaaL96 | 124 | usUfsuugGfaGfCfucguCfcAfgaaucscsa | 170 | UGGAUUCUGGACGAGCUCCAAAG | 216 |
| AD-68447.1 | asasagcuGfuGfAfUfucaguacagaL96 | 125 | usCfsuguAfcUfGfaaucAfcAfgcuuusgsu | 171 | ACAAAGCUGUGAUUCAGUACAGC | 217 |
| AD-68448.1 | csusggcuAfuGfAfGfcuucugcaaaL96 | 126 | usUfsugcAfgAfAfgcucAfuAfgccagsusc | 172 | GACUGGCUAUGAGCUUCUGCAAG | 218 |
| AD-68449.1 | uscsuggaCfuUfUfGfuggaguccuuL96 | 127 | asAfsggaCfuCfCfacaaAfgUfccagasasu | 173 | AUUCUGGACUUUGUGGAGUCCUU | 219 |
| AD-68450.1 | asgsguggUfuUfGfUfgggaggaauaL96 | 128 | usAfsuucCfuCfCfcacaAfaCfcaccuscsu | 174 | AGAGGUGGUUUGUGGGAGGAAUA | 220 |
| AD-68451.1 | usgsgauuCfuGfGfAfcgagcuccaaL96 | 129 | usUfsggaGfcUfCfguccAfgAfauccasusc | 175 | GAUGGAUUCUGGACGAGCUCCAA | 221 |
| AD-68452.1 | usgsauucAfgUfAfCfagcugugaaaL96 | 130 | usUfsucaCfaGfCfuguaCfuGfaaucascsa | 176 | UGUGAUUCAGUACAGCUGUGAAG | 222 |
| AD-68453.1 | csusacaaAfgCfUfGfugauucaguaL96 | 131 | usAfscugAfaUfCfacagCfuUfuguagsgsu | 177 | ACCUACAAAGCUGUGAUUCAGUA | 223 |
| AD-68454.1 | csusgugaUfuCfAfGfuacagcuguaL96 | 132 | usAfscagCfuGfUfacugAfaUfcacagscsu | 178 | AGCUGUGAUUCAGUACAGCUGUG | 224 |
| AD-68455.1 | csusggugAfuUfUfUfccuuggcaaaL96 | 133 | usUfsugcCfaAfGfgaaaAfuCfaccagsgsu | 179 | ACCUGGUGAUUUUCCUUGGCAAG | 225 |
| AD-68456.1 | gscsugauGfgAfUfUfcuggacgagaL96 | 134 | usCfsucgUfcCfAfgaauCfcAfucagcscsu | 180 | AGGCUGAUGGAUUCUGGACGAGC | 226 |
| AD-68457.1 | uscsuggaCfgAfGfCfuccaaaggaaL96 | 135 | usUfsccuUfuGfGfagcuCfgUfccagasasu | 181 | AUUCUGGACGAGCUCCAAAGGAG | 227 |
| AD-68458.1 | cscsacguUfuCfAfCfcugugcaagaL96 | 136 | usCfsuugCfaCfAfggugAfaAfcguggscsc | 182 | GGCCACGUUUCACCUGUGCAAGC | 228 |
| AD-68459.1 | asgscuguGfaUfUfCfaguacagcuaL96 | 137 | usAfsgcuGfuAfCfugaaUfcAfcagcusus u | 183 | AAAGCUGUGAUUCAGUACAGCUG | 229 |
| AD-68460.1 | uscscagcCfuGfGfAfcauuaccuuaL96 | 138 | usAfsaggUfaAfUfguccAfgGfcuggasgsc | 184 | GCUCCAGCCUGGACAUUACCUUC | 230 |
| AD-68461.1 | usascgucCfuGfCfAfccguaacaaaL96 | 139 | usUfsuguUfaCfGfgugcAfgGfacguasgsc | 185 | GCUACGUCCUGCACCGUAACAAG | 231 |
| AD-68462.1 | asgsccgaGfgAfCfAfuugacgaguaL96 | 140 | usAfscucGfuCfAfauguCfcUfcggcusgsc | 186 | GCAGCCGAGGACAUUGACGAGUG | 232 |

TABLE 3-continued

Modified Sense and Antisense Strand Sequences of MASP2 dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-68463.1 | asasguggCfcUfGfAfaccuguguuaL96 | 141 | usAfsacaCfaGfGfuucaGfgCfcacuuscsg | 187 | CGAAGUGGCCUGAACCUGUGUUC | 233 |
| AD-68464.1 | csuscugcGfaGfUfAfcgacuucguaL96 | 142 | usAfscgaAfgUfCfguacUfcGfcagagsgsu | 188 | ACCUCUGCGAGUACGACUUCGUC | 234 |
| AD-68465.1 | gsasguauGfcCfAfAfugaccaggaaL96 | 143 | usUfsccuGfgUfCfauugGfcAfuacucscsc | 189 | GGGAGUAUGCCAAUGACCAGGAG | 235 |
| AD-68466.1 | usgsggccCfgAfAfGfuggccugaaaL96 | 144 | usUfsucaGfgCfCfacuuCfgGfgcccasasg | 190 | CUUGGGCCCGAAGUGGCCUGAAC | 236 |
| AD-68467.1 | csusucguCfaAfGfCfugagcucggaL96 | 145 | usCfscgaGfcUfCfagcuUfgAfcgaagsusc | 191 | GACUUCGUCAAGCUGAGCUCGGG | 237 |
| AD-68468.1 | gscsagccGfaGfGfAfcauugacgaaL96 | 146 | usUfscguCfaAfUfguccUfcGfgcugcsasu | 192 | AUGCAGCCGAGGACAUUGACGAG | 238 |
| AD-68469.1 | usgsggcuCfcAfGfCfcuggacauuaL96 | 147 | usAfsaugUfcCfAfggcuGfgAfgcccasgsc | 193 | GCUGGGCUCCAGCCUGGACAUUA | 239 |
| AD-68470.1 | gscsacacCfaUfGfAfggcugcugaaL96 | 148 | usUfscagCfaGfCfcucaUfgGfugugcscsc | 194 | GGGCACACCAUGAGGCUGCUGAC | 240 |
| AD-68471.1 | csascuuuCfuAfCfUfcgcugggcuaL96 | 149 | usAfsgccCfaGfCfgaguAfgAfaagugsusc | 195 | GACACUUUCUACUCGCUGGGCUC | 241 |
| AD-68472.1 | gsasguauGfaCfUfUfugucaaguuaL96 | 150 | usAfsacuUfgAfCfaaagUfcAfuacucsgsc | 196 | GCGAGUAUGACUUUGUCAAGUUG | 242 |
| AD-68473.1 | csasggguUfuGfAfGfgccuucuauaL96 | 151 | usAfsuagAfaGfGfccucAfaAfcccugsusg | 197 | CACAGGGUUUGAGGCCUUCUAUG | 243 |
| AD-68474.1 | uscsccuuGfuGfAfCfcauuauugcaL96 | 152 | usGfscaaUfaAfUfggucAfcAfagggascsu | 198 | AGUCCCUUGUGACCAUUAUUGCC | 244 |
| AD-68475.1 | csgscugcGfaGfUfAfugacuuuguaL96 | 153 | usAfscaaAfgUfCfauacUfcGfcagcgsgsu | 199 | ACCGCUGCGAGUAUGACUUUGUC | 245 |
| AD-68476.1 | gsusaugaCfuUfUfGfucaaguugaaL96 | 154 | usUfscaaCfuUfGfacaaAfgUfcauacsusc | 200 | GAGUAUGACUUUGUCAAGUUGAG | 246 |
| AD-68477.1 | uscsugcuGfuGfGfAfguuugguggaL96 | 155 | usCfscacCfaAfAfcuccAfcAfgcagascsc | 201 | GGUCUGCUGUGGAGUUUGGUGGC | 247 |
| AD-68478.1 | gscsaccuGfgCfAfAfugacaccuuaL96 | 156 | usAfsaggUfgUfCfauugCfcAfggugcscsu | 202 | AGGCACCUGGCAAUGACACCUUC | 248 |
| AD-68479.1 | asgscggaGfgAfUfGfuggaugaauaL96 | 157 | usAfsuucAfuCfCfacauCfcUfccgcusgsc | 203 | GCAGCGGAGGAUGUGGAUGAAUG | 249 |
| AD-68480.1 | cscscagcCfuAfAfAfggucaccuuaL96 | 158 | usAfsaggUfgAfCfcuuuAfgGfcugggsasc | 204 | GUCCCAGCCUAAAGGUCACCUUC | 250 |
| AD-68481.1 | csascgugCfuCfAfGfcccuuuguuaL96 | 159 | usAfsacaAfaGfGfgcugAfgCfacgugsusg | 205 | CACACGUGCUCAGCCCUUUGUUC | 251 |
| AD-68482.1 | ascsugagCfaGfGfCfaccuggcaauL96 | 160 | asUfsugcCfaGfGfugccUfgCfucagusgsu | 206 | ACACUGAGCAGGCACCUGGCAAU | 252 |
| AD-68483.1 | ascscgcuGfcGfAfGfuaugacuuuaL96 | 161 | usAfsaagUfcAfUfacucGfcAfgcggusasa | 207 | UUACCGCUGCGAGUAUGACUUUG | 253 |

TABLE 4

| Unmodified Sense and Antisense Strand Sequences of MASP2 dsRNA Agents | | | | | | |
|---|---|---|---|---|---|---|
| Duplex Name | Sense Sequence 5' to 3' | SEQ ID NO: | Range in NM_006610.3 | Antisense Sequence 5' to 3' | SEQ ID NO: | Range in NM_006610.3 |
| AD-156804.1 | GACAAUGACAUAGCACUGAUU | 254 | 1620-1640 | AAUCAGUGCUAUGUCAUUGUCAA | 345 | 1618-1640 |
| AD-156950.1 | AUUGUUGACCAUCAAAAAUGU | 255 | 1806-1826 | ACAUUUUUGAUGGUCAACAAUCG | 346 | 1804-1826 |
| AD-156927.1 | AUCUAAUGUAUGUCGACAUAA | 256 | 1783-1803 | UUAUGUCGACAUACAUUAGAUUU | 347 | 1781-1803 |
| AD-156807.1 | AAUGACAUAGCACUGAUUAAA | 257 | 1623-1643 | UUUAAUCAGUGCUAUGUCAUUGU | 348 | 1621-1643 |
| AD-156581.1 | UUUUCCUUGGCAAGUCCUGAU | 258 | 1397-1417 | AUCAGGACUUGCCAAGGAAAAUC | 349 | 1395-1417 |
| AD-156926.1 | AAUCUAAUGUAUGUCGACAUA | 259 | 1782-1802 | UAUGUCGACAUACAUUAGAUUUC | 350 | 1780-1802 |
| AD-156921.1 | CUAGAAAUCUAAUGUAUGUCA | 260 | 1777-1797 | UGACAUACAUUAGAUUUCUAGCA | 351 | 1775-1797 |
| AD-156674.1 | UGAGCAAAAACAUGAUGCAUA | 261 | 1490-1510 | UAUGCAUCAUGUUUUUGCUCAUA | 352 | 1488-1510 |
| AD-156889.1 | CUUUAUGAGGACAGAUGACAU | 262 | 1712-1732 | AUGUCAUCUGUCCUCAUAAAGGA | 353 | 1710-1732 |
| AD-156853.1 | CACGCCUAUUUGUCUGCCAAA | 263 | 1676-1696 | UUUGGCAGACAAAUAGGCGUGAU | 354 | 1674-1696 |
| AD-156538.1 | ACAGGAGGGCGUAUAUAUGGA | 264 | 1353-1373 | UCCAUAUAUACGCCCUCCUGUUG | 355 | 1351-1373 |
| AD-157227.1 | ACAUGGCAGUUGUUGCUCCAA | 265 | 2189-2209 | UUGGAGCAACAACUGCCAUGUCC | 356 | 2187-2209 |
| AD-156622.1 | CAGGUGCACUUUUAUAUGACA | 266 | 1438-1458 | UGUCAUAUAAAAGUGCACCUGCU | 357 | 1436-1458 |
| AD-156964.1 | AAAAUGUACUGCUGCAUAUGA | 267 | 1820-1840 | UCAUAUGCAGCAGUACAUUUUUG | 358 | 1818-1840 |
| AD-156841.1 | CAAUAGCAACAUCACGCCUAU | 268 | 1664-1684 | AUAGGCGUGAUGUUGCUAUUGAU | 359 | 1662-1684 |
| AD-156571.1 | AAACCUGGUGAUUUUCCUUGA | 269 | 1386-1406 | UCAAGGAAAAUCACCAGGUUUUG | 360 | 1384-1406 |
| AD-156842.1 | AAUAGCAACAUCACGCCUAUU | 270 | 1665-1685 | AAUAGGCGUGAUGUUGCUAUUGA | 361 | 1663-1685 |
| AD-68457.2 | UCUGGACGAGCUCCAAAGGAA | 271 | 1282-1302 | UUCCUUUGGAGCUCGUCCAGAAU | 362 | 1280-1302 |
| AD-156990.1 | GUGUAACUGCUAACAUGCUUU | 272 | 1864-1884 | AAAGCAUGUUAGCAGUUACACUU | 363 | 1862-1884 |
| AD-156929.1 | CUAAUGUAUGUCGACAUACCA | 273 | 1785-1805 | UGGUAUGUCGACAUACAUUAGAU | 364 | 1783-1805 |
| AD-157334.1 | UGUAAUGUCACUGCUCAAAUU | 274 | 2333-2353 | AAUUUGAGCAGUGACAUUACACU | 365 | 2331-2353 |
| AD-156923.1 | AGAAAUCUAAUGUAUGUCGAA | 275 | 1779-1799 | UUCGACAUACAUUAGAUUUCUAG | 366 | 1777-1799 |
| AD-156536.1 | CAACAGGAGGGCGUAUAUAUA | 276 | 1351-1371 | UAUAUAUACGCCCUCCUGUUGUG | 367 | 1349-1371 |
| AD-156535.1 | ACAACAGGAGGGCGUAUAUAU | 277 | 1350-1370 | AUAUAUACGCCCUCCUGUUGUGC | 368 | 1348-1370 |
| AD-156255.1 | GCUUCUGCAAGGUCACUUGCA | 278 | 1031-1051 | UGCAAGUGACCUUGCAGAAGCUC | 369 | 1029-1051 |

TABLE 4-continued

| Duplex Name | Sense Sequence 5' to 3' | SEQ ID NO: | Range in NM_006610.3 | Antisense Sequence 5' to 3' | SEQ ID NO: | Range in NM_006610.3 |
|---|---|---|---|---|---|---|
| Unmodified Sense and Antisense Strand Sequences of MASP2 dsRNA Agents | | | | | | |
| AD-157093.1 | GUUAUUAACUAUAUUCCCUGA | 279 | 2046-2066 | UCAGGGAAUAUAGUUAAUAACUU | 370 | 2044-2066 |
| AD-156800.1 | CUUUGACAAUGACAUAGCACU | 280 | 1616-1636 | AGUGCUAUGUCAUUGUCAAAGCC | 371 | 1614-1636 |
| AD-157371.1 | AAGCCAGUCUCUUUUCAUACU | 281 | 2372-2392 | AGUAUGAAAAGAGACUGGCUUUU | 372 | 2370-2392 |
| AD-156844.1 | UAGCAACAUCACGCCUAUUUA | 282 | 1667-1687 | UAAAUAGGCGUGAUGUUGCUAUU | 373 | 1665-1687 |
| AD-156852.1 | UCACGCCUAUUUGUCUGCCAA | 283 | 1675-1695 | UUGGCAGACAAAUAGGCGUGAUG | 374 | 1673-1695 |
| AD-156924.1 | GAAAUCUAAUGUAUGUCGACA | 284 | 1780-1800 | UGUCGACAUACAUUAGAUUUCUA | 375 | 1778-1800 |
| AD-156725.1 | AAGACUAUCACCUCAUUAUAA | 285 | 1541-1561 | UUAUAAUGAGGUGAUAGUCUUUU | 376 | 1539-1561 |
| AD-156735.1 | CCUCAUUAUACACAAGCCUGA | 286 | 1551-1571 | UCAGGCUUGUGUAUAAUGAGGUG | 377 | 1549-1571 |
| AD-156583.1 | UUCCUUGGCAAGUCCUGAUAU | 287 | 1399-1419 | AUAUCAGGACUUGCCAAGGAAAA | 378 | 1397-1419 |
| AD-156878.1 | GAAGCUGAAUCCUUUAUGAGA | 288 | 1701-1721 | UCUCAUAAAGGAUUCAGCUUCUU | 379 | 1699-1721 |
| AD-156892.1 | UAUGAGGACAGAUGACAUUGA | 289 | 1715-1735 | UCAAUGUCAUCUGUCCUCAUAAA | 380 | 1713-1735 |
| AD-156877.1 | AGAAGCUGAAUCCUUUAUGAA | 290 | 1700-1720 | UUCAUAAAGGAUUCAGCUUCUUU | 381 | 1698-1720 |
| AD-156845.1 | AGCAACAUCACGCCUAUUUGU | 291 | 1668-1688 | ACAAAUAGGCGUGAUGUUGCUAU | 382 | 1666-1688 |
| AD-156551.1 | UAUAUGGAGGGCAAAAGGCAA | 292 | 1366-1386 | UUGCCUUUUGCCCUCCAUAUAUA | 383 | 1364-1386 |
| AD-157229.1 | AUGGCAGUUGUUGCUCCACCA | 293 | 2191-2211 | UGGUGGAGCAACAACUGCCAUGU | 384 | 2189-2211 |
| AD-157373.1 | GCCAGUCUCUUUUCAUACUGA | 294 | 2374-2394 | UCAGUAUGAAAAGAGACUGGCUU | 385 | 2372-2394 |
| AD-156584.1 | UCCUUGGCAAGUCCUGAUAUU | 295 | 1400-1420 | AAUAUCAGGACUUGCCAAGGAAA | 386 | 1398-1420 |
| AD-156499.1 | CCAGUCUGUGAGCCUGUUUGU | 296 | 1314-1334 | ACAAACAGGCUCACAGACUGGGA | 387 | 1312-1334 |
| AD-156965.1 | AAAUGUACUGCUGCAUAUGAA | 297 | 1821-1841 | UUCAUAUGCAGCAGUACAUUUUU | 388 | 1819-1841 |
| AD-156951.1 | UUGUUGACCAUCAAAAAUGUA | 298 | 1807-1827 | UACAUUUUUGAUGGUCAACAAUC | 389 | 1805-1827 |
| AD-156829.1 | CAAAGUUGUAAUCAAUAGCAA | 299 | 1652-1672 | UUGCUAUUGAUUACAACUUUGUU | 390 | 1650-1672 |
| AD-157167.1 | GAAAUGCCUGUGAAGACCUUA | 300 | 2129-2149 | UAAGGUCUUCACAGGCAUUUCUA | 391 | 2127-2149 |
| AD-156922.1 | UAGAAAUCUAAUGUAUGUCGA | 301 | 1778-1798 | UCGACAUACAUUAGAUUUCUAGC | 392 | 1776-1798 |
| AD-156879.1 | AAGCUGAAUCCUUUAUGAGGA | 302 | 1702-1722 | UCCUCAUAAAGGAUUCAGCUUCU | 393 | 1700-1722 |

TABLE 4-continued

Unmodified Sense and Antisense Strand Sequences of MASP2 dsRNA Agents

| Duplex Name | Sense Sequence 5' to 3' | SEQ ID NO: | Range in NM_006610.3 | Antisense Sequence 5' to 3' | SEQ ID NO: | Range in NM_006610.3 |
|---|---|---|---|---|---|---|
| AD-156588.1 | UGGCAAGUCCUGAUAUUAGGU | 303 | 1404-1424 | ACCUAAUAUCAGGACUUGCCAAG | 394 | 1402-1424 |
| AD-156777.1 | GAAGGUUAUACUCAUGAUGCU | 304 | 1593-1613 | AGCAUCAUGAGUAUAACCUUCAU | 395 | 1591-1613 |
| AD-156917.1 | CUUGCUAGAAAUCUAAUGUAU | 305 | 1773-1793 | AUACAUUAGAUUUCUAGCAAGAA | 396 | 1771-1793 |
| AD-157372.1 | AGCCAGUCUCUUUUCAUACUA | 306 | 2373-2393 | UAGUAUGAAAAGAGACUGGCUUU | 397 | 2371-2393 |
| AD-156729.1 | CUAUCACCUCAUUAUACACAA | 307 | 1545-1565 | UUGUGUAUAAUGAGGUGAUAGUC | 398 | 1543-1565 |
| AD-156956.1 | GACCAUCAAAAAUGUACUGCU | 308 | 1812-1832 | AGCAGUACAUUUUUGAUGGUCAA | 399 | 1810-1832 |
| AD-156854.1 | ACGCCUAUUUGUCUGCCAAGA | 309 | 1677-1697 | UCUUGGCAGACAAAUAGGCGUGA | 400 | 1675-1697 |
| AD-156544.1 | GGGCGUAUAUAUGGAGGGCAA | 310 | 1359-1379 | UUGCCCUCCAUAUAUACGCCCUC | 401 | 1357-1379 |
| AD-156840.1 | UCAAUAGCAACAUCACGCCUA | 311 | 1663-1683 | UAGGCGUGAUGUUGCUAUUGAUU | 402 | 1661-1683 |
| AD-156550.1 | AUAUAUGGAGGGCAAAAGGCA | 312 | 1365-1385 | UGCCUUUUGCCCUCCAUAUAUAC | 403 | 1363-1385 |
| AD-157232.1 | GCAGUUGUUGCUCCACCCAAA | 313 | 2194-2214 | UUUGGGUGGAGCAACAACUGCCA | 404 | 2192-2214 |
| AD-156577.1 | GUGAUUUUCCUUGGCAAGUCA | 314 | 1393-1413 | UGACUUGCCAAGGAAAAUCACCA | 405 | 1391-1413 |
| AD-156805.1 | ACAAUGACAUAGCACUGAUUA | 315 | 1621-1641 | UAAUCAGUGCUAUGUCAUUGUCA | 406 | 1619-1641 |
| AD-156850.1 | CAUCACGCCUAUUUGUCUGCA | 316 | 1673-1693 | UGCAGACAAAUAGGCGUGAUGUU | 407 | 1671-1693 |
| AD-156778.1 | AAGGUUAUACUCAUGAUGCUA | 317 | 1594-1614 | UAGCAUCAUGAGUAUAACCUUCA | 408 | 1592-1614 |
| AD-156572.1 | AACCUGGUGAUUUUCCUUGGA | 318 | 1387-1407 | UCCAAGGAAAAUCACCAGGUUUU | 409 | 1385-1407 |
| AD-156726.1 | AGACUAUCACCUCAUUAUACA | 319 | 1542-1562 | UGUAUAAUGAGGUGAUAGUCUUU | 410 | 1540-1562 |
| AD-157059.1 | GGUUUGUGGGAGGAAUAGUGU | 320 | 1972-1992 | ACACUAUUCCUCCCACAAACCAC | 411 | 1970-1992 |
| AD-156734.1 | ACCUCAUUAUACACAAGCCUA | 321 | 1550-1570 | UAGGCUUGUGUAUAAUGAGGUGA | 412 | 1548-1570 |
| AD-156508.1 | GAGCCUGUUUGUGGACUAUCA | 322 | 1323-1343 | UGAUAGUCCACAAACAGGCUCAC | 413 | 1321-1343 |
| AD-156542.1 | GAGGGCGUAUAUAUGGAGGGA | 323 | 1357-1377 | UCCCUCCAUAUAUACGCCCUCCU | 414 | 1355-1377 |
| AD-156545.1 | GGCGUAUAUAUGGAGGGCAAA | 324 | 1360-1380 | UUUGCCCUCCAUAUAUACGCCCU | 415 | 1358-1380 |
| AD-156888.1 | CCUUUAUGAGGACAGAUGACA | 325 | 1711-1731 | UGUCAUCUGUCCUCAUAAAGGAU | 416 | 1709-1731 |
| AD-156974.1 | GCUGCAUAUGAAAAGCCACCA | 326 | 1830-1850 | UGGUGGCUUUUCAUAUGCAGCAG | 417 | 1828-1850 |
| AD-156925.1 | AAAUCUAAUGUAUGUCGACAU | 327 | 1781-1801 | AUGUCGACAUACAUUAGAUUUCU | 418 | 1779-1801 |

TABLE 4-continued

Unmodified Sense and Antisense Strand Sequences of MASP2 dsRNA Agents

| Duplex Name | Sense Sequence 5' to 3' | SEQ ID NO: | Range in NM_006610.3 | Antisense Sequence 5' to 3' | SEQ ID NO: | Range in NM_006610.3 |
|---|---|---|---|---|---|---|
| AD-156589.1 | GGCAAGUCCUGAUAUUAGGUA | 328 | 1405-1425 | UACCUAAUAUCAGGACUUGCCAA | 419 | 1403-1425 |
| AD-157160.1 | AUUUUUAGAAAUGCCUGUGAA | 329 | 2122-2142 | UUCACAGGCAUUUCUAAAAAUGA | 420 | 2120-2142 |
| AD-156621.1 | GCAGGUGCACUUUUAUAUGAA | 330 | 1437-1457 | UUCAUAUAAAAGUGCACCUGCUG | 421 | 1435-1457 |
| AD-157060.1 | GUUUGUGGGAGGAAUAGUGUA | 331 | 1973-1993 | UACACUAUUCCUCCCACAAACCA | 422 | 1971-1993 |
| AD-157378.1 | UCUCUUUUCAUACUGGCUGUU | 332 | 2379-2399 | AACAGCCAGUAUGAAAAGAGACU | 423 | 2377-2399 |
| AD-156582.1 | UUUCCUUGGCAAGUCCUGAUA | 333 | 1398-1418 | UAUCAGGACUUGCCAAGGAAAAU | 424 | 1396-1418 |
| AD-156846.1 | GCAACAUCACGCCUAUUUGUA | 334 | 1669-1689 | UACAAAUAGGCGUGAUGUUGCUA | 425 | 1667-1689 |
| AD-156540.1 | AGGAGGGCGUAUAUAUGGAGA | 335 | 1355-1375 | UCUCCAUAUAUACGCCCUCCUGU | 426 | 1353-1375 |
| AD-157234.1 | AGUUGUUGCUCCACCCAAAAA | 336 | 2196-2216 | UUUUUGGGUGGAGCAACAACUGC | 427 | 2194-2216 |
| AD-156505.1 | UGUGAGCCUGUUUGUGGACUA | 337 | 1320-1340 | UAGUCCACAAACAGGCUCACAGA | 428 | 1318-1340 |
| AD-156591.1 | CAAGUCCUGAUAUUAGGUGGA | 338 | 1407-1427 | UCCACCUAAUAUCAGGACUUGCC | 429 | 1405-1427 |
| AD-156988.1 | AAGUGUAACUGCUAACAUGCU | 339 | 1862-1882 | AGCAUGUUAGCAGUUACACUUCC | 430 | 1860-1882 |
| AD-156843.1 | AUAGCAACAUCACGCCUAUUU | 340 | 1666-1686 | AAAUAGGCGUGAUGUUGCUAUUG | 431 | 1664-1686 |
| AD-156539.1 | CAGGAGGGCGUAUAUAUGGAA | 341 | 1354-1374 | UUCCAUAUAUACGCCCUCCUGUU | 432 | 1352-1374 |
| AD-157061.1 | UUUGUGGGAGGAAUAGUGUCA | 342 | 1974-1994 | UGACACUAUUCCUCCCACAAACC | 433 | 1972-1994 |
| AD-156839.1 | AUCAAUAGCAACAUCACGCCU | 343 | 1662-1682 | AGGCGUGAUGUUGCUAUUGAUUA | 434 | 1660-1682 |
| AD-156830.1 | AAAGUUGUAAUCAAUAGCAAA | 344 | 1653-1673 | UUUGCUAUUGAUUACAACUUUGU | 435 | 1651-1673 |

TABLE 5

Modified Sense and Antisense Strand Sequences of MASP2 dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-156804.1 | gsascaauGfaCfAfUfagcacugauuL96 | 436 | asAfsucaGfuGfCfuaugUfcAfuugucsasa | 527 | UUGACAAUGACAUAGCACUGAUU | 618 |
| AD-156950.1 | asusuguuGfaCfCfAfucaaaaauguL96 | 437 | asCfsauuUfuUfGfauggUfcAfacaauscsg | 528 | CGAUUGUUGACCAUCAAAAAUGU | 619 |
| AD-156927.1 | asuscuaaUfgUfAfUfgucgacauaaL96 | 438 | usUfsaugUfcGfAfcauaCfaUfuagaususu | 529 | AAAUCUAAUGUAUGUCGACAUAC | 620 |

TABLE 5-continued

| Modified Sense and Antisense Strand Sequences of MASP2 dsRNA Agents | | | | | | |
|---|---|---|---|---|---|---|
| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
| AD-156807.1 | asasugacAfuAfGfCfacugauuaaaL96 | 439 | usUfsuaaUfcAfGfugcuAfuGfucauusgsu | 530 | ACAAUGACAUAGCACUGAUUAAA | 621 |
| AD-156581.1 | ususuuccUfuGfGfCfaaguccugauL96 | 440 | asUfscagGfaCfUfugccAfaGfgaaaasusc | 531 | GAUUUUCCUUGGCAAGUCCUGAU | 622 |
| AD-156926.1 | asasucuaAfuGfUfAfugucgacauaL96 | 441 | usAfsuguCfgAfCfauacAfuUfagauusus c | 532 | GAAAUCUAAUGUAUGUCGACAUA | 623 |
| AD-156921.1 | csusagaaAfuCfUfAfauguaugucaL96 | 442 | usGfsacaUfaCfAfuuagAfuUfucuagscsa | 533 | UGCUAGAAAUCUAAUGUAUGUCG | 624 |
| AD-156674.1 | usgsagcaAfaAfAfCfaugaugcauaL96 | 443 | usAfsugcAfuCfAfuguuUfuUfgcucasusa | 534 | UAUGAGCAAAAACAUGAUGCAUC | 625 |
| AD-156889.1 | csusuuauGfaGfGfAfcagaugacauL96 | 444 | asUfsgucAfuCfUfguccUfcAfuaaagsgsa | 535 | UCCUUUAUGAGGACAGAUGACAU | 626 |
| AD-156853.1 | csascgccUfaUfUfUfgucugccaaaL96 | 445 | usUfsuggCfaGfAfcaaaUfaGfgcgugsasu | 536 | AUCACGCCUAUUUGUCUGCCAAG | 627 |
| AD-156538.1 | ascsaggaGfgGfCfGfuauauauggaL96 | 446 | usCfscauAfuAfUfacgcCfcUfccugusug | 537 | CAACAGGAGGGCGUAUAUAUGGA | 628 |
| AD-157227.1 | ascsauggCfaGfUfUfguugcuccaaL96 | 447 | usUfsggaGfcAfAfcaacUfgCfcaugucsc | 538 | GGACAUGGCAGUUGUUGCUCCAC | 629 |
| AD-156622.1 | csasggugCfaCfUfUfuuauaugacaL96 | 448 | usGfsucaUfaUfAfaaagUfgCfaccugscsu | 539 | AGCAGGUGCACUUUUAUAUGACA | 630 |
| AD-156964.1 | asasaaugUfaCfUfGfcugcauaugaL96 | 449 | usCfsauaUfgCfAfgcagUfaCfauuuusus g | 540 | CAAAAAUGUACUGCUGCAUAUGA | 631 |
| AD-156841.1 | csasauagCfaAfCfAfucacgccuauL96 | 450 | asUfsaggCfgUfGfauguUfgCfuauugsas u | 541 | AUCAAUAGCAACAUCACGCCUAU | 632 |
| AD-156571.1 | asasaccuGfgUfGfAfuuuuccuugaL96 | 451 | usCfsaagGfaAfAfaucaCfcAfgguuusus g | 542 | CAAAACCUGGUGAUUUUCCUUGG | 633 |
| AD-156842.1 | asasuagcAfaCfAfUfcacgccuauuL96 | 452 | asAfsuagGfcGfUfgaugUfuGfcuauugsg a | 543 | UCAAUAGCAACAUCACGCCUAUU | 634 |
| AD-68457.2 | uscsuggaCfgAfGfCfuccaaaggaaL96 | 453 | usUfsccuUfuGfGfagcuCfgUfccagasasu | 544 | AUUCUGGACGAGCUCCAAAGGAG | 635 |
| AD-156990.1 | gsusguaaCfuGfCfUfaacaugcuuuL96 | 454 | asAfsagcAfuGfUfuagcAfgUfuacacsusu | 545 | AAGUGUAACUGCUAACAUGCUUU | 636 |
| AD-156929.1 | csusaaugUfaUfGfUfcgacauaccaL96 | 455 | usGfsguaUfgUfCfgacaUfaCfauuagsasu | 546 | AUCUAAUGUAUGUCGACAUACCG | 637 |
| AD-157334.1 | usgsuaauGfuCfAfCfugcucaaauuL96 | 456 | asAfsuuuGfaGfCfagugAfcAfuuacascs u | 547 | AGUGUAAUGUCACUGCUCAAAUU | 638 |

TABLE 5-continued

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| Modified Sense and Antisense Strand Sequences of MASP2 dsRNA Agents | | | | | | |
| AD-156923.1 | asgsaaauCfuAfAfUfguaugucgaaL96 | 457 | usUfscgaCfaUfAfcauuAfgAfuuucusasg | 548 | CUAGAAAUCUAAUGUAUGUCGAC | 639 |
| AD-156536.1 | csasacagGfaGfGfGfcguauauauaL96 | 458 | usAfsuauAfuAfCfgcccUfcCfuguugsusg | 549 | CACAACAGGAGGGCGUAUAUAUG | 640 |
| AD-156535.1 | ascsaacaGfgAfGfGfgcguauauauL96 | 459 | asUfsauaUfaCfGfcccuCfcUfguugusgsc | 550 | GCACAACAGGAGGGCGUAUAUAU | 641 |
| AD-156255.1 | gscsuucuGfcAfAfGfgucacuugcaL96 | 460 | usGfscaaGfuGfAfccuuGfcAfgaagcsusc | 551 | GAGCUUCUGCAAGGUCACUUGCC | 642 |
| AD-157093.1 | gsusuauuAfaCfUfAfuauucccugaL96 | 461 | usCfsaggGfaAfUfauagUfuAfauaacsusu | 552 | AAGUUAUUAACUAUAUUCCCUGG | 643 |
| AD-156800.1 | csusuugaCfaAfUfGfacauagcacuL96 | 462 | asGfsugcUfaUfGfucauUfgUfcaaagscsc | 553 | GGCUUUGACAAUGACAUAGCACU | 644 |
| AD-157371.1 | asasgccaGfuCfUfCfuuuucauacuL96 | 463 | asGfsuauGfaAfAfagagAfcUfggcuusus u | 554 | AAAAGCCAGUCUCUUUUCAUACU | 645 |
| AD-156844.1 | usasgcaaCfaUfCfAfcgccuauuuaL96 | 464 | usAfsaauAfgGfCfgugaUfgUfugcuasusu | 555 | AAUAGCAACAUCACGCCUAUUUG | 646 |
| AD-156852.1 | uscsacgcCfuAfUfUfugucugccaaL96 | 465 | usUfsggcAfgAfCfaaauAfgGfcgugasusg | 556 | CAUCACGCCUAUUUGUCUGCCAA | 647 |
| AD-156924.1 | gsasaaucUfaAfUfGfuaugucgacaL96 | 466 | usGfsucgAfcAfUfacauUfaGfauuucsusa | 557 | UAGAAAUCUAAUGUAUGUCGACA | 648 |
| AD-156725.1 | asasgacuAfuCfAfCfcucauuauaaL96 | 467 | usUfsauaAfuGfAfggugAfuAfgucuusus u | 558 | AAAAGACUAUCACCUCAUUAUAC | 649 |
| AD-156735.1 | cscsucauUfaUfAfCfacaagccugaL96 | 468 | usCfsaggCfuUfGfuguaUfaAfugaggsusg | 559 | CACCUCAUUAUACACAAGCCUGG | 650 |
| AD-156583.1 | ususccuuGfgCfAfAfguccugauauL96 | 469 | asUfsaucAfgGfAfcuugCfcAfaggaasasa | 560 | UUUUCCUUGGCAAGUCCUGAUAU | 651 |
| AD-156878.1 | gsasagcuGfaAfUfCfcuuuaugagaL96 | 470 | usCfsucaUfaAfAfggauUfcAfgcuucsusu | 561 | AAGAAGCUGAAUCCUUUAUGAGG | 652 |
| AD-156892.1 | usasugagGfaCfAfGfaugacauugaL96 | 471 | usCfsaauGfuCfAfucugUfcCfucauasasa | 562 | UUUAUGAGGACAGAUGACAUUGG | 653 |
| AD-156877.1 | asgsaagcUfgAfAfUfccuuuaugaaL96 | 472 | usUfscauAfaAfGfgauuCfaGfcuucusus u | 563 | AAAGAAGCUGAAUCCUUUAUGAG | 654 |
| AD-156845.1 | asgscaacAfuCfAfCfgccuauuuguL96 | 473 | asCfsaaaUfaGfGfcgugAfuGfuugcusasu | 564 | AUAGCAACAUCACGCCUAUUUGU | 655 |
| AD-156551.1 | usasuaugGfaGfGfGfcaaaaggcaaL96 | 474 | usUfsgccUfuUfUfgcccUfcCfauauasusa | 565 | UAUAUAUGGAGGGCAAAAGGCAA | 656 |

TABLE 5-continued

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| Modified Sense and Antisense Strand Sequences of MASP2 dsRNA Agents | | | | | | |
| AD-157229.1 | asusggcaGfuUfGfUfugcuccaccaL96 | 475 | usGfsgugGfaGfCfaacaAfcUfgccausgsu | 566 | ACAUGGCAGUUGUUGCUCCACCC | 657 |
| AD-157373.1 | gscscaguCfuCfUfUfuucauacugaL96 | 476 | usCfsaguAfuGfAfaagAfgAfcuggcsusu | 567 | AAGCCAGUCUCUUUUCAUACUGG | 658 |
| AD-156584.1 | uscscuugGfcAfAfGfuccugauauuL96 | 477 | asAfsuauCfaGfGfacuuGfcCfaaggasasa | 568 | UUUCCUUGGCAAGUCCUGAUAUU | 659 |
| AD-156499.1 | cscsagucUfgUfGfAfgccuguuuguL96 | 478 | asCfsaaaCfaGfGfcucaCfaGfacuggsgsa | 569 | UCCCAGUCUGUGAGCCUGUUUGU | 660 |
| AD-156965.1 | asasauguAfcUfGfCfugcauaugaaL96 | 479 | usUfscauAfuGfCfagcaGfuAfcauuususu | 570 | AAAAAUGUACUGCUGCAUAUGAA | 661 |
| AD-156951.1 | ususguugAfcCfAfUfcaaaaauguaL96 | 480 | usAfscauUfuUfUfgaugGfuCfaacaasusc | 571 | GAUUGUUGACCAUCAAAAAUGUA | 662 |
| AD-156829.1 | csasaaguUfgUfAfAfucaauagcaaL96 | 481 | usUfsgcuAfuUfGfauuaCfaAfcuuugsusu | 572 | AACAAAGUUGUAAUCAAUAGCAA | 663 |
| AD-157167.1 | gsasaaugCfcUfGfUfgaagaccuuaL96 | 482 | usAfsaggUfcUfUfcacaGfgCfauuucsusa | 573 | UAGAAAUGCCUGUGAAGACCUUG | 664 |
| AD-156922.1 | usasgaaaUfcUfAfAfuguaugucgaL96 | 483 | usCfsgacAfuAfCfauuaGfaUfuucuasgsc | 574 | GCUAGAAAUCUAAUGUAUGUCGA | 665 |
| AD-156879.1 | asasgcugAfaUfCfCfuuuaugaggaL96 | 484 | usCfscucAfuAfAfaggaUfuCfagcuuscsu | 575 | AGAAGCUGAAUCCUUUAUGAGGA | 666 |
| AD-156588.1 | usgsgcaaGfuCfCfUfgauauuagguL96 | 485 | asCfscuaAfuAfUfcaggAfcUfugccasasg | 576 | CUUGGCAAGUCCUGAUAUUAGGU | 667 |
| AD-156777.1 | gsasagguUfaUfAfCfucaugaugcuL96 | 486 | asGfscauCfaUfGfaguaUfaAfccuucsasu | 577 | AUGAAGGUUAUACUCAUGAUGCU | 668 |
| AD-156917.1 | csusugcuAfgAfAfAfucuaauguauL96 | 487 | asUfsacaUfuAfGfauuuCfuAfgcaagsasa | 578 | UUCUUGCUAGAAAUCUAAUGUAU | 669 |
| AD-157372.1 | asgsccagUfcUfCfUfuuucauacuaL96 | 488 | usAfsguaUfgAfAfaagaGfaCfuggcus「susu | 579 | AAAGCCAGUCUCUUUUCAUACUG | 670 |
| AD-156729.1 | csusaucaCfcUfCfAfuuauacacaaL96 | 489 | usUfsgugUfaUfAfaugaGfgUfgauagsusc | 580 | GACUAUCACCUCAUUAUACACAA | 671 |
| AD-156956.1 | gsasccauCfaAfAfAfauguacugcuL96 | 490 | asGfscagUfaCfAfuuuuUfgAfuggucsasa | 581 | UUGACCAUCAAAAAUGUACUGCU | 672 |
| AD-156854.1 | ascsgccuAfuUfUfGfucugccaagaL96 | 491 | usCfsuugGfcAfGfacaaAfuAfggcgusgsa | 582 | UCACGCCUAUUUGUCUGCCAAGA | 673 |
| AD-156544.1 | gsgsgcguAfuAfUfAfuggagggcaaL96 | 492 | usUfsgccCfuCfCfauauAfuAfcgcccsusc | 583 | GAGGGCGUAUAUAUGGAGGGCAA | 674 |

TABLE 5-continued

| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
|---|---|---|---|---|---|---|
| Modified Sense and Antisense Strand Sequences of MASP2 dsRNA Agents | | | | | | |
| AD-156840.1 | uscsaauaGfcAfAfCfaucacgccuaL96 | 493 | usAfsggcGfuGfAfuguuGfcUfauugasusU | 584 | AAUCAAUAGCAACAUCACGCCUA | 675 |
| AD-156550.1 | asusauauGfgAfGfGfgcaaaaggcaL96 | 494 | usGfsccuUfuUfGfcccuCfcAfuauausasc | 585 | GUAUAUAUGGAGGGCAAAAGGCA | 676 |
| AD-157232.1 | gscsaguuGfuUfGfCfuccacccaaaL96 | 495 | usUfsuggGfuGfGfagcaAfcAfacugcscsa | 586 | UGGCAGUUGUUGCUCCACCCAAA | 677 |
| AD-156577.1 | gsusgauuUfuCfCfUfuggcaagucaL96 | 496 | usGfsacuUfgCfCfaaggAfaAfaucacscsa | 587 | UGGUGAUUUUCCUUGGCAAGUCC | 678 |
| AD-156805.1 | ascsaaugAfcAfUfAfgcacugauuaL96 | 497 | usAfsaucAfgUfGfcuauGfuCfauuguscsa | 588 | UGACAAUGACAUAGCACUGAUUA | 679 |
| AD-156850.1 | csasucacGfcCfUfAfuuugucugcaL96 | 498 | usGfscagAfcAfAfauagGfcGfugaugsusu | 589 | AACAUCACGCCUAUUUGUCUGCC | 680 |
| AD-156778.1 | asasgguuAfuAfCfUfcaugaugcuaL96 | 499 | usAfsgcaUfcAfUfgaguAfuAfaccuuscsa | 590 | UGAAGGUUAUACUCAUGAUGCUG | 681 |
| AD-156572.1 | asasccugGfuGfAfUfuuuccuuggaL96 | 500 | usCfscaaGfgAfAfaaucAfcCfagguususu | 591 | AAAACCUGGUGAUUUUCCUUGGC | 682 |
| AD-156726.1 | asgsacuaUfcAfCfCfucauuauacaL96 | 501 | usGfsuauAfaUfGfaggugGfaUfagucususu | 592 | AAAGACUAUCACCUCAUUAUACA | 683 |
| AD-157059.1 | gsgsuuugUfgGfGfAfggaauaguguL96 | 502 | asCfsacuAfuUfCfcucccCfaCfaaaccsasc | 593 | GUGGUUUGUGGGAGGAAUAGUGU | 684 |
| AD-156734.1 | ascsucaUfuAfUfAfcacaagccuaL96 | 503 | usAfsggcUfuGfUfguauAfaUfgaggusgsa | 594 | UCACCUCAUUAUACACAAGCCUG | 685 |
| AD-156508.1 | gsasgccuGfuUfUfGfuggacuaucaL96 | 504 | usGfsauaGfuCfCfacaaAfcAfggcucsasc | 595 | GUGAGCCUGUUUGUGGACUAUCA | 686 |
| AD-156542.1 | gsasgggcGfuAfUfAfuauggagggaL96 | 505 | usCfsccuCfcAfUfauauAfcGfcccucscsu | 596 | AGGAGGGCGUAUAUAUGGAGGGC | 687 |
| AD-156545.1 | gsgscguaUfaUfAfUfggagggcaaaL96 | 506 | usUfsugcCfcUfCfcauaUfaUfacgccscsu | 597 | AGGGCGUAUAUAUGGAGGGCAAA | 688 |
| AD-156888.1 | cscsuuuaUfgAfGfGfacagaugacaL96 | 507 | usGfsucaUfcUfGfuccuCfaUfaaaggsasu | 598 | AUCCUUUAUGAGGACAGAUGACA | 689 |
| AD-156974.1 | gscsugcaUfaUfGfAfaaagccaccaL96 | 508 | usGfsgugGfcUfUfuucaUfaUfgcagcsasg | 599 | CUGCUGCAUAUGAAAAGCCACCC | 690 |
| AD-156925.1 | asasaucuAfaUfGfUfaugucgacauL96 | 509 | asUfsgucGfaCfAfuacaUfuAfgauuuscsu | 600 | AGAAAUCUAAUGUAUGUCGACAU | 691 |
| AD-156589.1 | gsgscaagUfcCfUfGfauauuagguaL96 | 510 | usAfsccuAfaUfAfucagGfaCfuugccsasa | 601 | UUGGCAAGUCCUGAUAUUAGGUG | 692 |

TABLE 5-continued

Modified Sense and Antisense Strand Sequences of MASP2 dsRNA Agents

| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
|---|---|---|---|---|---|---|
| AD-157160.1 | asusuuuuAfgAfAfAfugccugugaaL96 | 511 | usUfscacAfgGfCfauuuCfuAfaaaausgsa | 602 | UCAUUUUUAGAAAUGCCUGUGAA | 693 |
| AD-156621.1 | gscsagguGfcAfCfUfuuuauaugaaL96 | 512 | usUfscauAfuAfAfaaguGfcAfccugcsusg | 603 | CAGCAGGUGCACUUUUAUAUGAC | 694 |
| AD-157060.1 | gsusuuguGfgGfAfGfgaauaguguaL96 | 513 | usAfscacUfaUfUfccucCfcAfcaaacscsa | 604 | UGGUUUGUGGGAGGAAUAGUGUC | 695 |
| AD-157378.1 | uscsucuuUfuCfAfUfacuggcuguuL96 | 514 | asAfscagCfcAfGfuaugAfaAfagagascsu | 605 | AGUCUCUUUUCAUACUGGCUGUU | 696 |
| AD-156582.1 | ususuccuUfgGfCfAfaguccugauaL96 | 515 | usAfsucaGfgAfCfuugcCfaAfggaaasasu | 606 | AUUUUCCUUGGCAAGUCCUGAUA | 697 |
| AD-156846.1 | gscsaacaUfcAfCfGfccuauuuguaL96 | 516 | usAfscaaAfuAfGfgcguGfaUfguugcsusa | 607 | UAGCAACAUCACGCCUAUUUGUC | 698 |
| AD-156540.1 | asgsgaggGfcGfUfAfuauauggagaL96 | 517 | usCfsuccAfuAfUfauacGfcCfcuccusgsu | 608 | ACAGGAGGGCGUAUAUAUGGAGG | 699 |
| AD-157234.1 | asgsuuguUfgCfUfCfcacccaaaaaL96 | 518 | usUfsuuuGfgGfUfggagCfaAfcaacusgsc | 609 | GCAGUUGUUGCUCCACCCAAAAA | 700 |
| AD-156505.1 | usgsugagCfcUfGfUfuuguggacuaL96 | 519 | usAfsgucCfaCfAfaacaGfgCfucacasgsa | 610 | UCUGUGAGCCUGUUUGUGGACUA | 701 |
| AD-156591.1 | csasagucCfuGfAfUfauuaggugga L96 | 520 | usCfscacCfuAfAfuaucAfgGfacuugscsc | 611 | GGCAAGUCCUGAUAUUAGGUGGA | 702 |
| AD-156988.1 | asasguguAfaCfUfGfcuaacaugcuL96 | 521 | asGfscauGfuUfAfgcagUfuAfcacuuscsc | 612 | GGAAGUGUAACUGCUAACAUGCU | 703 |
| AD-156843.1 | asusagcaAfcAfUfCfacgccuauuuL96 | 522 | asAfsauaGfgCfGfugauGfuUfgcuaususg | 613 | CAAUAGCAACAUCACGCCUAUUU | 704 |
| AD-156539.1 | csasggagGfgCfGfUfauauauggaaL96 | 523 | usUfsccaUfaUfAfuacgCfcCfuccugsusu | 614 | AACAGGAGGGCGUAUAUAUGGAG | 705 |
| AD-157061.1 | ususugugGfgAfGfGfaauagugucaL96 | 524 | usGfsacaCfuAfUfuccuCfcCfacaaascsc | 615 | GGUUUGUGGGAGGAAUAGUGUCC | 706 |
| AD-156839.1 | asuscaauAfgCfAfAfcaucacgccuL96 | 525 | asGfsgcgUfgAfUfguugCfuAfuugaususa | 616 | UAAUCAAUAGCAACAUCACGCCU | 707 |
| AD-156830.1 | asasaguuGfuAfAfUfcaauagcaaaL96 | 526 | usUfsugcUfaUfUfgauuAfcAfacuuusgsu | 617 | ACAAAGUUGUAAUCAAUAGCAAC | 708 |

TABLE 6

| Unmodified Sense and Antisense Strand Sequences of MASP2 dsRNA Agents | | | | | | |
|---|---|---|---|---|---|---|
| Duplex Name | Sense Sequence 5′ to 3′ | SEQ ID NO: | Range in NM_006610.4 | Antisense Sequence 5′ to 3′ | SEQ ID NO: | Range in NM_006610.4 |
| AD-1143337 | ACCAGGCCAGGCCAGCUGGAC | 709 | 3-23 | GUCCAGCUGGCCUGGCCUGGUCU | 844 | 1-23 |
| AD-1143348 | GACGGGCACACCAUGAGGCUG | 710 | 21-41 | CAGCCUCAUGGUGUGCCCGUCCA | 845 | 19-41 |
| AD-155520 | CUGCUGACCCUCCUGGGCCUU | 711 | 39-59 | AAGGCCCAGGAGGGUCAGCAGCC | 846 | 37-59 |
| AD-1143374 | CUUCUGUGUGGCUCGGUGGCC | 712 | 57-77 | GGCCACCGAGCCACACAGAAGGC | 847 | 55-77 |
| AD-1144836 | CCACCCCCUUGGGCCCGAAGU | 713 | 76-96 | ACUUCGGGCCCAAGGGGGUGGCC | 848 | 74-96 |
| AD-1143386 | AGUGGCCUGAACCUGUGUUCG | 714 | 94-114 | CGAACACAGGUUCAGGCCACUUC | 849 | 92-114 |
| AD-1144837 | UCGGGCGCCUGGCAUCCCCCG | 715 | 112-132 | CGGGGGAUGCCAGGCGCCCGAAC | 850 | 110-132 |
| AD-1144838 | CCGGCUUUCCAGGGGAGUAUG | 716 | 130-150 | CAUACUCCCCUGGAAAGCCGGGG | 851 | 128-150 |
| AD-1143406 | AUGCCAAUGACCAGGAGCGGC | 717 | 148-168 | GCCGCUCCUGGUCAUUGGCAUAC | 852 | 146-168 |
| AD-1143416 | GGCGCUGGACCCUGACUGCAC | 718 | 166-186 | GUGCAGUCAGGGUCCAGCGCCGC | 853 | 164-186 |
| AD-1144839 | CACCCCCCGGCUACCGCCUGC | 719 | 184-204 | GCAGGCGGUAGCCGGGGGGUGCA | 854 | 182-204 |
| AD-155599 | GCGCCUCUACUUCACCCACUU | 720 | 203-223 | AAGUGGGUGAAGUAGAGGCGCAG | 855 | 201-223 |
| AD-1143442 | CUUCGACCUGGAGCUCUCCCA | 721 | 221-241 | UGGGAGAGCUCCAGGUCGAAGUG | 856 | 219-241 |
| AD-155635 | CCACCUCUGCGAGUACGACUU | 722 | 239-259 | AAGUCGUACUCGCAGAGGUGGGA | 857 | 237-259 |
| AD-1143470 | CUUCGUCAAGCUGAGCUCGGG | 723 | 257-277 | CCCGAGCUCAGCUUGACGAAGUC | 858 | 255-277 |
| AD-1144840 | GGGGGCCAAGGUGCUGGCCAC | 724 | 275-295 | GUGGCCAGCACCUUGGCCCCCGA | 859 | 273-295 |
| AD-1143479 | CACGCUGUGCGGGCAGGAGAG | 725 | 293-313 | CUCUCCUGCCCGCACAGCGUGGC | 860 | 291-313 |
| AD-1143498 | AGCACAGACACGGAGCGGGCC | 726 | 312-332 | GGCCCGCUCCGUGUCUGUGCUCU | 861 | 310-332 |
| AD-1144841 | GCCCCUGGCAAGGACACUUUC | 727 | 330-350 | GAAAGUGUCCUUGCCAGGGGCCC | 862 | 328-350 |
| AD-1143511 | UUCUACUCGCUGGGCUCCAGC | 728 | 348-368 | GCUGGAGCCCAGCGAGUAGAAAG | 863 | 346-368 |
| AD-1143523 | AGCCUGGACAUUACCUUCCGC | 729 | 366-386 | GCGGAAGGUAAUGUCCAGGCUGG | 864 | 364-386 |
| AD-1143538 | CGCUCCGACUACUCCAACGAG | 730 | 384-404 | CUCGUUGGAGUAGUCGGAGCGGA | 865 | 382-404 |
| AD-1144842 | GAGAAGCCGUUCACGGGGUUC | 731 | 402-422 | GAACCCCGUGAACGGCUUCUCGU | 866 | 400-422 |
| AD-1143554 | UUCGAGGCCUUCUAUGCAGCC | 732 | 420-440 | GGCUGCAUAGAAGGCCUCGAACC | 867 | 418-440 |
| AD-1143570 | CCGAGGACAUUGACGAGUGCC | 733 | 439-459 | GGCACUCGUCAAUGUCCUCGGCU | 868 | 437-459 |

TABLE 6-continued

Unmodified Sense and Antisense Strand Sequences of MASP2 dsRNA Agents

| Duplex Name | Sense Sequence 5′ to 3′ | SEQ ID NO: | Range in NM_006610.4 | Antisense Sequence 5′ to 3′ | SEQ ID NO: | Range in NM_006610.4 |
|---|---|---|---|---|---|---|
| AD-1144843 | GCCAGGUGGCCCCGGGAGAGG | 734 | 457-477 | CCUCUCCCGGGGCCACCUGGCAC | 869 | 455-477 |
| AD-1144844 | AGGCGCCCACCUGCGACCACC | 735 | 475-495 | GGUGGUCGCAGGUGGGCGCCUCU | 870 | 473-495 |
| AD-1143594 | ACCACUGCCACAACCACCUGG | 736 | 493-513 | CCAGGUGGUUGUGGCAGUGGUGG | 871 | 491-513 |
| AD-155809 | UGGGCGGUUUCUACUGCUCCU | 737 | 511-531 | AGGAGCAGUAGAAACCGCCCAGG | 872 | 509-531 |
| AD-1143619 | CCUGCCGCGCAGGCUACGUCC | 738 | 529-549 | GGACGUAGCCUGCGCGGCAGGAG | 873 | 527-549 |
| AD-1143635 | UCCUGCACCGUAACAAGCGCA | 739 | 547-567 | UGCGCUUGUUACGGUGCAGGACG | 874 | 545-567 |
| AD-1143649 | CACCUGCUCAGCCCUGUGCUC | 740 | 566-586 | GAGCACAGGGCUGAGCAGGUGCG | 875 | 564-586 |
| AD-1143662 | CUCCGGCCAGGUCUUCACCCA | 741 | 584-604 | UGGGUGAAGACCUGGCCGGAGCA | 876 | 582-604 |
| AD-1144845 | CCAGAGGUCUGGGGAGCUCAG | 742 | 602-622 | CUGAGCUCCCCAGACCUCUGGGU | 877 | 600-622 |
| AD-1143677 | CAGCAGCCCUGAAUACCCACG | 743 | 620-640 | CGUGGGUAUUCAGGGCUGCUGAG | 878 | 618-640 |
| AD-1143691 | ACGGCCGUAUCCCAAACUCUC | 744 | 638-658 | GAGAGUUUGGGAUACGGCCGUGG | 879 | 636-658 |
| AD-155927 | CUCCAGUUGCACUUACAGCAU | 745 | 656-676 | AUGCUGUAAGUGCAACUGGAGAG | 880 | 654-676 |
| AD-1144846 | AUCAGCCUGGAGGAGGGGUUC | 746 | 675-695 | GAACCCCUCCUCCAGGCUGAUGC | 881 | 673-695 |
| AD-155946 | UUCAGUGUCAUUCUGGACUUU | 747 | 693-713 | AAAGUCCAGAAUGACACUGAACC | 882 | 691-713 |
| AD-1143731 | UUUGUGGAGUCCUUCGAUGUG | 748 | 711-731 | CACAUCGAAGGACUCCACAAAGU | 883 | 709-731 |
| AD-1143748 | GUGGAGACACACCCUGAAACC | 749 | 729-749 | GGUUUCAGGGUGUGUCUCCACAU | 884 | 727-749 |
| AD-155999 | ACCCUGUGUCCCUACGACUUU | 750 | 747-767 | AAAGUCGUAGGGACACAGGGUUU | 885 | 745-767 |
| AD-1143774 | UUUCUCAAGAUUCAAACAGAC | 751 | 765-785 | GUCUGUUUGAAUCUUGAGAAAGU | 886 | 763-785 |
| AD-1143789 | GACAGAGAAGAACAUGGCCCA | 752 | 783-803 | UGGGCCAUGUUCUUCUCUGUCUG | 887 | 781-803 |
| AD-1143802 | CAUUCUGUGGGAAGACAUUGC | 753 | 802-822 | GCAAUGUCUUCCCACAGAAUGGG | 888 | 800-822 |
| AD-1144847 | UGCCCCACAGGAUUGAAACAA | 754 | 820-840 | UUGUUUCAAUCCUGUGGGGCAAU | 889 | 818-840 |
| AD-1143816 | CAAAAAGCAACACGGUGACCA | 755 | 838-858 | UGGUCACCGUGUUGCUUUUUGUU | 890 | 836-858 |
| AD-1143828 | CCAUCACCUUUGUCACAGAUG | 756 | 856-876 | CAUCUGUGACAAAGGUGAUGGUC | 891 | 854-876 |
| AD-1143845 | AUGAAUCAGGAGACCACACAG | 757 | 874-894 | CUGUGUGGUCUCCUGAUUCAUCU | 892 | 872-894 |

TABLE 6-continued

Unmodified Sense and Antisense Strand Sequences of MASP2 dsRNA Agents

| Duplex Name | Sense Sequence 5′ to 3′ | SEQ ID NO: | Range in NM_006610.4 | Antisense Sequence 5′ to 3′ | SEQ ID NO: | Range in NM_006610.4 |
|---|---|---|---|---|---|---|
| AD-1143860 | CAGGCUGGAAGAUCCACUACA | 758 | 892-912 | UGUAGUGGAUCUUCCAGCCUGUG | 893 | 890-912 |
| AD-156136 | ACACGAGCACAGCGCAGCCUU | 759 | 910-930 | AAGGCUGCGCUGUGCUCGUGUAG | 894 | 908-930 |
| AD-1143891 | UUGCCCUUAUCCGAUGGCGCC | 760 | 929-949 | GGCGCCAUCGGAUAAGGGCAAGG | 895 | 927-949 |
| AD-1143904 | GCCACCUAAUGGCCACGUUUC | 761 | 947-967 | GAAACGUGGCCAUUAGGUGGCGC | 896 | 945-967 |
| AD-1143919 | UUCACCUGUGCAAGCCAAAUA | 762 | 965-985 | UAUUUGGCUUGCACAGGUGAAAC | 897 | 963-985 |
| AD-156208 | AUACAUCCUGAAAGACAGCUU | 763 | 983-1003 | AAGCUGUCUUUCAGGAUGUAUUU | 898 | 981-1003 |
| AD-1143945 | CUUCUCCAUCUUUUGCGAGAC | 764 | 1001-1021 | GUCUCGCAAAAGAUGGAGAAGCU | 899 | 999-1021 |
| AD-1143957 | GACUGGCUAUGAGCUUCUGCA | 765 | 1019-1039 | UGCAGAAGCUCAUAGCCAGUCUC | 900 | 1017-1039 |
| AD-1144848 | CAAGGUCACUUGCCCCUGAAA | 766 | 1038-1058 | UUUCAGGGGCAAGUGACCUUGCA | 901 | 1036-1058 |
| AD-156260 | AAAUCCUUUACUGCAGUUUGU | 767 | 1056-1076 | ACAAACUGCAGUAAAGGAUUUCA | 902 | 1054-1076 |
| AD-1143982 | UGUCAGAAAGAUGGAUCUUGG | 768 | 1074-1094 | CCAAGAUCCAUCUUUCUGACAAA | 903 | 1072-1094 |
| AD-1144849 | UGGGACCGGCCAAUGCCCGCG | 769 | 1092-1112 | CGCGGGCAUUGGCCGGUCCCAAG | 904 | 1090-1112 |
| AD-156308 | GCGUGCAGCAUUGUUGACUGU | 770 | 1110-1130 | ACAGUCAACAAUGCUGCACGCGG | 905 | 1108-1130 |
| AD-1144019 | UGUGGCCCUCCUGAUGAUCUA | 771 | 1128-1148 | UAGAUCAUCAGGAGGGCCACAGU | 906 | 1126-1148 |
| AD-1144035 | CUACCCAGUGGCCGAGUGGAG | 772 | 1146-1166 | CUCCACUCGGCCACUGGGUAGAU | 907 | 1144-1166 |
| AD-1144050 | AGUACAUCACAGGUCCUGGAG | 773 | 1165-1185 | CUCCAGGACCUGUGAUGUACUCC | 908 | 1163-1185 |
| AD-1144065 | GAGUGACCACCUACAAAGCUG | 774 | 1183-1203 | CAGCUUUGUAGGUGGUCACUCCA | 909 | 1181-1203 |
| AD-1144077 | CUGUGAUUCAGUACAGCUGUG | 775 | 1201-1221 | CACAGCUGUACUGAAUCACAGCU | 910 | 1199-1221 |
| AD-1144092 | GUGAAGAGACCUUCUACACAA | 776 | 1219-1239 | UUGUGUAGAAGGUCUCUUCACAG | 911 | 1217-1239 |
| AD-1144105 | CAAUGAAAGUGAAUGAUGGUA | 777 | 1237-1257 | UACCAUCAUUCACUUUCAUUGUG | 912 | 1235-1257 |
| AD-1144117 | GUAAAUAUGUGUGUGAGGCUG | 778 | 1255-1275 | CAGCCUCACACACAUAUUUACCA | 913 | 1253-1275 |
| AD-156460 | CUGAUGGAUUCUGGACGAGCU | 779 | 1273-1293 | AGCUCGUCCAGAAUCCAUCAGCC | 914 | 1271-1293 |
| AD-156477 | CUCCAAAGGAGAAAAAUCACU | 780 | 1292-1312 | AGUGAUUUUUCUCCUUUGGAGCU | 915 | 1290-1312 |
| AD-156495 | ACUCCCAGUCUGUGAGCCUGU | 781 | 1310-1330 | ACAGGCUCACAGACUGGGAGUGA | 916 | 1308-1330 |
| AD-1144173 | UGUUUGUGGACUAUCAGCCCG | 782 | 1328-1348 | CGGGCUGAUAGUCCACAAACAGG | 917 | 1326-1348 |

TABLE 6-continued

Unmodified Sense and Antisense Strand Sequences of MASP2 dsRNA Agents

| Duplex Name | Sense Sequence 5′ to 3′ | SEQ ID NO: | Range in NM_006610.4 | Antisense Sequence 5′ to 3′ | SEQ ID NO: | Range in NM_006610.4 |
|---|---|---|---|---|---|---|
| AD-156531 | CCGCACAACAGGAGGGCGUAU | 783 | 1346-1366 | AUACGCCCUCCUGUUGUGCGGGC | 918 | 1344-1366 |
| AD-1144205 | UAUAUAUGGAGGGCAAAAGGC | 784 | 1364-1384 | GCCUUUUGCCCUCCAUAUAUACG | 919 | 1362-1384 |
| AD-1144217 | GGCAAAACCUGGUGAUUUUCC | 785 | 1382-1402 | GGAAAAUCACCAGGUUUUGCCUU | 920 | 1380-1402 |
| AD-156584 | UCCUUGGCAAGUCCUGAUAUU | 786 | 1400-1420 | AAUAUCAGGACUUGCCAAGGAAA | 921 | 1398-1420 |
| AD-1144246 | UUAGGUGGAACCACAGCAGCA | 787 | 1419-1439 | UGCUGCUGUGGUUCCACCUAAUA | 922 | 1417-1439 |
| AD-1144257 | GCAGGUGCACUUUUAUAUGAC | 788 | 1437-1457 | GUCAUAUAAAAGUGCACCUGCUG | 923 | 1435-1457 |
| AD-156639 | GACAACUGGGUCCUAACAGCU | 789 | 1455-1475 | AGCUGUUAGGACCCAGUUGUCAU | 924 | 1453-1475 |
| AD-1144284 | GCUGCUCAUGCCGUCUAUGAG | 790 | 1473-1493 | CUCAUAGACGGCAUGAGCAGCUG | 925 | 1471-1493 |
| AD-1144299 | GAGCAAAAACAUGAUGCAUCC | 791 | 1491-1511 | GGAUGCAUCAUGUUUUUGCUCAU | 926 | 1489-1511 |
| AD-1144313 | UCCGCCCUGGACAUUCGAAUG | 792 | 1509-1529 | CAUUCGAAUGUCCAGGGCGGAUG | 927 | 1507-1529 |
| AD-156712 | UGGGCACCCUGAAAAGACUAU | 793 | 1528-1548 | AUAGUCUUUUCAGGGUGCCCAUU | 928 | 1526-1548 |
| AD-1144343 | UAUCACCUCAUUAUACACAAG | 794 | 1546-1566 | CUUGUGUAUAAUGAGGUGAUAGU | 929 | 1544-1566 |
| AD-156748 | AAGCCUGGUCUGAAGCUGUUU | 795 | 1564-1584 | AAACAGCUUCAGACCAGGCUUGU | 930 | 1562-1584 |
| AD-1144365 | UUUUUAUACAUGAAGGUUAUA | 796 | 1582-1602 | UAUAACCUUCAUGUAUAAAAACA | 931 | 1580-1602 |
| AD-1144376 | AUACUCAUGAUGCUGGCUUUG | 797 | 1600-1620 | CAAAGCCAGCAUCAUGAGUAUAA | 932 | 1598-1620 |
| AD-1144391 | UUGACAAUGACAUAGCACUGA | 798 | 1618-1638 | UCAGUGCUAUGUCAUUGUCAAAG | 933 | 1616-1638 |
| AD-1144850 | UGAUUAAAUUGAAUAACAAAG | 799 | 1636-1656 | CUUUGUUAUUCAAUUUAAUCAGU | 934 | 1634-1656 |
| AD-156832 | AGUUGUAAUCAAUAGCAACAU | 800 | 1655-1675 | AUGUUGCUAUUGAUUACAACUUU | 935 | 1653-1675 |
| AD-1144424 | CAUCACGCCUAUUUGUCUGCC | 801 | 1673-1693 | GGCAGACAAAUAGGCGUGAUGUU | 936 | 1671-1693 |
| AD-1144440 | GCCAAGAAAAGAAGCUGAAUC | 802 | 1691-1711 | GAUUCAGCUUCUUUUCUUGGCAG | 937 | 1689-1711 |
| AD-1144453 | AUCCUUUAUGAGGACAGAUGA | 803 | 1709-1729 | UCAUCUGUCCUCAUAAAGGAUUC | 938 | 1707-1729 |
| AD-1144466 | UGACAUUGGAACUGCAUCUGG | 804 | 1727-1747 | CCAGAUGCAGUUCCAAUGUCAUC | 939 | 1725-1747 |
| AD-1144851 | UGGAUGGGGAUUAACCCAAAG | 805 | 1745-1765 | CUUUGGGUUAAUCCCCAUCCAGA | 940 | 1743-1765 |
| AD-1144852 | AAGGGGUUUUCUUGCUAGAAA | 806 | 1763-1783 | UUUCUAGCAAGAAAACCCCUUUG | 941 | 1761-1783 |

TABLE 6-continued

| Duplex Name | Sense Sequence 5' to 3' | SEQ ID NO: | Range in NM_006610.4 | Antisense Sequence 5' to 3' | SEQ ID NO: | Range in NM_006610.4 |
|---|---|---|---|---|---|---|
| AD-1144481 | AAUCUAAUGUAUGUCGACAUA | 807 | 1782-1802 | UAUGUCGACAUACAUUAGAUUUC | 942 | 1780-1802 |
| AD-1144494 | AUACCGAUUGUUGACCAUCAA | 808 | 1800-1820 | UUGAUGGUCAACAAUCGGUAUGU | 943 | 1798-1820 |
| AD-156962 | CAAAAAUGUACUGCUGCAUAU | 809 | 1818-1838 | AUAUGCAGCAGUACAUUUUUGAU | 944 | 1816-1838 |
| AD-1144522 | UAUGAAAAGCCACCCUAUCCA | 810 | 1836-1856 | UGGAUAGGGUGGCUUUUCAUAUG | 945 | 1834-1856 |
| AD-1144853 | CCAAGGGGAAGUGUAACUGCU | 811 | 1854-1874 | AGCAGUUACACUUCCCCUUGGAU | 946 | 1852-1874 |
| AD-1144534 | GCUAACAUGCUUUGUGCUGGC | 812 | 1872-1892 | GCCAGCACAAAGCAUGUUAGCAG | 947 | 1870-1892 |
| AD-1144854 | GCUUAGAAAGUGGGGGCAAGG | 813 | 1891-1911 | CCUUGCCCCCACUUUCUAAGCCA | 948 | 1889-1911 |
| AD-1144548 | AGGACAGCUGCAGAGGUGACA | 814 | 1909-1929 | UGUCACCUCUGCAGCUGUCCUUG | 949 | 1907-1929 |
| AD-1144855 | ACAGCGGAGGGGCACUGGUGU | 815 | 1927-1947 | ACACCAGUGCCCCUCCGCUGUCA | 950 | 1925-1947 |
| AD-1144565 | UGUUUCUAGAUAGUGAAACAG | 816 | 1945-1965 | CUGUUUCACUAUCUAGAAACACC | 951 | 1943-1965 |
| AD-1144578 | CAGAGAGGUGGUUUGUGGGAG | 817 | 1963-1983 | CUCCCACAAACCACCUCUCUGUU | 952 | 1961-1983 |
| AD-1144856 | GAGGAAUAGUGUCCUGGGGUU | 818 | 1981-2001 | AACCCCAGGACACUAUUCCUCCC | 953 | 1979-2001 |
| AD-1144857 | GUUCCAUGAAUUGUGGGGAAG | 819 | 1999-2019 | CUUCCCCACAAUUCAUGGAACCC | 954 | 1997-2019 |
| AD-1144591 | AGCAGGUCAGUAUGGAGUCUA | 820 | 2018-2038 | UAGACUCCAUACUGACCUGCUUC | 955 | 2016-2038 |
| AD-1144604 | CUACACAAAAGUUAUUAACUA | 821 | 2036-2056 | UAGUUAAUAACUUUUGUGUAGAC | 956 | 2034-2056 |
| AD-1144614 | CUAUAUUCCCUGGAUCGAGAA | 822 | 2054-2074 | UUCUCGAUCCAGGGAAUAUAGUU | 957 | 2052-2074 |
| AD-1144858 | GAACAUAAUUAGUGAUUUUUA | 823 | 2072-2092 | UAAAAAUCACUAAUUAUGUUCUC | 958 | 2070-2092 |
| AD-1144631 | UUAACUUGCGUGUCUGCAGUC | 824 | 2090-2110 | GACUGCAGACACGCAAGUUAAAA | 959 | 2088-2110 |
| AD-1144640 | GUCAAGGAUUCUUCAUUUUUA | 825 | 2108-2128 | UAAAAAUGAAGAAUCCUUGACUG | 960 | 2106-2128 |
| AD-1144654 | UUAGAAAUGCCUGUGAAGACC | 826 | 2126-2146 | GGUCUUCACAGGCAUUUCUAAAA | 961 | 2124-2146 |
| AD-1144669 | CCUUGGCAGCGACGUGGCUCG | 827 | 2145-2165 | CGAGCCACGUCGCUGCCAAGGUC | 962 | 2143-2165 |
| AD-1144682 | UCGAGAAGCAUUCAUCAUUAC | 828 | 2163-2183 | GUAAUGAUGAAUGCUUCUCGAGC | 963 | 2161-2183 |
| AD-157219 | UACUGUGGACAUGGCAGUUGU | 829 | 2181-2201 | ACAACUGCCAUGUCCACAGUAAU | 964 | 2179-2201 |
| AD-1144859 | UGUUGCUCCACCCAAAAAAAC | 830 | 2199-2219 | GUUUUUUUGGGUGGAGCAACAAC | 965 | 2197-2219 |
| AD-1144708 | AACAGACUCCAGGUGAGGCUG | 831 | 2217-2237 | CAGCCUCACCUGGAGUCUGUUUU | 966 | 2215-2237 |

TABLE 6-continued

Unmodified Sense and Antisense Strand Sequences of MASP2 dsRNA Agents

| Duplex Name | Sense Sequence 5' to 3' | SEQ ID NO: | Range in NM_006610.4 | Antisense Sequence 5' to 3' | SEQ ID NO: | Range in NM_006610.4 |
|---|---|---|---|---|---|---|
| AD-1144718 | CUGCUGUCAUUUCUCCACUUG | 832 | 2235-2255 | CAAGUGGAGAAAUGACAGCAGCC | 967 | 2233-2255 |
| AD-157273 | UGCCAGUUUAAUUCCAGCCUU | 833 | 2254-2274 | AAGGCUGGAAUUAAACUGGCAAG | 968 | 2252-2274 |
| AD-1144860 | CUUACCCAUUGACUCAAGGGG | 834 | 2272-2292 | CCCCUUGAGUCAAUGGGUAAGGC | 969 | 2270-2292 |
| AD-1144745 | GGGACAUAAACCACGAGAGUG | 835 | 2290-2310 | CACUCUCGUGGUUUAUGUCCCCU | 970 | 2288-2310 |
| AD-1144758 | GUGACAGUCAUCUUUGCCCAC | 836 | 2308-2328 | GUGGGCAAAGAUGACUGUCACUC | 971 | 2306-2328 |
| AD-1144771 | CACCCAGUGUAAUGUCACUGC | 837 | 2326-2346 | GCAGUGACAUUACACUGGGUGGG | 972 | 2324-2346 |
| AD-1144781 | UGCUCAAAUUACAUUUCAUUA | 838 | 2344-2364 | UAAUGAAAUGUAAUUUGAGCAGU | 973 | 2342-2364 |
| AD-1144793 | UUACCUUAAAAAGCCAGUCUC | 839 | 2362-2382 | GAGACUGGCUUUUUAAGGUAAUG | 974 | 2360-2382 |
| AD-1144803 | UCUUUUCAUACUGGCUGUUGG | 840 | 2381-2401 | CCAACAGCCAGUAUGAAAAGAGA | 975 | 2379-2401 |
| AD-157398 | UGGCAUUUCUGUAAACUGCCU | 841 | 2399-2419 | AGGCAGUUUACAGAAAUGCCAAC | 976 | 2397-2419 |
| AD-157416 | CCUGUCCAUGCUCUUUGUUUU | 842 | 2417-2437 | AAAACAAAGAGCAUGGACAGGCA | 977 | 2415-2437 |
| AD-1144861 | UUUUAAACUUGUUCUUAUUGA | 843 | 2435-2455 | UCAAUAAGAACAAGUUUAAAAAC | 978 | 2433-2455 |

TABLE 7

Modified Sense and Antisense Strand Sequences of MASP2 dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1143337 | ascscaggCfAfGfGfccagcuggauL96 | 979 | asUfsccaGfcUfGfgccuGfgCfcuggusc su | 1114 | AGACCAGGCCAGGCCAGCTGGAC | 1249 |
| AD-1143348 | gsascgggCfaCfAfCfcaugaggcuuL96 | 980 | asAfsgccUfcAfUfggugUfgCfccgucscsa | 1115 | TGGACGGGCACACCATGAGGCTG | 1250 |
| AD-155520 | csusgcugAfcCfCfUfccugggccuuL96 | 981 | asAfsggcCfcAfGfgaggGfuCfagcagscsc | 1116 | GGCTGCTGACCCTCCTGGGCCTT | 1251 |
| AD-1143374 | csusucugUfgUfGfGfcucgguggcuL96 | 982 | asGfsccaCfcGfAfgccaCfaCfagaagsgsc | 1117 | GCCTTCTGTGTGGCTCGGTGGCC | 1252 |
| AD-1144836 | cscsacccCfcUfUfGfggcccgaaguL96 | 983 | asCfsuucGfgGfCfccaaGfgGfgguggscsc | 1118 | GGCCACCCCCTTGGGCCCGAAGT | 1253 |
| AD-1143386 | asgsuggcCfuGfAfAfccuguguucuL96 | 984 | asGfsaacAfcAfGfguucAfgGfccacususc | 1119 | GAAGTGGCCTGAACCTGTGTTCG | 1254 |
| AD-1144837 | uscsgggcGfcCfUfGfgcaucccccuL96 | 985 | asGfsgggGfaUfGfccagGfcGfcccgasasc | 1120 | GTTCGGGCGCCTGGCATCCCCCG | 1255 |
| AD-1144838 | cscsggcuUfuCfCfAfggggaguauuL96 | 986 | asAfsuacUfcCfCfcuggAfaAfgccggsgsg | 1121 | CCCCGGCTTTCCAGGGGAGTATG | 1256 |

TABLE 7-continued

| Modified Sense and Antisense Strand Sequences of MASP2 dsRNA Agents | | | | | | |
|---|---|---|---|---|---|---|
| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
| AD-1143406 | asusgccaAfuGfAfCfcaggagcgguL96 | 987 | asCfscgcUfcCfUfggucAfuUfggcausasc | 1122 | GTATGCCAATGACCAGGAGCGGC | 1257 |
| AD-1143416 | gsgscgcuGfgAfCfCfcugacugcauL96 | 988 | asUfsgcaGfuCfAfgggucCfcAfgcgccsgsc | 1123 | GCGGCGCTGGACCCTGACTGCAC | 1258 |
| AD-1144839 | csascccccCfcGfGfCfuaccgccuguL96 | 989 | asCfsaggCfgGfUfagccGfgGfgggugscsa | 1124 | TGCACCCCCCGGCTACCGCCTGC | 1259 |
| AD-155599 | gscsgccuCfuAfCfUfucacccacuuL96 | 990 | asAfsgugGfgUfGfaaguAfgAfggcgcsasg | 1125 | CTGCGCCTCTACTTCACCCACTT | 1260 |
| AD-1143442 | csusucgaCfcUfGfGfagcucucccuL96 | 991 | asGfsggaGfaGfCfuccaGfgUfcgaagsusg | 1126 | CACTTCGACCTGGAGCTCTCCCA | 1261 |
| AD-155635 | cscsaccuCfuGfCfGfaguacgacuuL96 | 992 | asAfsgucGfuAfCfucgcAfgAfgguggsgsa | 1127 | TCCCACCTCTGCGAGTACGACTT | 1262 |
| AD-1143470 | csusucguCfaAfGfCfugagcucgguL96 | 993 | asCfscgaGfcUfCfagcuUfgAfcgaagsusc | 1128 | GACTTCGTCAAGCTGAGCTCGGG | 1263 |
| AD-1144840 | gsgsgggcCfaAfGfGfugcuggccauL96 | 994 | asUfsggcCfaGfCfaccuUfgGfcccccsgsa | 1129 | TCGGGGGCCAAGGTGCTGGCCAC | 1264 |
| AD-1143479 | csascgcuGfuGfCfGfggcaggagauL96 | 995 | asUfscucCfuGfCfccgcAfcAfgcgugsgsc | 1130 | GCCACGCTGTGCGGGCAGGAGAG | 1265 |
| AD-1143498 | asgscacaGfaCfAfCfggagcgggcuL96 | 996 | asGfscccGfcUfCfcgugUfcUfgugcuscsu | 1131 | AGAGCACAGACACGGAGCGGGCC | 1266 |
| AD-1144841 | gscscccuGfgCfAfAfggacacuuuuL96 | 997 | asAfsaagUfgUfCfcuugCfcAfggggcscsc | 1132 | GGGCCCCTGGCAAGGACACTTTC | 1267 |
| AD-1143511 | ususcuacUfcGfCfUfgggcuccaguL96 | 998 | asCfsuggAfgCfCfcagcGfaGfuagaasasg | 1133 | CTTTCTACTCGCTGGGCTCCAGC | 1268 |
| AD-1143523 | asgsccugGfaCfAfUfuaccuuccguL96 | 999 | asCfsggaAfgGfUfaaugUfcCfaggcusgsg | 1134 | CCAGCCTGGACATTACCTTCCGC | 1269 |
| AD-1143538 | csgscuccGfaCfUfAfcuccaacgauL96 | 1000 | asUfscguUfgGfAfguagUfcGfgagcgsgsa | 1135 | TCCGCTCCGACTACTCCAACGAG | 1270 |
| AD-1144842 | gsasgaagCfcGfUfUfcacgggguuuL96 | 1001 | asAfsaccCfcGfUfgaacGfgCfuucucsgsu | 1136 | ACGAGAAGCCGTTCACGGGGTTC | 1271 |
| AD-1143554 | ususcgagGfcCfUfUfcuaugcagcuL96 | 1002 | asGfscugCfaUfAfgaagGfcCfucgaascsc | 1137 | GGTTCGAGGCCTTCTATGCAGCC | 1272 |
| AD-1143570 | cscsgaggAfcAfUfUfgacgagugcuL96 | 1003 | asGfscacUfcGfUfcaauGfuCfcucggscsu | 1138 | AGCCGAGGACATTGACGAGTGCC | 1273 |
| AD-1144843 | gscscaggUfgGfCfCfccgggagaguL96 | 1004 | asCfsucuCfcCfGfggccCfaCfcuggcsasc | 1139 | GTGCCAGGTGGCCCCGGGAGAGG | 1274 |
| AD-1144844 | asgsgcgcCfcAfCfCfugcgaccacuL96 | 1005 | asGfsuggUfcGfCfagguGfgGfcgccuscsu | 1140 | AGAGGCGCCCACCTGCGACCACC | 1275 |
| AD-1143594 | ascscacuGfcCfAfCfaaccaccuguL96 | 1006 | asCfsaggUfgGfUfugugGfcAfguggusgsg | 1141 | CCACCACTGCCACAACCACCTGG | 1276 |

TABLE 7-continued

Modified Sense and Antisense Strand Sequences of MASP2 dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-155809 | usgsggcgGfuUfUfCfuacugcuccuL96 | 1007 | asGfsgagCfaGfUfagaaAfcCfgcccasgsg | 1142 | CCTGGGCGGTTTCTACTGCTCCT | 1277 |
| AD-1143619 | cscsugccGfcGfCfAfggcuacgucuL96 | 1008 | asGfsacgUfaGfCfcugcGfcGfgcaggsasg | 1143 | CTCCTGCCGCGCAGGCTACGTCC | 1278 |
| AD-1143635 | uscscugcAfcCfGfUfaacaagcgcuL96 | 1009 | asGfscgcUfuGfUfuacgGfuGfcaggascsg | 1144 | CGTCCTGCACCGTAACAAGCGCA | 1279 |
| AD-1143649 | csasccugCfuCfAfGfcccugugcuuL96 | 1010 | asAfsgcaCfaGfGfgcugAfgCfaggugscsg | 1145 | CGCACCTGCTCAGCCCTGTGCTC | 1280 |
| AD-1143662 | csusccggCfcAfGfGfucuucacccuL96 | 1011 | asGfsgguGfaAfGfaccuGfgCfcggagscsa | 1146 | TGCTCCGGCCAGGTCTTCACCCA | 1281 |
| AD-1144845 | cscsagagGfuCfUfGfgggagcucauL96 | 1012 | asUfsgagCfuCfCfccagAfcCfucuggsgsu | 1147 | ACCCAGAGGTCTGGGGAGCTCAG | 1282 |
| AD-1143677 | csasgcagCfcCfUfGfaauacccacuL96 | 1013 | asGfsuggGfuAfUfucagGfgCfugcugsasg | 1148 | CTCAGCAGCCCTGAATACCCACG | 1283 |
| AD-1143691 | ascsggccGfuAfUfCfccaaacucuuL96 | 1014 | asAfsgagUfuUfGfggauAfcGfgccgusgsg | 1149 | CCACGGCCGTATCCCAAACTCTC | 1284 |
| AD-155927 | csusccagUfuGfCfAfcuuacagcauL96 | 1015 | asUfsgcuGfuAfAfgugcAfaCfuggagsasg | 1150 | CTCTCCAGTTGCACTTACAGCAT | 1285 |
| AD-1144846 | asuscagcCfuGfGfAfggaggguuuL96 | 1016 | asAfsaccCfcUfCfcuccAfgGfcugausgsc | 1151 | GCATCAGCCTGGAGGAGGGGTTC | 1286 |
| AD-155946 | ususcaguGfuCfAfUfucuggacuuuL96 | 1017 | asAfsaguCfcAfGfaaugAfcAfcugaascsc | 1152 | GGTTCAGTGTCATTCTGGACTTT | 1287 |
| AD-1143731 | ususugugGfaGfUfCfcuucgauguuL96 | 1018 | asAfscauCfgAfAfggacUfcCfacaaasgsu | 1153 | ACTTTGTGGAGTCCTTCGATGTG | 1288 |
| AD-1143748 | gsusggagAfcAfCfAfcccugaaacuL96 | 1019 | asGfsuuuCfaGfGfguguGfuCfuccacsasu | 1154 | ATGTGGAGACACACCCTGAAACC | 1289 |
| AD-155999 | ascsccugUfgUfCfCfcuacgacuuuL96 | 1020 | asAfsaguCfgUfAfggaCfaCfagggusu u | 1155 | AAACCCTGTGTCCCTACGACTTT | 1290 |
| AD-1143774 | ususucucAfaGfAfUfucaaacagauL96 | 1021 | asUfscugUfuUfGfaaucUfuGfagaaasgsu | 1156 | ACTTTCTCAAGATTCAAACAGAC | 1291 |
| AD-1143789 | gsascagaGfaAfGfAfacauggcccuL96 | 1022 | asGfsggcCfaUfGfuucuUfcUfcugucsusg | 1157 | CAGACAGAGAAGAACATGGCCCA | 1292 |
| AD-1143802 | csasuucuGfuGfGfGfaagacauuguL96 | 1023 | asCfsaauGfuCfUfucccAfcAfgaaugsgsg | 1158 | CCCATTCTGTGGGAAGACATTGC | 1293 |
| AD-1144847 | usgsccccAfcAfGfGfauugaaacauL96 | 1024 | asUfsguuUfcAfAfuccuGfuGfgggcasasu | 1159 | ATTGCCCCACAGGATTGAAACAA | 1294 |
| AD-1143816 | csasaaaaGfcAfAfCfacggugaccuL96 | 1025 | asGfsgucAfcCfGfuguuGfcUfuuuugsusu | 1160 | AACAAAAAGCAACACGGTGACCA | 1295 |
| AD-1143828 | cscsaucaCfcUfUfUfgucacagauuL96 | 1026 | asAfsucuGfuGfAfcaaaGfgUfgauggsusc | 1161 | GACCATCACCTTTGTCACAGATG | 1296 |
| AD-1143845 | asusgaauCfaGfGfAfgaccacacauL96 | 1027 | asUfsgugUfgGfUfcuccUfgAfuucauscsu | 1162 | AGATGAATCAGGAGACCACACAG | 1297 |

TABLE 7-continued

| Modified Sense and Antisense Strand Sequences of MASP2 dsRNA Agents | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-1143860 | csasggcuGfgAfAfGfauccacuacuL96 | 1028 | asGfsuagUfgGfAfucuuCfcAfgccugsusg | 1163 | CACAGGCTGGAAGATCCACTACA | 1298 |
| AD-156136 | ascsacgaGfcAfCfAfgcgcagccuuL96 | 1029 | asAfsggcUfgCfGfcuguGfcUfcgugusasg | 1164 | CTACACGAGCACAGCGCAGCCTT | 1299 |
| AD-1143891 | ususgcccUfuAfUfCfcgauggcgcuL96 | 1030 | asGfscgcCfaUfCfggauAfaGfggcaasgsg | 1165 | CCTTGCCCTTATCCGATGGCGCC | 1300 |
| AD-1143904 | gscscaccUfaAfUfGfgccacguuuuL96 | 1031 | asAfsaacGfuGfGfccauUfaGfguggcsgsc | 1166 | GCGCCACCTAATGGCCACGTTTC | 1301 |
| AD-1143919 | ususcaccUfgUfGfCfaagccaaauuL96 | 1032 | asAfsuuuGfgCfUfugcaCfaGfgugaasasc | 1167 | GTTTCACCTGTGCAAGCCAAATA | 1302 |
| AD-156208 | asusacauCfcUfGfAfaagacagcuuL96 | 1033 | asAfsgcuGfuCfUfuucaGfgAfuguausu | 1168 | AAATACATCCTGAAAGACAGCTT | 1303 |
| AD-1143945 | csusucucCfaUfCfUfuuugcgagauL96 | 1034 | asUfscucGfcAfAfaagaUfgGfagaagscsu | 1169 | AGCTTCTCCATCTTTTGCGAGAC | 1304 |
| AD-1143957 | gsascuggCfuAfUfGfagcuucugcuL96 | 1035 | asGfscagAfaGfCfucauAfgCfcagucsusc | 1170 | GAGACTGGCTATGAGCTTCTGCA | 1305 |
| AD-1144848 | csasagguCfaCfUfUfgccccugaauL96 | 1036 | asUfsucaGfgGfGfcaagUfgAfccuugscsa | 1171 | TGCAAGGTCACTTGCCCCTGAAA | 1306 |
| AD-156260 | asasauccUfuUfAfCfugcaguuuguL96 | 1037 | asCfsaaaCfuGfCfaguaAfaGfgauuuscsa | 1172 | TGAAATCCTTTACTGCAGTTTGT | 1307 |
| AD-1143982 | usgsucagAfaAfGfAfuggaucuuguL96 | 1038 | asCfsaagAfuCfCfaucuUfuCfugacasasa | 1173 | TTTGTCAGAAAGATGGATCTTGG | 1308 |
| AD-1144849 | usgsggacCfgGfCfCfaaugcccgcuL96 | 1039 | asGfscggGfcAfUfuggcCfgGfucccasasg | 1174 | CTTGGGACCGGCCAATGCCCGCG | 1309 |
| AD-156308 | gscsgugcAfgCfAfUfuguugacuguL96 | 1040 | asCfsaguCfaAfCfaaugCfuGfcacgcsgsg | 1175 | CCGCGTGCAGCATTGTTGACTGT | 1310 |
| AD-1144019 | usgsuggcCfcUfCfCfugaugaucuuL96 | 1041 | asAfsgauCfaUfCfaggaGfgGfccacasgsu | 1176 | ACTGTGGCCCTCCTGATGATCTA | 1311 |
| AD-1144035 | csusacccAfgUfGfGfccgaguggauL96 | 1042 | asUfsccaCfuCfGfgccaCfuGfgguagsasu | 1177 | ATCTACCCAGTGGCCGAGTGGAG | 1312 |
| AD-1144050 | asgsuacaUfcAfCfAfgguccuggauL96 | 1043 | asUfsccaGfgAfCfcuguGfaUfguacuscsc | 1178 | GGAGTACATCACAGGTCCTGGAG | 1313 |
| AD-1144065 | gsasgugaCfcAfCfCfuacaaagcuuL96 | 1044 | asAfsgcuUfuGfUfaggugGfgUfcacucscsa | 1179 | TGGAGTGACCACCTACAAAGCTG | 1314 |
| AD-1144077 | csusgugaUfuCfAfGfuacagcuguuL96 | 1045 | asAfscagCfuGfUfacugAfaUfcacagscsu | 1180 | AGCTGTGATTCAGTACAGCTGTG | 1315 |
| AD-1144092 | gsusgaagAfgAfCfCfuucuacacauL96 | 1046 | asUfsgugUfaGfAfagguCfuCfuucacsasg | 1181 | CTGTGAAGAGACCTTCTACACAA | 1316 |
| AD-1144105 | csasaugaAfaGfUfGfaaugaugguuL96 | 1047 | asAfsccaUfcAfUfucacUfuUfcauugsusg | 1182 | CACAATGAAAGTGAATGATGGTA | 1317 |
| AD-1144117 | gsusaaauAfuGfUfGfugugaggcuuL96 | 1048 | asAfsgccUfcAfCfacacAfuAfuuuacscsa | 1183 | TGGTAAATATGTGTGTGAGGCTG | 1318 |
| AD-156460 | csusgaugGfaUfUfCfuggacgagcuL96 | 1049 | asGfscucGfuCfCfagaaUfcCfaucagscsc | 1184 | GGCTGATGGATTCTGGACGAGCT | 1319 |

TABLE 7-continued

| Modified Sense and Antisense Strand Sequences of MASP2 dsRNA Agents | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-156477 | csusccaaAfgGfAfGfaaaaaucacuL96 | 1050 | asGfsugaUfuUfUfucucCfuUfuggagscsu | 1185 | AGCTCCAAAGGAGAAAAATCACT | 1320 |
| AD-156495 | ascsucccAfgUfCfUfgugagccuguL96 | 1051 | asCfsaggCfuCfAfcagaCfuGfggagusgsa | 1186 | TCACTCCCAGTCTGTGAGCCTGT | 1321 |
| AD-1144173 | usgsuuugUfgGfAfCfuaucagcccuL96 | 1052 | asGfsggcUfgAfUfagucCfaCfaaacasgsg | 1187 | CCTGTTTGTGGACTATCAGCCCG | 1322 |
| AD-156531 | cscsgcacAfaCfAfGfgagggcguauL96 | 1053 | asUfsacgCfcCfUfccugUfuGfugcggsgsc | 1188 | GCCCGCACAACAGGAGGGCGTAT | 1323 |
| AD-1144205 | usasuauaUfgGfAfGfggcaaaagguL96 | 1054 | asCfscuuUfuGfCfcucuCfaUfauauascsg | 1189 | CGTATATATGGAGGGCAAAAGGC | 1324 |
| AD-1144217 | gsgscaaaAfcCfUfGfgugauuuucuL96 | 1055 | asGfsaaaAfuCfAfccagGfuUfuugccsusu | 1190 | AAGGCAAAACCTGGTGATTTTCC | 1325 |
| AD-156584 | uscscuugGfcAfAfGfuccugauauuL96 | 1056 | asAfsuauCfaGfGfacuuGfcCfaaggasasa | 1191 | TTTCCTTGGCAAGTCCTGATATT | 1326 |
| AD-1144246 | ususagguGfgAfAfCfcacagcagcuL96 | 1057 | asGfscugCfuGfUfgguuCfcAfccuaasusa | 1192 | TATTAGGTGGAACCACAGCAGCA | 1327 |
| AD-1144257 | gscsagguGfcAfCfUfuuuauaugauL96 | 1058 | asUfscauAfuAfAfaaguGfcAfccugcsusg | 1193 | CAGCAGGTGCACTTTTATATGAC | 1328 |
| AD-156639 | gsascaacUfgGfGfUfccuaacagcuL96 | 1059 | asGfscugUfuAfGfgacccCfaGfuugucsasu | 1194 | ATGACAACTGGGTCCTAACAGCT | 1329 |
| AD-1144284 | gscsugcuCfaUfGfCfcgucuaugauL96 | 1060 | asUfscauAfgAfCfggcaUfgAfgcagcsusg | 1195 | CAGCTGCTCATGCCGTCTATGAG | 1330 |
| AD-1144299 | gsasgcaaAfaAfCfAfugaugcaucuL96 | 1061 | asGfsaugCfaUfCfauguUfuUfugcucsasu | 1196 | ATGAGCAAAAACATGATGCATCC | 1331 |
| AD-1144313 | uscscgccCfuGfGfAfcauucgaauuL96 | 1062 | asAfsuucGfaAfUfguccAfgGfgcggasusg | 1197 | CATCCGCCCTGGACATTCGAATG | 1332 |
| AD-156712 | usgsggcaCfcCfUfGfaaaagacuauL96 | 1063 | asUfsaguCfuUfUfucagGfgUfgcccasusu | 1198 | AATGGGCACCCTGAAAAGACTAT | 1333 |
| AD-1144343 | usasucacCfuCfAfUfuauacacaauL96 | 1064 | asUfsuguGfuAfUfaaugAfgGfugauasgsu | 1199 | ACTATCACCTCATTATACACAAG | 1334 |
| AD-156748 | asasgccuGfgUfCfUfgaagcuguuuL96 | 1065 | asAfsacaGfcUfUfcagaCfcAfggcuusgsu | 1200 | ACAAGCCTGGTCTGAAGCTGTTT | 1335 |
| AD-1144365 | ususuuuaUfaCfAfUfgaagguuauuL96 | 1066 | asAfsuaaCfcUfUfcaugUfaUfaaaaascsa | 1201 | TGTTTTTATACATGAAGGTTATA | 1336 |
| AD-1144376 | asusacucAfuGfAfUfgcuggcuuuuL96 | 1067 | asAfsaagCfcAfGfcaucAfuGfaguausasa | 1202 | TTATACTCATGATGCTGGCTTTG | 1337 |
| AD-1144391 | ususgacaAfuGfAfCfauagcacuguL96 | 1068 | asCfsaguGfcUfAfugucAfuUfgucaasasg | 1203 | CTTTGACAATGACATAGCACTGA | 1338 |
| AD-1144850 | usgsauuaAfaUfUfGfaauaacaaauL96 | 1069 | asUfsuugUfuAfUfucaaUfuUfaaucasgsu | 1204 | ACTGATTAAATTGAATAACAAAG | 1339 |
| AD-156832 | asgsuuguAfaUfCfAfauagcaacauL96 | 1070 | asUfsguuGfcUfAfuugaUfuAfcaacusus u | 1205 | AAAGTTGTAATCAATAGCAACAT | 1340 |

TABLE 7-continued

Modified Sense and Antisense Strand Sequences of MASP2 dsRNA Agents

| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
|---|---|---|---|---|---|---|
| AD-1144424 | csasucacGfcCfUfAfuuugucugcuL96 | 1071 | asGfscagAfcAfAfauagGfcGfugaugsusu | 1206 | AACATCACGCCTATTTGTCTGCC | 1341 |
| AD-1144440 | gscscaagAfaAfAfGfaagcugaauuL96 | 1072 | asAfsuucAfgCfUfucuuUfuCfuuggcsasg | 1207 | CTGCCAAGAAAAGAAGCTGAATC | 1342 |
| AD-1144453 | asusccuuUfaUfGfAfggacagauguL96 | 1073 | asCfsaucUfgUfCfcucaUfaAfaggaususc | 1208 | GAATCCTTTATGAGGACAGATGA | 1343 |
| AD-1144466 | usgsacauUfgGfAfAfcugcaucuguL96 | 1074 | asCfsagaUfgCfAfguucCfaAfugucasusc | 1209 | GATGACATTGGAACTGCATCTGG | 1344 |
| AD-1144851 | usgsgaugGfgGfAfUfuaacccaaauL96 | 1075 | asUfsuugGfgUfUfaaucCfcCfauccasgsa | 1210 | TCTGGATGGGGATTAACCCAAAG | 1345 |
| AD-1144852 | asasggggUfuUfUfCfuugcuagaauL96 | 1076 | asUfsucuAfgCfAfagaaAfaCfcccuususg | 1211 | CAAAGGGGTTTTCTTGCTAGAAA | 1346 |
| AD-1144481 | asasucuaAfuGfUfAfugucgacauuL96 | 1077 | asAfsuguCfgAfCfauacAfuUfagauusus c | 1212 | GAAATCTAATGTATGTCGACATA | 1347 |
| AD-1144494 | asusaccgAfuUfGfUfugaccaucauL96 | 1078 | asUfsgauGfgUfCfaacaAfuCfgguausgsu | 1213 | ACATACCGATTGTTGACCATCAA | 1348 |
| AD-156962 | csasaaaaUfgUfAfCfugcugcauauL96 | 1079 | asUfsaugCfaGfCfaguaCfaUfuuuugsasu | 1214 | ATCAAAAATGTACTGCTGCATAT | 1349 |
| AD-1144522 | usasugaaAfaGfCfCfacccuauccuL96 | 1080 | asGfsgauAfgGfGfuggcUfuUfucauasusg | 1215 | CATATGAAAAGCCACCCTATCCA | 1350 |
| AD-1144853 | cscsaaggGfgAfAfGfuguaacugcuL96 | 1081 | asGfscagUfuAfCfacuuCfcCfcuuggsasu | 1216 | ATCCAAGGGGAAGTGTAACTGCT | 1351 |
| AD-1144534 | gscsuaacAfuGfCfUfuugugcugguL96 | 1082 | asCfscagCfaCfAfaagcAfuGfuuagcsasg | 1217 | CTGCTAACATGCTTTGTGCTGGC | 1352 |
| AD-1144854 | gscsuuagAfaAfGfUfgggggcaaguL96 | 1083 | asCfsuugCfcCfCfcacuUfuCfuaagcscsa | 1218 | TGGCTTAGAAAGTGGGGGCAAGG | 1353 |
| AD-1144548 | asgsgacaGfcUfGfCfagaggugacuL96 | 1084 | asGfsucaCfcUfCfugcaGfcUfguccusus g | 1219 | CAAGGACAGCTGCAGAGGTGACA | 1354 |
| AD-1144855 | ascsagcgGfaGfGfGfgcacugguguL96 | 1085 | asCfsaccAfgUfGfcccccUfcCfgcuguscsa | 1220 | TGACAGCGGAGGGGCACTGGTGT | 1355 |
| AD-1144565 | usgsuuucUfaGfAfUfagugaaacauL96 | 1086 | asUfsguuUfcAfCfuaucUfaGfaaacascsc | 1221 | GGTGTTTCTAGATAGTGAAACAG | 1356 |
| AD-1144578 | csasgagaGfgUfGfGfuuuguggggauL96 | 1087 | asUfscccAfcAfAfaccaCfcUfcucugsusu | 1222 | AACAGAGAGGTGGTTTGTGGGAG | 1357 |
| AD-1144856 | gsasggaaUfaGfUfGfuccuggggguuL96 | 1088 | asAfsccccCfaGfGfacacUfaUfuccucscsc | 1223 | GGGAGGAATAGTGTCCTGGGGTT | 1358 |
| AD-1144857 | gsusuccaUfgAfAfUfuguggggaauL96 | 1089 | asUfsuccCfcAfCfaauuCfaUfggaacscsc | 1224 | GGGTTCCATGAATTGTGGGGAAG | 1359 |
| AD-1144591 | asgscaggUfcAfGfUfauggagucuuL96 | 1090 | asAfsgacUfcCfAfuacuGfaCfcugcususc | 1225 | GAAGCAGGTCAGTATGGAGTCTA | 1360 |
| AD-1144604 | csusacacAfaAfAfGfuuauuaacuuL96 | 1091 | asAfsguuAfaUfAfacuuUfuGfuguagsasc | 1226 | GTCTACACAAAAGTTATTAACTA | 1361 |
| AD-1144614 | csusauauUfcCfCfUfggaucgagauL96 | 1092 | asUfscucGfaUfCfcaggGfaAfuauagsusu | 1227 | AACTATATTCCCTGGATCGAGAA | 1362 |

TABLE 7-continued

Modified Sense and Antisense Strand Sequences of MASP2 dsRNA Agents

| Duplex ID | Sense Sequence 5′ to 3′ | SEQ ID NO: | Antisense Sequence 5′ to 3′ | SEQ ID NO: | mRNA Target Sequence 5′ to 3′ | SEQ ID NO: |
|---|---|---|---|---|---|---|
| AD-1144858 | gsasacauAfaUfUfAfgugauuuuuL96 | 1093 | asAfsaaaAfuCfAfcuaaUfuAfuguucsusc | 1228 | GAGAACATAATTAGTGATTTTTA | 1363 |
| AD-1144631 | ususaacuUfgCfGfUfgucugcaguuL96 | 1094 | asAfscugCfaGfAfcacgCfaAfguuaasasa | 1229 | TTTTAACTTGCGTGTCTGCAGTC | 1364 |
| AD-1144640 | gsuscaagGfaUfUfCfuucauuuuuL96 | 1095 | asAfsaaaAfuGfAfagaaUfcCfuugacsusg | 1230 | CAGTCAAGGATTCTTCATTTTTA | 1365 |
| AD-1144654 | ususagaaAfuGfCfCfugugaagacuL96 | 1096 | asGfsucuUfcAfCfaggcAfuUfucuaasasa | 1231 | TTTTAGAAATGCCTGTGAAGACC | 1366 |
| AD-1144669 | cscsuuggCfaGfCfGfacguggcucuL96 | 1097 | asGfsagcCfaCfGfucgcUfgCfcaaggsusc | 1232 | GACCTTGGCAGCGACGTGGCTCG | 1367 |
| AD-1144682 | uscsgagaAfgCfAfUfucaucauuauL96 | 1098 | asUfsaauGfaUfGfaaugCfuUfcucgasgsc | 1233 | GCTCGAGAAGCATTCATCATTAC | 1368 |
| AD-157219 | usascuguGfgAfCfAfuggcaguuguL96 | 1099 | asCfsaacUfgCfCfauguCfcAfcaguasasu | 1234 | ATTACTGTGGACATGGCAGTTGT | 1369 |
| AD-1144859 | usgsuugcUfcCfAfCfccaaaaaaauL96 | 1100 | asUfsuuuUfuUfGfggugGfaGfcaacasasc | 1235 | GTTGTTGCTCCACCCAAAAAAAC | 1370 |
| AD-1144708 | asascagaCfuCfCfAfggugaggcuuL96 | 1101 | asAfsgccUfcAfCfcuggAfgUfcuguusus u | 1236 | AAAACAGACTCCAGGTGAGGCTG | 1371 |
| AD-1144718 | csusgcugUfcAfUfUfucuccacuuuL96 | 1102 | asAfsaguGfgAfGfaaauGfaCfagcagscsc | 1237 | GGCTGCTGTCATTTCTCCACTTG | 1372 |
| AD-157273 | usgsccagUfuUfAfAfuuccagccuuL96 | 1103 | asAfsggcUfgGfAfauuaAfaCfuggcasasg | 1238 | CTTGCCAGTTTAATTCCAGCCTT | 1373 |
| AD-1144860 | csusuaccCfaUfUfGfacucaaggguL96 | 1104 | asCfsccuUfg$_A$fGfucaaUfgGfguaagsgsc | 1239 | GCCTTACCCATTGACTCAAGGGG | 1374 |
| AD-1144745 | gsgsgacaUfa$_A$f$_A$fCfcacgagaguuL96 | 1105 | asAfscucUfcGfUfgguuUfaUfgucccscs u | 1240 | AGGGGACATAAACCACGAGAGTG | 1375 |
| AD-1144758 | gsusgacaGfuCfAfUfcuuugcccauL96 | 1106 | asUfsgggCfa$_A$f$_A$fgaugAfcUfgucacsusc | 1241 | GAGTGACAGTCATCTTTGCCCAC | 1376 |
| AD-1144771 | csascccaGfuGfUfAfaugucacuguL96 | 1107 | asCfsaguGfaCfAfuuac$_A$fcUfgggugsgs g | 1242 | CCCACCCAGTGTAATGTCACTGC | 1377 |
| AD-1144781 | usgscucaAfaUfUfAfcauuucauuuL96 | 1108 | as$_A$fsaug$_A$fa$_A$fUfguaaUfuUfgagcasgs u | 1243 | ACTGCTCAAATTACATTTCATTA | 1378 |
| AD-1144793 | ususaccuUfa$_A$f$_A$fAfagccagucuuL96 | 1109 | as$_A$fsgacUfgGfCfuuuuUfa$_A$fgguaasus g | 1244 | CATTACCTTAAAAAGCCAGTCTC | 1379 |
| AD-1144803 | uscsuuuuCfaUf$_A$fCfuggcuguuguL96 | 1110 | asCfsaacAfgCfCfaguaUfg$_A$faaagasgsa | 1245 | TCTCTTTTCATACTGGCTGTTGG | 1380 |
| AD-157398 | usgsgcauUfuCfUfGfuaaacugccuL96 | 1111 | asGfsgcaGfuUfUfacagAfaAfugccasasc | 1246 | GTTGGCATTTCTGTAAACTGCCT | 1381 |
| AD-157416 | cscsugucCfaUfGfCfucuuuguuuuL96 | 1112 | asAfsaacAfaAfGfagcaUfgGfacaggscsa | 1247 | TGCCTGTCCATGCTCTTTGTTTT | 1382 |
| AD-1144861 | ususuuaa$_A$fcUfUfGfuucuuauuguL96 | 1113 | asCfsaauAfaGfAfacaaGfuUfuaaaasasc | 1248 | G$_{TTTTTAAACTT}$GrTCTT$_A$TTG$_A$ | 1383 |

TABLE 8

MASP2 Single Dose Screens in Primary Cynomolgus Monkey Hepatocytes

| | Probe Detects Both MASP2 Isoforms | | | | Probe Detects Long MASP2 Isoform | | | | |
|---|---|---|---|---|---|---|---|---|---|
| | 10 nM Dose | | 0.1 nM Dose | | 10 nM Dose | | 0.1 nM Dose | | |
| Duplex | Avg % MASP2 mRNA Remaining | SD | Avg % MASP2 mRNA Remaining | SD | Avg % MASP2 mRNA Remaining | SD | Avg % MASP2 mRNA Remaining | SD | Cross-reactivity |
| AD-68438.1 | 76.4 | 8.1 | 84.7 | 11.5 | 5.7 | 1.2 | 47.1 | 8.9 | hcmr, long-specific |
| AD-68439.1 | 64.8 | 6.5 | 91.4 | 8.6 | 7.8 | 0.6 | 58.4 | 2.5 | hcmr, long-specific |
| AD-68440.1 | 79.4 | 4.8 | 80.6 | 11.1 | 5.8 | 0.5 | 30.5 | 5.2 | hcmr, long-specific |
| AD-68441.1 | 70.9 | 10.8 | 101.5 | 12.7 | 17.2 | 0.9 | 85.1 | 12.7 | hcmr, long-specific |
| AD-68442.1 | 65.4 | 7.7 | 104.7 | 11.2 | 10.1 | 1.4 | 83.0 | 10.4 | hcmr, long-specific |
| AD-68443.1 | 69.8 | 9.3 | 101.8 | 3.5 | 23.3 | 2.4 | 91.5 | 8.1 | hcmr, long-specific |
| AD-68444.1 | 64.4 | 6.7 | 72.5 | 8.0 | 6.2 | 0.8 | 15.8 | 1.5 | hcmr, long-specific |
| AD-68445.1 | 70.1 | 5.4 | 78.3 | 6.9 | 13.1 | 1.8 | 81.8 | 9.4 | hcmr, long-specific |
| AD-68446.1 | 83.4 | 7.8 | 94.8 | 10.2 | 58.8 | 6.4 | 102.6 | 8.6 | hcmr, long-specific |
| AD-68447.1 | 77.2 | 5.2 | 95.8 | 8.0 | 15.6 | 1.0 | 84.9 | 6.9 | hcmr, long-specific |
| AD-68448.1 | 76.0 | 5.9 | 104.7 | 36.7 | 14.1 | 0.9 | 75.7 | 7.2 | hcmr, long-specific |
| AD-68449.1 | 75.3 | 4.0 | 92.1 | 11.5 | 9.2 | 1.6 | 61.4 | 12.8 | hcmr, long-specific |
| AD-68450.1 | 75.9 | 4.2 | 104.0 | 13.5 | 11.0 | 1.1 | 60.5 | 8.1 | hcmr, long-specific |
| AD-68451.1 | 67.6 | 6.6 | 91.8 | 11.2 | 6.1 | 1.2 | 30.3 | 5.3 | hcmr, long-specific |
| AD-68452.1 | 68.3 | 3.5 | 82.1 | 5.2 | 15.7 | 1.5 | 64.6 | 11.2 | hcmr, long-specific |
| AD-68453.1 | 64.4 | 7.4 | 66.4 | 12.4 | 6.3 | 0.5 | 58.8 | 10.4 | hcmr, long-specific |
| AD-68454.1 | 66.7 | 4.9 | 88.1 | 7.9 | 11.0 | 3.2 | 79.8 | 6.6 | hcmr, long-specific |
| AD-68455.1 | 83.5 | 4.6 | 79.2 | 8.7 | 9.0 | 1.9 | 45.8 | 4.7 | hcmr, long-specific |
| AD-68456.1 | 79.1 | 12.1 | 99.1 | 6.7 | 16.8 | 1.9 | 89.4 | 7.9 | hcmr, long-specific |
| AD-68457.1 | 85.4 | 5.7 | 113.7 | 21.8 | 30.4 | 2.7 | 89.9 | 7.7 | hcmr, long-specific |
| AD-68458.1 | 72.2 | 10.3 | 98.6 | 16.2 | 15.8 | 3.3 | 91.6 | 11.3 | hcmr, long-specific |
| AD-68459.1 | 84.6 | 7.0 | 101.1 | 18.0 | 39.2 | 2.0 | 90.8 | 4.1 | hcmr, long-specific |
| AD-68460.1 | 1.5 | 0.3 | 15.9 | 4.5 | 5.5 | 1.0 | 33.7 | 6.6 | hc, shared |
| AD-68461.1 | 1.3 | 0.3 | 8.5 | 3.3 | 4.6 | 0.8 | 23.0 | 7.6 | hc, shared |
| AD-68462.1 | 3.9 | 0.7 | 36.2 | 11.5 | 13.6 | 0.8 | 64.0 | 12.4 | hc, shared |
| AD-68463.1 | 7.5 | 0.3 | 54.5 | 5.2 | 17.4 | 2.1 | 70.1 | 6.7 | hc, shared |
| AD-68464.1 | 4.0 | 0.3 | 37.9 | 5.6 | 8.5 | 0.7 | 58.2 | 5.7 | hc, shared |
| AD-68465.1 | 17.5 | 0.9 | 84.9 | 3.3 | 28.3 | 2.8 | 88.4 | 8.5 | hc, shared |
| AD-68466.1 | 14.8 | 2.8 | 81.1 | 11.4 | 26.0 | 3.4 | 79.0 | 7.9 | hc, shared |
| AD-68467.1 | 6.5 | 1.4 | 80.4 | 9.4 | 14.8 | 1.5 | 83.8 | 8.5 | hc, shared |
| AD-68468.1 | 1.9 | 0.3 | 22.0 | 3.6 | 7.0 | 1.5 | 46.9 | 5.0 | hc, shared |
| AD-68469.1 | 17.4 | 2.4 | 59.8 | 9.6 | 40.9 | 2.0 | 80.5 | 11.1 | hc, shared |
| AD-68470.1 | 5.3 | 1.2 | 44.2 | 6.7 | 15.4 | 2.7 | 60.6 | 8.1 | hc, shared |
| AD-68471.1 | 9.7 | 0.7 | 72.6 | 2.5 | 24.6 | 2.2 | 92.4 | 8.0 | hc, shared |
| AD-68472.1 | 65.5 | 6.3 | 91.5 | 9.9 | 82.1 | 8.1 | 102.0 | 2.9 | mr, shared |
| AD-68473.1 | 15.4 | 0.8 | 66.6 | 3.5 | 40.8 | 3.1 | 87.4 | 4.2 | mr, shared |
| AD-68474.1 | 103.5 | 6.8 | 95.6 | 9.1 | 103.2 | 10.4 | 98.2 | 12.4 | mr, shared |
| AD-68475.1 | 14.4 | 2.4 | 79.6 | 11.7 | 30.8 | 4.3 | 87.1 | 2.8 | mr, shared |
| AD-68476.1 | 78.0 | 10.0 | 87.4 | 4.5 | 91.6 | 3.3 | 93.5 | 3.8 | mr, shared |
| AD-68477.1 | 80.4 | 5.6 | 74.5 | 5.8 | 93.7 | 8.3 | 92.8 | 5.8 | mr, shared |
| AD-68478.1 | 16.5 | 3.2 | 85.5 | 12.3 | 41.0 | 4.0 | 89.2 | 5.5 | mr, shared |
| AD-68479.1 | 108.8 | 9.5 | 100.1 | 5.5 | 111.0 | 8.1 | 100.6 | 5.5 | mr, shared |

TABLE 8-continued

MASP2 Single Dose Screens in Primary Cynomolgus Monkey Hepatocytes

| | Probe Detects Both MASP2 Isoforms | | | | Probe Detects Long MASP2 Isoform | | | | |
|---|---|---|---|---|---|---|---|---|---|
| | 10 nM Dose | | 0.1 nM Dose | | 10 nM Dose | | 0.1 nM Dose | | |
| Duplex | Avg % MASP2 mRNA Remaining | SD | Avg % MASP2 mRNA Remaining | SD | Avg % MASP2 mRNA Remaining | SD | Avg % MASP2 mRNA Remaining | SD | Cross-reactivity |
| AD-68480.1 | 108.2 | 9.4 | 97.6 | 9.9 | 109.2 | 6.2 | 100.8 | 8.9 | mr, shared |
| AD-68481.1 | 102.0 | 7.5 | 86.7 | 7.5 | 99.5 | 7.6 | 95.2 | 8.8 | mr, shared |
| AD-68482.1 | 85.6 | 5.7 | 87.1 | 9.0 | 94.5 | 7.4 | 91.2 | 7.9 | mr, shared |
| AD-68483.1 | 101.6 | 13.8 | 88.3 | 11.0 | 105.7 | 6.6 | 93.0 | 3.8 | mr, shared |
| AD-1955 | 100.7 | 9.3 | | | 100.1 | 4.4 | | | |

TABLE 9

MASP2 Single Dose Screens in Primary Mouse Hepatocytes

| | Probe Detects Both MASP2 Isoforms | | | | |
|---|---|---|---|---|---|
| | 10 nM Dose | | 0.1 nM Dose | | |
| Duplex | Avg % MASP2 mRNA Remaining | SD | Avg % MASP2 mRNA Remaining | SD | Cross-reactivity |
| AD-68438.1 | 76.4 | 8.1 | 84.7 | 11.5 | hcmr,long-specific |
| AD-68439.1 | 64.8 | 6.5 | 91.4 | 8.6 | hcmr,long-specific |
| AD-68440.1 | 79.4 | 4.8 | 80.6 | 11.1 | hcmr,long-specific |
| AD-68441.1 | 70.9 | 10.8 | 101.5 | 12.7 | hcmr,long-specific |
| AD-68442.1 | 65.4 | 7.7 | 104.7 | 11.2 | hcmr,long-specific |
| AD-68443.1 | 69.8 | 9.3 | 101.8 | 3.5 | hcmr,long-specific |
| AD-68444.1 | 64.4 | 6.7 | 72.5 | 8.0 | hcmr,long-specific |
| AD-68445.1 | 70.1 | 5.4 | 78.3 | 6.9 | hcmr,long-specific |
| AD-68446.1 | 83.4 | 7.8 | 94.8 | 10.2 | hcmr,long-specific |
| AD-68447.1 | 77.2 | 5.2 | 95.8 | 8.0 | hcmr,long-specific |
| AD-68448.1 | 76.0 | 5.9 | 104.7 | 36.7 | hcmr,long-specific |
| AD-68449.1 | 75.3 | 4.0 | 92.1 | 11.5 | hcmr,long-specific |
| AD-68450.1 | 75.9 | 4.2 | 104.0 | 13.5 | hcmr,long-specific |
| AD-68451.1 | 67.6 | 6.6 | 91.8 | 11.2 | hcmr,long-specific |
| AD-68452.1 | 68.3 | 3.5 | 82.1 | 5.2 | hcmr,long-specific |
| AD-68453.1 | 64.4 | 7.4 | 66.4 | 12.4 | hcmr,long-specific |
| AD-68454.1 | 66.7 | 4.9 | 88.1 | 7.9 | hcmr,long-specific |
| AD-68455.1 | 83.5 | 4.6 | 79.2 | 8.7 | hcmr,long-specific |
| AD-68456.1 | 79.1 | 12.1 | 99.1 | 6.7 | hcmr,long-specific |
| AD-68457.1 | 85.4 | 5.7 | 113.7 | 21.8 | hcmr,long-specific |
| AD-68458.1 | 72.2 | 10.3 | 98.6 | 16.2 | hcmr,long-specific |
| AD-68459.1 | 84.6 | 7.0 | 101.1 | 18.0 | hcmr,long-specific |
| AD-68460.1 | 1.5 | 0.3 | 15.9 | 4.5 | hc,shared |
| AD-68461.1 | 1.3 | 0.3 | 8.5 | 3.3 | hc,shared |

TABLE 9-continued

MASP2 Single Dose Screens in Primary Mouse Hepatocytes

| | Probe Detects Both MASP2 Isoforms | | | | |
|---|---|---|---|---|---|
| | 10 nM Dose | | 0.1 nM Dose | | |
| Duplex | Avg % MASP2 mRNA Remaining | SD | Avg % MASP2 mRNA Remaining | SD | Cross-reactivity |
| AD-68462.1 | 3.9 | 0.7 | 36.2 | 11.5 | hc,shared |
| AD-68463.1 | 7.5 | 0.3 | 54.5 | 5.2 | hc,shared |
| AD-68464.1 | 4.0 | 0.3 | 37.9 | 5.6 | hc,shared |
| AD-68465.1 | 17.5 | 0.9 | 84.9 | 3.3 | hc,shared |
| AD-68466.1 | 14.8 | 2.8 | 81.1 | 11.4 | hc,shared |
| AD-68467.1 | 6.5 | 1.4 | 80.4 | 9.4 | hc,shared |
| AD-68468.1 | 1.9 | 0.3 | 22.0 | 3.6 | hc,shared |
| AD-68469.1 | 17.4 | 2.4 | 59.8 | 9.6 | hc,shared |
| AD-68470.1 | 5.3 | 1.2 | 44.2 | 6.7 | hc,shared |
| AD-68471.1 | 9.7 | 0.7 | 72.6 | 2.5 | hc,shared |
| AD-68472.1 | 65.5 | 6.3 | 91.5 | 9.9 | mr,shared |
| AD-68473.1 | 15.4 | 0.8 | 66.6 | 3.5 | mr,shared |
| AD-68474.1 | 103.5 | 6.8 | 95.6 | 9.1 | mr,shared |
| AD-68475.1 | 14.4 | 2.4 | 79.6 | 11.7 | mr,shared |
| AD-68476.1 | 78.0 | 10.0 | 87.4 | 4.5 | mr,shared |
| AD-68477.1 | 80.4 | 5.6 | 74.5 | 5.8 | mr,shared |
| AD-68478.1 | 16.5 | 3.2 | 85.5 | 12.3 | mr,shared |
| AD-68479.1 | 108.8 | 9.5 | 100.1 | 5.5 | mr,shared |
| AD-68480.1 | 108.2 | 9.4 | 97.6 | 9.9 | mr,shared |
| AD-68481.1 | 102.0 | 7.5 | 86.7 | 7.5 | mr,shared |
| AD-68482.1 | 85.6 | 5.7 | 87.1 | 9.0 | mr,shared |
| AD-68483.1 | 101.6 | 13.8 | 88.3 | 11.0 | mr,shared |
| AD-1955 | 100.7 | 9.3 | | | |

TABLE 10

MASP2 Single Dose Screens in Hep3B Cells

| | 10 nM Dose | | 0.1 nM Dose | |
|---|---|---|---|---|
| Duplex | Avg % MASP2 mRNA Remaining | SD | Avg % MASP2 mRNA Remaining | SD |
| AD-156804.1 | 29.6 | 3.4 | 109.4 | 12.5 |
| AD-156950.1 | 35.3 | 2.2 | 100.3 | 16.6 |
| AD-156927.1 | 37.9 | 5.7 | 115.5 | 9.9 |
| AD-156807.1 | 41.5 | 15.9 | 100.3 | 13.0 |
| AD-156581.1 | 41.6 | 7.9 | 102.3 | 25.0 |
| AD-156926.1 | 41.7 | 8.7 | 102.3 | 3.6 |
| AD-156921.1 | 43.8 | 8.4 | 75.7 | 9.5 |
| AD-156674.1 | 43.9 | 10.2 | 125.0 | 38.2 |
| AD-156889.1 | 44.1 | 2.6 | 104.3 | 19.8 |

TABLE 10-continued

| MASP2 Single Dose Screens in Hep3B Cells | | | | |
|---|---|---|---|---|
| | 10 nM Dose | | 0.1 nM Dose | |
| Duplex | Avg % MASP2 mRNA Remaining | SD | Avg % MASP2 mRNA Remaining | SD |
| AD-156853.1 | 44.4 | 7.7 | 114.5 | 21.5 |
| AD-156538.1 | 47.1 | 5.5 | 135.7 | 9.9 |
| AD-157227.1 | 48.1 | 13.0 | 101.5 | 16.7 |
| AD-156622.1 | 48.3 | 9.9 | 105.3 | 8.4 |
| AD-156964.1 | 48.6 | 12.4 | 99.3 | 6.4 |
| AD-156841.1 | 49.7 | 5.9 | 82.1 | 7.8 |
| AD-156571.1 | 49.9 | 8.8 | 96.5 | 44.5 |
| AD-156842.1 | 50.3 | 10.0 | 95.7 | 19.0 |
| AD-68457.2 | 51.8 | 14.0 | 139.9 | 48.9 |
| AD-156990.1 | 51.9 | 15.4 | 101.2 | 7.1 |
| AD-156929.1 | 52.5 | 6.1 | 101.7 | 11.9 |
| AD-157334.1 | 52.7 | 7.7 | 84.6 | 11.4 |
| AD-156923.1 | 53.1 | 13.0 | 93.5 | 7.8 |
| AD-156536.1 | 54.0 | 16.7 | 94.6 | 26.8 |
| AD-156535.1 | 55.7 | 7.2 | 119.8 | 35.4 |
| AD-156255.1 | 55.8 | 6.1 | 88.5 | 12.1 |
| AD-157093.1 | 56.6 | 7.3 | 97.3 | 7.4 |
| AD-156800.1 | 57.9 | 19.2 | 76.2 | 14.1 |
| AD-157371.1 | 58.6 | 3.4 | 95.2 | 11.3 |
| AD-156844.1 | 59.0 | 18.0 | 107.2 | 7.2 |
| AD-156852.1 | 59.1 | 5.4 | 105.8 | 6.6 |
| AD-156924.1 | 60.0 | 5.8 | 97.7 | 6.9 |
| AD-156725.1 | 60.3 | 5.5 | 92.3 | 15.0 |
| AD-156735.1 | 60.6 | 16.3 | 126.2 | 14.7 |
| AD-156583.1 | 60.7 | 20.4 | 107.2 | 21.2 |
| AD-156878.1 | 61.2 | 6.2 | 101.3 | 16.2 |
| AD-156892.1 | 62.8 | 13.3 | 106.1 | 17.2 |
| AD-156877.1 | 63.7 | 6.5 | 91.1 | 9.6 |
| AD-156845.1 | 64.1 | 5.9 | 103.7 | 4.6 |
| AD-156551.1 | 64.2 | 16.4 | 90.6 | 20.5 |
| AD-157229.1 | 64.6 | 15.9 | 92.9 | 18.7 |
| AD-157373.1 | 65.0 | 3.8 | 126.1 | 37.3 |
| AD-156584.1 | 65.1 | 5.4 | 103.7 | 16.3 |
| AD-156499.1 | 65.2 | 14.4 | 113.8 | 31.3 |
| AD-156965.1 | 65.7 | 18.5 | 108.3 | 5.3 |
| AD-156951.1 | 67.2 | 11.2 | 108.8 | 12.5 |
| AD-156829.1 | 67.7 | 19.7 | 104.0 | 8.9 |
| AD-157167.1 | 68.4 | 18.9 | 119.9 | 25.4 |
| AD-156922.1 | 68.5 | 15.9 | 102.3 | 5.1 |
| AD-156879.1 | 69.4 | 11.0 | 100.0 | 9.7 |
| AD-156588.1 | 69.5 | 9.7 | 94.1 | 13.1 |
| AD-156777.1 | 71.2 | 8.9 | 106.0 | 14.0 |
| AD-156917.1 | 72.0 | 7.9 | 76.0 | 15.9 |
| AD-157372.1 | 74.6 | 4.1 | 98.6 | 18.1 |
| AD-156729.1 | 74.8 | 29.7 | 91.8 | 31.6 |
| AD-156956.1 | 75.3 | 33.0 | 110.4 | 22.5 |
| AD-156854.1 | 75.8 | 11.3 | 101.3 | 7.1 |

TABLE 10-continued

| MASP2 Single Dose Screens in Hep3B Cells | | | | |
|---|---|---|---|---|
| | 10 nM Dose | | 0.1 nM Dose | |
| Duplex | Avg % MASP2 mRNA Remaining | SD | Avg % MASP2 mRNA Remaining | SD |
| AD-156544.1 | 75.8 | 7.0 | 102.6 | 15.6 |
| AD-156840.1 | 78.1 | 22.2 | 88.5 | 23.6 |
| AD-156550.1 | 78.5 | 20.8 | 107.0 | 43.9 |
| AD-157232.1 | 78.7 | 26.9 | 107.8 | 34.6 |
| AD-156577.1 | 79.0 | 9.3 | 107.2 | 23.8 |
| AD-156805.1 | 79.1 | 10.2 | 91.3 | 18.1 |
| AD-156850.1 | 79.2 | 9.6 | 114.5 | 13.7 |
| AD-156778.1 | 79.5 | 10.1 | 98.7 | 16.2 |
| AD-156572.1 | 80.0 | 17.3 | 127.6 | 12.0 |
| AD-156726.1 | 81.2 | 17.2 | 74.8 | 5.8 |
| AD-157059.1 | 82.4 | 15.9 | 76.4 | 18.6 |
| AD-156734.1 | 84.3 | 17.5 | 98.2 | 9.1 |
| AD-156508.1 | 84.7 | 11.8 | 90.5 | 4.3 |
| AD-156542.1 | 85.8 | 12.1 | 141.9 | 27.3 |
| AD-156545.1 | 86.8 | 9.0 | 100.6 | 6.6 |
| AD-156888.1 | 86.9 | 38.8 | 106.0 | 11.7 |
| AD-156974.1 | 87.3 | 14.8 | 102.4 | 8.7 |
| AD-156925.1 | 90.2 | 28.0 | 139.3 | 49.7 |
| AD-156589.1 | 91.3 | 17.4 | 115.6 | 7.5 |
| AD-157160.1 | 91.3 | 21.4 | 114.7 | 19.7 |
| AD-156621.1 | 91.8 | 26.1 | 86.1 | 21.5 |
| AD-157060.1 | 93.3 | 9.6 | 99.1 | 11.7 |
| AD-157378.1 | 94.7 | 8.7 | 94.5 | 1.2 |
| AD-156582.1 | 94.7 | 10.2 | 105.7 | 20.0 |
| AD-156846.1 | 96.2 | 9.4 | 98.1 | 14.5 |
| AD-156540.1 | 96.5 | 67.5 | 89.5 | 30.1 |
| AD-157234.1 | 96.7 | 4.8 | 114.0 | 12.8 |
| AD-156505.1 | 97.7 | 14.2 | 98.9 | 12.9 |
| AD-156591.1 | 98.1 | 32.9 | 101.3 | 21.8 |
| AD-156988.1 | 98.9 | 24.1 | 128.3 | 32.9 |
| AD-156843.1 | 99.8 | 20.9 | 104.7 | 13.4 |
| AD-156539.1 | 103.2 | 12.7 | 98.4 | 12.9 |
| AD-157061.1 | 125.8 | 15.9 | 91.8 | 13.1 |
| AD-156839.1 | 127.2 | 47.7 | 95.8 | 18.9 |
| AD-157486.1 | 128.6 | 14.4 | 110.3 | 28.9 |
| AD-156830.1 | 144.4 | 28.6 | 120.8 | 8.5 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

| MASP2 Sequences |
|---|
| SEQ ID NO: 1<br>>NM_006610.4 *Homo sapiens* mannan binding lectin serine peptidase 2 (MASP2) long isoform, mRNA<br>AGACCAGGCCAGGCCAGCTGGACGGGCACACCATGAGGCTGCTGACCCTCCTGGGCCTTCTGTGTGGCTCGGTGGCC<br>ACCCCCTTGGGCCCGAAGTGGCCTGAACCTGTGTTCGGGCGCCTGGCATCCCCCGGCTTTCCAGGGGAGTATGCCAA<br>TGACCAGGAGCGGCGCTGGACCCTGACTGCACCCCCCGGCTACCGCCTGCGCCTCTACTTCACCCACTTCGACCTGG<br>AGCTCTCCCACCTCTGCGAGTACGACTTCGTCAAGCTGAGCTCGGGGGCCAAGGTGCTGGCCACGCTGTGCGGGCAG<br>GAGAGCACAGACACGGAGCGGGCCCCTGGCAAGGACACTTTCTACTCGCTGGGCTCCAGCCTGGACATTACCTTCCG<br>CTCCGACTACTCCAACGAGAAGCCGTTCACGGGGTTCGAGGCCTTCTATGCAGCCGAGGACATTGACGAGTGCCAGG<br>TGGCCCCGGGAGAGGCGCCCACCTGCGACCACCACTGCCACAACCACCTGGGCGGTTTCTACTGCTCCTGCCGCGCA<br>GGCTACGTCCTGCACCGTAACAAGCGCACCTGCTCAGCCCTGTGCTCCGGCCAGGTCTTCACCCAGAGGTCTGGGGA<br>GCTCAGCAGCCCTGAATACCCACGGCCGTATCCCAAACTCTCCAGTTGCACTTACAGCATCAGCCTGGAGGAGGGGT<br>TCAGTGTCATTCTGGACTTTGTGGAGTCCTTCGATGTGGAGACACACCCTGAAACCCTGTGTCCCTACGACTTTCTC<br>AAGATTCAAACAGACAGAGAAGAACATGGCCCATTCTGTGGGAAGACATTGCCCCACAGGATTGAAACAAAAAGCAA<br>CACGGTGACCATCACCTTTGTCACAGATGAATCAGGAGACCACACAGGCTGGAAGATCCACTACACGAGCACAGCGC<br>AGCCTTGCCCTTATCCGATGGCGCCACCTAATGGCCACGTTTCACCTGTGCAAGCCAAATACATCCTGAAAGACAGC<br>TTCTCCATCTTTTGCGAGACTGGCTATGAGCTTCTGCAAGGTCACTTGCCCCTGAAATCCTTTACTGCAGTTTGTCA<br>GAAAGATGGATCTTGGGACCGGCCAATGCCCGCGTGCAGCATTGTTGACTGTGGCCCTCCTGATGATCTACCCAGTG |

-continued

MASP2 Sequences

GCCGAGTGGAGTACATCACAGGTCCTGGAGTGACCACCTACAAAGCTGTGATTCAGTACAGCTGTGAAGAGACCTTC
TACACAATGAAAGTGAATGATGGTAAATATGTGTGTGAGGCTGATGGATTCTGGACGAGCTCCAAAGGAGAAAAATC
ACTCCCAGTCTGTGAGCCTGTTTGTGGACTATCAGCCCGCACAACAGGAGGGCGTATATATGGAGGGCAAAAGGCAA
AACCTGGTGATTTTCCTTGGCAAGTCCTGATATTAGGTGGAACCACAGCAGCAGGTGCACTTTTATATGACAACTGG
GTCCTAACAGCTGCTCATGCCGTCTATGAGCAAAAACATGATGCATCCGCCCTGGACATTCGAATGGGCACCCTGAA
AAGACTATCACCTCATTATACACAAGCCTGGTCTGAAGCTGTTTTTATACATGAAGGTTATACTCATGATGCTGGCT
TTGACAATGACATAGCACTGATTAAATTGAATAACAAAGTTGTAATCAATAGCAACATCACGCCTATTTGTCTGCCA
AGAAAAGAAGCTGAATCCTTTATGAGGACAGATGACATTGGAACTGCATCTGGATGGGGATTAACCCAAAGGGGTTT
TCTTGCTAGAAATCTAATGTATGTCGACATACCGATTGTTGACCATCAAAAATGTACTGCTGCATATGAAAAGCCAC
CCTATCCAAGGGGAAGTGTAACTGCTAACATGCTTTGTGCTGGCTTAGAAAGTGGGGGCAAGGACAGCTGCAGAGGT
GACAGCGGAGGGGCACTGGTGTTTCTAGATAGTGAAACAGAGAGGTGGTTTGTGGGAGGAATAGTGTCCTGGGGTTC
CATGAATTGTGGGGAAGCAGGTCAGTATGGAGTCTACACAAAAGTTATTAACTATATTCCCTGGATCGAGAACATAA
TTAGTGATTTTTAACTTGCGTGTCTGCAGTCAAGGATTCTTCATTTTTAGAAATGCCTGTGAAGACCTTGGCAGCGA
CGTGGCTCGAGAAGCATTCATCATTACTGTGGACATGGCAGTTGTTGCTCCACCCAAAAAAACAGACTCCAGGTGAG
GCTGCTGTCATTTCTCCACTTGCCAGTTTAATTCCAGCCTTACCCATTGACTCAAGGGGACATAAACCACGAGAGTG
ACAGTCATCTTTGCCCACCCAGTGTAATGTCACTGCTCAAATTACATTTCATTACCTTAAAAAGCCAGTCTCTTTTC
ATACTGGCTGTTGGCATTTCTGTAAACTGCCTGTCCATGCTCTTTGTTTTTAAACTTGTTCTTATTGA

SEQ ID NO: 2
>Reverse complement of SEQ ID NO: 1
TCAATAAGAACAAGTTTAAAAACAAAGAGCATGGACAGGCAGTTTACAGAAATGCCAACAGCCAGTATGAAAAGAGA
CTGGCTTTTTAAGGTAATGAAATGTAATTTGAGCAGTGACATTACACTGGGTGGGCAAAGATGACTGTCACTCTCGT
GGTTTATGTCCCCTTGAGTCAATGGGTAAGGCTGGAATTAAACTGGCAAGTGGAGAAATGACAGCAGCCTCACCTGG
AGTCTGTTTTTTTGGGTGGAGCAACAACTGCCATGTCCACAGTAATGATGAATGCTTCTCGAGCCACGTCGCTGCCA
AGGTCTTCACAGGCATTTCTAAAAATGAAGAATCCTTGACTGCAGACACGCAAGTTAAAAATCACTAATTATGTTCT
CGATCCAGGGAATATAGTTAATAACTTTTGTGTAGACTCCATACTGACCTGCTTCCCCACAATTCATGGAACCCCAG
GACACTATTCCTCCCACAAACCACCTCTCTGTTTCACTATCTAGAAACACCAGTGCCCCTCCGCTGTCACCTCTGCA
GCTGTCCTTGCCCCCACTTTCTAAGCCAGCACAAAGCATGTTAGCAGTTACACTTCCCCTTGGATAGGGTGGCTTTT
CATATGCAGCAGTACATTTTTGATGGTCAACAATCGGTATGTCGACATACATTAGATTTCTAGCAAGAAAACCCCTT
TGGGTTAATCCCCATCCAGATGCAGTTCCAATGTCATCTGTCCTCATAAAGGATTCAGCTTCTTTTCTTGGCAGACA
AATAGGCGTGATGTTGCTATTGATTACAACTTTGTTATTCAATTTAATCAGTGCTATGTCATTGTCAAAGCCAGCAT
CATGAGTATAACCTTCATGTATAAAAACAGCTTCAGACCAGGCTTGTGTATAATGAGGTGATAGTCTTTTCAGGGTG
CCCATTCGAATGTCCAGGGCGGATGCATCATGTTTTTGCTCATAGACGGCATGAGCAGCTGTTAGGACCCAGTTGTC
ATATAAAAGTGCACCTGCTGCTGTGGTTCCACCTAATATCAGGACTTGCCAAGGAAAATCACCAGGTTTTGCCTTTT
GCCCTCCATATATACGCCCTCCTGTTGTGCGGGCTGATAGTCCACAAACAGGCTCACAGACTGGGAGTGATTTTTCT
CCTTTGGAGCTCGTCCAGAATCCATCAGCCTCACACACATATTTACCATCATTCACTTTCATTGTGTAGAAGGTCTC
TTCACAGCTGTACTGAATCACAGCTTTGTAGGTGGTCACTCCAGGACCTGTGATGTACTCCACTCGGCCACTGGGTA
GATCATCAGGAGGGCCACAGTCAACAATGCTGCACGCGGGCATTGGCCGGTCCCAAGATCCATCTTTCTGACAAACT
GCAGTAAAGGATTTCAGGGGCAAGTGACCTTGCAGAAGCTCATAGCCAGTCTCGCAAAAGATGGAGAAGCTGTCTTT
CAGGATGTATTTGGCTTGCACAGGTGAAACGTGGCCATTAGGTGGCGCCATCGGATAAGGGCAAGGCTGCGCTGTGC
TCGTGTAGTGGATCTTCCAGCCTGTGTGGTCTCCTGATTCATCTGTGACAAAGGTGATGGTCACCGTGTTGCTTTTT
GTTTCAATCCTGTGGGGCAATGTCTTCCCACAGAATGGGCCATGTTCTTCTCTGTCTGTTTGAATCTTGAGAAAGTC
GTAGGGACACAGGGTTTCAGGGTGTGTCTCCACATCGAAGGACTCCACAAAGTCCAGAATGACACTGAACCCCTCCT
CCAGGCTGATGCTGTAAGTGCAACTGGAGAGTTTGGGATACGGCCGTGGGTATTCAGGGCTGCTGAGCTCCCCAGAC
CTCTGGGTGAAGACCTGGCCGGAGCACAGGGCTGAGCAGGTGCGCTTGTTACGGTGCAGGACGTAGCCTGCGCGGCA
GGAGCAGTAGAAACCGCCCAGGTGGTTGTGGCAGTGGTGGTCGCAGGTGGGCGCCTCTCCCGGGGCCACCTGGCACT
CGTCAATGTCCTCGGCTGCATAGAAGGCCTCGAACCCCGTGAACGGCTTCTCGTTGGAGTAGTCGGAGCGGAAGGTA
ATGTCCAGGCTGGAGCCCAGCGAGTAGAAAGTGTCCTTGCCAGGGGCCCGCTCCGTGTCTGTGCTCTCCTGCCCGCA
CAGCGTGGCCAGCACCTTGGCCCCCGAGCTCAGCTTGACGAAGTCGTACTCGCAGAGGTGGGAGAGCTCCAGGTCGA
AGTGGGTGAAGTAGAGGCGCAGGCGGTAGCCGGGGGGTGCAGTCAGGGTCCAGCGCCGCTCCTGGTCATTGGCATAC
TCCCCTGGAAAGCCGGGGGATGCCAGGCGCCCGAACACAGGTTCAGGCCACTTCGGGCCCAAGGGGGTGGCCACCGA
GCCACACAGAAGGCCCAGGAGGGTCAGCAGCCTCATGGTGTGCCCGTCCAGCTGGCCTGGCCTGGTCT SEQ ID NO: 3
>NM_006610.3 *Homo sapiens* mannan binding lectin serine peptidase 2 (MASP2)
long isoform, mRNA
AGACCAGGCCAGGCCAGCTGGACGGGCACACCATGAGGCTGCTGACCCTCCTGGGCCTTCTGTGTGGCTCGGTGGCC
ACCCCCTTGGGCCCGAAGTGGCCTGAACCTGTGTTCGGGCGCCTGGCATCCCCCGGCTTTCCAGGGGAGTATGCCAA
TGACCAGGAGCGGCGCTGGACCCTGACTGCACCCCCCGGCTACCGCCTGCGCCTCTACTTCACCCACTTCGACCTGG
AGCTCTCCCACCTCTGCGAGTACGACTTCGTCAAGCTGAGCTCGGGGGCCAAGGTGCTGGCCACGCTGTGCGGGCAG
GAGAGCACAGACACGGAGCGGGCCCCTGGCAAGGACACTTTCTACTCGCTGGGCTCCAGCCTGGACATTACCTTCCG
CTCCGACTACTCCAACGAGAAGCCGTTCACGGGGTTCGAGGCCTTCTATGCAGCCGAGGACATTGACGAGTGCCAGG
TGGCCCCGGGAGAGGCGCCCACCTGCGACCACCACTGCCACAACCACCTGGGCGGTTTCTACTGCTCCTGCCGCGCA
GGCTACGTCCTGCACCGTAACAAGCGCACCTGCTCAGCCCTGTGCTCCGGCCAGGTCTTCACCCAGAGGTCTGGGGA
GCTCAGCAGCCCTGAATACCCACGGCCGTATCCCAAACTCTCCAGTTGCACTTACAGCATCAGCCTGGAGGAGGGGT
TCAGTGTCATTCTGGACTTTGTGGAGTCCTTCGATGTGGAGACACACCCTGAAACCCTGTGTCCCTACGACTTTCTC
AAGATTCAAACAGACAGAGAAGAACATGGCCCATTCTGTGGGAAGACATTGCCCCACAGGATTGAAACAAAAAGCAA
CACGGTGACCATCACCTTTGTCACAGATGAATCAGGAGACCACACAGGCTGGAAGATCCACTACACGAGCACAGCGC
AGCCTTGCCCTTATCCGATGGCGCCACCTAATGGCCACGTTTCACCTGTGCAAGCCAAATACATCCTGAAAGACAGC
TTCTCCATCTTTTGCGAGACTGGCTATGAGCTTCTGCAAGGTCACTTGCCCCTGAAATCCTTTACTGCAGTTTGTCA
GAAAGATGGATCTTGGGACCGGCCAATGCCCGCGTGCAGCATTGTTGACTGTGGCCCTCCTGATGATCTACCCAGTG
GCCGAGTGGAGTACATCACAGGTCCTGGAGTGACCACCTACAAAGCTGTGATTCAGTACAGCTGTGAAGAGACCTTC
TACACAATGAAAGTGAATGATGGTAAATATGTGTGTGAGGCTGATGGATTCTGGACGAGCTCCAAAGGAGAAAAATC
ACTCCCAGTCTGTGAGCCTGTTTGTGGACTATCAGCCCGCACAACAGGAGGGCGTATATATGGAGGGCAAAAGGCAA
AACCTGGTGATTTTCCTTGGCAAGTCCTGATATTAGGTGGAACCACAGCAGCAGGTGCACTTTTATATGACAACTGG
GTCCTAACAGCTGCTCATGCCGTCTATGAGCAAAAACATGATGCATCCGCCCTGGACATTCGAATGGGCACCCTGAA
AAGACTATCACCTCATTATACACAAGCCTGGTCTGAAGCTGTTTTTATACATGAAGGTTATACTCATGATGCTGGCT -continued

| MASP2 Sequences |
|---|

TTGACAATGACATAGCACTGATTAAATTGAATAACAAAGTTGTAATCAATAGCAACATCACGCCTATTTGTCTGCCA
AGAAAAGAAGCTGAATCCTTTATGAGGACAGATGACATTGGAACTGCATCTGGATGGGGATTAACCCAAAGGGGTTT
TCTTGCTAGAAATCTAATGTATGTCGACATACCGATTGTTGACCATCAAAAATGTACTGCTGCATATGAAAAGCCAC
CCTATCCAAGGGGAAGTGTAACTGCTAACATGCTTTGTGCTGGCTTAGAAAGTGGGGGCAAGGACAGCTGCAGAGGT
GACAGCGGAGGGGCACTGGTGTTTCTAGATAGTGAAACAGAGAGGTGGTTTGTGGGAGGAATAGTGTCCTGGGGTTC
CATGAATTGTGGGGAAGCAGGTCAGTATGGAGTCTACACAAAAGTTATTAACTATATTCCCTGGATCGAGAACATAA
TTAGTGATTTTTAACTTGCGTGTCTGCAGTCAAGGATTCTTCATTTTTAGAAATGCCTGTGAAGACCTTGGCAGCGA
CGTGGCTCGAGAAGCATTCATCATTACTGTGGACATGGCAGTTGTTGCTCCACCCAAAAAAACAGACTCCAGGTGAG
GCTGCTGTCATTTCTCCACTTGCCAGTTTAATTCCAGCCTTACCCATTGACTCAAGGGGACATAAACCACGAGAGTG
ACAGTCATCTTTGCCCACCCAGTGTAATGTCACTGCTCAAATTACATTTCATTACCTTAAAAGCCAGTCTCTTTTC
ATACTGGCTGTTGGCATTTCTGTAAACTGCCTGTCCATGCTCTTTGTTTTTAAACTTGTTCTTATTGAAAAAAAAAA
AAAAAAA

SEQ ID NO: 4
>Reverse complement of SEQ ID NO: 3
TTTTTTTTTTTTTTTTTCAATAAGAACAAGTTTAAAAACAAAGAGCATGGACAGGCAGTTTACAGAAATGCCAACAG
CCAGTATGAAAAGAGACTGGCTTTTAAGGTAATGAAATGTAATTTGAGCAGTGACATTACACTGGGTGGGCAAAGA
TGACTGTCACTCTCGTGGTTTATGTCCCCTTGAGTCAATGGGTAAGGCTGGAATTAAACTGGCAAGTGGAGAAATGA
CAGCAGCCTCACCTGGAGTCTGTTTTTTTGGGTGGAGCAACAACTGCCATGTCCACAGTAATGATGAATGCTTCTCG
AGCCACGTCGCTGCCAAGGTCTTCACAGGCATTTCTAAAAATGAAGAATCCTTGACTGCAGACACGCAAGTTAAAAA
TCACTAATTATGTTCTCGATCCAGGGAATATAGTTAATAACTTTTGTGTAGACTCCATACTGACCTGCTTCCCCACA
ATTCATGGAACCCCAGGACACTATTCCTCCCACAAACCACCTCTCTGTTTCACTATCTAGAAACACCAGTGCCCCTC
CGCTGTCACCTCTGCAGCTGTCCTTGCCCCCACTTTCTAAGCCAGCACAAAGCATGTTAGCAGTTACACTTCCCCTT
GGATAGGGTGGCTTTTCATATGCAGCAGTACATTTTTGATGGTCAACAATCGGTATGTCGACATACATTAGATTTCT
AGCAAGAAAACCCCTTTGGGTTAATCCCCATCCAGATGCAGTTCCAATGTCATCTGTCCTCATAAAGGATTCAGCTT
CTTTTCTTGGCAGACAAATAGGCGTGATGTTGCTATTGATTACAACTTTGTTATTCAATTTAATCAGTGCTATGTCA
TTGTCAAAGCCAGCATCATGAGTATAACCTTCATGTATAAAAACAGCTTCAGACCAGGCTTGTGTATAATGAGGTGA
TAGTCTTTTCAGGGTGCCCATTCGAATGTCCAGGGCGGATGCATCATGTTTTTGCTCATAGACGGCATGAGCAGCTG
TTAGGACCCAGTTGTCATATAAAAGTGCACCTGCTGCTGTGGTTCCACCTAATATCAGGACTTGCCAAGGAAAATCA
CCAGGTTTTGCCTTTTGCCCTCCATATATACGCCCTCCTGTTGTGCGGGCTGATAGTCCACAAACAGGCTCACAGAC
TGGGAGTGATTTTTCTCCTTTGGAGCTCGTCCAGAATCCATCAGCCTCACACACATATTTACCATCATTCACTTTCA
TTGTGTAGAAGGTCTCTTCACAGCTGTACTGAATCACAGCTTTGTAGGTGGTCACTCCAGGACCTGTGATGTACTCC
ACTCGGCCACTGGGTAGATCATCAGGAGGGCCACAGTCAACAATGCTGCACGCGGGCATTGGCCGGTCCCAAGATCC
ATCTTTCTGACAAACTGCAGTAAAGGATTTCAGGGGCAAGTGACCTTGCAGAAGCTCATAGCCAGTCTCGCAAAAGA
TGGAGAAGCTGTCTTTCAGGATGTATTTGGCTTGCACAGGTGAAACGTGGCCATTAGGTGGCGCCATCGGATAAGGG
CAAGGCTGCGCTGTGCTCGTGTAGTGGATCTTCCAGCCTGTGTGGTCTCCTGATTCATCTGTGACAAAGGTGATGGT
CACCGTGTTGCTTTTTGTTTCAATCCTGTGGGGCAATGTCTTCCCACAGAATGGGCCATGTTCTTCTCTGTCTGTTT
GAATCTTGAGAAAGTCTGTAGGGACACAGGGTTTCAGGGTGTGTCTCCACATCGAAGGACTCCACAAAGTCCAGAATG
ACACTGAACCCCTCCTCCAGGCTGATGCTGTAAGTGCAACTGGAGAGTTTGGGATACGGCCGTGGGTATTCAGGGCT
GCTGAGCTCCCCAGACCTCTGGGTGAAGACCTGGCCGGAGCACAGGGCTGAGCAGGTGCGCTTGTTACGGTGCAGGA
CGTAGCCTGCGCGGCAGGAGCAGTAGAAACCGCCCAGGTGGTTGTGGCAGTGGTGGTCGCAGGTGGGCGCCTCTCCC
GGGGCCACCTGGCACTCGTCAATGTCCTCGGCTGCATAGAAGGCCTCGAACCCCGTGAACGGCTTCTCGTTGGAGTA
GTCGGAGCGGAAGGTAATGTCCAGGCTGGAGCCCAGCGAGTAGAAAGTGTCCTTGCCAGGGGCCCGCTCCGTGTCTG
TGCTCTCCTGCCCGCACAGCGTGGCCAGCACCTTGGCCCCCGAGCTCAGCTTGACGAAGTCGTACTCGCAGAGGTGG
GAGAGCTCCAGGTCGAAGTGGGTGAAGTAGAGGCGCAGGCGGTAGCCGGGGGGTGCAGTCAGGGTCCAGCGCCGCTC
CTGGTCATTGGCATACTCCCCTGGAAAGCCGGGGGATGCCAGGCGCCCGAACACAGGTTCAGGCCACTTCGGGCCCA
AGGGGGTGGCCACCGAGCCACACAGAAGGCCCAGGAGGGTCAGCAGCCTCATGGTGTGCCCGTCCAGCTGGCCTGGC
CTGGTCT SEQ ID NO: 5
>NM_139208.2 *Homo sapiens* mannan binding lectin serine peptidase 2 (MASP2)
short isoform,
mRNAAGACCAGGCCAGGCCAGCTGGACGGGCACACCATGAGGCTGCTGACCCTCCTGGGCCTTCTGTGTGGCTCGGT
GGCCACCCCCTTGGGCCCGAAGTGGCCTGAACCTGTGTTCGGGCGCCTGGCATCCCCCGGCTTTCCAGGGGAGTATG
CCAATGACCAGGAGCGGCGCTGGACCCTGACTGCACCCCCCGGCTACCGCCTGCGCCTCTACTTCACCCACTTCGAC
CTGGAGCTCTCCCACCTCTGCGAGTACGACTTCGTCAAGCTGAGCTCGGGGGCCAAGGTGCTGGCCACGCTGTGCGG
GCAGGAGAGCACAGACACGGAGCGGGCCCCTGGCAAGGACACTTTCTACTCGCTGGGCTCCAGCCTGGACATTACCT
TCCGCTCCGACTACTCCAACGAGAAGCCGTTCACGGGGTTCGAGGCCTTCTATGCAGCCGAGGACATTGACGAGTGC
CAGGTGGCCCCGGGAGAGGCGCCCACCTGCGACCACCACTGCCACAACCACCTGGGCGGTTTCTACTGCTCCTGCCG
CGCAGGCTACGTCCTGCACCGTAACAAGCGCACCTGCTCAGAGCAGAGCCTCTAGCCTCCCCTGGAGCTCCGGCCTG
CCCAGCAGGTCAGAAGCCAGAGCCAGCCTGCTGGCCTCAGCTCCGGGTTGGGCTGAGATGGCTGTGCCCCAACTCCC
ATTCACCCACCATGGACCCAATAATAAACCTGGCCCCACCCCAAAAAAAAAAAAAAAAA SEQ ID NO: 6
Reverse Complement of SEQ ID NO: 5
TTTTTTTTTTTTTTTTTGGGGTGGGGCCAGGTTTATTATTGGGTCCATGGTGGGTGAATGGGAGTTGGGGCACAGC
CATCTCAGCCCAACCCGGAGCTGAGGCCAGCAGGCTGGCTCTGGCTTCTGACCTGCTGGGCAGGCCGGAGCTCCAGG
GGAGGCTAGAGGCTCTGCTCTGAGCAGGTGCGCTTGTTACGGTGCAGGACGTAGCCTGCGCGGCAGGAGCAGTAGAA
ACCGCCCAGGTGGTTGTGGCAGTGGTGGTCGCAGGTGGGCGCCTCTCCCGGGGCCACCTGGCACTCGTCAATGTCCT
CGGCTGCATAGAAGGCCTCGAACCCCGTGAACGGCTTCTCGTTGGAGTAGTCGGAGCGGAAGGTAATGTCCAGGCTG
GAGCCCAGCGAGTAGAAAGTGTCCTTGCCAGGGGCCCGCTCCGTGTCTGTGCTCTCCTGCCCGCACAGCGTGGCCAG
CACCTTGGCCCCCGAGCTCAGCTTGACGAAGTCGTACTCGCAGAGGTGGGAGAGCTCCAGGTCGAAGTGGGTGAAGT
AGAGGCGCAGGCGGTAGCCGGGGGGTGCAGTCAGGGTCCAGCGCCGCTCCTGGTCATTGGCATACTCCCCTGGAAAG
CCGGGGGATGCCAGGCGCCCGAACACAGGTTCAGGCCACTTCGGGCCCAAGGGGGTGGCCACCGAGCCACACAGAAG
GCCCAGGAGGGTCAGCAGCCTCATGGTGTGCCCGTCCAGCTGGCCTGGCCTGGTCT -continued

| MASP2 Sequences |
|---|

SEQ ID NO: 7
>NM_001003893.2 *Mus musculus* mannan binding lectin serine peptidase 2 (MASP2) long isoform, mRNA
AAAGGTGATAGGCGCTGGACCTGCAGAGCTAGGTGGCACACCATGAGGCTACTCATCTTCCTGGGTCTGCTGTGGAG
TTTGGTGGCCACACTTCTGGGTTCAAAGTGGCCTGAACCTGTATTCGGGCGCCTGGTGTCCCCTGGCTTCCCAGAGA
AGTATGCTGACCATCAAGATCGATCCTGGACACTGACTGCACCCCCTGGCTACCGCCTGCGCCTCTACTTCACCCAC
TTTGACCTGGAACTCTCTTACCGCTGCGAGTATGACTTTGTCAAGTTGAGCTCAGGGACCAAGGTGCTGGCCACACT
GTGTGGGCAGGAGAGTACAGACACTGAGCAGGCACCTGGCAATGACACCTTCTACTCACTGGGTCCCAGCCTAAAGG
TCACCTTCCACTCCGACTACTCCAATGAGAAGCCGTTCACAGGGTTTGAGGCCTTCTATGCAGCGGAGGATGTGGAT
GAATGCAGAGTGTCTCTGGGAGACTCAGTCCCTTGTGACCATTATTGCCACAACTACTTGGGCGGCTACTATTGCTC
CTGCAGAGCGGGCTACGTTCTCCACCAGAACAAGCACACGTGCTCAGCCCTTTGTTCAGGCCAGGTGTTCACAGGAA
GATCTGGGTATCTCAGTAGCCCTGAGTACCCACAGCCATACCCCAAGCTCTCCAGCTGCACCTACAGCATCCGCCTG
GAGGACGGCTTCAGTGTCATCCTGGACTTCGTGGAGTCCTTCGATGTGGAGACGCACCCTGAAGCCCAGTGCCCCTA
TGACTCCCTCAAGATTCAAACAGACAAGGGGGAACACGGCCCATTTTGTGGGAAGACGCTGCCTCCCAGGATTGAAA
CTGACAGCCACAAGGTGACCATCACCTTTGCCACTGACGAGTCGGGGAACCACACAGGCTGGAAGATACACTACACA
AGCACAGCACGGCCCTGCCCTGATCCAACGGCGCCACCTAATGGCAGCATTTCACCTGTGCAAGCCATATATGTCCT
GAAGGACAGGTTTTCTGTCTTCTGCAAGACAGGCTTCGAGCTTCTGCAAGGTTCTGTCCCCCTGAAATCATTCACTG
CTGTCTGTCAGAAAGATGGATCTTGGGACCGGCCGATGCCAGAGTGCAGCATTATTGATTGTGGCCCTCCTGATGAC
CTACCCAATGGCCATGTGGACTATATCACAGGCCCTGAAGTGACTACCTACAAAGCTGTGATTCAGTACAGCTGTGA
AGAGACTTTCTACACAATGAGCAGCAATGGTAAATATGTGTGTGAGGCTGATGGATTCTGGACGAGCTCCAAAGGAG
AAAAACTCCCCCCGGTTTGTGAGCCTGTTTGTGGGCTGTCCACACACACTATAGGAGGACGCATAGTTGGAGGGCAG
CCTGCAAAGCCTGGTGACTTTCCTTGGCAAGTCTTGTTGCTGGGTCAAACTACAGCAGCAGCAGGTGCACTTATACA
TGACAATTGGGTCCTAACAGCCGCTCATGCTGTATATGAGAAAAGAATGGCAGCGTCCTCCCTGAACATCCGAATGG
GCATCCTCAAAAGGCTCTCACCTCATTACACTCAAGCCTGGCCCGAGGAAATCTTTATACATGAAGGCTACACTCAC
GGTGCTGGTTTTGACAATGATATAGCATTGATTAAACTCAAGAACAAAGTCACAATCAACGGAAGCATCATGCCTGT
TTGCCTACCGCGAAAAGAAGCTGCATCCTTAATGAGAACAGACTTCACTGGAACTGTGGCTGGCTGGGGGTTAACCC
AGAAGGGGCTTCTTGCTAGAAACCTAATGTTTGTGGACATACCAATTGCTGACCACCAAAAATGTACCGCCGTGTAT
GAAAAGCTCTATCCAGGAGTAAGAGTAAGCGCTAACATGCTCTGTGCTGGCTTAGAGACTGGTGGCAAGGACAGCTG
CAGAGGTGACAGTGGGGGGCATTAGTGTTTCTAGATAATGAGACACAGCGATGGTTTGTGGGAGGAATAGTTTCCT
GGGGTTCCATTAATTGTGGGGCGGCAGACCAGTATGGGGTCTACACAAAAGTCATCAACTATATTCCCTGGATTGAG
AACATAATAAGTAATTTCTAATTTGCATCGTCCAATCATTGTTCCTCATATCGCCAAGTACCTGGGAAGCTTAGTAA
CAAACCTAAGAATGACAGCCTACCCCAAAATCAGAGCAGGTGAGATTGTTACAGGTCCAAACACTTGCCAATATCAG
CTTTGATTTGTGTTTAACAGTGCTTGGCCAACCCCCAACACAGAAAAAACAAGTTGTATTTGATTCCCTACAATCTA
CTTATTTTATACTGGCTGTTTCCATTTCTGGCCAACAAAGGGCTTGTTGTGTCTAGTGTGTAGATTTGGTCTTAATG
AGCTCAGAAAGTGCTCTTACTTTCTGAGTAACTTCTGAGTGGTTCCAGAATACCTTTTGGAAGGTAAGCGGAAAGCA
GGTGTGTGACCTTCACATTAGATCAGCTATTAAATTAACACCAAGTCCATTCCAGAATATTGGGATATAGGCATGTT
CTACCAGATTCACCAAATTGTCAGATAAAAAGAACACGAAACAGCATTTTACCCTTTACAAGGGCAATTTAGCAAAT
CATTCCAAAAACCTTAACAGGTGTTTCACTATACCCAGCCCACTTTTCTTAGGTGAGCGTTGGGCTCAGGGAAGTCA
ACCGTAACTGTACAAGGTACAGTCATTTGCTTATGTATCAAAAACAGTAAGTTATCCTGAAATAAACTGCTCTTCTG
CTAAGATGCTGACCTTAAAGGTCATGTTTGATTTTAACTGGCTCTTCCAACAAGGCAAGACAGGGTGCCTCAAGATG
GGGAAATAGCTGGCCTACAACTCATTTACACCAATTCTGGGATTAAAAGCATGGGCCACCACACCCACCTGGAGACT
CAAATTTTAAAGGATGAAAATGCTATATTGCATCTTCCCACATAAGTCACCTTAACTTTTCTAGCATTGTCATGATA
TAGAATTTTTTTTTCTTCCAGTAAGACTCCAGACACTAAACTGTTGGTGGCAAGAAAA SEQ ID NO: 8
Reverse Complement of SEQ ID NO: 7
TTTTCTTGCCACCAACAGTTTAGTGTCTGGAGTCTTACTGGAAGAAAAAAAAATTCTATATCATGACAATGCTAGAA
AAGTTAAGGTGACTTATGTGGGAAGATGCAATATAGCATTTTCATCCTTTAAAATTTGAGTCTCCAGGTGGGTGTGG
TGGCCCATGCTTTTAATCCCAGAATTGGTGTAAATGAGTTGTAGGCCAGCTATTTCCCCATCTTGAGGCACCCTGTC
TTGCCTTGTTGGAAGAGCCAGTTAAAATCAAACATGACCTTTAAGGTCAGCATCTTAGCAGAAGAGCAGTTTATTTC
AGGATAACTTACTGTTTTTGATACATAAGCAAATGACTGTACCTTGTACAGTTACGGTTGACTTCCCTGAGCCCAAC
GCTCACCTAAGAAAAGTGGGCTGGGTATAGTGAAACACCTGTTAAGGTTTTTGGAATGATTTGCTAAATTGCCCTTG
TAAAGGGTAAAATGCTGTTTCGTGTTCTTTTTATCTGACAATTTGGTGAATCTGGTAGAACATGCCTATATCCCAAT
ATTCTGGAATGGACTTGGTGTTAATTTAATAGCTGATCTAATGTGAAGGTCACACACCTGCTTTCCGCTTACCTTCC
AAAAGGTATTCTGGAACCACTCAGAAGTTACTCAGAAAGTAAGAGCACTTTCTGAGCTCATTAAGACCAAATCTACA
CACTAGACACAACAAGCCCTTTGTTGGCCAGAAATGGAAACAGCCAGTATAAAATAAGTAGATTGTAGGGAATCAAA
TACAACTTGTTTTTTCTGTGTTGGGGGTTGGCCAAGCACTGTTAAACACAAATCAAAGCTGATATTGGCAAGTGTTT
GGACCTGTAACAATCTCACCTGCTCTGATTTTGGGGTAGGCTGTCATTCTTAGGTTTGTTACTAAGCTTCCCAGGTA
CTTGGCGATATGAGGAACAATGATTGGACGATGCAAATTAGAAATTACTTATTATGTTCTCAATCCAGGGAATATAG
TTGATGACTTTTGTGTAGACCCCATACTGGTCTGCCGCCCCACAATTAATGGAACCCCAGGAAACTATTCCTCCCAC
AAACCATCGCTGTGTCTCATTATCTAGAAACACTAATGCCCCCCCACTGTCACCTCTGCAGCTGTCCTTGCCACCAG
TCTCTAAGCCAGCACAGAGCATGTTAGCGCTTACTCTTACTCCTGGATAGAGCTTTTCATACACGGCGGTACATTTT
TGGTGGTCAGCAATTGGTATGTCCACAAACATTAGGTTTCTAGCAAGAAGCCCCTTCTGGGTTAACCCCCAGCCAGC
CACAGTTCCAGTGAAGTCTGTTCTCATTAAGGATGCAGCTTCTTTTCGCGGTAGGCAAACAGGCATGATGCTTCCGT
TGATTGTGACTTTGTTCTTGAGTTTAATCAATGCTATATCATTGTCAAAACCAGCACCGTGAGTGTAGCCTTCATGT
ATAAAGATTTCCTCGGGCCAGGCTTGAGTGTAATGAGGTGAGAGCCTTTTGAGGATGCCCATTCGGATGTTCAGGGA
GGACGCTGCCATTCTTTTCTCATATACAGCATGAGCGGCTGTTAGGACCCAATTGTCATGTATAAGTGCACCTGCTG
CTGCTGTAGTTTGACCCAGCAACAAGACTTGCCAAGGAAAGTCACCAGGCTTTGCAGGCTGCCCTCCAACTATGCGT
CCTCCTATAGTGTGTGTGGACAGCCCACAAACAGGCTCACAAACCGGGGGGAGTTTTTCTCCTTTGGAGCTCGTCCA
GAATCCATCAGCCTCACACACATATTTACCATTGCTGCTCATTGTGTAGAAAGTCTCTTCACAGCTGTACTGAATCA
CAGCTTTGTAGGTAGTCACTTCAGGGCCTGTGATATAGTCCACATGGCCATTGGGTAGGTCATCAGGAGGGCCACAA
TCAATAATGCTGCACTCTGGCATCGGCCGGTCCCAAGATCCATCTTTCTGACAGACAGCAGTGAATGATTTCAGGGG
GACAGAACCTTGCAGAAGCTCGAAGCCTGTCTTGCAGAAGACAGAAAACCTGTCCTTCAGGACATATATGGCTTGCA
CAGGTGAAATGCTGCCATTAGGTGGCGCCGTTGGATCAGGGCAGGGCCGTGCTGTGCTTGTGTAGTGTATCTTCCAG
CCTGTGTGGTTCCCCGACTCGTCAGTGGCAAAGGTGATGGTCACCTTGTGGCTGTCAGTTTCAATCCTGGGAGGCAG
CGTCTTCCCACAAAATGGGCCGTGTTCCCCCTTGTCTGTTTGAATCTTGAGGGAGTCATAGGGGCACTGGGCTTCAG
GGTGCGTCTCCACATCGAAGGACTCCACGAAGTCCAGGATGACACTGAAGCCGTCCTCCAGGCGGATGCTGTAGGTG -continued MASP2 Sequences CAGCTGGAGAGCTTGGGGTATGGCTGTGGGTACTCAGGGCTACTGAGATACCCAGATCTTCCTGTGAACACCTGGCC
TGAACAAAGGGCTGAGCACGTGTGCTTGTTCTGGTGGAGAACGTAGCCCGCTCTGCAGGAGCAATAGTAGCCGCCCA
AGTAGTTGTGGCAATAATGGTCACAAGGGACTGAGTCTCCCAGAGACACTCTGCATTCATCCACATCCTCCGCTGCA
TAGAAGGCCTCAAACCCTGTGAACGGCTTCTCATTGGAGTAGTCGGAGTGGAAGGTGACCTTTAGGCTGGGACCCAG
TGAGTAGAAGGTGTCATTGCCAGGTGCCTGCTCAGTGTCTGTACTCTCCTGCCCACACAGTGTGGCCAGCACCTTGG
TCCCTGAGCTCAACTTGACAAAGTCATACTCGCAGCGGTAAGAGAGTTCCAGGTCAAAGTGGGTGAAGTAGAGGCGC
AGGCGGTAGCCAGGGGGTGCAGTCAGTGTCCAGGATCGATCTTGATGGTCAGCATACTTCTCTGGGAAGCCAGGGGA
CACCAGGCGCCCGAATACAGGTTCAGGCCACTTTGAACCCAGAAGTGTGGCCACCAAACTCCACAGCAGACCCAGGA
AGATGAGTAGCCTCATGGTGTGCCACCTAGCTCTGCAGGTCCAGCGCCTATCACCTTT SEQ ID NO: 9
>NM_010767.3 *Mus musculus* mannan binding lectin serine peptidase 2 (MASP2)
short isoform, mRNA
AAAGGTGATAGGCGCTGGACCTGCAGAGCTAGGTGGCACACCATGAGGCTACTCATCTTCCTGGGTCTGCTGTGGAG
TTTGGTGGCCACACTTCTGGGTTCAAAGTGGCCTGAACCTGTATTCGGGCGCCTGGTGTCCCCTGGCTTCCCAGAGA
AGTATGCTGACCATCAAGATCGATCCTGGACACTGACTGCACCCCCTGGCTACCGCCTGCGCCTCTACTTCACCCAC
TTTGACCTGGAACTCTCTTACCGCTGCGAGTATGACTTTGTCAAGTTGAGCTCAGGGACCAAGGTGCTGGCCACACT
GTGTGGGCAGGAGAGTACAGACACTGAGCAGGCACCTGGCAATGACACCTTCTACTCACTGGGTCCCAGCCTAAAGG
TCACCTTCCACTCCGACTACTCCAATGAGAAGCCGTTCACAGGGTTTGAGGCCTTCTATGCAGCGGAGGATGTGGAT
GAATGCAGAGTGTCTCTGGGAGACTCAGTCCCTTGTGACCATTATTGCCACAACTACTTGGGCGGCTACTATTGCTC
CTGCAGAGCGGGCTACGTTCTCCACCAGAACAAGCACACGTGCTCAGAGCAGAGCCTCTAAACCTCCCTCAGCAACA
GCCCGCCCACCCCAGTGAGTCAGATACCAGTCAGTACATGCCCACACGATGCTGCTCTGTCAGGCTGGAATGACTGC
CAGCTACAGCACCCATTCACCTTAACCATGACAATAATAAACCTGCCTCCG SEQ ID NO: 10
Reverse Complement of SEQ ID NO: 9
CGGAGGCAGGTTTATTATTGTCATGGTTAAGGTGAATGGGTGCTGTAGCTGGCAGTCATTCCAGCCTGACAGAGCAG
CATCGTGTGGGCATGTACTGACTGGTATCTGACTCACTGGGGTGGGCGGGCTGTTGCTGAGGGAGGTTTAGAGGCTC
TGCTCTGAGCACGTGTGCTTGTTCTGGTGGAGAACGTAGCCCGCTCTGCAGGAGCAATAGTAGCCGCCCAAGTAGTT
GTGGCAATAATGGTCACAAGGGACTGAGTCTCCCAGAGACACTCTGCATTCATCCACATCCTCCGCTGCATAGAAGG
CCTCAAACCCTGTGAACGGCTTCTCATTGGAGTAGTCGGAGTGGAAGGTGACCTTTAGGCTGGGACCCAGTGAGTAG
AAGGTGTCATTGCCAGGTGCCTGCTCAGTGTCTGTACTCTCCTGCCCACACAGTGTGGCCAGCACCTTGGTCCCTGA
GCTCAACTTGACAAAGTCATACTCGCAGCGGTAAGAGAGTTCCAGGTCAAAGTGGGTGAAGTAGAGGCGCAGGCGGT
AGCCAGGGGGTGCAGTCAGTGTCCAGGATCGATCTTGATGGTCAGCATACTTCTCTGGGAAGCCAGGGGACACCAGG
CGCCCGAATACAGGTTCAGGCCACTTTGAACCCAGAAGTGTGGCCACCAAACTCCACAGCAGACCCAGGAAGATGAG
TAGCCTCATGGTGTGCCACCTAGCTCTGCAGGTCCAGCGCCTATCACCTTT SEQ ID NO: 11
>XM_005544812.2 *Macaca fascicularis* mannan binding lectin serine peptidase 2
(MASP2) long isoform, mRNA
CAGAGTCAGGGAGGCTGGGGGCAGGGGCAGGTCACTGGACAAACAGATCAAAGGTGAGACCAGTGTAGGGCTGCAGA
CCAGGCCAGGCCAGCTGGACGGGCACACCATGAGGCTGCTGACCCTCCTGGGCCTGCTGTGTGGCTCGGTGGCCACC
CCCTTGGGCCCGAAGTGGCCTGAACCTGTGTTTGGGCGCCTGGCATCCCCTGGCTTTCCAGGGGAGTACGCCAATGA
CCAGGAGCGGCGCTGGACCCTGACCGCACCCCCCGGTTACCGCCTGCGCCTCTACTTCACCCACTTTGACCTGGAGC
TCTCCCACCTCTGCGAGTACGACTTCGTCAAGCTGAGCTCGGGGGCCAAGGTGCTGGCCACGCTGTGTGGGCATGAG
AGCACAGACACGGAGCGGGCCCCTGGCAACGACACCTTCTACTCGCTGGGCTCCAGCCTGGACATTACCTTCCGCTC
CGACTACTCCAACGAGAAGCCGTTCACAGGGTTCGAGGCCTTCTACGCAGCCGAGGACATTGACGAGTGCCAGGTGG
CCCCGGGAGAGGCGCCCGCCTGCGACCACCACTGCCACAACCACCTGGGTGGTTTCTACTGCTCCTGCCGTGTAGGC
TACATCCTGCACCGTAACAAGCGCACCTGCTCAGCCCTGTGCTCCGGCCAGGTCTTCACCCAGCGGTCTGGGGAGCT
CAGCAGCCCTGAATACCCACAGCCGTACCCCAAACTCTCCAGTTGTACTTACAGCATCCGCCTGGAGGAGGGGTTCA
GTGTCATTCTGGACTTTGTGGAGTCCTTCGATGTGGAGACGCACCCTGAAACCCTGTGTCCCTACGACTTTCTCAAG
ATTCAAATAGACAGTGAAGAACACGGCCCGTTCTGTGGGAAGACATTGCCCCGCAGGATTGAAACAAAAAGCAACAC
GGTGACCATCACCTTTGTCACAGATGAGTCAGGAGACCACACAGGCTGGAAGATCCACTACACGAGCACAGCGCAGC
CTTGCCCTTATCCGATGGCGCCACCTAATGGCCACCTTTCACCTGTGCAAGCCAAATACATCCTGAAAGACAGCTTC
TCCATCTTTTGCGAGCCTGGCTATGAGCTTCTGCAAGGTCACTTGCCCCTGAAATCATTTGCCGCAGTTTGTCAGAA
AGACGGATCTTGGGACCAGCCAATGCCCTCGTGCAGCATTGTTGACTGTGGCCCTCCTGATGATCTACCCAGTGGCC
GAGTGGAGTACATCACAGGTCCTGAAGTGACCACCTACAAAGCTGTGATTCAGTACAGCTGTGAAGAGACCTTCTAC
ACAATGAAAGTGAATGATGGTAAATATGTGTGTGAGGCTGATGGATTCTGGACGAGCTCCAAAGGAGAAAGATCACC
GCCAGTCTGTGAGCCTGTTTGTGGACTATCAGCCCGTACAACAGGAGGGCGTATATATGGAGGGCAAAAGGCAAAAC
CTGGTGATTTTCCTTGGCAAGTCCTGATATTAGGTGGAAGCACAGCAGCAGGTGCACTTTTATATGACAACTGGGTC
CTCACAGCTGCTCATGCCATATATGAGCAAAAACATGATGCATCCTCCCTGGACATTCGATTGGGCGCCCTGAAGAG
ACTATCGCCTCATTATACACAAGCCTGGGCTGAAGCTGTTTTTATACATGAAGGTTATACTCATGATGCTGGCTTTG
ACAATGACATAGCACTGATTAAATTGAATAACAAAGTTGTAATCAATAGCAACATCACGCCTATTTGTCTGCCAAGA
AAAGAAGCTGAATCCTTTATGAGGACAGATGACATTGGAACTGCATCTGGATGGGGATTAACCCAAAGAGGCCTTCT
TGCTAGAAATCTAATGTATGTCGACATACCAATTGTTGACCATCAAAAATGTACTGCTGCATATGAAAAGCCACCCT
ATTCAGGGGGAAGTGTAACTGCTAACATGCTTTGCGCTGGCTTAGAAAGTGGGGGCAAGGACAGCTGCAGAGGTGAC
AGCGGAGGGGCACTGGTGTTTCTAGATAATGAAACACAGAGGTGGTTTGTGGGAGGAATAGTGTCCTGGGGTTCCAT
GAATTGTGGGGAAGCAGGTCAGTACGGAGTCTATACAAAAGTCATTAACTATATTCCCTGGATCAAGAACATAATTA
GTAATTTTTAATTCGCATGTCTGCAGTCAGTCAAGGATTCCTCATTTTTAGAAATGCCTGTGAAGACCTTGGCAGCA
ACGTGACCTGAGAAGCATTAATCATTACTATGAACATGGCAGTTGTTGCTCCACCCAAAAAACAGACTCCAGGTGAG
ACTGCTGTCGTTTCTCCACTTACCAGTTTAATTCCAACCTTACCCACTGACTCAAGGGGACATAAGCTACGAGTGAT
AGTCACCTTTGCCAACCCAATGTAATGTGACTGCTCAAATTACATTTTGTTACTTTAAAAGGCCAGTCTCTTTTCAT
ACTGGCTGTTGGCATTTCTGTGAACTGCCTGTCCATGGTCTTTGACTGTTTTTAAACTTGTTCTTATTGATCTCTGT
AAGTGCTTTATATATTATAGCAGTATTGATTCAA -continued MASP2 Sequences SEQ ID NO: 12
Reverse Complement of SEQ ID NO: 11
TTGAATCAATACTGCTATAATATATAAAGCACTTACAGAGATCAATAAGAACAAGTTTAAAAACAGTCAAAGACCAT
GGACAGGCAGTTCACAGAAATGCCAACAGCCAGTATGAAAAGAGACTGGCCTTTTAAAGTAACAAAATGTAATTTGA
GCAGTCACATTACATTGGGTTGGCAAAGGTGACTATCACTCGTAGCTTATGTCCCCTTGAGTCAGTGGGTAAGGTTG
GAATTAAACTGGTAAGTGGAGAAACGACAGCAGTCTCACCTGGAGTCTGTTTTTTGGGTGGAGCAACAACTGCCATG
TTCATAGTAATGATTAATGCTTCTCAGGTCACGTTGCTGCCAAGGTCTTCACAGGCATTTCTAAAAATGAGGAATCC
TTGACTGACTGCAGACATGCGAATTAAAAATTACTAATTATGTTCTTGATCCAGGGAATATAGTTAATGACTTTTGT
ATAGACTCCGTACTGACCTGCTTCCCCACAATTCATGGAACCCCAGGACACTATTCCTCCCACAAACCACCTCTGTG
TTTCATTATCTAGAAACACCAGTGCCCCTCCGCTGTCACCTCTGCAGCTGTCCTTGCCCCCACTTTCTAAGCCAGCG
CAAAGCATGTTAGCAGTTACACTTCCCCCTGAATAGGGTGGCTTTTCATATGCAGCAGTACATTTTTGATGGTCAAC
AATTGGTATGTCGACATACATTAGATTTCTAGCAAGAAGGCCTCTTTGGGTTAATCCCCATCCAGATGCAGTTCCAA
TGTCATCTGTCCTCATAAAGGATTCAGCTTCTTTTCTTGGCAGACAAATAGGCGTGATGTTGCTATTGATTACAACT
TTGTTATTCAATTTAATCAGTGCTATGTCATTGTCAAAGCCAGCATCATGAGTATAACCTTCATGTATAAAAACAGC
TTCAGCCCAGGCTTGTGTATAATGAGGCGATAGTCTCTTCAGGGCGCCCAATCGAATGTCCAGGGAGGATGCATCAT
GTTTTTGCTCATATATGGCATGAGCAGCTGTGAGGACCCAGTTGTCATATAAAAGTGCACCTGCTGCTGTGCTTCCA
CCTAATATCAGGACTTGCCAAGGAAAATCACCAGGTTTTGCCTTTTGCCCTCCATATATACGCCCTCCTGTTGTACG
GGCTGATAGTCCACAAACAGGCTCACAGACTGGCGGTGATCTTTCTCCTTTGGAGCTCGTCCAGAATCCATCAGCCT
CACACACATATTTACCATCATTCACTTTCATTGTGTAGAAGGTCTCTTCACAGCTGTACTGAATCACAGCTTTGTAG
GTGGTCACTTCAGGACCTGTGATGTACTCCACTCGGCCACTGGGTAGATCATCAGGAGGGCCACAGTCAACAATGCT
GCACGAGGGCATTGGCTGGTCCCAAGATCCGTCTTTCTGACAAACTGCGGCAAATGATTTCAGGGGCAAGTGACCTT
GCAGAAGCTCATAGCCAGGCTCGCAAAAGATGGAGAAGCTGTCTTTCAGGATGTATTTGGCTTGCACAGGTGAAAGG
TGGCCATTAGGTGGCGCCATCGGATAAGGGCAAGGCTGCGCTGTGCTCGTGTAGTGGATCTTCCAGCCTGTGTGGTC
TCCTGACTCATCTGTGACAAAGGTGATGGTCACCGTGTTGCTTTTTGTTTCAATCCTGCGGGGCAATGTCTTCCCAC
AGAACGGGCCGTGTTCTTCACTGTCTATTTGAATCTTGAGAAAGTCGTAGGGACACAGGGTTTCAGGGTGCGTCTCC
ACATCGAAGGACTCCACAAAGTCCAGAATGACACTGAACCCCTCCTCCAGGCGGATGCTGTAAGTACAACTGGAGAG
TTTGGGGTACGGCTGTGGGTATTCAGGGCTGCTGAGCTCCCCAGACCGCTGGGTGAAGACCTGGCCGGAGCACAGGG
CTGAGCAGGTGCGCTTGTTACGGTGCAGGATGTAGCCTACACGGCAGGAGCAGTAGAAACCACCCAGGTGGTTGTGG
CAGTGGTGGTCGCAGGCGGGCGCCTCTCCCGGGGCCACCTGGCACTCGTCAATGTCCTCGGCTGCGTAGAAGGCCTC
GAACCCTGTGAACGGCTTCTCGTTGGAGTAGTCGGAGCGGAAGGTAATGTCCAGGCTGGAGCCCAGCGAGTAGAAGG
TGTCGTTGCCAGGGGCCCGCTCCGTGTCTGTGCTCTCATGCCCACACAGCGTGGCCAGCACCTTGGCCCCCGAGCTC
AGCTTGACGAAGTCGTACTCGCAGAGGTGGGAGAGCTCCAGGTCAAAGTGGGTGAAGTAGAGGCGCAGGCGGTAACC
GGGGGGTGCGGTCAGGGTCCAGCGCCGCTCCTGGTCATTGGCGTACTCCCCTGGAAAGCCAGGGGATGCCAGGCGCC
CAAACACAGGTTCAGGCCACTTCGGGCCCAAGGGGGTGGCCACCGAGCCACACAGCAGGCCCAGGAGGGTCAGCAGC
CTCATGGTGTGCCCGTCCAGCTGGCCTGGCCTGGTCTGCAGCCCTACACTGGTCTCACCTTTGATCTGTTTGTCCAG
TGACCTGCCCCTGCCCCCAGCCTCCCTGACTCTG SEQ ID NO: 13
>XR_001487411.1 *Macaca fascicularis* mannan binding lectin serine peptidase 2 (MASP2) short isoform, mRNA
CAGAGTCAGGGAGGCTGGGGGCAGGGGCAGGTCACTGGACAAACAGATCAAAGGTGAGACCAGTGTAGGGCTGCAGA
CCAGGCCAGGCCAGCTGGACGGGCACACCATGAGGCTGCTGACCCTCCTGGGCCTGCTGTGTGGCTCGGTGGCCACC
CCCTTGGGCCCGAAGTGGCCTGAACCTGTGTTTGGGCGCCTGGCATCCCCTGGCTTTCCAGGGGAGTACGCCAATGA
CCAGGAGCGGCGCTGGACCCTGACCGCACCCCCCGGTTACCGCCTGCGCCTCTACTTCACCCACTTTGACCTGGAGC
TCTCCCACCTCTGCGAGTACGACTTCGTCAAGCTGAGCTCGGGGGCCAAGGTGCTGGCCACGCTGTGTGGGCATGAG
AGCACAGACACGGAGCGGGCCCCTGGCAACGACACCTTCTACTCGCTGGGCTCCAGCCTGGACATTACCTTCCGCTC
CGACTACTCCAACGAGAAGCCGTTCACAGGGTTCGAGGCCTTCTACGCAGCCGAGGACATTGACGAGTGCCAGGTGG
CCCCGGGAGAGGCGCCCGCCTGCGACCACCACTGCCACAACCACCTGGGTGGTTTCTACTGCTCCTGCCGTGTAGGC
TACATCCTGCACCGTAACAAGCGCACCTGCTCAGATTCAAATAGACAGTGAAGAACACGGCCCGTTCTGTGGGAAGA
CATTGCCCCGCAGGATTGAAACAAAAAGCAACACGGTGACCATCACCTTTGTCACAGATGAGTCAGGAGACCACACA
GGCTGGAAGATCCACTACACGAGCACAGCGCAGCCTTGCCCTTATCCGATGGCGCCACCTAATGGCCACCTTTCACC
TGTGCAAGCCAAATACATCCTGAAAGACAGCTTCTCCATCTTTTGCGAGCCTGGCTATGAGCTTCTGCAA SEQ ID NO: 14
Reverse Complement of SEQ ID NO: 13
TTGCAGAAGCTCATAGCCAGGCTCGCAAAAGATGGAGAAGCTGTCTTTCAGGATGTATTTGGCTTGCACAGGTGAAA
GGTGGCCATTAGGTGGCGCCATCGGATAAGGGCAAGGCTGCGCTGTGCTCGTGTAGTGGATCTTCCAGCCTGTGTGG
TCTCCTGACTCATCTGTGACAAAGGTGATGGTCACCGTGTTGCTTTTTGTTTCAATCCTGCGGGGCAATGTCTTCCC
ACAGAACGGGCCGTGTTCTTCACTGTCTATTTGAATCTGAGCAGGTGCGCTTGTTACGGTGCAGGATGTAGCCTACA
CGGCAGGAGCAGTAGAAACCACCCAGGTGGTTGTGGCAGTGGTGGTCGCAGGCGGGCGCCTCTCCCGGGGCCACCTG
GCACTCGTCAATGTCCTCGGCTGCGTAGAAGGCCTCGAACCCTGTGAACGGCTTCTCGTTGGAGTAGTCGGAGCGGA
AGGTAATGTCCAGGCTGGAGCCCAGCGAGTAGAAGGTGTCGTTGCCAGGGGCCCGCTCCGTGTCTGTGCTCTCATGC
CCACACAGCGTGGCCAGCACCTTGGCCCCCGAGCTCAGCTTGACGAAGTCGTACTCGCAGAGGTGGGAGAGCTCCAG
GTCAAAGTGGGTGAAGTAGAGGCGCAGGCGGTAACCGGGGGGTGCGGTCAGGGTCCAGCGCCGCTCCTGGTCATTGG
CGTACTCCCCTGGAAAGCCAGGGGATGCCAGGCGCCCAAACACAGGTTCAGGCCACTTCGGGCCCAAGGGGGTGGCC
ACCGAGCCACACAGCAGGCCCAGGAGGGTCAGCAGCCTCATGGTGTGCCCGTCCAGCTGGCCTGGCCTGGTCTGCAG
CCCTACACTGGTCTCACCTTTGATCTGTTTGTCCAGTGACCTGCCCCTGCCCCCAGCCTCCCTGACTCTG SEQ ID NO: 15
>NM_172043.1 *Rattus norvegicus* mannan binding lectin serine peptidase 2 (MASP2) long isoform, mRNA
TGACAGGCGCTGGACCTGCAGAGCTGGGTGGCACACCATGAGGCTACTGATCGTCCTGGGTCTGCTTTGGAGTTTGG
TGGCCACACTTTTGGGCTCCAAGTGGCCTGAGCCTGTATTCGGGCGCCTGGTGTCCCCTGGCTTCCCAGAGAAGTAT
GGCAACCATCAGGATCGATCCTGGACGCTGACTGCACCCCCTGGCTTCCGCCTGCGCCTCTACTTCACCCACTTCAA
CCTGGAACTCTCTTACCGCTGCGAGTATGACTTTGTCAAGTTGACCTCAGGGACCAAGGTGCTAGCCACGCTGTGTG
GGCAGGAGAGTACAGATACTGAGCGGGCACCTGGCAATGACACCTTCTACTCACTGGGTCCCAGCCTAAAGGTCACC
TTCCACTCCGACTACTCCAATGAGAAGCCATTCACAGGATTTGAGGCCTTCTATGCAGCGGAGGATGTGGATGAATG -continued MASP2 Sequences CAGAACATCCCTGGGAGACTCAGTCCCTTGTGACCATTATTGCCACAACTACCTGGGCGGCTACTACTGCTCCTGCC
GAGTGGGCTACATTCTGCACCAGAACAAGCATACCTGCTCAGCCCTTTGTTCAGGCCAGGTGTTCACTGGGAGGTCT
GGCTTTCTCAGTAGCCCTGAGTACCCACAGCCATACCCCAAACTCTCCAGCTGCGCCTACAACATCCGCCTGGAGGA
AGGCTTCAGTATCACCCTGGACTTCGTGGAGTCCTTTGATGTGGAGATGCACCCTGAAGCCCAGTGCCCCTACGACT
CCCTCAAGATTCAAACAGACAAGAGGGAATACGGCCCGTTTTGTGGGAAGACGCTGCCCCCCAGGATTGAAACTGAC
AGCAACAAGGTGACCATTACCTTTACCACCGACGAGTCAGGGAACCACACAGGCTGGAAGATACACTACACAAGCAC
AGCACAGCCCTGCCCTGATCCAACGGCGCCACCTAATGGTCACATTTCACCTGTGCAAGCCACGTATGTCCTGAAGG
ACAGCTTTTCTGTCTTCTGCAAGACTGGCTTCGAGCTTCTGCAAGGTTCTGTCCCCCTGAAGTCATTCACTGCTGTC
TGTCAGAAAGATGGATCTTGGGACCGGCCGATACCAGAGTGCAGCATTATTGACTGTGGCCCTCCCGATGACCTACC
CAATGGCCACGTGGACTATATCACAGGCCCTGAAGTGACCACCTACAAAGCTGTGATTCAGTACAGCTGTGAAGAGA
CTTTCTACACAATGAGCAGCAATGGTAAATATGTGTGTGAGGCTGATGGATTCTGGACGAGCTCCAAAGGAGAAAAA
TCCCTCCCGGTTTGCAAGCCTGTCTGTGGACTGTCCACACACACTTCAGGAGGCCGTATAATTGGAGGACAGCCTGC
AAAGCCTGGTGACTTTCCTTGGCAAGTCTTGTTACTGGGTGAAACTACAGCAGCAGGTGCTCTTATACATGACGACT
GGGTCCTAACAGCGGCTCATGCTGTATATGGGAAAACAGAGGCGATGTCCTCCCTGGACATCCGCATGGGCATCCTC
AAAAGGCTCTCCCCTCATTACACTCAAGCCTGGCCAGAGGCTGTCTTTATCCATGAAGGCTACACTCACGGAGCTGG
TTTTGACAATGATATAGCACTGATTAAACTCAAGAACAAAGTCACAATCAACAGAAACATCATGCCGATTTGTCTAC
CAAGAAAAGAAGCTGCATCCTTAATGAAAACAGACTTCGTTGGAACTGTGGCTGGCTGGGGGTTAACCCAGAAGGGG
TTTCTTGCTAGAAACCTAATGTTTGTGGACATACCAATTGTTGACCACCAAAAATGTGCTACTGCGTATACAAAGCA
GCCCTACCCAGGAGCAAAAGTGACTGTTAACATGCTCTGTGCTGGCCTAGACGCCGGTGGCAAGGACAGCTGCAGAG
GTGACAGCGGAGGGGCATTAGTGTTTCTAGACAATGAAACACAGAGATGGTTTGTGGGAGGAATAGTTTCCTGGGGT
TCTATTAACTGTGGGGGGTCAGAACAGTATGGGGTCTACACGAAAGTCACGAACTATATTCCCTGGATTGAGAACAT
AATAAATAATTTCTAA SEQ ID NO: 6
Reverse Complement of SEQ ID NO: 15
TTAGAAATTATTTATTATGTTCTCAATCCAGGGAATATAGTTCGTGACTTTCGTGTAGACCCCATACTGTTCTGACC
CCCCACAGTTAATAGAACCCCAGGAAACTATTCCTCCCACAAACCATCTCTGTGTTTCATTGTCTAGAAACACTAAT
GCCCCTCCGCTGTCACCTCTGCAGCTGTCCTTGCCACCGGCGTCTAGGCCAGCACAGAGCATGTTAACAGTCACTTT
TGCTCCTGGGTAGGGCTGCTTTGTATACGCAGTAGCACATTTTTGGTGGTCAACAATTGGTATGTCCACAAACATTA
GGTTTCTAGCAAGAAACCCCTTCTGGGTTAACCCCCAGCCAGCCACAGTTCCAACGAAGTCTGTTTTCATTAAGGAT
GCAGCTTCTTTTCTTGGTAGACAAATCGGCATGATGTTTCTGTTGATTGTGACTTTGTTCTTGAGTTTAATCAGTGC
TATATCATTGTCAAAACCAGCTCCGTGAGTGTAGCCTTCATGGATAAAGACAGCCTCTGGCCAGGCTTGAGTGTAAT
GAGGGGAGAGCCTTTTGAGGATGCCCATGCGGATGTCCAGGGAGGACATCGCCTCTGTTTTCCCATATACAGCATGA
GCCGCTGTTAGGACCCAGTCGTCATGTATAAGAGCACCTGCTGCTGTAGTTTCACCCAGTAACAAGACTTGCCAAGG
AAAGTCACCAGGCTTTGCAGGCTGTCCTCCAATTATACGGCCTCCTGAAGTGTGTGTGGACAGTCCACAGACAGGCT
TGCAAACCGGGAGGGATTTTTCTCCTTTGGAGCTCGTCCAGAATCCATCAGCCTCACACACATATTTACCATTGCTG
CTCATTGTGTAGAAAGTCTCTTCACAGCTGTACTGAATCACAGCTTTGTAGGTGGTCACTTCAGGGCCTGTGATATA
GTCCACGTGGCCATTGGGTAGGTCATCGGGAGGGCCACAGTCAATAATGCTGCACTCTGGTATCGGCCGGTCCCAAG
ATCCATCTTTCTGACAGACAGCAGTGAATGACTTCAGGGGGACAGAACCTTGCAGAAGCTCGAAGCCAGTCTTGCAG
AAGACAGAAAAGCTGTCCTTCAGGACATACGTGGCTTGCACAGGTGAAATGTGACCATTAGGTGGCGCCGTTGGATC
AGGGCAGGGCTGTGCTGTGCTTGTGTAGTGTATCTTCCAGCCTGTGTGGTTCCCTGACTCGTCGGTGGTAAAGGTAA
TGGTCACCTTGTTGCTGTCAGTTTCAATCCTGGGGGGCAGCGTCTTCCCACAAAACGGGCCGTATTCCCTCTTGTCT
GTTTGAATCTTGAGGGAGTCGTAGGGGCACTGGGCTTCAGGGTGCATCTCCACATCAAAGGACTCCACGAAGTCCAG
GGTGATACTGAAGCCTTCCTCCAGGCGGATGTTGTAGGCGCAGCTGGAGAGTTTGGGGTATGGCTGTGGGTACTCAG
GGCTACTGAGAAAGCCAGACCTCCCAGTGAACACCTGGCCTGAACAAAGGGCTGAGCAGGTATGCTTGTTCTGGTGC
AGAATGTAGCCCACTCGGCAGGAGCAGTAGTAGCCGCCCAGGTAGTTGTGGCAATAATGGTCACAAGGGACTGAGTC
TCCCAGGGATGTTCTGCATTCATCCACATCCTCCGCTGCATAGAAGGCCTCAAATCCTGTGAATGGCTTCTCATTGG
AGTAGTCGGAGTGGAAGGTGACCTTTAGGCTGGGACCCAGTGAGTAGAAGGTGTCATTGCCAGGTGCCCGCTCAGTA
TCTGTACTCTCCTGCCCACACAGCGTGGCTAGCACCTTGGTCCCTGAGGTCAACTTGACAAAGTCATACTCGCAGCG
GTAAGAGAGTTCCAGGTTGAAGTGGGTGAAGTAGAGGCGCAGGCGGAAGCCAGGGGGTGCAGTCAGCGTCCAGGATC
GATCCTGATGGTTGCCATACTTCTCTGGGAAGCCAGGGGACACCAGGCGCCCGAATACAGGCTCAGGCCACTTGGAG
CCCAAAAGTGTGGCCACCAAACTCCAAAGCAGACCCAGGACGATCAGTAGCCTCATGGTGTGCCACCCAGCTCTGCA
GGTCCAGCGCCTGTCA SEQ ID NO: 17
>AJ542538.1 *Rattus norvegicus* mannan binding lectin serine peptidase 2 (MASP2) short isoform, mRNA
CTTCTCTCCTCAGTCTTCCTGATGCATCCCCCACCCCATCTCTCTTCCAGAGCAGAGCCTCTAACCTCCCTCGCTCC
AGCCTGCCCACCCCAGTGAGTCAGACACCAGTCAATACATGCCCACACGACTCAGCTCTGTCAGGCTGGAGTGGCTG
CCAGCACCCATTCACCTTTCCCAGACAATAAACCTGCCTCCACTTCCACTGTGGCTCTGTGTCTCTTGCCAGGGTTG
GGGTGATGGGCTTGGAGGGCACTAGAGCATCCTGGGTGTCCCCTCATTTAATCCTCATCTCACAGCCCGGATGCAGG
AACTCCCTGAGCTCACACAGGGAGATGCGCCCCCGCCCCCCGTCCCCCCGTCCCCCCCCCCCCCCCCGTCCCCTGA
GGCTGATCTCAGGACTCGGTAGCCAGTTCTTGTTCATAGGTCACCGCAGGTCTTTGTTCTCTAACCCTGGGGAGCTT
GATTCAGCACAGAGAGCAAAGGGGGTGTTACTGAGGGATCAGGCTAGTCGCCCTGCATCCGGGGTGTACTCTCTGCT
GGTATGGAGAGCCTTCAGTTCCATAAGCCCTCCTCCTAGCCTGTCCCTCC SEQ ID NO: 18
Reverse Complement of SEQ ID NO:17
GGAGGGACAGGCTAGGAGGAGGGCTTATGGAACTGAAGGCTCTCCATACCAGCAGAGAGTACACCCCGGATGCAGGG
CGACTAGCCTGATCCCTCAGTAACACCCCCTTTGCTCTCTGTGCTGAATCAAGCTCCCCAGGGTTAGAGAACAAAGA
CCTGCGGTGACCTATGAACAAGAACTGGCTACCGAGTCCTGAGATCAGCCTCAGGGGACGGGGGGGGGGGGGGGGA
CGGGGGGACGGGGGGCGGGGGCGCATCTCCCTGTGTGAGCTCAGGGAGTTCCTGCATCCGGGCTGTGAGATGAGGAT
TAAATGAGGGGACACCCAGGATGCTCTAGTGCCCTCCAAGCCCATCACCCCAACCCTGGCAAGAGACACAGAGCCAC
AGTGGAAGTGGAGGCAGGTTTATTGTCTGGGAAAGGTGAATGGGTGCTGGCAGCCACTCCAGCCTGACAGAGCTGAG
TCGTGTGGGCATGTATTGACTGGTGTCTGACTCACTGGGGTGGGCAGGCTGGAGCGAGGGAGGTTAGAGGCTCTGCT
CTGGAAGAGAGATGGGGTGGGGGATGCATCAGGAAGACTGAGGAGAGAAG

We claim:

1. A double stranded ribonucleic acid (dsRNA) agent for inhibiting expression of mannan binding lectin serine peptidase 2 (MASP2) in a cell, wherein said dsRNA comprises a sense strand and an antisense strand forming a double stranded region, wherein the antisense strand comprises a region of complementarity to an mRNA encoding MASP2, and wherein the antisense strand comprises the nucleotide sequence set forth as SEQ ID NO: 93, 92, 100, 94, 96, 70, 71, 72, 76, or 83, and the sense strand comprises the nucleotide sequence set forth as SEQ ID NO: 47, 46, 54, 48, 50, 24, 25, 26, 30, or 37 that corresponds to the antisense sequence.

2. The dsRNA agent of claim 1, wherein (a) the dsRNA agent comprises at least one modified nucleotide;

(b) substantially all of the nucleotides of the sense strand comprise a modification, substantially all of the nucleotides of the antisense strand comprise a modification, or substantially all of the nucleotides of the sense strand and substantially all of the nucleotides of the antisense strand comprise a modification;

(c) all of the nucleotides of the sense strand comprise a modification, all of the nucleotides of the antisense strand comprise a modification, or all of the nucleotides of the sense strand and all of the nucleotides of the antisense strand comprise a modification;

(d) the dsRNA agent comprises at least one modified nucleotide selected from the group consisting of a deoxy-nucleotide, a 3'-terminal deoxythymidine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a nucleotide comprising a phosphoramidate, a nucleotide comprising a non-natural nucleotide base, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide, and combinations thereof;

(e) the dsRNA agent comprises at least one modified nucleotide selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and glycol, and combinations thereof;

(f) the dsRNA agent comprises at least one modified nucleotide selected from the group consisting of a deoxy-nucleotide, a 2'-O-methyl modified nucleotide, a 2'-fluoro modified nucleotide, a 2'-deoxy-modified nucleotide, a GNA, and, a vinyl-phosphonate nucleotide, and combinations thereof;

(g) the dsRNA agent comprises at least one modified nucleotide, wherein the modified nucleotide is a thermally destabilizing nucleotide; and/or (h) the dsRNA agent comprises at least one modified nucleotide, wherein the modified nucleotide is a thermally destabilizing nucleotide modification, and wherein the thermally destabilizing nucleotide modification is selected from the group consisting of an abasic modification, a mismatch with the opposing nucleotide in the duplex, a destabilizing sugar modification, a 2'-deoxy modification, an acyclic modification, an unlocked nucleic acid (UNA), and GNA.

3. The dsRNA agent of claim 1, wherein (a) the double stranded region is 23-27 nucleotide pairs in length;

(b) wherein the double stranded region is 21-23 nucleotide pairs in length;

(c) each strand is independently no more than 30 nucleotides in length;

(d) the sense strand is 21 nucleotides in length and the antisense strand is 23 nucleotides in length;

(e) the region of complementarity is at least 17 nucleotides in length;

(f) the region of complementarity is between 19 and 23 nucleotides in length;

(g) the region of complementarity is 19 nucleotides in length;

(h) at least one strand comprises a 3' overhang of at least 1 nucleotide; and/or (i) at least one strand comprises a 3' overhang of at least 2 nucleotides.

4. The dsRNA agent of claim 1, further comprising a ligand.

5. The dsRNA agent of claim 4, wherein (a) the ligand is conjugated to the 3' end of the sense strand of the dsRNA agent;

(b) the ligand is an N-acetylgalactosamine (GalNAc) derivative;

(c) the ligand is one or more GalNAc derivatives attached through a monovalent, bivalent, or trivalent branched linker; and/or (d) the ligand is

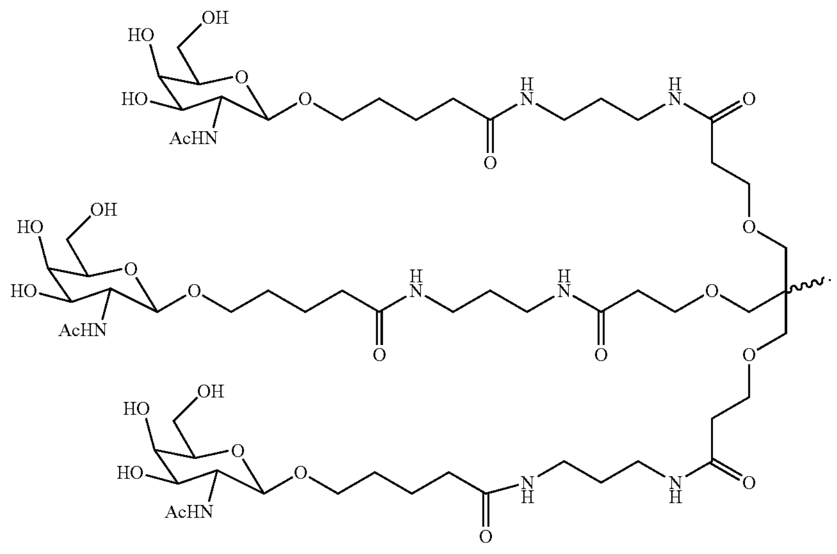

6. The dsRNA agent of claim 1, wherein the dsRNA agent is conjugated to a ligand as shown in the following schematic (e) introducing the dsRNA agent into the cell inhibits the expression of MASP2 by at least 50%, 60%, 70%, 80%, 90%, or 95%; and/or

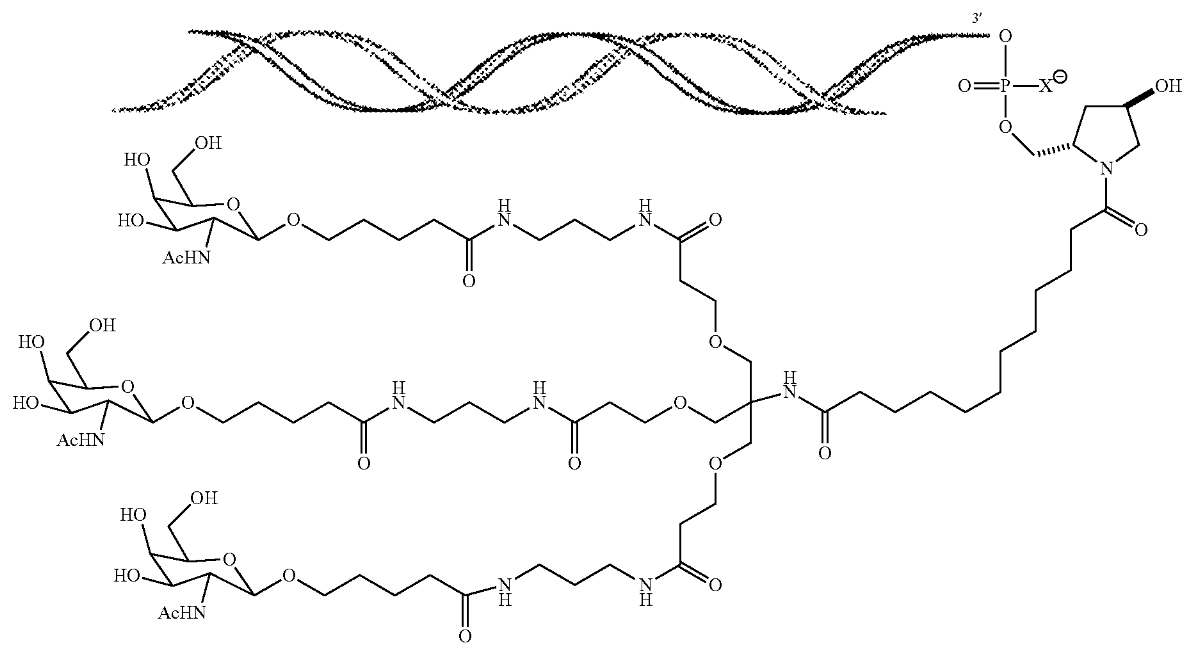

and, wherein X is O or S.

7. The dsRNA agent of claim 1, wherein
(a) the dsRNA agent further comprises at least one phosphorothioate or methylphosphonate internucleotide linkage at the 3'-terminus and/or 5'-terminus of the sense strand and/or the antisense strand; and/or
(b) the base pair at the 1 position of the 5'-end of the antisense strand of the duplex is an AU base pair.

8. A cell containing the dsRNA agent of claim 1.

9. A pharmaceutical composition for inhibiting expression of a gene encoding MASP2 comprising the dsRNA agent of claim 2.

10. The pharmaceutical composition of claim 9, wherein
(a) the dsRNA agent is in an unbuffered solution;
(b) the dsRNA agent is in an unbuffered solution, wherein the unbuffered solution is saline or water;
(c) the dsRNA agent is in a buffer solution;
(d) the dsRNA agent is in a buffer solution, wherein the buffer solution comprises acetate, citrate, prolamine, carbonate, or phosphate or any combination thereof; or
(e) the dsRNA agent is in a buffer solution, wherein the buffer solution is phosphate buffered saline (PBS).

11. A method of inhibiting expression of a MASP2 gene in a cell, the method comprising introducing into the cell the dsRNA agent of claim 1, thereby inhibiting expression of the MASP2 gene in the cell.

12. The method of claim 11, wherein
(a) the cell is within a subject;
(b) the cell is within a subject, wherein the subject is a human;
(c) the cell is within a subject, wherein the subject has a MASP2-associated disorder;
(d) the cell is within a subject having a MASP2-associated disorder, wherein the MASP2-associated disorder is selected from the group consisting of arthritis, IgA nephropathy, thrombotic microangiopathy, diabetic nephropathy and membranous nephropathy;
(f) inhibiting expression of MASP2 decreases MASP2 protein level in serum of the subject by at least 50%, 60%, 70%, 80%, 90%, or 95%.

13. A method of treating a subject having a disorder that would benefit from reduction in MASP2 expression, comprising administering to the subject a therapeutically effective amount of the dsRNA agent of claim 1, thereby treating the subject having the disorder that would benefit from reduction in MASP2 expression.

14. A method of preventing at least one symptom in a subject having a disorder that would benefit from reduction in MASP2, comprising administering to the subject a prophylactically effective amount of the dsRNA agent of claim 1, thereby preventing at least one symptom in the subject having the disorder that would benefit from reduction in MASP2 expression.

15. The method of claim 13, wherein
(a) the disorder is a MASP2-associated disorder;
(b) the disorder is a MASP2-associated disorder selected from the group consisting of arthritis, IgA nephropathy, thrombotic microangiopathy, diabetic nephropathy and membranous nephropathy;
(c) the subject is human;
(d) the administration of the agent to the subject causes a decrease in inflammation and/or a decrease in proteinuria;
(e) the dsRNA agent is administered to the subject at a dose of about 0.01 mg/kg to about 50 mg/kg;
(f) the dsRNA agent is administered to the subject subcutaneously;
(g) the method further comprises determining the level of MASP2 in a sample(s) from the subject;
(h) the method further comprises determining the MASP2 protein level in a blood or serum sample(s); and/or
(i) the method further comprises administering to the subject an additional therapeutic agent for treatment of inflammation.

16. A kit comprising the dsRNA agent of claim 1.

17. A vial comprising the dsRNA agent of claim 1.

18. A syringe comprising the dsRNA agent of claim 1.

19. The method of claim 14, wherein (a) the disorder is a MASP2-associated disorder;

(b) the disorder is a MASP2-associated disorder selected from the group consisting of arthritis, IgA nephropathy, thrombotic microangiopathy, diabetic nephropathy and membranous nephropathy;

(c) the subject is human;

(d) the administration of the agent to the subject causes a decrease in inflammation and/or a decrease in proteinuria;

(e) the dsRNA agent is administered to the subject at a dose of about 0.01 mg/kg to about 50 mg/kg;

(f) the dsRNA agent is administered to the subject subcutaneously;

(g) the method further comprises determining the level of MASP2 in a sample(s) from the subject;

(h) the method further comprises determining the level of MASP2 protein level in a blood or serum sample(s); and/or (i) the method further comprises administering to the subject an additional therapeutic agent for treatment of inflammation.

20. The dsRNA of claim 1, wherein (a) the sense strand comprises the sequence and all of the modifications of SEQ ID NO: 139 and the antisense strand comprises the sequence and all of the modifications of SEQ ID NO: 185;

(b) the sense strand comprises the sequence and all of the modifications of SEQ ID NO: 138 and the antisense strand comprises the sequence and all of the modifications of SEQ ID NO: 184;

(c) the sense strand comprises the sequence and all of the modifications of SEQ ID NO: 146 and the antisense strand comprises the sequence and all of the modifications of SEQ ID NO: 192;

(d) the sense strand comprises the sequence and all of the modifications of SEQ ID NO: 140 and the antisense strand comprises the sequence and all of the modifications of SEQ ID NO: 186;

(e) the sense strand comprises the sequence and all of the modifications of SEQ ID NO: 142 and the antisense strand comprises the sequence and all of the modifications of SEQ ID NO: 188;

(f) the sense strand comprises the sequence and all of the modifications of SEQ ID NO: 116 and the antisense strand comprises the sequence and all of the modifications of SEQ ID NO: 162;

(g) the sense strand comprises the sequence and all of the modifications of SEQ ID NO: 117 and the antisense strand comprises the sequence and all of the modifications of SEQ ID NO: 163;

(h) the sense strand comprises the sequence and all of the modifications of SEQ ID NO: 118 and the antisense strand comprises the sequence and all of the modifications of SEQ ID NO: 164;

(i) the sense strand comprises the sequence and all of the modifications of SEQ ID NO: 122 and the antisense strand comprises the sequence and all of the modifications of SEQ ID NO: 168; or (j) the sense strand comprises the sequence and all of the modifications of SEQ ID NO: 129 and the antisense strand comprises the sequence and all of the modifications of SEQ ID NO: 175.

* * * * *

SEQUENCE LISTING

<160> NUMBER OF SEQ ID NOS: 1383

<210> SEQ ID NO 1
<211> LENGTH: 2455
<212> TYPE: DNA
<213> ORGANISM: Homo sapiens

<400> SEQUENCE: 1
agaccaggcc aggccagctg gacgggcaca ccatgaggct gctgaccctc ctgggccttc 60
tgtgtggctc ggtggccacc cccttgggcc cgaagtggcc tgaacctgtg ttcgggcgcc 120
tggcatcccc cggctttcca ggggagtatg ccaatgacca ggagcggcgc tggaccctga 180
ctgcaccccc cggctaccgc ctgcgcctct acttcaccca cttcgacctg gagctctccc 240
acctctgcga gtacgacttc gtcaagctga gctcgggggc caaggtgctg gccacgctgt 300
gcgggcagga gagcacagac acggagcggg cccctggcaa ggacactttc tactcgctgg 360
gctccagcct ggacattacc ttccgctccg actactccaa cgagaagccg ttcacggggt 420
tcgaggcctt ctatgcagcc gaggacattg acgagtgcca ggtggccccg ggagaggcgc 480
ccacctgcga ccaccactgc cacaaccacc tgggcggttt ctactgctcc tgccgcgcag 540
gctacgtcct gcaccgtaac aagcgcacct gctcagccct gtgctccggc caggtcttca 600
cccagaggtc tggggagctc agcagccctg aatacccacg gccgtatccc aaactctcca 660
gttgcactta cagcatcagc ctggaggagg ggttcagtgt cattctggac tttgtggagt 720
ccttcgatgt ggagacacac cctgaaaccc tgtgtcccta cgactttctc aagattcaaa 780
cagacagaga agaacatggc ccattctgtg ggaagacatt gccccacagg attgaaacaa 840
aaagcaacac ggtgaccatc acctttgtca cagatgaatc aggagaccac acaggctgga 900
agatccacta cacgagcaca gcgcagcctt gcccttatcc gatggcgcca cctaatggcc 960
acgtttcacc tgtgcaagcc aaatacatcc tgaaagacag cttctccatc ttttgcgaga 1020
ctggctatga gcttctgcaa ggtcacttgc ccctgaaatc ctttactgca gtttgtcaga 1080
aagatggatc ttgggaccgg ccaatgcccg cgtgcagcat tgttgactgt ggccctcctg 1140
atgatctacc cagtggccga gtggagtaca tcacaggtcc tggagtgacc acctacaaag 1200
ctgtgattca gtacagctgt gaagagacct tctacacaat gaaagtgaat gatggtaaat 1260
atgtgtgtga ggctgatgga ttctggacga gctccaaagg agaaaaatca ctcccagtct 1320
gtgagcctgt ttgtggacta tcagcccgca caacaggagg gcgtatatat ggagggcaaa 1380
aggcaaaacc tggtgatttt ccttggcaag tcctgatatt aggtggaacc acagcagcag 1440
gtgcactttt atatgacaac tggtcctaa cagctgctca tgccgtctat gagcaaaaac 1500
atgatgcatc cgccctggac attcgaatgg gcaccctgaa aagactatca cctcattata 1560
cacaagcctg gtctgaagct gtttttatac atgaaggtta tactcatgat gctggctttg 1620
acaatgacat agcactgatt aaattgaata acaaagttgt aatcaatagc aacatcacgc 1680
ctatttgtct gccaagaaaa gaagctgaat cctttatgag gacagatgac attggaactg 1740
catctggatg gggattaacc caaaggggtt ttcttgctag aaatctaatg tatgtcgaca 1800
taccgattgt tgaccatcaa aaatgtactg ctgcatatga aaagccaccc tatccaaggg 1860
gaagtgtaac tgctaacatg ctttgtgctg gcttagaaag tgggggcaag gacagctgca 1920
gaggtgacag cggaggggca ctggtgtttc tagatagtga aacagagagg tggtttgtgg 1980
gaggaatagt gtcctggggt tccatgaatt gtggggaagc aggtcagtat ggagtctaca 2040
caaaagttat taactatatt ccctggatcg agaacataat tagtgatttt taacttgcgt 2100

```
gtctgcagtc aaggattctt catttttaga aatgcctgtg aagaccttgg cagcgacgtg   2160

gctcgagaag cattcatcat tactgtggac atggcagttg ttgctccacc caaaaaaaca   2220

gactccaggt gaggctgctg tcatttctcc acttgccagt ttaattccag ccttacccat   2280

tgactcaagg ggacataaac cacgagagtg acagtcatct ttgcccaccc agtgtaatgt   2340

cactgctcaa attacatttc attaccttaa aaagccagtc tcttttcata ctggctgttg   2400

gcatttctgt aaactgcctg tccatgctct ttgtttttaa acttgttctt attga        2455
```

```
<210> SEQ ID NO 2
<211> LENGTH: 2455
<212> TYPE: DNA
<213> ORGANISM: Homo sapiens

<400> SEQUENCE: 2

tcaataagaa caagtttaaa aacaaagagc atggacaggc agtttacaga aatgccaaca     60

gccagtatga aaagagactg gctttttaag gtaatgaaat gtaatttgag cagtgacatt    120

acactgggtg ggcaaagatg actgtcactc tcgtggttta tgtccccttg agtcaatggg    180

taaggctgga attaaactgg caagtggaga aatgacagca gcctcacctg gagtctgttt    240

ttttgggtgg agcaacaact gccatgtcca cagtaatgat gaatgcttct cgagccacgt    300

cgctgccaag gtcttcacag gcatttctaa aaatgaagaa tccttgactg cagacacgca    360

agttaaaaat cactaattat gttctcgatc cagggaatat agttaataac ttttgtgtag    420

actccatact gacctgcttc cccacaattc atggaacccc aggacactat tcctcccaca    480

aaccacctct ctgtttcact atctagaaac accagtgccc ctccgctgtc acctctgcag    540

ctgtccttgc ccccactttc taagccagca caaagcatgt tagcagttac acttcccctt    600

ggatagggtg gcttttcata tgcagcagta catttttgat ggtcaacaat cggtatgtcg    660

acatacatta gatttctagc aagaaaaccc ctttgggtta atccccatcc agatgcagtt    720

ccaatgtcat ctgtcctcat aaaggattca gcttcttttc ttggcagaca aataggcgtg    780

atgttgctat tgattacaac tttgttattc aatttaatca gtgctatgtc attgtcaaag    840

ccagcatcat gagtataacc ttcatgtata aaaacagctt cagaccaggc ttgtgtataa    900

tgaggtgata gtcttttcag ggtgcccatt cgaatgtcca gggcggatgc atcatgtttt    960

tgctcataga cggcatgagc agctgttagg acccagttgt catataaaag tgcacctgct   1020

gctgtggttc cacctaatat caggacttgc caaggaaaat caccaggttt tgccttttgc   1080

cctccatata tacgccctcc tgttgtgcgg gctgatagtc cacaaacagg ctcacagact   1140

gggagtgatt tttctccttt ggagctcgtc cagaatccat cagcctcaca cacatattta   1200

ccatcattca ctttcattgt gtagaaggtc tcttcacagc tgtactgaat cacagctttg   1260

taggtggtca ctccaggacc tgtgatgtac tccactcggc cactgggtag atcatcagga   1320

gggccacagt caacaatgct gcacgcgggc attggccggt cccaagatcc atctttctga   1380

caaactgcag taaaggattt caggggcaag tgaccttgca gaagctcata gccagtctcg   1440

caaaagatgg agaagctgtc tttcaggatg tatttggctt gcacaggtga aacgtggcca   1500

ttaggtggcg ccatcggata agggcaaggc tgcgctgtgc tcgtgtagtg gatcttccag   1560

cctgtgtggt ctcctgattc atctgtgaca aaggtgatgg tcaccgtgtt gctttttgtt   1620

tcaatcctgt ggggcaatgt cttcccacag aatgggccat gttcttctct gtctgtttga   1680

atcttgagaa agtcgtaggg acacagggtt tcagggtgtg tctccacatc gaaggactcc   1740
```

-continued acaaagtcca gaatgacact gaacccctcc tccaggctga tgctgtaagt gcaactggag 1800
agtttgggat acggccgtgg gtattcaggg ctgctgagct ccccagacct ctgggtgaag 1860
acctggccgg agcacagggc tgagcaggtg cgcttgttac ggtgcaggac gtagcctgcg 1920
cggcaggagc agtagaaacc gcccaggtgg ttgtggcagt ggtggtcgca ggtgggcgcc 1980
tctcccgggg ccacctggca ctcgtcaatg tcctcggctg catagaaggc ctcgaacccc 2040
gtgaacggct tctcgttgga gtagtcggag cggaaggtaa tgtccaggct ggagcccagc 2100
gagtagaaag tgtccttgcc aggggcccgc tccgtgtctg tgctctcctg cccgcacagc 2160
gtggccagca ccttggcccc cgagctcagc ttgacgaagt cgtactcgca gaggtgggag 2220
agctccaggt cgaagtgggt gaagtagagg cgcaggcggt agccgggggg tgcagtcagg 2280
gtccagcgcc gctcctggtc attggcatac tcccctggaa agccggggga tgccaggcgc 2340
ccgaacacag gttcaggcca cttcgggccc aagggggtgg ccaccgagcc acacagaagg 2400
cccaggaggg tcagcagcct catggtgtgc ccgtccagct ggcctggcct ggtct 2455

<210> SEQ ID NO 3
<211> LENGTH: 2471
<212> TYPE: DNA
<213> ORGANISM: Homo sapiens

<400> SEQUENCE: 3
agaccaggcc aggccagctg gacgggcaca ccatgaggct gctgaccctc ctgggccttc 60
tgtgtggctc ggtggccacc cccttgggcc cgaagtggcc tgaacctgtg ttcgggcgcc 120
tggcatcccc cggctttcca ggggagtatg ccaatgacca ggagcggcgc tggaccctga 180
ctgcaccccc cggctaccgc ctgcgcctct acttcaccca cttcgacctg gagctctccc 240
acctctgcga gtacgacttc gtcaagctga gctcgggggc caaggtgctg gccacgctgt 300
gcgggcagga gagcacagac acggagcggg cccctggcaa ggacactttc tactcgctgg 360
gctccagcct ggacattacc ttccgctccg actactccaa cgagaagccg ttcacggggt 420
tcgaggcctt ctatgcagcc gaggacattg acgagtgcca ggtggccccg ggagaggcgc 480
ccacctgcga ccaccactgc cacaaccacc tgggcggttt ctactgctcc tgccgcgcag 540
gctacgtcct gcaccgtaac aagcgcacct gctcagccct gtgctccggc caggtcttca 600
cccagaggtc tggggagctc agcagccctg aatacccacg gccgtatccc aaactctcca 660
gttgcactta cagcatcagc ctggaggagg ggttcagtgt cattctggac tttgtggagt 720
ccttcgatgt ggagacacac cctgaaaccc tgtgtcccta cgactttctc aagattcaaa 780
cagacagaga agaacatggc ccattctgtg ggaagacatt gccccacagg attgaaacaa 840
aaagcaacac ggtgaccatc acctttgtca cagatgaatc aggagaccac acaggctgga 900
agatccacta cacgagcaca gcgcagcctt gcccttatcc gatggcgcca cctaatggcc 960
acgtttcacc tgtgcaagcc aaatacatcc tgaaagacag cttctccatc ttttgcgaga 1020
ctggctatga gcttctgcaa ggtcacttgc ccctgaaatc ctttactgca gtttgtcaga 1080
aagatggatc ttgggaccgg ccaatgcccg cgtgcagcat tgttgactgt ggccctcctg 1140
atgatctacc cagtggccga gtggagtaca tcacaggtcc tggagtgacc acctacaaag 1200
ctgtgattca gtacagctgt gaagagacct tctacacaat gaaagtgaat gatggtaaat 1260
atgtgtgtga ggctgatgga ttctggacga gctccaaagg agaaaaatca ctcccagtct 1320
gtgagcctgt ttgtggacta tcagcccgca caacaggagg gcgtatatat ggagggcaaa 1380
aggcaaaacc tggtgatttt ccttggcaag tcctgatatt aggtggaacc acagcagcag 1440

```
gtgcactttt atatgacaac tgggtcctaa cagctgctca tgccgtctat gagcaaaaac   1500

atgatgcatc cgccctggac attcgaatgg gcaccctgaa aagactatca cctcattata   1560

cacaagcctg gtctgaagct gtttttatac atgaaggtta tactcatgat gctggctttg   1620

acaatgacat agcactgatt aaattgaata acaaagttgt aatcaatagc aacatcacgc   1680

ctatttgtct gccaagaaaa gaagctgaat cctttatgag gacagatgac attggaactg   1740

catctggatg ggggattaacc caaaggggtt ttcttgctag aaatctaatg tatgtcgaca   1800

taccgattgt tgaccatcaa aaatgtactg ctgcatatga aaagccaccc tatccaaggg   1860

gaagtgtaac tgctaacatg ctttgtgctg gcttagaaag tgggggcaag gacagctgca   1920

gaggtgacag cggaggggca ctggtgtttc tagatagtga aacagagagg tggtttgtgg   1980

gaggaatagt gtcctggggt tccatgaatt gtggggaagc aggtcagtat ggagtctaca   2040

caaaagttat taactatatt ccctggatcg agaacataat tagtgatttt taacttgcgt   2100

gtctgcagtc aaggattctt catttttaga aatgcctgtg aagaccttgg cagcgacgtg   2160

gctcgagaag cattcatcat tactgtggac atggcagttg ttgctccacc caaaaaaaca   2220

gactccaggt gaggctgctg tcatttctcc acttgccagt ttaattccag ccttacccat   2280

tgactcaagg ggacataaac cacgagagtg acagtcatct ttgcccaccc agtgtaatgt   2340

cactgctcaa attacatttc attaccttaa aaagccagtc tcttttcata ctggctgttg   2400

gcatttctgt aaactgcctg tccatgctct ttgtttttaa acttgttctt attgaaaaaa   2460

aaaaaaaaaa a                                                         2471
```

<210> SEQ ID NO 4
<211> LENGTH: 2471
<212> TYPE: DNA
<213> ORGANISM: Homo sapiens

<400> SEQUENCE: 4

```
tttttttttt ttttttcaa taagaacaag tttaaaaaca aagagcatgg acaggcagtt     60

tacagaaatg ccaacagcca gtatgaaaag agactggctt tttaaggtaa tgaaatgtaa    120

tttgagcagt gacattacac tgggtgggca aagatgactg tcactctcgt ggtttatgtc    180

cccttgagtc aatgggtaag gctggaatta aactggcaag tggagaaatg acagcagcct    240

cacctggagt ctgttttttt gggtggagca acaactgcca tgtccacagt aatgatgaat    300

gcttctcgag ccacgtcgct gccaaggtct tcacaggcat ttctaaaaat gaagaatcct    360

tgactgcaga cacgcaagtt aaaaatcact aattatgttc tcgatccagg gaatatagtt    420

aataactttt gtgtagactc catactgacc tgcttcccca caattcatgg aaccccagga    480

cactattcct cccacaaacc acctctctgt ttcactatct agaaacacca gtgcccctcc    540

gctgtcacct ctgcagctgt ccttgccccc actttctaag ccagcacaaa gcatgttagc    600

agttacactt ccccttggat agggtggctt ttcatatgca gcagtacatt tttgatggtc    660

aacaatcggt atgtcgacat acattagatt tctagcaaga aaaccccttt gggttaatcc    720

ccatccagat gcagttccaa tgtcatctgt cctcataaag gattcagctt cttttcttgg    780

cagacaaata ggcgtgatgt tgctattgat tacaactttg ttattcaatt taatcagtgc    840

tatgtcattg tcaaagccag catcatgagt ataaccttca tgtataaaaa cagcttcaga    900

ccaggcttgt gtataatgag gtgatagtct tttcagggtg cccattcgaa tgtccagggc    960

ggatgcatca tgtttttgct catagacggc atgagcagct gttaggaccc agttgtcata   1020
```

-continued taaaagtgca cctgctgctg tggttccacc taatatcagg acttgccaag gaaaatcacc 1080
aggttttgcc ttttgccctc catatatacg ccctcctgtt gtgcgggctg atagtccaca 1140
aacaggctca cagactggga gtgatttttc tcctttggag ctcgtccaga atccatcagc 1200
ctcacacaca tatttaccat cattcacttt cattgtgtag aaggtctctt cacagctgta 1260
ctgaatcaca gctttgtagg tggtcactcc aggacctgtg atgtactcca ctcggccact 1320
gggtagatca tcaggagggc cacagtcaac aatgctgcac gcgggcattg gccggtccca 1380
agatccatct ttctgacaaa ctgcagtaaa ggatttcagg ggcaagtgac cttgcagaag 1440
ctcatagcca gtctcgcaaa agatggagaa gctgtctttc aggatgtatt tggcttgcac 1500
aggtgaaacg tggccattag gtggcgccat cggataaggg caaggctgcg ctgtgctcgt 1560
gtagtggatc ttccagcctg tgtggtctcc tgattcatct gtgacaaagg tgatggtcac 1620
cgtgttgctt tttgtttcaa tcctgtgggg caatgtcttc ccacagaatg ggccatgttc 1680
ttctctgtct gtttgaatct tgagaaagtc gtagggacac agggtttcag ggtgtgtctc 1740
cacatcgaag gactccacaa agtccagaat gacactgaac ccctcctcca ggctgatgct 1800
gtaagtgcaa ctggagagtt tgggatacgg ccgtgggtat tcagggctgc tgagctcccc 1860
agacctctgg gtgaagacct ggccggagca cagggctgag caggtgcgct tgttacggtg 1920
caggacgtag cctgcgcggc aggagcagta gaaaccgccc aggtggttgt ggcagtggtg 1980
gtcgcaggtg ggcgcctctc ccggggccac ctggcactcg tcaatgtcct cggctgcata 2040
gaaggcctcg aaccccgtga acggcttctc gttggagtag tcggagcgga aggtaatgtc 2100
caggctggag cccagcgagt agaaagtgtc cttgccaggg gcccgctccg tgtctgtgct 2160
ctcctgcccg cacagcgtgg ccagcacctt ggcccccgag ctcagcttga cgaagtcgta 2220
ctcgcagagg tgggagagct ccaggtcgaa gtgggtgaag tagaggcgca ggcggtagcc 2280
ggggggtgca gtcagggtcc agcgccgctc ctggtcattg gcatactccc ctggaaagcc 2340
gggggatgcc aggcgcccga acacaggttc aggccacttc gggcccaagg gggtggccac 2400
cgagccacac agaaggccca ggagggtcag cagcctcatg gtgtgcccgt ccagctggcc 2460
tggcctggtc t 2471

<210> SEQ ID NO 5
<211> LENGTH: 749
<212> TYPE: DNA
<213> ORGANISM: Homo sapiens

<400> SEQUENCE: 5
agaccaggcc aggccagctg gacgggcaca ccatgaggct gctgaccctc ctgggccttc 60
tgtgtggctc ggtggccacc cccttgggcc cgaagtggcc tgaacctgtg ttcgggcgcc 120
tggcatcccc cggctttcca ggggagtatg ccaatgacca ggagcggcgc tggaccctga 180
ctgcaccccc cggctaccgc ctgcgcctct acttcaccca cttcgacctg gagctctccc 240
acctctgcga gtacgacttc gtcaagctga gctcgggggc caaggtgctg gccacgctgt 300
gcgggcagga gagcacagac acggagcggg cccctggcaa ggacactttc tactcgctgg 360
gctccagcct ggacattacc ttccgctccg actactccaa cgagaagccg ttcacggggt 420
tcgaggcctt ctatgcagcc gaggacattg acgagtgcca ggtggccccg ggagaggcgc 480
ccacctgcga ccaccactgc cacaaccacc tgggcggttt ctactgctcc tgccgcgcag 540
gctacgtcct gcaccgtaac aagcgcacct gctcagagca gagcctctag cctcccctgg 600
agctccggcc tgcccagcag gtcagaagcc agagccagcc tgctggcctc agctccgggt 660
tgggctgaga tggctgtgcc ccaactccca ttcacccacc atggacccaa taataaacct 720
ggccccaccc caaaaaaaaa aaaaaaaaa 749

<210> SEQ ID NO 6
<211> LENGTH: 749
<212> TYPE: DNA
<213> ORGANISM: Homo sapiens

<400> SEQUENCE: 6 ttttttttt tttttttgg ggtggggcca ggtttattat tgggtccatg gtgggtgaat 60
gggagttggg gcacagccat ctcagcccaa cccggagctg aggccagcag gctggctctg 120
gcttctgacc tgctgggcag gccggagctc caggggaggc tagaggctct gctctgagca 180
ggtgcgcttg ttacggtgca ggacgtagcc tgcgcggcag gagcagtaga aaccgcccag 240
gtggttgtgg cagtggtggt cgcaggtggg cgcctctccc ggggccacct ggcactcgtc 300
aatgtcctcg gctgcataga aggcctcgaa ccccgtgaac ggcttctcgt tggagtagtc 360
ggagcggaag gtaatgtcca ggctggagcc cagcgagtag aaagtgtcct tgccaggggc 420
ccgctccgtg tctgtgctct cctgcccgca cagcgtggcc agcaccttgg cccccgagct 480
cagcttgacg aagtcgtact cgcagaggtg ggagagctcc aggtcgaagt gggtgaagta 540
gaggcgcagg cggtagccgg ggggtgcagt cagggtccag cgccgctcct ggtcattggc 600
atactcccct ggaaagccgg gggatgccag gcgcccgaac acaggttcag gccacttcgg 660
gcccaagggg gtggccaccg agccacacag aaggcccagg agggtcagca gcctcatggt 720
gtgcccgtcc agctggcctg gcctggtct 749

<210> SEQ ID NO 7
<211> LENGTH: 3061
<212> TYPE: DNA
<213> ORGANISM: Mus musculus

<400> SEQUENCE: 7
aaaggtgata ggcgctggac ctgcagagct aggtggcaca ccatgaggct actcatcttc 60
ctgggtctgc tgtggagttt ggtggccaca cttctgggtt caaagtggcc tgaacctgta 120
ttcgggcgcc tggtgtcccc tggcttccca gagaagtatg ctgaccatca agatcgatcc 180
tggacactga ctgcaccccc tggctaccgc ctgcgcctct acttcaccca ctttgacctg 240
gaactctctt accgctgcga gtatgacttt gtcaagttga gctcagggac caaggtgctg 300
gccacactgt gtgggcagga gagtacagac actgagcagg cacctggcaa tgacaccttc 360
tactcactgg gtcccagcct aaaggtcacc ttccactccg actactccaa tgagaagccg 420
ttcacagggt ttgaggcctt ctatgcagcg gaggatgtgg atgaatgcag agtgtctctg 480
ggagactcag tcccttgtga ccattattgc cacaactact tgggcggcta ctattgctcc 540
tgcagagcgg gctacgttct ccaccagaac aagcacacgt gctcagccct ttgttcaggc 600
caggtgttca caggaagatc tgggtatctc agtagccctg agtacccaca gccataccc 660 aagctctcca gctgcaccta cagcatccgc ctggaggacg gcttcagtgt catcctggac 720
ttcgtggagt ccttcgatgt ggagacgcac cctgaagccc agtgccccta tgactccctc 780
aagattcaaa cagacaaggg ggaacacggc ccattttgtg ggaagacgct gcctcccagg 840
attgaaactg acagccacaa ggtgaccatc acctttgcca ctgacgagtc ggggaaccac 900
acaggctgga agatacacta cacaagcaca gcacggccct gccctgatcc aacggcgcca 960

-continued

```
cctaatggca gcatttcacc tgtgcaagcc atatatgtcc tgaaggacag gttttctgtc   1020
ttctgcaaga caggcttcga gcttctgcaa ggttctgtcc ccctgaaatc attcactgct   1080
gtctgtcaga aagatggatc ttgggaccgg ccgatgccag agtgcagcat tattgattgt   1140
ggccctcctg atgacctacc caatggccat gtggactata tcacaggccc tgaagtgact   1200
acctacaaag ctgtgattca gtacagctgt gaagagactt tctacacaat gagcagcaat   1260
ggtaaatatg tgtgtgaggc tgatggattc tggacgagct ccaaaggaga aaaactcccc   1320
ccggtttgtg agcctgtttg tgggctgtcc acacacacta taggaggacg catagttgga   1380
gggcagcctg caaagcctgg tgactttcct tggcaagtct tgttgctggg tcaaactaca   1440
gcagcagcag gtgcacttat acatgacaat tgggtcctaa cagccgctca tgctgtatat   1500
gagaaaagaa tggcagcgtc ctccctgaac atccgaatgg gcatcctcaa aaggctctca   1560
cctcattaca ctcaagcctg gcccgaggaa atctttatac atgaaggcta cactcacggt   1620
gctggttttg acaatgatat agcattgatt aaactcaaga acaaagtcac aatcaacgga   1680
agcatcatgc ctgtttgcct accgcgaaaa gaagctgcat ccttaatgag aacagacttc   1740
actggaactg tggctggctg gggggttaacc cagaaggggc ttcttgctag aaacctaatg  1800
tttgtggaca taccaattgc tgaccaccaa aaatgtaccg ccgtgtatga aaagctctat   1860
ccaggagtaa gagtaagcgc taacatgctc tgtgctggct tagagactgg tggcaaggac   1920
agctgcagag gtgacagtgg gggggcatta gtgtttctag ataatgagac acagcgatgg   1980
tttgtgggag gaatagtttc ctggggttcc attaattgtg ggcggcaga ccagtatggg    2040
gtctacacaa aagtcatcaa ctatattccc tggattgaga acataataag taatttctaa   2100
tttgcatcgt ccaatcattg ttcctcatat cgccaagtac ctgggaagct tagtaacaaa   2160
cctaagaatg acagcctacc ccaaaatcag agcaggtgag attgttacag gtccaaacac   2220
ttgccaatat cagctttgat ttgtgtttaa cagtgcttgg ccaaccccca acacagaaaa   2280
aacaagttgt atttgattcc ctacaatcta cttattttat actggctgtt tccatttctg   2340
gccaacaaag ggcttgttgt gtctagtgtg tagatttggt cttaatgagc tcagaaagtg   2400
ctcttacttt ctgagtaact tctgagtggt tccagaatac cttttggaag gtaagcggaa   2460
agcaggtgtg tgaccttcac attagatcag ctattaaatt aacaccaagt ccattccaga   2520
atattgggat ataggcatgt tctaccagat tcaccaaatt gtcagataaa aagaacacga   2580
aacagcattt taccctttac aagggcaatt tagcaaatca ttccaaaaac cttaacaggt   2640
gtttcactat acccagccca cttttcttag gtgagcgttg ggctcaggga agtcaaccgt   2700
aactgtacaa ggtacagtca tttgcttatg tatcaaaaac agtaagttat cctgaaataa   2760
actgctcttc tgctaagatg ctgaccttaa aggtcatgtt tgattttaac tggctcttcc   2820
aacaaggcaa gacagggtgc ctcaagatgg ggaaatagct ggcctacaac tcatttacac   2880
caattctggg attaaaagca tgggccacca cacccacctg gagactcaaa ttttaaagga   2940
tgaaaatgct atattgcatc ttcccacata agtcacctta acttttctag cattgtcatg   3000
atatagaatt ttttttcttt ccagtaagac tccagacact aaactgttgg tggcaagaaa   3060
a                                                                   3061
```

<210> SEQ ID NO 8
<211> LENGTH: 3061
<212> TYPE: DNA
<213> ORGANISM: Mus musculus

<400> SEQUENCE: 8

```
ttttcttgcc accaacagtt tagtgtctgg agtcttactg gaagaaaaaa aaattctata     60
tcatgacaat gctagaaaag ttaaggtgac ttatgtggga agatgcaata tagcattttc    120
atcctttaaa atttgagtct ccaggtgggt gtggtggccc atgcttttaa tcccagaatt    180
ggtgtaaatg agttgtaggc cagctatttc cccatcttga ggcaccctgt cttgccttgt    240
tggaagagcc agttaaaatc aaacatgacc tttaaggtca gcatcttagc agaagagcag    300
tttatttcag gataacttac tgtttttgat acataagcaa atgactgtac cttgtacagt    360
tacggttgac ttccctgagc ccaacgctca cctaagaaaa gtgggctggg tatagtgaaa    420
cacctgttaa ggtttttgga atgatttgct aaattgccct tgtaaagggt aaaatgctgt    480
ttcgtgttct ttttatctga caatttggtg aatctggtag aacatgccta tatcccaata    540
ttctggaatg gacttggtgt taatttaata gctgatctaa tgtgaaggtc acacacctgc    600
tttccgctta ccttccaaaa ggtattctgg aaccactcag aagttactca gaaagtaaga    660
gcactttctg agctcattaa gaccaaatct acacactaga cacaacaagc cctttgttgg    720
ccagaaatgg aaacagccag tataaaataa gtagattgta gggaatcaaa tacaacttgt    780
tttttctgtg ttgggggttg gccaagcact gttaaacaca aatcaaagct gatattggca    840
agtgtttgga cctgtaacaa tctcacctgc tctgattttg gggtaggctg tcattcttag    900
gtttgttact aagcttccca ggtacttggc gatatgagga acaatgattg gacgatgcaa    960
attagaaatt acttattatg ttctcaatcc agggaatata gttgatgact tttgtgtaga   1020
ccccatactg gtctgccgcc ccacaattaa tggaacccca ggaaactatt cctcccacaa   1080
accatcgctg tgtctcatta tctagaaaca ctaatgcccc cccactgtca cctctgcagc   1140
tgtccttgcc accagtctct aagccagcac agagcatgtt agcgcttact cttactcctg   1200
gatagagctt ttcatacacg gcggtacatt tttggtggtc agcaattggt atgtccacaa   1260
acattaggtt tctagcaaga agccccttct gggttaaccc ccagccagcc acagttccag   1320
tgaagtctgt tctcattaag gatgcagctt cttttcgcgg taggcaaaca ggcatgatgc   1380
ttccgttgat tgtgactttg ttcttgagtt taatcaatgc tatatcattg tcaaaaccag   1440
caccgtgagt gtagccttca tgtataaaga tttcctcggg ccaggcttga gtgtaatgag   1500
gtgagagcct tttgaggatg cccattcgga tgttcaggga ggacgctgcc attcttttct   1560
catatacagc atgagcggct gttaggaccc aattgtcatg tataagtgca cctgctgctg   1620
ctgtagtttg acccagcaac aagacttgcc aaggaaagtc accaggcttt gcaggctgcc   1680
ctccaactat gcgtcctcct atagtgtgtg tggacagccc acaaacaggc tcacaaaccg   1740
gggggagttt ttctcctttg gagctcgtcc agaatccatc agcctcacac acatatttac   1800
cattgctgct cattgtgtag aaagtctctt cacagctgta ctgaatcaca gctttgtagg   1860
tagtcacttc agggcctgtg atatagtcca catggccatt gggtaggtca tcaggagggc   1920
cacaatcaat aatgctgcac tctggcatcg gccggtccca agatccatct ttctgacaga   1980
cagcagtgaa tgatttcagg gggacagaac cttgcagaag ctcgaagcct gtcttgcaga   2040
agacagaaaa cctgtccttc aggacatata tggcttgcac aggtgaaatg ctgccattag   2100
gtggcgccgt tggatcaggg cagggccgtg ctgtgcttgt gtagtgtatc ttccagcctg   2160
tgtggttccc cgactcgtca gtggcaaagg tgatggtcac cttgtggctg tcagtttcaa   2220
tcctgggagg cagcgtcttc ccacaaaatg ggccgtgttc ccccttgtct gtttgaatct   2280
tgagggagtc ataggggcac tgggcttcag ggtgcgtctc cacatcgaag gactccacga   2340
```

-continued agtccaggat gacactgaag ccgtcctcca ggcggatgct gtaggtgcag ctggagagct 2400
tggggtatgg ctgtgggtac tcagggctac tgagataccc agatcttcct gtgaacacct 2460
ggcctgaaca aagggctgag cacgtgtgct tgttctggtg gagaacgtag cccgctctgc 2520
aggagcaata gtagccgccc aagtagttgt ggcaataatg gtcacaaggg actgagtctc 2580
ccagagacac tctgcattca tccacatcct ccgctgcata gaaggcctca aaccctgtga 2640
acggcttctc attggagtag tcggagtgga aggtgacctt taggctggga cccagtgagt 2700
agaaggtgtc attgccaggt gcctgctcag tgtctgtact ctcctgccca cacagtgtgg 2760
ccagcacctt ggtccctgag ctcaacttga caaagtcata ctcgcagcgg taagagagtt 2820
ccaggtcaaa gtgggtgaag tagaggcgca ggcggtagcc agggggtgca gtcagtgtcc 2880
aggatcgatc ttgatggtca gcatacttct ctgggaagcc aggggacacc aggcgcccga 2940
atacaggttc aggccacttt gaacccagaa gtgtggccac caaactccac agcagaccca 3000
ggaagatgag tagcctcatg gtgtgccacc tagctctgca ggtccagcgc ctatcacctt 3060
t 3061

<210> SEQ ID NO 9
<211> LENGTH: 744
<212> TYPE: DNA
<213> ORGANISM: Mus musculus

<400> SEQUENCE: 9
aaaggtgata ggcgctggac ctgcagagct aggtggcaca ccatgaggct actcatcttc 60
ctgggtctgc tgtggagttt ggtggccaca cttctgggtt caaagtggcc tgaacctgta 120
ttcgggcgcc tggtgtcccc tggcttccca gagaagtatg ctgaccatca agatcgatcc 180
tggacactga ctgcaccccc tggctaccgc ctgcgcctct acttcaccca ctttgacctg 240
gaactctctt accgctgcga gtatgacttt gtcaagttga gctcagggac caaggtgctg 300
gccacactgt gtgggcagga gagtacagac actgagcagg cacctggcaa tgacaccttc 360
tactcactgg gtcccagcct aaaggtcacc ttccactccg actactccaa tgagaagccg 420
ttcacagggt ttgaggcctt ctatgcagcg gaggatgtgg atgaatgcag agtgtctctg 480
ggagactcag tcccttgtga ccattattgc cacaactact tgggcggcta ctattgctcc 540
tgcagagcgg gctacgttct ccaccagaac aagcacacgt gctcagagca gagcctctaa 600
acctccctca gcaacagccc gcccacccca gtgagtcaga taccagtcag tacatgccca 660
cacgatgctg ctctgtcagg ctggaatgac tgccagctac agcacccatt caccttaacc 720
atgacaataa taaacctgcc tccg 744

<210> SEQ ID NO 10
<211> LENGTH: 744
<212> TYPE: DNA
<213> ORGANISM: Mus musculus

<400> SEQUENCE: 10
cggaggcagg tttattattg tcatggttaa ggtgaatggg tgctgtagct ggcagtcatt 60
ccagcctgac agagcagcat cgtgtgggca tgtactgact ggtatctgac tcactggggt 120
gggcgggctg ttgctgaggg aggtttagag gctctgctct gagcacgtgt gcttgttctg 180
gtggagaacg tagcccgctc tgcaggagca atagtagccg cccaagtagt tgtggcaata 240
atggtcacaa gggactgagt ctcccagaga cactctgcat tcatccacat cctccgctgc 300
atagaaggcc tcaaaccctg tgaacggctt ctcattggag tagtcggagt ggaaggtgac 360

```
ctttaggctg ggacccagtg agtagaaggt gtcattgcca ggtgcctgct cagtgtctgt    420

actctcctgc ccacacagtg tggccagcac cttggtccct gagctcaact tgacaaagtc    480

atactcgcag cggtaagaga gttccaggtc aaagtgggtg aagtagaggc gcaggcggta    540

gccagggggt gcagtcagtg tccaggatcg atcttgatgg tcagcatact tctctgggaa    600

gccaggggac accaggcgcc cgaatacagg ttcaggccac tttgaaccca gaagtgtggc    660

caccaaactc cacagcagac ccaggaagat gagtagcctc atggtgtgcc acctagctct    720

gcaggtccag cgcctatcac cttt                                           744
```

<210> SEQ ID NO 11
<211> LENGTH: 2575
<212> TYPE: DNA
<213> ORGANISM: Macaca fascicularis

<400> SEQUENCE: 11

```
cagagtcagg gaggctgggg gcaggggcag gtcactggac aaacagatca aaggtgagac     60

cagtgtaggg ctgcagacca ggccaggcca gctggacggg cacaccatga ggctgctgac    120

cctcctgggc ctgctgtgtg gctcggtggc cacccccttg ggcccgaagt ggcctgaacc    180

tgtgtttggg cgcctggcat cccctggctt tccaggggag tacgccaatg accaggagcg    240

gcgctggacc ctgaccgcac cccccggtta ccgcctgcgc ctctacttca cccactttga    300

cctggagctc tcccacctct gcgagtacga cttcgtcaag ctgagctcgg gggccaaggt    360

gctggccacg ctgtgtgggc atgagagcac agacacggag cgggcccctg gcaacgacac    420

cttctactcg ctgggctcca gcctggacat taccttccgc tccgactact ccaacgagaa    480

gccgttcaca gggttcgagg ccttctacgc agccgaggac attgacgagt gccaggtggc    540

cccgggagag gcgcccgcct gcgaccacca ctgccacaac cacctgggtg gtttctactg    600

ctcctgccgt gtaggctaca tcctgcaccg taacaagcgc acctgctcag ccctgtgctc    660

cggccaggtc ttcacccagc ggtctgggga gctcagcagc cctgaatacc cacagccgta    720

ccccaaactc tccagttgta cttacagcat ccgcctggag gaggggttca gtgtcattct    780

ggactttgtg gagtccttcg atgtggagac gcaccctgaa accctgtgtc cctacgactt    840

tctcaagatt caaatagaca gtgaagaaca cggcccgttc tgtgggaaga cattgccccg    900

caggattgaa acaaaaagca acacggtgac catcaccttt gtcacagatg agtcaggaga    960

ccacacaggc tggaagatcc actacacgag cacagcgcag ccttgccctt atccgatggc   1020

gccacctaat ggccaccttt cacctgtgca agccaaatac atcctgaaag acagcttctc   1080

catcttttgc gagcctggct atgagcttct gcaaggtcac ttgcccctga aatcatttgc   1140

cgcagtttgt cagaaagacg gatcttggga ccagccaatg ccctcgtgca gcattgttga   1200

ctgtggccct cctgatgatc tacccagtgg ccgagtggag tacatcacag gtcctgaagt   1260

gaccacctac aaagctgtga ttcagtacag ctgtgaagag accttctaca caatgaaagt   1320

gaatgatggt aaatatgtgt gtgaggctga tggattctgg acgagctcca aaggagaaag   1380

atcaccgcca gtctgtgagc ctgtttgtgg actatcagcc cgtacaacag gagggcgtat   1440

atatggaggg caaaaggcaa aacctggtga ttttccttgg caagtcctga tattaggtgg   1500

aagcacagca gcaggtgcac ttttatatga caactgggtc ctcacagctg ctcatgccat   1560

atatgagcaa aaacatgatg catcctccct ggacattcga ttgggcgccc tgaagagact   1620

atcgcctcat tatacacaag cctgggctga agctgttttt atacatgaag gttatactca   1680
```

-continued

```
tgatgctggc tttgacaatg acatagcact gattaaattg aataacaaag ttgtaatcaa   1740
tagcaacatc acgcctattt gtctgccaag aaaagaagct gaatccttta tgaggacaga   1800
tgacattgga actgcatctg gatggggatt aacccaaaga ggccttcttg ctagaaatct   1860
aatgtatgtc gacataccaa ttgttgacca tcaaaaatgt actgctgcat atgaaaagcc   1920
accctattca gggggaagtg taactgctaa catgctttgc gctggcttag aaagtggggg   1980
caaggacagc tgcagaggtg acagcggagg ggcactggtg tttctagata atgaaacaca   2040
gaggtggttt gtgggaggaa tagtgtcctg gggttccatg aattgtgggg aagcaggtca   2100
gtacggagtc tatacaaaag tcattaacta tattccctgg atcaagaaca taattagtaa   2160
tttttaattc gcatgtctgc agtcagtcaa ggattcctca tttttagaaa tgcctgtgaa   2220
gaccttggca gcaacgtgac ctgagaagca ttaatcatta ctatgaacat ggcagttgtt   2280
gctccaccca aaaaacagac tccaggtgag actgctgtcg tttctccact taccagttta   2340
attccaacct tacccactga ctcaagggga cataagctac gagtgatagt cacctttgcc   2400
aacccaatgt aatgtgactg ctcaaattac attttgttac tttaaaaggc cagtctcttt   2460
tcatactggc tgttggcatt tctgtgaact gcctgtccat ggtctttgac tgtttttaaa   2520
cttgttctta ttgatctctg taagtgcttt atatattata gcagtattga ttcaa        2575
```

<210> SEQ ID NO 12
<211> LENGTH: 2575
<212> TYPE: DNA
<213> ORGANISM: Macaca fascicularis

<400> SEQUENCE: 12

```
ttgaatcaat actgctataa tatataaagc acttacagag atcaataaga acaagtttaa     60
aaacagtcaa agaccatgga caggcagttc acagaaatgc caacagccag tatgaaaaga    120
gactggcctt ttaaagtaac aaaatgtaat ttgagcagtc acattacatt gggttggcaa    180
aggtgactat cactcgtagc ttatgtcccc ttgagtcagt gggtaaggtt ggaattaaac    240
tggtaagtgg agaaacgaca gcagtctcac ctggagtctg tttttgggt ggagcaacaa    300
ctgccatgtt catagtaatg attaatgctt ctcaggtcac gttgctgcca aggtcttcac    360
aggcatttct aaaaatgagg aatccttgac tgactgcaga catgcgaatt aaaaattact    420
aattatgttc ttgatccagg gaatatagtt aatgactttt gtatagactc cgtactgacc    480
tgcttcccca caattcatgg aaccccagga cactattcct cccacaaacc acctctgtgt    540
ttcattatct agaaacacca gtgcccctcc gctgtcacct ctgcagctgt ccttgccccc    600
actttctaag ccagcgcaaa gcatgttagc agttacactt ccccctgaat agggtggctt    660
ttcatatgca gcagtacatt tttgatggtc aacaattggt atgtcgacat acattagatt    720
tctagcaaga aggcctcttt gggttaatcc ccatccagat gcagttccaa tgtcatctgt    780
cctcataaag gattcagctt cttttcttgg cagacaaata ggcgtgatgt tgctattgat    840
tacaactttg ttattcaatt taatcagtgc tatgtcattg tcaaagccag catcatgagt    900
ataaccttca tgtataaaaa cagcttcagc ccaggcttgt gtataatgag gcgatagtct    960
cttcagggcg cccaatcgaa tgtccaggga ggatgcatca tgtttttgct catatatggc   1020
atgagcagct gtgaggaccc agttgtcata taaaagtgca cctgctgctg tgcttccacc   1080
taatatcagg acttgccaag gaaaatcacc aggttttgcc ttttgccctc catatatacg   1140
ccctcctgtt gtacgggctg atagtccaca aacaggctca cagactggcg gtgatctttc   1200
tcctttggag ctcgtccaga atccatcagc ctcacacaca tatttaccat cattcacttt   1260
```

```
cattgtgtag aaggtctctt cacagctgta ctgaatcaca gctttgtagg tggtcacttc   1320

aggacctgtg atgtactcca ctcggccact gggtagatca tcaggagggc cacagtcaac   1380

aatgctgcac gagggcattg gctggtccca agatccgtct ttctgacaaa ctgcggcaaa   1440

tgatttcagg ggcaagtgac cttgcagaag ctcatagcca ggctcgcaaa agatggagaa   1500

gctgtctttc aggatgtatt tggcttgcac aggtgaaagg tggccattag gtggcgccat   1560

cggataaggg caaggctgcg ctgtgctcgt gtagtggatc ttccagcctg tgtggtctcc   1620

tgactcatct gtgacaaagg tgatggtcac cgtgttgctt tttgtttcaa tcctgcgggg   1680

caatgtcttc ccacagaacg ggccgtgttc ttcactgtct atttgaatct tgagaaagtc   1740

gtagggacac agggtttcag ggtgcgtctc cacatcgaag gactccacaa agtccagaat   1800

gacactgaac ccctcctcca ggcggatgct gtaagtacaa ctggagagtt tggggtacgg   1860

ctgtgggtat tcagggctgc tgagctcccc agaccgctgg gtgaagacct ggccggagca   1920

cagggctgag caggtgcgct tgttacggtg caggatgtag cctacacggc aggagcagta   1980

gaaaccaccc aggtggttgt ggcagtggtg gtcgcaggcg ggcgcctctc ccggggccac   2040

ctggcactcg tcaatgtcct cggctgcgta gaaggcctcg aaccctgtga acggcttctc   2100

gttggagtag tcggagcgga aggtaatgtc caggctggag cccagcgagt agaaggtgtc   2160

gttgccaggg gcccgctccg tgtctgtgct ctcatgccca cacagcgtgg ccagcacctt   2220

ggcccccgag ctcagcttga cgaagtcgta ctcgcagagg tgggagagct ccaggtcaaa   2280

gtgggtgaag tagaggcgca ggcggtaacc ggggggtgcg gtcagggtcc agcgccgctc   2340

ctggtcattg gcgtactccc ctggaaagcc aggggatgcc aggcgcccaa acacaggttc   2400

aggccacttc gggcccaagg gggtggccac cgagccacac agcaggccca ggagggtcag   2460

cagcctcatg gtgtgcccgt ccagctggcc tggcctggtc tgcagcccta cactggtctc   2520

acctttgatc tgtttgtcca gtgacctgcc cctgccccca gcctccctga ctctg        2575
```

```
<210> SEQ ID NO 13
<211> LENGTH: 917
<212> TYPE: DNA
<213> ORGANISM: Macaca fascicularis

<400> SEQUENCE: 13

cagagtcagg gaggctgggg gcaggggcag gtcactggac aaacagatca aaggtgagac     60

cagtgtaggg ctgcagacca ggccaggcca gctggacggg cacaccatga ggctgctgac    120

cctcctgggc ctgctgtgtg gctcggtggc cacccccttg ggcccgaagt ggcctgaacc    180

tgtgtttggg cgcctggcat cccctggctt tccaggggag tacgccaatg accaggagcg    240

gcgctggacc ctgaccgcac cccccggtta ccgcctgcgc ctctacttca cccactttga    300

cctggagctc tcccacctct gcgagtacga cttcgtcaag ctgagctcgg gggccaaggt    360

gctggccacg ctgtgtgggc atgagagcac agacacggag cgggcccctg gcaacgacac    420

cttctactcg ctgggctcca gcctggacat taccttccgc tccgactact ccaacgagaa    480

gccgttcaca gggttcgagg ccttctacgc agccgaggac attgacgagt gccaggtggc    540

cccgggagag gcgcccgcct gcgaccacca ctgccacaac cacctgggtg gtttctactg    600

ctcctgccgt gtaggctaca tcctgcaccg taacaagcgc acctgctcag attcaaatag    660

acagtgaaga acacggcccg ttctgtggga agacattgcc ccgcaggatt gaaacaaaaa    720

gcaacacggt gaccatcacc tttgtcacag atgagtcagg agaccacaca ggctggaaga    780
```

-continued tccactacac gagcacagcg cagccttgcc cttatccgat ggcgccacct aatggccacc 840
tttcacctgt gcaagccaaa tacatcctga aagacagctt ctccatcttt tgcgagcctg 900
gctatgagct tctgcaa 917

<210> SEQ ID NO 14
<211> LENGTH: 917
<212> TYPE: DNA
<213> ORGANISM: Macaca fascicularis

<400> SEQUENCE: 14
ttgcagaagc tcatagccag gctcgcaaaa gatggagaag ctgtctttca ggatgtattt 60
ggcttgcaca ggtgaaaggt ggccattagg tggcgccatc ggataagggc aaggctgcgc 120
tgtgctcgtg tagtggatct tccagcctgt gtggtctcct gactcatctg tgacaaaggt 180
gatggtcacc gtgttgcttt ttgtttcaat cctgcggggc aatgtcttcc cacagaacgg 240
gccgtgttct tcactgtcta tttgaatctg agcaggtgcg cttgttacgg tgcaggatgt 300
agcctacacg gcaggagcag tagaaaccac ccaggtggtt gtggcagtgg tggtcgcagg 360
cgggcgcctc tcccggggcc acctggcact cgtcaatgtc ctcggctgcg tagaaggcct 420
cgaaccctgt gaacggcttc tcgttggagt agtcggagcg gaaggtaatg tccaggctgg 480
agcccagcga gtagaaggtg tcgttgccag gggcccgctc cgtgtctgtg ctctcatgcc 540
cacacagcgt ggccagcacc ttggccccccg agctcagctt gacgaagtcg tactcgcaga 600
ggtgggagag ctccaggtca aagtgggtga agtagaggcg caggcggtaa ccgggggggtg 660 cggtcagggt ccagcgccgc tcctggtcat tggcgtactc ccctggaaag ccaggggatg 720
ccaggcgccc aaacacaggt tcaggccact tcgggcccaa gggggtggcc accgagccac 780
acagcaggcc caggagggtc agcagcctca tggtgtgccc gtccagctgg cctggcctgg 840
tctgcagccc tacactggtc tcacctttga tctgtttgtc cagtgacctg cccctgcccc 900
cagcctccct gactctg 917

<210> SEQ ID NO 15
<211> LENGTH: 2095
<212> TYPE: DNA
<213> ORGANISM: Rattus norvegicus

<400> SEQUENCE: 15
tgacaggcgc tggacctgca gagctgggtg gcacaccatg aggctactga tcgtcctggg 60
tctgctttgg agtttggtgg ccacactttt gggctccaag tggcctgagc ctgtattcgg 120
gcgcctggtg tcccctggct tcccagagaa gtatggcaac catcaggatc gatcctggac 180
gctgactgca ccccctggct tccgcctgcg cctctacttc acccacttca acctggaact 240
ctcttaccgc tgcgagtatg actttgtcaa gttgacctca gggaccaagg tgctagccac 300
gctgtgtggg caggagagta cagatactga gcgggcacct ggcaatgaca ccttctactc 360
actgggtccc agcctaaagg tcaccttcca ctccgactac tccaatgaga agccattcac 420
aggatttgag gccttctatg cagcggagga tgtggatgaa tgcagaacat ccctgggaga 480
ctcagtccct tgtgaccatt attgccacaa ctacctgggc ggctactact gctcctgccg 540
agtgggctac attctgcacc agaacaagca tacctgctca gcccctttgtt caggccaggt 600 gttcactggg aggtctggct ttctcagtag ccctgagtac ccacagccat accccaaact 660
ctccagctgc gcctacaaca tccgcctgga ggaaggcttc agtatcaccc tggacttcgt 720
ggagtccttt gatgtggaga tgcaccctga agcccagtgc ccctacgact ccctcaagat 780
tcaaacagac aagagggaat acggcccgtt ttgtgggaag acgctgcccc ccaggattga 840
aactgacagc aacaaggtga ccattacctt taccaccgac gagtcaggga accacacagg 900
ctggaagata cactacacaa gcacagcaca gccctgccct gatccaacgg cgccacctaa 960
tggtcacatt tcacctgtgc aagccacgta tgtcctgaag gacagctttt ctgtcttctg 1020
caagactggc ttcgagcttc tgcaaggttc tgtcccccctg aagtcattca ctgctgtctg 1080
tcagaaagat ggatcttggg accggccgat accagagtgc agcattattg actgtggccc 1140
tcccgatgac ctacccaatg gccacgtgga ctatatcaca ggccctgaag tgaccaccta 1200
caaagctgtg attcagtaca gctgtgaaga gactttctac acaatgagca gcaatggtaa 1260
atatgtgtgt gaggctgatg gattctggac gagctccaaa ggagaaaaat ccctcccggt 1320
ttgcaagcct gtctgtggac tgtccacaca cacttcagga ggccgtataa ttggaggaca 1380
gcctgcaaag cctggtgact ttccttggca agtcttgtta ctgggtgaaa ctacagcagc 1440
aggtgctctt atacatgacg actgggtcct aacagcggct catgctgtat atgggaaaac 1500
agaggcgatg tcctccctgg acatccgcat gggcatcctc aaaaggctct cccctcatta 1560
cactcaagcc tggccagagg ctgtctttat ccatgaaggc tacactcacg gagctggttt 1620
tgacaatgat atagcactga ttaaactcaa gaacaaagtc acaatcaaca gaaacatcat 1680
gccgatttgt ctaccaagaa aagaagctgc atccttaatg aaaacagact tcgttggaac 1740
tgtggctggc tgggggttaa cccagaaggg gtttcttgct agaaacctaa tgtttgtgga 1800
cataccaatt gttgaccacc aaaaatgtgc tactgcgtat acaaagcagc cctacccagg 1860
agcaaaagtg actgttaaca tgctctgtgc tggcctagac gccggtggca aggacagctg 1920
cagaggtgac agcggagggg cattagtgtt tctagacaat gaaacacaga gatggtttgt 1980
gggaggaata gtttcctggg gttctattaa ctgtgggggg tcagaacagt atggggtcta 2040
cacgaaagtc acgaactata ttccctggat tgagaacata ataaataatt tctaa 2095

<210> SEQ ID NO 16
<211> LENGTH: 2095
<212> TYPE: DNA
<213> ORGANISM: Rattus norvegicus

<400> SEQUENCE: 16
ttagaaatta tttattatgt tctcaatcca gggaatatag ttcgtgactt tcgtgtagac 60
cccatactgt tctgaccccc cacagttaat agaaccccag gaaactattc ctcccacaaa 120
ccatctctgt gtttcattgt ctagaaacac taatgcccct ccgctgtcac ctctgcagct 180
gtccttgcca ccggcgtcta ggccagcaca gagcatgtta acagtcactt ttgctcctgg 240
gtagggctgc tttgtatacg cagtagcaca tttttggtgg tcaacaattg gtatgtccac 300
aaacattagg tttctagcaa gaaacccctt ctgggttaac ccccagccag ccacagttcc 360
aacgaagtct gttttcatta aggatgcagc ttcttttctt ggtagacaaa tcggcatgat 420
gtttctgttg attgtgactt tgttcttgag tttaatcagt gctatatcat tgtcaaaacc 480
agctccgtga gtgtagcctt catggataaa gacagcctct ggccaggctt gagtgtaatg 540
aggggagagc cttttgagga tgcccatgcg gatgtccagg gaggacatcg cctctgtttt 600
cccatataca gcatgagccg ctgttaggac ccagtcgtca tgtataagag cacctgctgc 660
tgtagtttca cccagtaaca agacttgcca aggaaagtca ccaggctttg caggctgtcc 720
tccaattata cggcctcctg aagtgtgtgt ggacagtcca cagacaggct tgcaaaccgg 780

-continued gagggatttt tctcctttgg agctcgtcca gaatccatca gcctcacaca catatttacc 840
attgctgctc attgtgtaga aagtctcttc acagctgtac tgaatcacag ctttgtaggt 900
ggtcacttca gggcctgtga tatagtccac gtggccattg ggtaggtcat cgggagggcc 960
acagtcaata atgctgcact ctggtatcgg ccggtcccaa gatccatctt tctgacagac 1020
agcagtgaat gacttcaggg ggacagaacc ttgcagaagc tcgaagccag tcttgcagaa 1080
gacagaaaag ctgtccttca ggacatacgt ggcttgcaca ggtgaaatgt gaccattagg 1140
tggcgccgtt ggatcagggc agggctgtgc tgtgcttgtg tagtgtatct tccagcctgt 1200
gtggttccct gactcgtcgg tggtaaaggt aatggtcacc ttgttgctgt cagtttcaat 1260 cctgggggc agcgtcttcc cacaaaacgg gccgtattcc ctcttgtctg tttgaatctt 1320
gagggagtcg taggggcact gggcttcagg gtgcatctcc acatcaaagg actccacgaa 1380
gtccagggtg atactgaagc cttcctccag gcggatgttg taggcgcagc tggagagttt 1440
ggggtatggc tgtgggtact cagggctact gagaaagcca gacctcccag tgaacacctg 1500
gcctgaacaa agggctgagc aggtatgctt gttctggtgc agaatgtagc ccactcggca 1560
ggagcagtag tagccgccca ggtagttgtg gcaataatgg tcacaaggga ctgagtctcc 1620
cagggatgtt ctgcattcat ccacatcctc cgctgcatag aaggcctcaa atcctgtgaa 1680
tggcttctca ttggagtagt cggagtggaa ggtgaccttt aggctgggac ccagtgagta 1740
gaaggtgtca ttgccaggtg cccgctcagt atctgtactc tcctgcccac acagcgtggc 1800
tagcaccttg gtccctgagg tcaacttgac aaagtcatac tcgcagcggt aagagagttc 1860
caggttgaag tgggtgaagt agaggcgcag gcggaagcca gggggtgcag tcagcgtcca 1920
ggatcgatcc tgatggttgc catacttctc tgggaagcca ggggacacca ggcgcccgaa 1980
tacaggctca ggccacttgg agcccaaaag tgtggccacc aaactccaaa gcagacccag 2040
gacgatcagt agcctcatgg tgtgccaccc agctctgcag gtccagcgcc tgtca 2095

<210> SEQ ID NO 17
<211> LENGTH: 589
<212> TYPE: DNA
<213> ORGANISM: Rattus norvegicus

<400> SEQUENCE: 17
cttctctcct cagtcttcct gatgcatccc ccaccccatc tctcttccag agcagagcct 60
ctaacctccc tcgctccagc ctgcccaccc cagtgagtca gacaccagtc aatacatgcc 120
cacacgactc agctctgtca ggctggagtg gctgccagca cccattcacc tttcccagac 180
aataaacctg cctccacttc cactgtggct ctgtgtctct tgccagggtt ggggtgatgg 240
gcttggaggg cactagagca tcctgggtgt cccctcattt aatcctcatc tcacagcccg 300
gatgcaggaa ctccctgagc tcacacaggg agatgcgccc ccgccccccg tccccccgtc 360
cccccccccc ccccccgtcc cctgaggctg atctcaggac tcggtagcca gttcttgttc 420
ataggtcacc gcaggtcttt gttctctaac cctggggagc ttgattcagc acagagagca 480
aagggggtgt tactgaggga tcaggctagt cgccctgcat ccggggtgta ctctctgctg 540
gtatggagag ccttcagttc cataagccct cctcctagcc tgtccctcc 589

<210> SEQ ID NO 18
<211> LENGTH: 589
<212> TYPE: DNA
<213> ORGANISM: Rattus norvegicus

<400> SEQUENCE: 18

```
ggagggacag gctaggagga gggcttatgg aactgaaggc tctccatacc agcagagagt      60

acaccccgga tgcagggcga ctagcctgat ccctcagtaa cacccccttt gctctctgtg     120

ctgaatcaag ctccccaggg ttagagaaca aagacctgcg gtgacctatg aacaagaact     180

ggctaccgag tcctgagatc agcctcaggg gacgggggg gggggggggg acgggggac      240

ggggggcggg ggcgcatctc cctgtgtgag ctcagggagt tcctgcatcc gggctgtgag     300

atgaggatta aatgagggga cacccaggat gctctagtgc cctccaagcc catcacccca     360

accctggcaa gagacacaga gccacagtgg aagtggaggc aggtttattg tctgggaaag     420

gtgaatgggt gctggcagcc actccagcct gacagagctg agtcgtgtgg gcatgtattg     480

actggtgtct gactcactgg ggtgggcagg ctggagcgag ggaggttaga ggctctgctc     540

tggaagagag atggggtggg ggatgcatca ggaagactga ggagagaag                589


<210> SEQ ID NO 19
<211> LENGTH: 16
<212> TYPE: PRT
<213> ORGANISM: Unknown
<220> FEATURE:
<223> OTHER INFORMATION: Description of Unknown: RFGF peptide

<400> SEQUENCE: 19

Ala Ala Val Ala Leu Leu Pro Ala Val Leu Leu Ala Leu Leu Ala Pro
1               5                   10                  15


<210> SEQ ID NO 20
<211> LENGTH: 11
<212> TYPE: PRT
<213> ORGANISM: Unknown
<220> FEATURE:
<223> OTHER INFORMATION: Description of Unknown: RFGF analogue peptide

<400> SEQUENCE: 20

Ala Ala Leu Leu Pro Val Leu Leu Ala Ala Pro
1               5                   10


<210> SEQ ID NO 21
<211> LENGTH: 13
<212> TYPE: PRT
<213> ORGANISM: Human immunodeficiency virus

<400> SEQUENCE: 21

Gly Arg Lys Lys Arg Arg Gln Arg Arg Arg Pro Pro Gln
1               5                   10


<210> SEQ ID NO 22
<211> LENGTH: 16
<212> TYPE: PRT
<213> ORGANISM: Drosophila sp.

<400> SEQUENCE: 22

Arg Gln Ile Lys Ile Trp Phe Gln Asn Arg Arg Met Lys Trp Lys Lys
1               5                   10                  15


<210> SEQ ID NO 23

<400> SEQUENCE: 23

000


<210> SEQ ID NO 24
<211> LENGTH: 21
```

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
gugugugagg cugauggauu a 21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
caccuacaaa gcugugauuc a 21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
accuacaaag cugugauuca a 21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
agaaagaugg aucuugggac a 21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
aggcugaugg auucuggacg a 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
gaccacacag gcuggaagau a 21

<210> SEQ ID NO 30
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 30
cgacuuucuc aagauucaaa a 21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 31
guaaauaugu gugugaggcu a 21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
gauucuggac gagcuccaaa a 21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
aaagcuguga uucaguacag a 21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
cuggcuauga gcuucugcaa a 21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
ucuggacuuu guggaguccu u 21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
aggugguuug ugggaggaau a 21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37
uggauucugg acgagcucca a 21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38
ugauucagua cagcugugaa a 21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 39
cuacaaagcu gugauucagu a 21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 40
cugugauuca guacagcugu a 21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 41
cuggugauuu uccuuggcaa a 21

<210> SEQ ID NO 42
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 42
gcugauggau ucuggacgag a                                                21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ucuggacgag cuccaaagga a                                                21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccacguuuca ccugugcaag a                                                21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agcugugauu caguacagcu a                                                21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uccagccugg acauuaccuu a                                                21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uacguccugc accguaacaa a                                                21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 48
agccgaggac auugacgagu a 21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49
aaguggccug aaccuguguu a 21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50
cucugcgagu acgacuucgu a 21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51
gaguaugcca augaccagga a 21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
ugggcccgaa guggccugaa a 21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
cuucgucaag cugagcucgg a 21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54
gcagccgagg acauugacga a 21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
ugggcuccag ccuggacauu a 21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
gcacaccaug aggcugcuga a 21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
cacuuucuac ucgcugggcu a 21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
gaguaugacu uugucaaguu a 21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59 cagguuuga ggccuucuau a 21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 60
ucccuuguga ccauuauugc a 21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 61
cgcugcgagu augacuuugu a 21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
guaugacuuu gucaaguuga a 21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
ucugcugugg aguuuggugg a 21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
gcaccuggca augacaccuu a 21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
agcggaggau guggaugaau a 21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
cccagccuaa aggucaccuu a 21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
cacgugcuca gcccuuuguu a 21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 68
acugagcagg caccuggcaa u 21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 69
accgcugcga guaugacuuu a 21

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 70
uaauccauca gccucacaca cau 23

<210> SEQ ID NO 71
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
ugaaucacag cuuuguaggu ggu 23

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
uugaaucaca gcuuuguagg ugg 23

<210> SEQ ID NO 73
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
ugucccaaga uccaucuuuc uga 23

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
ucguccagaa uccaucagcc uca 23

<210> SEQ ID NO 75
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
uaucuuccag ccuguguggu cuc 23

<210> SEQ ID NO 76
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
uuuugaaucu ugagaaaguc gua 23

<210> SEQ ID NO 77
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
uagccucaca cacauauuua cca 23

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
uuuuggagcu cguccagaau cca 23

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
ucuguacuga aucacagcuu ugu 23

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80
uuugcagaag cucauagcca guc 23

<210> SEQ ID NO 81
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 81
aaggacucca caaaguccag aau 23

<210> SEQ ID NO 82
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 82
uauuccuccc acaaaccacc ucu 23

<210> SEQ ID NO 83
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 83
uuggagcucg uccagaaucc auc 23

<210> SEQ ID NO 84
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 84
uuucacagcu guacugaauc aca 23

<210> SEQ ID NO 85
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 85
uacugaauca cagcuuugua ggu 23

<210> SEQ ID NO 86
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 86
uacagcugua cugaaucaca gcu 23

<210> SEQ ID NO 87
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
uuugccaagg aaaaucacca ggu 23

<210> SEQ ID NO 88
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
ucucguccag aauccaucag ccu 23

<210> SEQ ID NO 89
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
uuccuuugga gcucguccag aau 23

<210> SEQ ID NO 90
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 90
ucuugcacag gugaaacgug gcc 23

<210> SEQ ID NO 91
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
uagcuguacu gaaucacagc uuu 23

<210> SEQ ID NO 92
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 92
uaagguaaug uccaggcugg agc 23

<210> SEQ ID NO 93
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
uuuguuacgg ugcaggacgu agc 23

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 94
uacucgucaa uguccucggc ugc 23

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
uaacacaggu ucaggccacu ucg 23

<210> SEQ ID NO 96
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 96
uacgaagucg uacucgcaga ggu 23

<210> SEQ ID NO 97

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 97
uuccugguca uuggcauacu ccc 23

<210> SEQ ID NO 98
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
uuucaggcca cuucgggccc aag 23

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
uccgagcuca gcuugacgaa guc 23

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 100
uucgucaaug uccucggcug cau 23

<210> SEQ ID NO 101
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 101
uaauguccag gcuggagccc agc 23

<210> SEQ ID NO 102
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
uucagcagcc ucauggugug ccc 23

<210> SEQ ID NO 103
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103

uagcccagcg aguagaaagu guc                                              23


<210> SEQ ID NO 104
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104

uaacuugaca aagucauacu cgc                                              23


<210> SEQ ID NO 105
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105

uauagaaggc cucaaacccu gug                                              23


<210> SEQ ID NO 106
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106

ugcaauaaug gucacaaggg acu                                              23


<210> SEQ ID NO 107
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107

uacaaaguca uacucgcagc ggu                                              23


<210> SEQ ID NO 108
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108

uucaacuuga caaagucaua cuc                                              23


<210> SEQ ID NO 109
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 109
uccaccaaac uccacagcag acc 23

<210> SEQ ID NO 110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uaaggaguca uugccaggug ccu 23

<210> SEQ ID NO 111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uauucaucca cauccuccgc ugc 23

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uaaggugacc uuuaggcugg gac 23

<210> SEQ ID NO 113
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uaacaaaggg cugagcacgu gug 23

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
auugccaggu gccugcucag ugu 23

<210> SEQ ID NO 115
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
uaaagucaua cucgcagcgg uaa 23

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
gugugugagg cugauggauu a 21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
caccuacaaa gcugugauuc a 21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
accuacaaag cugugauuca a 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
agaaagaugg aucuugggac a 21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
aggcugaugg auucuggacg a 21

<210> SEQ ID NO 121
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 121
gaccacacag gcuggaagau a                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cgacuuucuc aagauucaaa a                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
guaaauaugu gugugaggcu a                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gauucuggac gagcuccaaa a                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aaagcuguga uucaguacag a                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
cuggcuauga gcuucugcaa a                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 127
ucuggacuuu guggaguccu u 21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 128
aggugguuug ugggaggaau a 21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 129
uggauucugg acgagcucca a 21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 130
ugauucagua cagcugugaa a 21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 131
cuacaaagcu gugauucagu a 21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 132
cugugauuca guacagcugu a 21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 133
cuggugauuu uccuuggcaa a 21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 134
gcugauggau ucuggacgag a 21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 135
ucuggacgag cuccaaagga a 21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 136
ccacguuuca ccugugcaag a 21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 137
agcugugauu caguacagcu a 21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 138
uccagccugg acauuaccuu a 21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 139
uacguccugc accguaacaa a 21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 140
agccgaggac auugacgagu a 21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 141
aaguggccug aaccuguguu a 21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 142
cucugcgagu acgacuucgu a 21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 143
gaguaugcca augaccagga a 21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 144
ugggcccgaa guggccugaa a 21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 145
cuucgucaag cugagcucgg a 21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 146
gcagccgagg acauugacga a 21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
ugggcuccag ccuggacauu a 21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
gcacaccaug aggcugcuga a 21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 149
cacuuucuac ucgcugggcu a 21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
gaguaugacu uugucaaguu a 21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
caggguuuga ggccuucuau a 21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
ucccuuguga ccauuauugc a 21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
cgcugcgagu augacuuugu a 21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
guaugacuuu gucaaguuga a 21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
ucugcugugg aguuuggugg a 21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
gcaccuggca augacaccuu a 21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
agcggaggau guggaugaau a 21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
cccagccuaa aggucaccuu a 21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
cacgugcuca gcccuuuguu a 21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 160
acugagcagg caccuggcaa u 21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 161
accgcugcga guaugacuuu a 21

<210> SEQ ID NO 162
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 162
uaauccauca gccucacaca cau 23

<210> SEQ ID NO 163
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 163
ugaaucacag cuuuguaggu ggu 23

<210> SEQ ID NO 164
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 164
uugaaucaca gcuuuguagg ugg 23

<210> SEQ ID NO 165
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 165
ugucccaaga uccaucuuuc uga 23

<210> SEQ ID NO 166
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
ucguccagaa uccaucagcc uca 23

<210> SEQ ID NO 167
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
uaucuuccag ccuguguggu cuc 23

<210> SEQ ID NO 168
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
uuuugaaucu ugagaaaguc gua 23

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
uagccucaca cacauauuua cca 23

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 170
uuuuggagcu cguccagaau cca 23

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 171
ucuguacuga aucacagcuu ugu 23

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 172
uuugcagaag cucauagcca guc 23

<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 173
aaggacucca caaaguccag aau 23

<210> SEQ ID NO 174
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 174
uauuccuccc acaaaccacc ucu 23

<210> SEQ ID NO 175
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 175
uuggagcucg uccagaaucc auc 23

<210> SEQ ID NO 176

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 176
uuucacagcu guacugaauc aca 23

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 177
uacugaauca cagcuuugua ggu 23

<210> SEQ ID NO 178
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 178
uacagcugua cugaaucaca gcu 23

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 179
uuugccaagg aaaaucacca ggu 23

<210> SEQ ID NO 180
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 180
ucucguccag aauccaucag ccu 23

<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 181
uuccuuugga gcucguccag aau 23

<210> SEQ ID NO 182
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 182
ucuugcacag gugaaacgug gcc 23

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 183
uagcuguacu gaaucacagc uuu 23

<210> SEQ ID NO 184
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 184
uaagguaaug uccaggcugg agc 23

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 185
uuuguuacgg ugcaggacgu agc 23

<210> SEQ ID NO 186
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 186
uacucgucaa uguccucggc ugc 23

<210> SEQ ID NO 187
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 187
uaacacaggu ucaggccacu ucg 23

<210> SEQ ID NO 188
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 188
uacgaagucg uacucgcaga ggu 23

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 189
uuccugguca uuggcauacu ccc 23

<210> SEQ ID NO 190
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 190
uuucaggcca cuucgggccc aag 23

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
uccgagcuca gcuugacgaa guc 23

<210> SEQ ID NO 192
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 192
uucgucaaug uccucggcug cau 23

<210> SEQ ID NO 193
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 193
uaauguccag gcuggagccc agc 23

<210> SEQ ID NO 194
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 194
uucagcagcc ucauggugug ccc 23

<210> SEQ ID NO 195
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 195
uagcccagcg aguagaaagu guc 23

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 196
uaacuugaca aagucauacu cgc 23

<210> SEQ ID NO 197
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 197
uauagaaggc cucaaacccu gug 23

<210> SEQ ID NO 198
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 198
ugcaauaaug gucacaaggg acu 23

<210> SEQ ID NO 199
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 199
uacaaaguca uacucgcagc ggu 23

<210> SEQ ID NO 200
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 200
uucaacuuga caaagucaua cuc 23

<210> SEQ ID NO 201
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uccaccaaac uccacagcag acc 23

<210> SEQ ID NO 202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uaagguguca uugccaggug ccu 23

<210> SEQ ID NO 203
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uauucaucca cauccuccgc ugc 23

<210> SEQ ID NO 204
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uaaggugacc uuuaggcugg gac 23

<210> SEQ ID NO 205
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uaacaaaggg cugagcacgu gug 23

<210> SEQ ID NO 206
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 206
auugccaggu gccugcucag ugu 23

<210> SEQ ID NO 207
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 207
uaaagucaua cucgcagcgg uaa 23

<210> SEQ ID NO 208
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 208 augugugu ga ggcugaugga uuc 23

<210> SEQ ID NO 209
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 209
accaccuaca aagcugugau uca 23

<210> SEQ ID NO 210
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 210
ccaccuacaa agcugugauu cag 23

<210> SEQ ID NO 211
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 211
ucagaaagau ggaucuuggg acc 23

<210> SEQ ID NO 212
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 212
ugaggcugau ggauucugga cga 23

<210> SEQ ID NO 213
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 213
gagaccacac aggcuggaag auc 23

<210> SEQ ID NO 214
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 214
uacgacuuuc ucaagauuca aac 23

<210> SEQ ID NO 215
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 215
ugguaaauau gugugugagg cug 23

<210> SEQ ID NO 216
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 216
uggauucugg acgagcucca aag 23

<210> SEQ ID NO 217
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 217
acaaagcugu gauucaguac agc 23

<210> SEQ ID NO 218
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 218
gacuggcuau gagcuucugc aag 23

<210> SEQ ID NO 219
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 219
auucuggacu uuguggaguc cuu 23

<210> SEQ ID NO 220
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 220
agaggugguu ugugggagga aua 23

<210> SEQ ID NO 221
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 221
gauggauucu ggacgagcuc caa 23

<210> SEQ ID NO 222
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 222
ugugauucag uacagcugug aag 23

<210> SEQ ID NO 223
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 223
accuacaaag cugugauuca gua 23

<210> SEQ ID NO 224
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 224
agcugugauu caguacagcu gug 23

<210> SEQ ID NO 225
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 225
accuggugau uuuccuuggc aag 23

<210> SEQ ID NO 226

<211> LENGTH: 23
<212> TYPE: RNA
<213> ORGANISM: Unknown
<220> FEATURE:
<223> OTHER INFORMATION: Description of Unknown: Target sequence

<400> SEQUENCE: 226
aggcugaugg auucuggacg agc 23

<210> SEQ ID NO 227
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 227
auucuggacg agcuccaaag gag 23

<210> SEQ ID NO 228
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 228
ggccacguuu caccugugca agc 23

<210> SEQ ID NO 229
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 229
aaagcuguga uucaguacag cug 23

<210> SEQ ID NO 230
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 230
gcuccagccu ggacauuacc uuc 23

<210> SEQ ID NO 231
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 231
gcuacguccu gcaccguaac aag 23

<210> SEQ ID NO 232
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 232
gcagccgagg acauugacga gug 23

<210> SEQ ID NO 233
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 233
cgaaguggcc ugaaccugug uuc 23

<210> SEQ ID NO 234
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 234
accucugcga guacgacuuc guc 23

<210> SEQ ID NO 235
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 235
gggaguaugc caaugaccag gag 23

<210> SEQ ID NO 236
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 236
cuugggcccg aaguggccug aac 23

<210> SEQ ID NO 237
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 237
gacuucguca agcugagcuc ggg 23

<210> SEQ ID NO 238
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 238
augcagccga ggacauugac gag 23

<210> SEQ ID NO 239
<211> LENGTH: 23
<212> TYPE: RNA

<213> ORGANISM: Unknown
<220> FEATURE:
<223> OTHER INFORMATION: Description of Unknown: Target sequence

<400> SEQUENCE: 239
gcugggcucc agccuggaca uua 23

<210> SEQ ID NO 240
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 240
gggcacacca ugaggcugcu gac 23

<210> SEQ ID NO 241
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 241
gacacuuucu acucgcuggg cuc 23

<210> SEQ ID NO 242
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 242
gcgaguauga cuuugucaag uug 23

<210> SEQ ID NO 243
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 243
cacaggguuu gaggccuucu aug 23

<210> SEQ ID NO 244
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 244
agucccuugu gaccauuauu gcc 23

<210> SEQ ID NO 245
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 245
accgcugcga guaugacuuu guc 23

<210> SEQ ID NO 246
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 246
gaguaugacu uugucaaguu gag 23

<210> SEQ ID NO 247
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 247
ggucugcugu ggaguuuggu ggc 23

<210> SEQ ID NO 248
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 248
aggcaccugg caaugacacc uuc 23

<210> SEQ ID NO 249
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 249
gcagcggagg auguggauga aug 23

<210> SEQ ID NO 250
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 250
gucccagccu aaaggucacc uuc 23

<210> SEQ ID NO 251
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 251
cacacgugcu cagcccuuug uuc 23

<210> SEQ ID NO 252
<211> LENGTH: 23
<212> TYPE: RNA
<213> ORGANISM: Unknown
<220> FEATURE:

<223> OTHER INFORMATION: Description of Unknown: Target sequence

<400> SEQUENCE: 252
acacugagca ggcaccuggc aau 23

<210> SEQ ID NO 253
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 253
uuaccgcugc gaguaugacu uug 23

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 254
gacaaugaca uagcacugau u 21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 255
auuguugacc aucaaaaaug u 21

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 256
aucuaaugua ugucgacaua a 21

<210> SEQ ID NO 257
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 257
aaugacauag cacugauuaa a 21

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 258
uuuuccuugg caaguccuga u 21

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 259
aaucuaaugu augucgacau a 21

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 260
cuagaaaucu aauguauguc a 21

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 261
ugagcaaaaa caugaugcau a 21

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 262
cuuuaugagg acagaugaca u 21

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 263
cacgccuauu ugucugccaa a 21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 264
acaggagggc guauauaugg a 21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 265
acauggcagu uguugcucca a 21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 266
caggugcacu uuuauaugac a 21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 267
aaaauguacu gcugcauaug a 21

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 268
caauagcaac aucacgccua u 21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 269
aaaccuggug auuuuccuug a 21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 270

-continued aauagcaaca ucacgccuau u 21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 271
ucuggacgag cuccaaagga a 21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
guguaacugc uaacaugcuu u 21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 273
cuaauguaug ucgacauacc a 21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 274
uguaauguca cugcucaaau u 21

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 275
agaaaucuaa uguaugucga a 21

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
caacaggagg gcguauauau a 21

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
acaacaggag ggcguauaua u 21

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
gcuucugcaa ggucacuugc a 21

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279
guuauuaacu auauucccug a 21

<210> SEQ ID NO 280
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 280
cuuugacaau gacauagcac u 21

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 281
aagccagucu cuuuucauac u 21

<210> SEQ ID NO 282
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 282
uagcaacauc acgccuauuu a 21

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 283
ucacgccuau uugucugcca a 21

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 284
gaaaucuaau guaugucgac a 21

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 285
aagacuauca ccucauuaua a 21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 286
ccucauuaua cacaagccug a 21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 287
uuccuuggca aguccugaua u 21

<210> SEQ ID NO 288
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
gaagcugaau ccuuuaugag a 21

```
<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289

uaugaggaca gaugacauug a                                              21


<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290

agaagcugaa uccuuuauga a                                              21


<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291

agcaacauca cgccuauuug u                                              21


<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292

uauauggagg gcaaaaggca a                                              21


<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293

auggcaguug uugcuccacc a                                              21


<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294

gccagucucu uuucauacug a                                              21


<210> SEQ ID NO 295
```

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 295
uccuuggcaa guccugauau u 21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 296
ccagucugug agccuguuug u 21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 297
aaauguacug cugcauauga a 21

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 298
uuguugacca ucaaaaaugu a 21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 299
caaaguugua aucaauagca a 21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 300
gaaaugccug ugaagaccuu a 21

<210> SEQ ID NO 301
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301
uagaaaucua auguaugucg a 21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302
aagcugaauc cuuuaugagg a 21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303
uggcaagucc ugauauuagg u 21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304
gaagguuaua cucaugaugc u 21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305
cuugcuagaa aucuaaugua u 21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
agccagucuc uuuucauacu a 21

<210> SEQ ID NO 307
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 307
cuaucaccuc auuauacaca a 21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308
gaccaucaaa aauguacugc u 21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309
acgccuauuu gucugccaag a 21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 310
gggcguauau auggagggca a 21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 311
ucaauagcaa caucacgccu a 21

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 312
auauauggag ggcaaaaggc a 21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 313
gcaguuguug cuccacccaa a 21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 314
gugauuuucc uuggcaaguc a 21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 315
acaaugacau agcacugauu a 21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
caucacgccu auuugucugc a 21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
aagguuauac ucaugaugcu a 21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
aaccugguga uuuuccuugg a 21

<210> SEQ ID NO 319
<211> LENGTH: 21
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 319
agacuaucac cucauuauac a 21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
gguuuguggg aggaauagug u 21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
accucauuau acacaagccu a 21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
gagccuguuu guggacuauc a 21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 323
gagggcguau auauggaggg a 21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 324
ggcguauaua uggagggcaa a 21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 325
ccuuuaugag gacagaugac a 21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 326
gcugcauaug aaaagccacc a 21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 327
aaaucuaaug uaugucgaca u 21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 328
ggcaaguccu gauauuaggu a 21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 329
auuuuuagaa augccuguga a 21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 330
gcaggugcac uuuuauauga a 21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 331
guuuguggga ggaauagugu a 21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 332
ucucuuuuca uacuggcugu u 21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 333
uuuccuuggc aaguccugau a 21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 334
gcaacaucac gccuauuugu a 21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
aggagggcgu auauauggag a 21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 336
aguuguugcu ccacccaaaa a 21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 337
ugugagccug uuuguggacu a 21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
caaguccuga uauuaggugg a 21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 339
aaguguaacu gcuaacaugc u 21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 340
auagcaacau cacgccuauu u 21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 341
caggagggcg uauauaugga a 21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 342
uuugugggag gaauaguguc a 21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 343
aucaauagca acaucacgcc u 21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 344
aaaguuguaa ucaauagcaa a 21

<210> SEQ ID NO 345
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 345
aaucagugcu augucauugu caa 23

<210> SEQ ID NO 346
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
acauuuuuga uggucaacaa ucg 23

<210> SEQ ID NO 347
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 347
uuaugucgac auacauuaga uuu 23

<210> SEQ ID NO 348
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
uuuaaucagu gcuaugucau ugu 23

<210> SEQ ID NO 349
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 349
aucaggacuu gccaaggaaa auc 23

<210> SEQ ID NO 350
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 350
uaugucgaca uacauuagau uuc 23

<210> SEQ ID NO 351
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 351
ugacauacau uagauuucua gca 23

<210> SEQ ID NO 352
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 352
uaugcaucau guuuuugcuc aua 23

<210> SEQ ID NO 353
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 353
augucaucug uccucauaaa gga 23

<210> SEQ ID NO 354
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 354
uuuggcagac aaauaggcgu gau 23

<210> SEQ ID NO 355
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 355
uccauauaua cgcccuccug uug 23

<210> SEQ ID NO 356
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 356
uuggagcaac aacugccaug ucc 23

<210> SEQ ID NO 357
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
ugucauauaa aagugcaccu gcu 23

<210> SEQ ID NO 358
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
ucauaugcag caguacauuu uug 23

<210> SEQ ID NO 359
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
auaggcguga uguugcuauu gau 23

<210> SEQ ID NO 360
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
ucaaggaaaa ucaccagguu uug 23

<210> SEQ ID NO 361
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 361
aauaggcgug auguugcuau uga 23

<210> SEQ ID NO 362
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 362
uuccuuugga gcucguccag aau 23

<210> SEQ ID NO 363
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 363
aaagcauguu agcaguuaca cuu 23

<210> SEQ ID NO 364
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 364
ugguaugucg acauacauua gau 23

<210> SEQ ID NO 365
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 365
aauuugagca gugacauuac acu 23

<210> SEQ ID NO 366
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 366
uucgacauac auuagauuuc uag 23

<210> SEQ ID NO 367
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 367
uauauauacg cccuccuguu gug 23

<210> SEQ ID NO 368
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
auauauacgc ccuccuguug ugc 23

<210> SEQ ID NO 369
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
ugcaagugac cuugcagaag cuc 23

<210> SEQ ID NO 370
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
ucagggaaua uaguuaauaa cuu 23

<210> SEQ ID NO 371
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
agugcuaugu cauugucaaa gcc 23

<210> SEQ ID NO 372
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372
aguaugaaaa gagacuggcu uuu 23

<210> SEQ ID NO 373
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 373
uaaauaggcg ugauguugcu auu 23

<210> SEQ ID NO 374

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
uuggcagaca aauaggcgug aug 23

<210> SEQ ID NO 375
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
ugucgacaua cauuagauuu cua 23

<210> SEQ ID NO 376
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
uuauaaugag gugauagucu uuu 23

<210> SEQ ID NO 377
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
ucaggcuugu guauaaugag gug 23

<210> SEQ ID NO 378
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
auaucaggac uugccaagga aaa 23

<210> SEQ ID NO 379
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
ucucauaaag gauucagcuu cuu 23

<210> SEQ ID NO 380
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 380
ucaaugucau cuguccucau aaa 23

<210> SEQ ID NO 381
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 381
uucauaaagg auucagcuuc uuu 23

<210> SEQ ID NO 382
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 382
acaaauaggc gugauguugc uau 23

<210> SEQ ID NO 383
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 383
uugccuuuug cccuccauau aua 23

<210> SEQ ID NO 384
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 384
ugguggagca acaacugcca ugu 23

<210> SEQ ID NO 385
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 385
ucaguaugaa aagagacugg cuu 23

<210> SEQ ID NO 386
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 386
aauaucagga cuugccaagg aaa 23

<210> SEQ ID NO 387
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
acaaacaggc ucacagacug gga 23

<210> SEQ ID NO 388
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
uucauaugca gcaguacauu uuu 23

<210> SEQ ID NO 389
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389
uacauuuuug auggucaaca auc 23

<210> SEQ ID NO 390
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
uugcuauuga uuacaacuuu guu 23

<210> SEQ ID NO 391
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
uaaggucuuc acaggcauuu cua 23

<210> SEQ ID NO 392
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucgacauaca uuagauuucu agc 23

<210> SEQ ID NO 393
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
uccucauaaa ggauucagcu ucu 23

<210> SEQ ID NO 394
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
accuaauauc aggacuugcc aag 23

<210> SEQ ID NO 395
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
agcaucauga guauaaccuu cau 23

<210> SEQ ID NO 396
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
auacauuaga uuucuagcaa gaa 23

<210> SEQ ID NO 397
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uaguaugaaa agagacuggc uuu 23

<210> SEQ ID NO 398
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 398
uuguguauaa ugaggugaua guc 23

<210> SEQ ID NO 399
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 399
agcaguacau uuuugauggu caa 23

<210> SEQ ID NO 400
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
ucuuggcaga caaauaggcg uga 23

<210> SEQ ID NO 401
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
uugcccucca uauauacgcc cuc 23

<210> SEQ ID NO 402
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 402
uaggcgugau guugcuauug auu 23

<210> SEQ ID NO 403
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 403
ugccuuuugc ccuccauaua uac 23

<210> SEQ ID NO 404
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 404
uuugggugga gcaacaacug cca 23

<210> SEQ ID NO 405
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 405
ugacuugcca aggaaaauca cca 23

<210> SEQ ID NO 406
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 406
uaaucagugc uaugucauug uca 23

<210> SEQ ID NO 407
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 407
ugcagacaaa uaggcgugau guu 23

<210> SEQ ID NO 408
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 408
uagcaucaug aguauaaccu uca 23

<210> SEQ ID NO 409
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
uccaaggaaa aucaccaggu uuu 23

<210> SEQ ID NO 410
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
uguauaauga ggugauaguc uuu 23

<210> SEQ ID NO 411
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
acacuauucc ucccacaaac cac 23

<210> SEQ ID NO 412
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
uaggcuugug uauaaugagg uga 23

<210> SEQ ID NO 413
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 413
ugauagucca caaacaggcu cac 23

<210> SEQ ID NO 414
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 414
ucccuccaua uauacgcccu ccu 23

<210> SEQ ID NO 415
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
uuugcccucc auauauacgc ccu 23

<210> SEQ ID NO 416
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
ugucaucugu ccucauaaag gau 23

<210> SEQ ID NO 417
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417 uggugg cuuu ucauaugcag cag 23

<210> SEQ ID NO 418
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
augucgacau acauuagauu ucu 23

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 419
uaccuaauau caggacuugc caa 23

<210> SEQ ID NO 420
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
uucacaggca uuucuaaaaa uga 23

<210> SEQ ID NO 421
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 421
uucauauaaa agugcaccug cug 23

<210> SEQ ID NO 422
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 422
uacacuauuc cucccacaaa cca 23

<210> SEQ ID NO 423
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 423
aacagccagu augaaaagag acu 23

<210> SEQ ID NO 424
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 424
uaucaggacu ugccaaggaa aau 23

<210> SEQ ID NO 425
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 425
uacaaauagg cgugauguug cua 23

<210> SEQ ID NO 426
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 426
ucuccauaua uacgcccucc ugu 23

<210> SEQ ID NO 427
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 427
uuuuugggug gagcaacaac ugc 23

<210> SEQ ID NO 428
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 428
uaguccacaa acaggcucac aga 23

<210> SEQ ID NO 429
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
uccaccuaau aucaggacuu gcc 23

<210> SEQ ID NO 430
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
agcauguuag caguuacacu ucc 23

<210> SEQ ID NO 431
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 431
aaauaggcgu gauguugcua uug 23

<210> SEQ ID NO 432
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 432
uuccauauau acgcccuccu guu 23

<210> SEQ ID NO 433
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 433
ugacacuauu ccucccacaa acc 23

<210> SEQ ID NO 434
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 434
aggcgugaug uugcuauuga uua 23

<210> SEQ ID NO 435
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 435
uuugcuauug auuacaacuu ugu 23

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 436
gacaaugaca uagcacugau u 21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 437
auuguugacc aucaaaaaug u 21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 438
aucuaaugua ugucgacaua a 21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 439
aaugacauag cacugauuaa a 21

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 440
uuuuccuugg caaguccuga u 21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 441
aaucuaaugu augucgacau a 21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 442
cuagaaaucu aauguauguc a 21

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 443
ugagcaaaaa caugaugcau a 21

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 444
cuuuaugagg acagaugaca u 21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 445
cacgccuauu ugucugccaa a 21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
acaggagggc guauauaugg a 21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 447
acauggcagu uguugcucca a 21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 448
caggugcacu uuuauaugac a 21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 449
aaaauguacu gcugcauaug a 21

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 450
caauagcaac aucacgccua u 21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 451
aaaccuggug auuuuccuug a 21

<210> SEQ ID NO 452
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 452
aauagcaaca ucacgccuau u 21

<210> SEQ ID NO 453

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 453
ucuggacgag cuccaaagga a 21

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 454
guguaacugc uaacaugcuu u 21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 455
cuaauguaug ucgacauacc a 21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 456
uguaauguca cugcucaaau u 21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 457
agaaaucuaa uguaugucga a 21

<210> SEQ ID NO 458
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 458
caacaggagg gcguauauau a 21

<210> SEQ ID NO 459
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 459
acaacaggag ggcguauaua u 21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 460
gcuucugcaa ggucacuugc a 21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 461
guuauuaacu auauucccug a 21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 462
cuuugacaau gacauagcac u 21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 463
aagccagucu cuuuucauac u 21

<210> SEQ ID NO 464
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 464
uagcaacauc acgccuauuu a 21

<210> SEQ ID NO 465
<211> LENGTH: 21
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 465
ucacgccuau uugucugcca a 21

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 466
gaaaucuaau guaugucgac a 21

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 467
aagacuauca ccucauuaua a 21

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 468
ccucauuaua cacaagccug a 21

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 469
uuccuuggca aguccugaua u 21

<210> SEQ ID NO 470
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 470
gaagcugaau ccuuuaugag a 21

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 471
uaugaggaca gaugacauug a 21

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 472
agaagcugaa uccuuuauga a 21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 473
agcaacauca cgccuauuug u 21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 474
uauauggagg gcaaaaggca a 21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 475
auggcaguug uugcuccacc a 21

<210> SEQ ID NO 476
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 476
gccagucucu uuucauacug a 21

<210> SEQ ID NO 477
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 477
uccuuggcaa guccugauau u 21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
ccagucugug agccuguuug u 21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
aaauguacug cugcauauga a 21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 480
uuguugacca ucaaaaaugu a 21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 481
caaaguugua aucaauagca a 21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 482
gaaaugccug ugaagaccuu a 21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 483
uagaaaucua auguaugucg a 21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 484
aagcugaauc cuuuaugagg a 21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
uggcaagucc ugauauuagg u 21

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 486
gaagguuaua cucaugaugc u 21

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 487
cuugcuagaa aucuaaugua u 21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 488
agccagucuc uuuucauacu a 21

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 489
cuaucaccuc auuauacaca a 21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 490
gaccaucaaa aauguacugc u 21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 491
acgccuauuu gucugccaag a 21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
gggcguauau auggagggca a 21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
ucaauagcaa caucacgccu a 21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 494
auauauggag ggcaaaaggc a 21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 495
gcaguuguug cuccacccaa a 21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 496
gugauuuucc uuggcaaguc a 21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 497
acaaugacau agcacugauu a 21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 498
caucacgccu auuugucugc a 21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 499
aagguuauac ucaugaugcu a 21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 500
aaccugguga uuuuccuugg a 21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 501
agacuaucac cucauuauac a 21

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
gguuuguggg aggaauagug u 21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 503
accucauuau acacaagccu a 21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 504
gagccuguuu guggacuauc a 21

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 505
gagggcguau auauggaggg a 21

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 506
ggcguauaua uggagggcaa a 21

<210> SEQ ID NO 507
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 507
ccuuuaugag gacagaugac a 21

<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 508
gcugcauaug aaaagccacc a 21

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 509
aaaucuaaug uaugucgaca u 21

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 510
ggcaaguccu gauauuaggu a 21

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 511
auuuuuagaa augccuguga a 21

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 512
gcaggugcac uuuuauauga a 21

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 513
guuuguggga ggaauagugu a 21

<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 514
ucucuuuuca uacuggcugu u 21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 515
uuuccuuggc aaguccugau a 21

<210> SEQ ID NO 516
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 516
gcaacaucac gccuauuugu a 21

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 517
aggagggcgu auauauggag a 21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 518
aguuguugcu ccacccaaaa a 21

<210> SEQ ID NO 519
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 519
ugugagccug uuuguggacu a 21

<210> SEQ ID NO 520
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 520
caaguccuga uauuaggugg a 21

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 521
aaguguaacu gcuaacaugc u 21

<210> SEQ ID NO 522
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 522
auagcaacau cacgccuauu u 21

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 523
caggagggcg uauauaugga a 21

<210> SEQ ID NO 524
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 524
uuugugggag gaauaguguc a 21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 525
aucaauagca acaucacgcc u 21

<210> SEQ ID NO 526
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 526
aaaguuguaa ucaauagcaa a 21

<210> SEQ ID NO 527
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 527
aaucagugcu augucauugu caa 23

<210> SEQ ID NO 528
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 528
acauuuuuga uggucaacaa ucg 23

<210> SEQ ID NO 529
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 529
uuaugucgac auacauuaga uuu 23

<210> SEQ ID NO 530
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 530
uuuaaucagu gcuaugucau ugu 23

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 531
aucaggacuu gccaaggaaa auc 23

<210> SEQ ID NO 532

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 532
uaugucgaca uacauuagau uuc 23

<210> SEQ ID NO 533
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 533
ugacauacau uagauuucua gca 23

<210> SEQ ID NO 534
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 534
uaugcaucau guuuuugcuc aua 23

<210> SEQ ID NO 535
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 535
augucaucug uccucauaaa gga 23

<210> SEQ ID NO 536
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 536
uuuggcagac aaauaggcgu gau 23

<210> SEQ ID NO 537
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 537
uccauauaua cgcccuccug uug 23

<210> SEQ ID NO 538
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 538
uuggagcaac aacugccaug ucc 23

<210> SEQ ID NO 539
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 539
ugucauauaa aagugcaccu gcu 23

<210> SEQ ID NO 540
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 540
ucauaugcag caguacauuu uug 23

<210> SEQ ID NO 541
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 541
auaggcguga uguugcuauu gau 23

<210> SEQ ID NO 542
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 542
ucaaggaaaa ucaccagguu uug 23

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 543
aauaggcgug auguugcuau uga 23

<210> SEQ ID NO 544
<211> LENGTH: 23
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 544
uuccuuugga gcucguccag aau                                              23

<210> SEQ ID NO 545
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
aaagcauguu agcaguuaca cuu                                              23

<210> SEQ ID NO 546
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
ugguaugucg acauacauua gau                                              23

<210> SEQ ID NO 547
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
aauuugagca gugacauuac acu                                              23

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
uucgacauac auuagauuuc uag                                              23

<210> SEQ ID NO 549
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
uauauauacg cccuccuguu gug                                              23

<210> SEQ ID NO 550
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 550
auauauacgc ccuccuguug ugc 23

<210> SEQ ID NO 551
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 551
ugcaagugac cuugcagaag cuc 23

<210> SEQ ID NO 552
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 552
ucagggaaua uaguuaauaa cuu 23

<210> SEQ ID NO 553
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 553
agugcuaugu cauugucaaa gcc 23

<210> SEQ ID NO 554
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 554
aguaugaaaa gagacuggcu uuu 23

<210> SEQ ID NO 555
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 555
uaaauaggcg ugauguugcu auu 23

<210> SEQ ID NO 556
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 556
uuggcagaca aauaggcgug aug 23

<210> SEQ ID NO 557
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 557
ugucgacaua cauuagauuu cua 23

<210> SEQ ID NO 558
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 558
uuauaaugag gugauagucu uuu 23

<210> SEQ ID NO 559
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 559
ucaggcuugu guauaaugag gug 23

<210> SEQ ID NO 560
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 560
auaucaggac uugccaagga aaa 23

<210> SEQ ID NO 561
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 561
ucucauaaag gauucagcuu cuu 23

<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
ucaaugucau cuguccucau aaa 23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
uucauaaagg auucagcuuc uuu 23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
acaaauaggc gugauguugc uau 23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
uugccuuuug cccuccauau aua 23

<210> SEQ ID NO 566
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 566
ugguggagca acaacugcca ugu 23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
ucaguaugaa aagagacugg cuu 23

<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 568
aauaucagga cuugccaagg aaa 23

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 569
acaaacaggc ucacagacug gga 23

<210> SEQ ID NO 570
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 570
uucauaugca gcaguacauu uuu 23

<210> SEQ ID NO 571
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 571
uacauuuuug auggucaaca auc 23

<210> SEQ ID NO 572
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 572
uugcuauuga uuacaacuuu guu 23

<210> SEQ ID NO 573
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 573
uaaggucuuc acaggcauuu cua 23

<210> SEQ ID NO 574
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 574
ucgacauaca uuagauuucu agc 23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 575
uccucauaaa ggauucagcu ucu 23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 576
accuaauauc aggacuugcc aag 23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 577
agcaucauga guauaaccuu cau 23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 578
auacauuaga uuucuagcaa gaa 23

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 579
uaguaugaaa agagacuggc uuu 23

<210> SEQ ID NO 580
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 580
uuguguauaa ugaggugaua guc 23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 581
agcaguacau uuuugauggu caa 23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 582
ucuuggcaga caaauaggcg uga 23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 583
uugcccucca uauauacgcc cuc 23

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 584
uaggcgugau guugcuauug auu 23

<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 585
ugccuuuugc ccuccauaua uac 23

<210> SEQ ID NO 586
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 586
uuugggugga gcaacaacug cca 23

<210> SEQ ID NO 587
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 587
ugacuugcca aggaaaauca cca 23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 588
uaaucagugc uaugucauug uca 23

<210> SEQ ID NO 589
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 589
ugcagacaaa uaggcgugau guu 23

<210> SEQ ID NO 590
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 590
uagcaucaug aguauaaccu uca 23

<210> SEQ ID NO 591
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 591
uccaaggaaa aucaccaggu uuu 23

<210> SEQ ID NO 592
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 592
uguauaauga ggugauaguc uuu 23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 593
acacuauucc ucccacaaac cac 23

<210> SEQ ID NO 594
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 594
uaggcuugug uauaaugagg uga 23

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 595
ugauagucca caaacaggcu cac 23

<210> SEQ ID NO 596
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 596
ucccuccaua uauacgcccu ccu 23

<210> SEQ ID NO 597
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 597
uuugcccucc auauauacgc ccu 23

<210> SEQ ID NO 598
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 598
ugucaucugu ccucauaaag gau 23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 599
ugguggcuuu ucauaugcag cag 23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 600
augucgacau acauuagauu ucu 23

<210> SEQ ID NO 601
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 601
uaccuaauau caggacuugc caa 23

<210> SEQ ID NO 602
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 602
uucacaggca uuucuaaaaa uga 23

<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 603
uucauauaaa agugcaccug cug 23

<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 604
uacacuauuc cucccacaaa cca 23

<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 605
aacagccagu augaaaagag acu 23

<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 606
uaucaggacu ugccaaggaa aau 23

<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 607
uacaaauagg cgugauguug cua 23

<210> SEQ ID NO 608
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 608
ucuccauaua uacgcccucc ugu 23

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 609
uuuuugggug gagcaacaac ugc 23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 610
uaguccacaa acaggcucac aga 23

<210> SEQ ID NO 611

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 611
uccaccuaau aucaggacuu gcc 23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 612
agcauguuag caguuacacu ucc 23

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 613
aaauaggcgu gauguugcua uug 23

<210> SEQ ID NO 614
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 614
uuccauauau acgcccuccu guu 23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 615
ugacacuauu ccucccacaa acc 23

<210> SEQ ID NO 616
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 616
aggcgugaug uugcuauuga uua 23

<210> SEQ ID NO 617
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 617
uuugcuauug auuacaacuu ugu 23

<210> SEQ ID NO 618
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 618
uugacaauga cauagcacug auu 23

<210> SEQ ID NO 619
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 619
cgauuguuga ccaucaaaaa ugu 23

<210> SEQ ID NO 620
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 620
aaaucuaaug uaugucgaca uac 23

<210> SEQ ID NO 621
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 621
acaaugacau agcacugauu aaa 23

<210> SEQ ID NO 622
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 622
gauuuuccuu ggcaaguccu gau 23

<210> SEQ ID NO 623
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 623
gaaaucuaau guaugucgac aua 23

<210> SEQ ID NO 624
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 624
ugcuagaaau cuaauguaug ucg 23

<210> SEQ ID NO 625
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 625
uaugagcaaa aacaugaugc auc 23

<210> SEQ ID NO 626
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 626
uccuuuauga ggacagauga cau 23

<210> SEQ ID NO 627
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 627
aucacgccua uuugucugcc aag 23

<210> SEQ ID NO 628
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 628
caacaggagg gcguauauau gga 23

<210> SEQ ID NO 629
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 629
ggacauggca guuguugcuc cac 23

<210> SEQ ID NO 630
<211> LENGTH: 23
<212> TYPE: RNA

<213> ORGANISM: Unknown
<220> FEATURE:
<223> OTHER INFORMATION: Description of Unknown: Target sequence

<400> SEQUENCE: 630
agcaggugca cuuuuauaug aca 23

<210> SEQ ID NO 631
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 631
caaaaaugua cugcugcaua uga 23

<210> SEQ ID NO 632
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 632
aucaauagca acaucacgcc uau 23

<210> SEQ ID NO 633
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 633
caaaaccugg ugauuuuccu ugg 23

<210> SEQ ID NO 634
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 634
ucaauagcaa caucacgccu auu 23

<210> SEQ ID NO 635
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 635
auucuggacg agcuccaaag gag 23

<210> SEQ ID NO 636
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 636
aaguguaacu gcuaacaugc uuu 23

<210> SEQ ID NO 637
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 637
aucuaaugua ugucgacaua ccg 23

<210> SEQ ID NO 638
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 638
aguguaaugu cacugcucaa auu 23

<210> SEQ ID NO 639
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 639
cuagaaaucu aauguauguc gac 23

<210> SEQ ID NO 640
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 640
cacaacagga gggcguauau aug 23

<210> SEQ ID NO 641
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 641
gcacaacagg agggcguaua uau 23

<210> SEQ ID NO 642
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 642
gagcuucugc aaggucacuu gcc 23

<210> SEQ ID NO 643
<211> LENGTH: 23
<212> TYPE: RNA
<213> ORGANISM: Unknown
<220> FEATURE:

<223> OTHER INFORMATION: Description of Unknown: Target sequence

<400> SEQUENCE: 643
aaguuauuaa cuauauuccc ugg 23

<210> SEQ ID NO 644
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 644
ggcuuugaca augacauagc acu 23

<210> SEQ ID NO 645
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 645
aaaagccagu cucuuuucau acu 23

<210> SEQ ID NO 646
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 646
aauagcaaca ucacgccuau uug 23

<210> SEQ ID NO 647
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 647
caucacgccu auuugucugc caa 23

<210> SEQ ID NO 648
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 648
uagaaaucua auguaugucg aca 23

<210> SEQ ID NO 649
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 649
aaaagacuau caccucauua uac 23

<210> SEQ ID NO 650
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 650
caccucauua uacacaagcc ugg 23

<210> SEQ ID NO 651
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 651
uuuuccuugg caaguccuga uau 23

<210> SEQ ID NO 652
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 652
aagaagcuga auccuuuaug agg 23

<210> SEQ ID NO 653
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 653
uuuaugagga cagaugacau ugg 23

<210> SEQ ID NO 654
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 654
aaagaagcug aauccuuuau gag 23

<210> SEQ ID NO 655
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 655
auagcaacau cacgccuauu ugu 23

<210> SEQ ID NO 656
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 656
uauauaugga gggcaaaagg caa 23

<210> SEQ ID NO 657
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 657
acauggcagu uguugcucca ccc 23

<210> SEQ ID NO 658
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 658
aagccagucu cuuuucauac ugg 23

<210> SEQ ID NO 659
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 659
uuuccuuggc aaguccugau auu 23

<210> SEQ ID NO 660
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 660
ucccagucug ugagccuguu ugu 23

<210> SEQ ID NO 661
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 661
aaaaauguac ugcugcauau gaa 23

<210> SEQ ID NO 662
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 662
gauuguugac caucaaaaau gua 23

<210> SEQ ID NO 663
<211> LENGTH: 23

<212> TYPE: RNA
<213> ORGANISM: Unknown
<220> FEATURE:
<223> OTHER INFORMATION: Description of Unknown: Target sequence

<400> SEQUENCE: 663
aacaaaguug uaaucaauag caa 23

<210> SEQ ID NO 664
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 664
uagaaaugcc ugugaagacc uug 23

<210> SEQ ID NO 665
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 665
gcuagaaauc uaauguaugu cga 23

<210> SEQ ID NO 666
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 666
agaagcugaa uccuuuauga gga 23

<210> SEQ ID NO 667
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 667
cuuggcaagu ccugauauua ggu 23

<210> SEQ ID NO 668
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 668
augaagguua uacucaugau gcu 23

<210> SEQ ID NO 669
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 669
uucuugcuag aaaucuaaug uau 23

<210> SEQ ID NO 670
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 670
aaagccaguc ucuuuucaua cug 23

<210> SEQ ID NO 671
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 671
gacuaucacc ucauuauaca caa 23

<210> SEQ ID NO 672
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 672
uugaccauca aaaauguacu gcu 23

<210> SEQ ID NO 673
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 673
ucacgccuau uugucugcca aga 23

<210> SEQ ID NO 674
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 674
gagggcguau auauggaggg caa 23

<210> SEQ ID NO 675
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 675
aaucaauagc aacaucacgc cua 23

<210> SEQ ID NO 676
<211> LENGTH: 23
<212> TYPE: RNA
<213> ORGANISM: Unknown

<220> FEATURE:
<223> OTHER INFORMATION: Description of Unknown: Target sequence

<400> SEQUENCE: 676
guauauaugg agggcaaaag gca 23

<210> SEQ ID NO 677
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 677
uggcaguugu ugcuccaccc aaa 23

<210> SEQ ID NO 678
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 678
uggugauuuu ccuuggcaag ucc 23

<210> SEQ ID NO 679
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 679
ugacaaugac auagcacuga uua 23

<210> SEQ ID NO 680
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 680
aacaucacgc cuauuugucu gcc 23

<210> SEQ ID NO 681
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 681
ugaagguuau acucaugaug cug 23

<210> SEQ ID NO 682
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 682
aaaaccuggu gauuuuccuu ggc 23

<210> SEQ ID NO 683
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 683
aaagacuauc accucauuau aca 23

<210> SEQ ID NO 684
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 684
gugguuugug ggaggaauag ugu 23

<210> SEQ ID NO 685
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 685
ucaccucauu auacacaagc cug 23

<210> SEQ ID NO 686
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 686
gugagccugu uuguggacua uca 23

<210> SEQ ID NO 687
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 687
aggagggcgu auauauggag ggc 23

<210> SEQ ID NO 688
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 688
agggcguaua uauggagggc aaa 23

<210> SEQ ID NO 689
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 689
auccuuuaug aggacagaug aca 23

<210> SEQ ID NO 690
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 690
cugcugcaua ugaaaagcca ccc 23

<210> SEQ ID NO 691
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 691
agaaaucuaa uguaugucga cau 23

<210> SEQ ID NO 692
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 692
uuggcaaguc cugauauuag gug 23

<210> SEQ ID NO 693
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 693
ucauuuuuag aaaugccugu gaa 23

<210> SEQ ID NO 694
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 694
cagcaggugc acuuuuauau gac 23

<210> SEQ ID NO 695
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 695
ugguuugugg gaggaauagu guc 23

<210> SEQ ID NO 696

<211> LENGTH: 23
<212> TYPE: RNA
<213> ORGANISM: Unknown
<220> FEATURE:
<223> OTHER INFORMATION: Description of Unknown: Target sequence

<400> SEQUENCE: 696
agucucuuuu cauacuggcu guu 23

<210> SEQ ID NO 697
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 697
auuuuccuug gcaaguccug aua 23

<210> SEQ ID NO 698
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 698
uagcaacauc acgccuauuu guc 23

<210> SEQ ID NO 699
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 699
acaggagggc guauauaugg agg 23

<210> SEQ ID NO 700
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 700
gcaguuguug cuccacccaa aaa 23

<210> SEQ ID NO 701
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 701
ucugugagcc uguuugugga cua 23

<210> SEQ ID NO 702
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 702 ggcaagugccu gauauuaggu gga 23

<210> SEQ ID NO 703
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 703
ggaaguguaa cugcuaacau gcu 23

<210> SEQ ID NO 704
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 704
caauagcaac aucacgccua uuu 23

<210> SEQ ID NO 705
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 705
aacaggaggg cguauauaug gag 23

<210> SEQ ID NO 706
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 706
gguuuguggg aggaauagug ucc 23

<210> SEQ ID NO 707
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 707
uaaucaauag caacaucacg ccu 23

<210> SEQ ID NO 708
<211> LENGTH: 23
<212> TYPE: RNA
<213> ORGANISM: Unknown
<220> FEATURE:
<223> OTHER INFORMATION: Description of Unknown: Target sequence

<400> SEQUENCE: 708
acaaaguugu aaucaauagc aac 23

<210> SEQ ID NO 709
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 709
accaggccag gccagcugga c 21

<210> SEQ ID NO 710
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710
gacgggcaca ccaugaggcu g 21

<210> SEQ ID NO 711
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 711
cugcugaccc uccugggccu u 21

<210> SEQ ID NO 712
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712
cuucugugug gcucgguggc c 21

<210> SEQ ID NO 713
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 713
ccacccccuu gggcccgaag u 21

<210> SEQ ID NO 714
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714
aguggccuga accuguguuc g 21

<210> SEQ ID NO 715
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 715
ucgggcgccu ggcauccccc g 21

<210> SEQ ID NO 716
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716
ccggcuuucc aggggaguau g 21

<210> SEQ ID NO 717
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717
augccaauga ccaggagcgg c 21

<210> SEQ ID NO 718
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 718
ggcgcuggac ccugacugca c 21

<210> SEQ ID NO 719
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719
caccccccgg cuaccgccug c 21

<210> SEQ ID NO 720
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
gcgccucuac uucacccacu u 21

<210> SEQ ID NO 721
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 721
cuucgaccug gagcucuccc a                                               21

<210> SEQ ID NO 722
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
ccaccucugc gaguacgacu u                                               21

<210> SEQ ID NO 723
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
cuucgucaag cugagcucgg g                                               21

<210> SEQ ID NO 724
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
gggggccaag gugcuggcca c                                               21

<210> SEQ ID NO 725
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
cacgcugugc gggcaggaga g                                               21

<210> SEQ ID NO 726
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 726
agcacagaca cggagcgggc c                                               21

<210> SEQ ID NO 727
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
gccccuggca aggacacuuu c 21

<210> SEQ ID NO 728
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 728
uucuacucgc ugggcuccag c 21

<210> SEQ ID NO 729
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 729
agccuggaca uuaccuuccg c 21

<210> SEQ ID NO 730
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 730
cgcuccgacu acuccaacga g 21

<210> SEQ ID NO 731
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 731
gagaagccgu ucacggggua c 21

<210> SEQ ID NO 732
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 732
uucgaggccu ucuaugcagc c 21

<210> SEQ ID NO 733
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 733
ccgaggacau ugacgagugc c 21

<210> SEQ ID NO 734
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 734
gccagguggc cccgggagag g 21

<210> SEQ ID NO 735
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 735
aggcgcccac cugcgaccac c 21

<210> SEQ ID NO 736
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736
accacugcca caaccaccug g 21

<210> SEQ ID NO 737
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 737
ugggcgguuu cuacugcucc u 21

<210> SEQ ID NO 738
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 738
ccugccgcgc aggcuacguc c 21

<210> SEQ ID NO 739
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 739
uccugcaccg uaacaagcgc a 21

<210> SEQ ID NO 740
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
caccugcuca gcccugugcu c 21

<210> SEQ ID NO 741
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 741
cuccggccag gucuucaccc a 21

<210> SEQ ID NO 742
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 742
ccagaggucu ggggagcuca g 21

<210> SEQ ID NO 743
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 743
cagcagcccu gaauacccac g 21

<210> SEQ ID NO 744
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 744
acggccguau cccaaacucu c 21

<210> SEQ ID NO 745
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 745
cuccaguugc acuuacagca u 21

<210> SEQ ID NO 746
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 746
aucagccugg aggaggggguu c 21

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 747
uucaguguca uucuggacuu u 21

<210> SEQ ID NO 748
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 748
uuuguggagu ccuucgaugu g 21

<210> SEQ ID NO 749
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 749
guggagacac acccugaaac c 21

<210> SEQ ID NO 750
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 750
acccuguguc ccuacgacuu u 21

<210> SEQ ID NO 751
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 751
uuucucaaga uucaaacaga c 21

<210> SEQ ID NO 752
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 752
gacagagaag aacauggccc a 21

<210> SEQ ID NO 753
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 753
cauucugugg gaagacauug c 21

<210> SEQ ID NO 754
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 754
ugccccacag gauugaaaca a 21

<210> SEQ ID NO 755
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 755
caaaaagcaa cacggugacc a 21

<210> SEQ ID NO 756
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 756
ccaucaccuu ugucacagau g 21

<210> SEQ ID NO 757
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 757
augaaucagg agaccacaca g 21

<210> SEQ ID NO 758
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
caggcuggaa gauccacuac a 21

<210> SEQ ID NO 759
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
acacgagcac agcgcagccu u 21

<210> SEQ ID NO 760
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
uugcccuuau ccgauggcgc c 21

<210> SEQ ID NO 761
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761
gccaccuaau ggccacguuu c 21

<210> SEQ ID NO 762
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 762
uucaccugug caagccaaau a 21

<210> SEQ ID NO 763
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 763
auacauccug aaagacagcu u 21

<210> SEQ ID NO 764
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 764
cuucuccauc uuuugcgaga c 21

<210> SEQ ID NO 765
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 765
gacuggcuau gagcuucugc a 21

<210> SEQ ID NO 766
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 766
caaggucacu ugccccugaa a 21

<210> SEQ ID NO 767
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 767
aaauccuuua cugcaguuug u 21

<210> SEQ ID NO 768
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 768
ugucagaaag auggaucuug g 21

<210> SEQ ID NO 769
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 769
ugggaccggc caaugcccgc g 21

<210> SEQ ID NO 770

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 770
gcgugcagca uuguugacug u 21

<210> SEQ ID NO 771
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 771
uguggcccuc cugaugaucu a 21

<210> SEQ ID NO 772
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 772
cuacccagug gccgagugga g 21

<210> SEQ ID NO 773
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 773
aguacaucac agguccugga g 21

<210> SEQ ID NO 774
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 774
gagugaccac cuacaaagcu g 21

<210> SEQ ID NO 775
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 775
cugugauuca guacagcugu g 21

<210> SEQ ID NO 776
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 776
gugaagagac cuucuacaca a 21

<210> SEQ ID NO 777
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 777
caaugaaagu gaaugauggu a 21

<210> SEQ ID NO 778
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 778
guaaauaugu gugugaggcu g 21

<210> SEQ ID NO 779
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 779
cugauggauu cuggacgagc u 21

<210> SEQ ID NO 780
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 780
cuccaaagga gaaaaaucac u 21

<210> SEQ ID NO 781
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 781
acucccaguc ugugagccug u 21

<210> SEQ ID NO 782
<211> LENGTH: 21
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 782
uguuugugga cuaucagccc g 21

<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 783
ccgcacaaca ggagggcgua u 21

<210> SEQ ID NO 784
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 784
uauauaugga gggcaaaagg c 21

<210> SEQ ID NO 785
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 785
ggcaaaaccu ggugauuuuc c 21

<210> SEQ ID NO 786
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 786
uccuuggcaa guccugauau u 21

<210> SEQ ID NO 787
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 787
uuagguggaa ccacagcagc a 21

<210> SEQ ID NO 788
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 788
gcaggugcac uuuuauauga c 21

<210> SEQ ID NO 789
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 789
gacaacuggg uccuaacagc u 21

<210> SEQ ID NO 790
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 790
gcugcucaug ccgucuauga g 21

<210> SEQ ID NO 791
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 791
gagcaaaaac augaugcauc c 21

<210> SEQ ID NO 792
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 792
uccgcccugg acauucgaau g 21

<210> SEQ ID NO 793
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 793
ugggcacccu gaaaagacua u 21

<210> SEQ ID NO 794
<211> LENGTH: 21
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 794
uaucaccuca uuauacacaa g 21

<210> SEQ ID NO 795
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 795
aagccugguc ugaagcuguu u 21

<210> SEQ ID NO 796
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 796
uuuuuauaca ugaagguuau a 21

<210> SEQ ID NO 797
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 797
auacucauga ugcuggcuuu g 21

<210> SEQ ID NO 798
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 798
uugacaauga cauagcacug a 21

<210> SEQ ID NO 799
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 799
ugauuaaauu gaauaacaaa g 21

<210> SEQ ID NO 800
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 800
aguuguaauc aauagcaaca u 21

<210> SEQ ID NO 801
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 801
caucacgccu auuugucugc c 21

<210> SEQ ID NO 802
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 802
gccaagaaaa gaagcugaau c 21

<210> SEQ ID NO 803
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 803
auccuuuaug aggacagaug a 21

<210> SEQ ID NO 804
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 804
ugacauugga acugcaucug g 21

<210> SEQ ID NO 805
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 805
uggaugggga uuaacccaaa g 21

<210> SEQ ID NO 806
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 806 aaggggguuuu cuugcuagaa a 21

<210> SEQ ID NO 807
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 807
aaucuaaugu augucgacau a 21

<210> SEQ ID NO 808
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 808
auaccgauug uugaccauca a 21

<210> SEQ ID NO 809
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 809
caaaaaugua cugcugcaua u 21

<210> SEQ ID NO 810
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 810
uaugaaaagc cacccuaucc a 21

<210> SEQ ID NO 811
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 811
ccaaggggaa guguaacugc u 21

<210> SEQ ID NO 812
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 812
gcuaacaugc uuugugcugg c 21

<210> SEQ ID NO 813
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 813
gcuuagaaag ugggggcaag g 21

<210> SEQ ID NO 814
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 814
aggacagcug cagaggugac a 21

<210> SEQ ID NO 815
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 815
acagcggagg ggcacuggug u 21

<210> SEQ ID NO 816
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 816
uguuucuaga uagugaaaca g 21

<210> SEQ ID NO 817
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
cagagaggug guuuguggga g 21

<210> SEQ ID NO 818
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818
gaggaauagu guccuggggu u 21

<210> SEQ ID NO 819
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
guuccaugaa uuguggggaa g 21

<210> SEQ ID NO 820
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 820
agcaggucag uauggagucu a 21

<210> SEQ ID NO 821
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 821
cuacacaaaa guuauuaacu a 21

<210> SEQ ID NO 822
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 822
cuauauuccc uggaucgaga a 21

<210> SEQ ID NO 823
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 823
gaacauaauu agugauuuuu a 21

<210> SEQ ID NO 824
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 824

-continued uuaacuugcg ugucugcagu c 21

<210> SEQ ID NO 825
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 825
gucaaggauu cuucauuuuu a 21

<210> SEQ ID NO 826
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 826
uuagaaaugc cugugaagac c 21

<210> SEQ ID NO 827
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 827
ccuuggcagc gacguggcuc g 21

<210> SEQ ID NO 828
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 828
ucgagaagca uucaucauua c 21

<210> SEQ ID NO 829
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 829
uacuguggac auggcaguug u 21

<210> SEQ ID NO 830
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 830
uguugcucca cccaaaaaaa c 21

<210> SEQ ID NO 831
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 831
aacagacucc aggugaggcu g 21

<210> SEQ ID NO 832
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 832
cugcugucau uucuccacuu g 21

<210> SEQ ID NO 833
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 833
ugccaguuua auuccagccu u 21

<210> SEQ ID NO 834
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 834
cuuacccauu gacucaaggg g 21

<210> SEQ ID NO 835
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 835
gggacauaaa ccacgagagu g 21

<210> SEQ ID NO 836
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 836
gugacaguca ucuuugccca c 21

<210> SEQ ID NO 837
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 837
cacccagugu aaugucacug c 21

<210> SEQ ID NO 838
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 838
ugcucaaauu acauuucauu a 21

<210> SEQ ID NO 839
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 839
uuaccuuaaa aagccagucu c 21

<210> SEQ ID NO 840
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 840
ucuuuucaua cuggcuguug g 21

<210> SEQ ID NO 841
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 841
uggcauuucu guaaacugcc u 21

<210> SEQ ID NO 842
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 842
ccuguccaug cucuuuguuu u 21

<210> SEQ ID NO 843
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 843
uuuuaaacuu guucuuauug a 21

<210> SEQ ID NO 844
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 844
guccagcugg ccuggccugg ucu 23

<210> SEQ ID NO 845
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 845
cagccucaug gugugcccgu cca 23

<210> SEQ ID NO 846
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 846
aaggcccagg agggucagca gcc 23

<210> SEQ ID NO 847
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 847
ggccaccgag ccacacagaa ggc 23

<210> SEQ ID NO 848
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 848
acuucgggcc caagggggug gcc 23

<210> SEQ ID NO 849
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 849
cgaacacagg uucaggccac uuc 23

<210> SEQ ID NO 850
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 850
cgggggaugc caggcgcccg aac 23

<210> SEQ ID NO 851
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 851
cauacucccc uggaaagccg ggg 23

<210> SEQ ID NO 852
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 852
gccgcuccug gucauuggca uac 23

<210> SEQ ID NO 853
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 853
gugcagucag gguccagcgc cgc 23

<210> SEQ ID NO 854
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 854
gcaggcggua gccgggggu gca 23

<210> SEQ ID NO 855
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 855
aaguggguga aguagaggcg cag 23

<210> SEQ ID NO 856
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 856
ugggagagcu ccaggucgaa gug 23

<210> SEQ ID NO 857
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 857
aagucguacu cgcagaggug gga 23

<210> SEQ ID NO 858
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 858
cccgagcuca gcuugacgaa guc 23

<210> SEQ ID NO 859
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 859
guggccagca ccuuggcccc cga 23

<210> SEQ ID NO 860
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 860
cucuccugcc cgcacagcgu ggc 23

<210> SEQ ID NO 861
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 861
ggcccgcucc gugucugugc ucu 23

<210> SEQ ID NO 862
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 862 gaaaguguce uugccagggg ccc 23

<210> SEQ ID NO 863
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 863
gcuggagccc agcgaguaga aag 23

<210> SEQ ID NO 864
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 864
gcggaaggua auguccaggc ugg 23

<210> SEQ ID NO 865
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 865
cucguuggag uagucggagc gga 23

<210> SEQ ID NO 866
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 866
gaaccccgug aacggcuucu cgu 23

<210> SEQ ID NO 867
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 867
ggcugcauag aaggccucga acc 23

<210> SEQ ID NO 868
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
ggcacucguc aauguccucg gcu 23

<210> SEQ ID NO 869
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
ccucucccgg ggccaccugg cac 23

<210> SEQ ID NO 870
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
gguggucgca ggugggcgcc ucu 23

<210> SEQ ID NO 871
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
ccaggugguu guggcagugg ugg 23

<210> SEQ ID NO 872
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
aggagcagua gaaaccgccc agg 23

<210> SEQ ID NO 873
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 873
ggacguagcc ugcgcggcag gag 23

<210> SEQ ID NO 874
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 874
ugcgcuuguu acggugcagg acg 23

<210> SEQ ID NO 875
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 875
gagcacaggg cugagcaggu gcg 23

<210> SEQ ID NO 876
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 876
ugggugaaga ccuggccgga gca 23

<210> SEQ ID NO 877
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 877
cugagcuccc cagaccucug ggu 23

<210> SEQ ID NO 878
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 878 cgugggguauu cagggcugcu gag 23

<210> SEQ ID NO 879
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 879
gagaguuugg gauacggccg ugg 23

<210> SEQ ID NO 880
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 880
augcuguaag ugcaacugga gag 23

<210> SEQ ID NO 881
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 881
gaaccccucc uccaggcuga ugc 23

<210> SEQ ID NO 882
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 882
aaaguccaga augacacuga acc 23

<210> SEQ ID NO 883
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 883
cacaucgaag gacuccacaa agu 23

<210> SEQ ID NO 884
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 884
gguuucaggg ugugucucca cau 23

<210> SEQ ID NO 885
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 885
aaagucguag ggacacaggg uuu 23

<210> SEQ ID NO 886
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 886
gucuguuuga aucuugagaa agu 23

<210> SEQ ID NO 887
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 887
ugggccaugu ucuucucugu cug 23

<210> SEQ ID NO 888
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 888
gcaaugucuu cccacagaau ggg 23

<210> SEQ ID NO 889
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 889
uuguuucaau ccuguggggc aau 23

<210> SEQ ID NO 890
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 890
uggucaccgu guugcuuuuu guu 23

<210> SEQ ID NO 891
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 891
caucugugac aaaggugaug guc 23

<210> SEQ ID NO 892
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 892
cugugugguc uccugauuca ucu 23

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 893
uguaguggau cuuccagccu gug 23

<210> SEQ ID NO 894
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
aaggcugcgc ugugcucgug uag 23

<210> SEQ ID NO 895
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 895
ggcgccaucg gauaagggca agg 23

<210> SEQ ID NO 896
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 896
gaaacguggc cauuaggugg cgc 23

<210> SEQ ID NO 897
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 897
uauuuggcuu gcacagguga aac 23

<210> SEQ ID NO 898
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 898
aagcugucuu ucaggaugua uuu 23

<210> SEQ ID NO 899
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 899
gucucgcaaa agauggagaa gcu 23

<210> SEQ ID NO 900
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 900
ugcagaagcu cauagccagu cuc 23

<210> SEQ ID NO 901
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 901
uuucaggggc aagugaccuu gca 23

<210> SEQ ID NO 902
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 902
acaaacugca guaaaggauu uca 23

<210> SEQ ID NO 903
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 903
ccaagaucca ucuuucugac aaa 23

<210> SEQ ID NO 904
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 904
cgcgggcauu ggccgguccc aag 23

<210> SEQ ID NO 905
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 905
acagucaaca augcugcacg cgg 23

<210> SEQ ID NO 906
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906
uagaucauca ggagggccac agu 23

<210> SEQ ID NO 907
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 907
cuccacucgg ccacugggua gau 23

<210> SEQ ID NO 908
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 908
cuccaggacc ugugauguac ucc 23

<210> SEQ ID NO 909
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 909
cagcuuugua gguggucacu cca 23

<210> SEQ ID NO 910
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 910
cacagcugua cugaaucaca gcu 23

<210> SEQ ID NO 911
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 911
uuguguagaa ggucucuuca cag 23

<210> SEQ ID NO 912
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 912
uaccaucauu cacuuucauu gug 23

<210> SEQ ID NO 913
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 913
cagccucaca cacauauuua cca 23

<210> SEQ ID NO 914
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 914
agcucgucca gaauccauca gcc 23

<210> SEQ ID NO 915
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 915
agugauuuuu cuccuuugga gcu 23

<210> SEQ ID NO 916
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 916
acaggcucac agacugggag uga 23

<210> SEQ ID NO 917
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
cgggcugaua guccacaaac agg 23

<210> SEQ ID NO 918
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918
auacgcccuc cuguugugcg ggc 23

<210> SEQ ID NO 919
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 919
gccuuuugcc cuccauauau acg 23

<210> SEQ ID NO 920
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 920
ggaaaaucac cagguuuugc cuu 23

<210> SEQ ID NO 921
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 921
aauaucagga cuugccaagg aaa 23

<210> SEQ ID NO 922

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 922
ugcugcugug guuccaccua aua 23

<210> SEQ ID NO 923
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 923
gucauauaaa agugcaccug cug 23

<210> SEQ ID NO 924
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 924
agcuguuagg acccaguugu cau 23

<210> SEQ ID NO 925
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 925
cucauagacg gcaugagcag cug 23

<210> SEQ ID NO 926
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 926
ggaugcauca uguuuuugcu cau 23

<210> SEQ ID NO 927
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 927
cauucgaaug uccagggcgg aug 23

<210> SEQ ID NO 928
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 928
auagucuuuu cagggugccc auu 23

<210> SEQ ID NO 929
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 929
cuuguguaua augaggugau agu 23

<210> SEQ ID NO 930
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 930
aaacagcuuc agaccaggcu ugu 23

<210> SEQ ID NO 931
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 931
uauaaccuuc auguauaaaa aca 23

<210> SEQ ID NO 932
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 932
caaagccagc aucaugagua uaa 23

<210> SEQ ID NO 933
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 933
ucagugcuau gucauuguca aag 23

<210> SEQ ID NO 934
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 934
cuuuguuauu caauuuaauc agu 23

<210> SEQ ID NO 935
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 935
auguugcuau ugauuacaac uuu 23

<210> SEQ ID NO 936
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 936
ggcagacaaa uaggcgugau guu 23

<210> SEQ ID NO 937
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 937
gauucagcuu cuuuucuugg cag 23

<210> SEQ ID NO 938
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 938
ucaucugucc ucauaaagga uuc 23

<210> SEQ ID NO 939
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 939
ccagaugcag uuccaauguc auc 23

<210> SEQ ID NO 940
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 940
cuuuggguua auccccaucc aga 23

<210> SEQ ID NO 941
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 941
uuucuagcaa gaaaaccccu uug 23

<210> SEQ ID NO 942
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 942
uaugucgaca uacauuagau uuc 23

<210> SEQ ID NO 943
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
uugaugguca acaaucggua ugu 23

<210> SEQ ID NO 944
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 944
auaugcagca guacauuuuu gau 23

<210> SEQ ID NO 945
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 945
uggauagggu ggcuuuucau aug 23

<210> SEQ ID NO 946
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 946
agcaguuaca cuuccccuug gau 23

<210> SEQ ID NO 947
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 947
gccagcacaa agcauguuag cag 23

<210> SEQ ID NO 948
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 948
ccuugccccc acuuucuaag cca 23

<210> SEQ ID NO 949
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 949
ugucaccucu gcagcugucc uug 23

<210> SEQ ID NO 950
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 950
acaccagugc cccuccgcug uca 23

<210> SEQ ID NO 951
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 951
cuguuucacu aucuagaaac acc 23

<210> SEQ ID NO 952
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 952
cucccacaaa ccaccucucu guu 23

<210> SEQ ID NO 953
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953
aaccccagga cacuauuccu ccc 23

<210> SEQ ID NO 954
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 954
cuuccccaca auucauggaa ccc 23

<210> SEQ ID NO 955
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 955
uagacuccau acugaccugc uuc 23

<210> SEQ ID NO 956
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 956
uaguuaauaa cuuuugugua gac 23

<210> SEQ ID NO 957
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 957
uucucgaucc agggaauaua guu 23

<210> SEQ ID NO 958
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 958
uaaaaaucac uaauuauguu cuc 23

<210> SEQ ID NO 959
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 959
gacugcagac acgcaaguua aaa 23

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 960
uaaaaaugaa gaauccuuga cug 23

<210> SEQ ID NO 961
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 961
ggucuucaca ggcauuucua aaa 23

<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 962
cgagccacgu cgcugccaag guc 23

<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 963
guaaugauga augcuucucg agc 23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 964
acaacugcca uguccacagu aau 23

<210> SEQ ID NO 965
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 965
guuuuuuugg guggagcaac aac 23

<210> SEQ ID NO 966
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 966
cagccucacc uggagucugu uuu 23

<210> SEQ ID NO 967
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 967
caaguggaga aaugacagca gcc 23

<210> SEQ ID NO 968
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 968
aaggcuggaa uuaaacuggc aag 23

<210> SEQ ID NO 969
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 969
ccccuugagu caaugggua ggc 23

<210> SEQ ID NO 970
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 970
cacucucgug guuuaugucc ccu 23

<210> SEQ ID NO 971
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971
gugggcaaag augacuguca cuc 23

<210> SEQ ID NO 972
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 972
gcagugacau uacacugggu ggg 23

<210> SEQ ID NO 973
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 973
uaaugaaaug uaauuugagc agu 23

<210> SEQ ID NO 974
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 974
gagacuggcu uuuuaaggua aug 23

<210> SEQ ID NO 975
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 975
ccaacagcca guaugaaaag aga 23

<210> SEQ ID NO 976
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 976
aggcaguuua cagaaaugcc aac 23

<210> SEQ ID NO 977
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 977
aaaacaaaga gcauggacag gca 23

<210> SEQ ID NO 978
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 978
ucaauaagaa caaguuuaaa aac 23

<210> SEQ ID NO 979
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 979
accaggccag gccagcugga u 21

<210> SEQ ID NO 980
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 980
gacgggcaca ccaugaggcu u 21

<210> SEQ ID NO 981
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 981
cugcugaccc uccugggccu u 21

<210> SEQ ID NO 982
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 982
cuucugugug gcucggugge u 21

<210> SEQ ID NO 983
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 983
ccacccccuu gggcccgaag u 21

<210> SEQ ID NO 984
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 984
aguggccuga accuguguuc u 21

<210> SEQ ID NO 985
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 985
ucgggcgccu ggcauccccc u 21

<210> SEQ ID NO 986
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
ccggcuuucc aggggaguau u 21

<210> SEQ ID NO 987
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 987
augccaauga ccaggagcgg u 21

<210> SEQ ID NO 988
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 988
ggcgcuggac ccugacugca u 21

<210> SEQ ID NO 989
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 989
caccccccgg cuaccgccug u 21

<210> SEQ ID NO 990
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 990
gcgccucuac uucacccacu u 21

<210> SEQ ID NO 991
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 991
cuucgaccug gagcucuccc u 21

<210> SEQ ID NO 992
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 992
ccaccucugc gaguacgacu u 21

<210> SEQ ID NO 993
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 993
cuucgucaag cugagcucgg u 21

<210> SEQ ID NO 994
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 994
gggggccaag gugcuggcca u 21

<210> SEQ ID NO 995
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 995
cacgcugugc gggcaggaga u 21

<210> SEQ ID NO 996
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 996
agcacagaca cggagcgggc u 21

<210> SEQ ID NO 997
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 997
gccccuggca aggacacuuu u 21

<210> SEQ ID NO 998
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 998
uucuacucgc ugggcuccag u 21

<210> SEQ ID NO 999
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 999
agccuggaca uuaccuuccg u 21

<210> SEQ ID NO 1000
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1000
cgcuccgacu acuccaacga u 21

<210> SEQ ID NO 1001

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
gagaagccgu ucacggggu u 21

<210> SEQ ID NO 1002
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002
uucgaggccu ucuaugcagc u 21

<210> SEQ ID NO 1003
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003
ccgaggacau ugacgagugc u 21

<210> SEQ ID NO 1004
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1004
gccagguggc cccgggagag u 21

<210> SEQ ID NO 1005
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005
aggcgcccac cugcgaccac u 21

<210> SEQ ID NO 1006
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006
accacugcca caaccaccug u 21

<210> SEQ ID NO 1007
<211> LENGTH: 21

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
ugggcgguuu cuacugcucc u 21

<210> SEQ ID NO 1008
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
ccugccgcgc aggcuacguc u 21

<210> SEQ ID NO 1009
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
uccugcaccg uaacaagcgc u 21

<210> SEQ ID NO 1010
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
caccugcuca gcccugugcu u 21

<210> SEQ ID NO 1011
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
cuccggccag gucuucaccc u 21

<210> SEQ ID NO 1012
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
ccagaggucu ggggagcuca u 21

<210> SEQ ID NO 1013
<211> LENGTH: 21
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 1013
cagcagcccu gaauacccac u 21

<210> SEQ ID NO 1014
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1014
acggccguau cccaaacucu u 21

<210> SEQ ID NO 1015
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1015
cuccaguugc acuuacagca u 21

<210> SEQ ID NO 1016
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1016
aucagccugg aggaggggguu u 21

<210> SEQ ID NO 1017
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1017
uucaguguca uucuggacuu u 21

<210> SEQ ID NO 1018
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1018
uuuguggagu ccuucgaugu u 21

<210> SEQ ID NO 1019
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1019
guggagacac acccugaaac u 21

<210> SEQ ID NO 1020
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1020
acccuguguc ccuacgacuu u 21

<210> SEQ ID NO 1021
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1021
uuucucaaga uucaaacaga u 21

<210> SEQ ID NO 1022
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1022
gacagagaag aacauggccc u 21

<210> SEQ ID NO 1023
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1023
cauucugugg gaagacauug u 21

<210> SEQ ID NO 1024
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1024
ugccccacag gauugaaaca u 21

<210> SEQ ID NO 1025
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1025
caaaaagcaa cacggugacc u 21

<210> SEQ ID NO 1026
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
ccaucaccuu ugucacagau u 21

<210> SEQ ID NO 1027
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
augaaucagg agaccacaca u 21

<210> SEQ ID NO 1028
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
caggcuggaa gauccacuac u 21

<210> SEQ ID NO 1029
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
acacgagcac agcgcagccu u 21

<210> SEQ ID NO 1030
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
uugcccuuau ccgauggcgc u 21

<210> SEQ ID NO 1031
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1031
gccaccuaau ggccacguuu u 21

<210> SEQ ID NO 1032
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1032
uucaccugug caagccaaau u 21

<210> SEQ ID NO 1033
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1033
auacauccug aaagacagcu u 21

<210> SEQ ID NO 1034
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1034
cuucuccauc uuuugcgaga u 21

<210> SEQ ID NO 1035
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1035
gacuggcuau gagcuucugc u 21

<210> SEQ ID NO 1036
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1036
caaggucacu ugccccugaa u 21

<210> SEQ ID NO 1037
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1037
aaauccuuua cugcaguuug u 21

<210> SEQ ID NO 1038
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1038
ugucagaaag auggaucuug u 21

<210> SEQ ID NO 1039
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1039
ugggaccggc caaugcccgc u 21

<210> SEQ ID NO 1040
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1040
gcgugcagca uuguugacug u 21

<210> SEQ ID NO 1041
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1041
uguggcccuc cugaugaucu u 21

<210> SEQ ID NO 1042
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1042
cuacccagug gccgagugga u 21

<210> SEQ ID NO 1043
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1043
aguacaucac agguccugga u 21

<210> SEQ ID NO 1044
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1044
gagugaccac cuacaaagcu u 21

<210> SEQ ID NO 1045
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1045
cugugauuca guacagcugu u 21

<210> SEQ ID NO 1046
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1046
gugaagagac cuucuacaca u 21

<210> SEQ ID NO 1047
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1047
caaugaaagu gaaugauggu u 21

<210> SEQ ID NO 1048
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1048
guaaauaugu gugugaggcu u 21

<210> SEQ ID NO 1049
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1049
cugauggauu cuggacgagc u 21

<210> SEQ ID NO 1050
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1050
cuccaaagga gaaaaaucac u 21

<210> SEQ ID NO 1051
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1051
acucccaguc ugugagccug u 21

<210> SEQ ID NO 1052
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1052
uguuugugga cuaucagccc u 21

<210> SEQ ID NO 1053
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1053
ccgcacaaca ggagggcgua u 21

<210> SEQ ID NO 1054
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1054
uauauaugga gggcaaaagg u 21

<210> SEQ ID NO 1055
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1055
ggcaaaaccu ggugauuuuc u 21

<210> SEQ ID NO 1056
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1056
uccuuggcaa guccugauau u 21

<210> SEQ ID NO 1057
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1057
uuagguggaa ccacagcagc u 21

<210> SEQ ID NO 1058
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1058
gcaggugcac uuuuauauga u 21

<210> SEQ ID NO 1059
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1059
gacaacuggg uccuaacagc u 21

<210> SEQ ID NO 1060
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1060
gcugcucaug ccgucuauga u 21

<210> SEQ ID NO 1061
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1061
gagcaaaaac augaugcauc u 21

<210> SEQ ID NO 1062
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1062
uccgcccugg acauucgaau u 21

<210> SEQ ID NO 1063
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1063
ugggcacccu gaaaagacua u 21

<210> SEQ ID NO 1064
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1064
uaucaccuca uuauacacaa u 21

<210> SEQ ID NO 1065
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1065
aagccugguc ugaagcuguu u 21

<210> SEQ ID NO 1066
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1066
uuuuuauaca ugaagguuau u 21

<210> SEQ ID NO 1067
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1067
auacucauga ugcuggcuuu u 21

<210> SEQ ID NO 1068
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1068
uugacaauga cauagcacug u 21

<210> SEQ ID NO 1069
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
ugauuaaauu gaauaacaaa u 21

<210> SEQ ID NO 1070
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
aguuguaauc aauagcaaca u 21

<210> SEQ ID NO 1071
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1071
caucacgccu auuugucugc u 21

<210> SEQ ID NO 1072
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1072
gccaagaaaa gaagcugaau u 21

<210> SEQ ID NO 1073
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1073
auccuuuaug aggacagaug u 21

<210> SEQ ID NO 1074
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1074
ugacauugga acugcaucug u 21

<210> SEQ ID NO 1075
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1075
uggaugggga uuaacccaaa u 21

<210> SEQ ID NO 1076
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1076 aaggggguuuu cuugcuagaa u 21

<210> SEQ ID NO 1077
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
aaucuaaugu augucgacau u 21

<210> SEQ ID NO 1078
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
auaccgauug uugaccauca u 21

<210> SEQ ID NO 1079
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
caaaaaugua cugcugcaua u 21

<210> SEQ ID NO 1080

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1080
uaugaaaagc cacccuaucc u 21

<210> SEQ ID NO 1081
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1081
ccaaggggaa guguaacugc u 21

<210> SEQ ID NO 1082
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1082
gcuaacaugc uuugugcugg u 21

<210> SEQ ID NO 1083
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1083
gcuuagaaag ugggggcaag u 21

<210> SEQ ID NO 1084
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1084
aggacagcug cagaggugac u 21

<210> SEQ ID NO 1085
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1085
acagcggagg ggcacuggug u 21

<210> SEQ ID NO 1086
<211> LENGTH: 21

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1086
uguuucuaga uagugaaaca u 21

<210> SEQ ID NO 1087
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1087
cagagaggug guuuguggga u 21

<210> SEQ ID NO 1088
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1088
gaggaauagu guccuggggu u 21

<210> SEQ ID NO 1089
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1089
guuccaugaa uuguggggaa u 21

<210> SEQ ID NO 1090
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1090
agcaggucag uauggagucu u 21

<210> SEQ ID NO 1091
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1091
cuacacaaaa guuauuaacu u 21

<210> SEQ ID NO 1092
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1092
cuauauuccc uggaucgaga u 21

<210> SEQ ID NO 1093
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1093
gaacauaauu agugauuuuu u 21

<210> SEQ ID NO 1094
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1094
uuaacuugcg ugucugcagu u 21

<210> SEQ ID NO 1095
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1095
gucaaggauu cuucauuuuu u 21

<210> SEQ ID NO 1096
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096
uuagaaaugc cugugaagac u 21

<210> SEQ ID NO 1097
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097
ccuuggcagc gacguggcuc u 21

<210> SEQ ID NO 1098
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1098
ucgagaagca uucaucauua u 21

<210> SEQ ID NO 1099
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1099
uacuguggac auggcaguug u 21

<210> SEQ ID NO 1100
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1100
uguugcucca cccaaaaaaa u 21

<210> SEQ ID NO 1101
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1101
aacagacucc aggugaggcu u 21

<210> SEQ ID NO 1102
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1102
cugcugucau uucuccacuu u 21

<210> SEQ ID NO 1103
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1103
ugccaguuua auuccagccu u 21

<210> SEQ ID NO 1104
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1104
cuuacccauu gacucaaggg u 21

<210> SEQ ID NO 1105
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
gggacauaaa ccacgagagu u 21

<210> SEQ ID NO 1106
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
gugacaguca ucuuugccca u 21

<210> SEQ ID NO 1107
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107
cacccagugu aaugucacug u 21

<210> SEQ ID NO 1108
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1108
ugcucaaauu acauuucauu u 21

<210> SEQ ID NO 1109
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1109
uuaccuuaaa aagccagucu u 21

<210> SEQ ID NO 1110
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1110
ucuuuucaua cuggcuguug u 21

<210> SEQ ID NO 1111
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1111
uggcauuucu guaaacugcc u 21

<210> SEQ ID NO 1112
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1112
ccuguccaug cucuuuguuu u 21

<210> SEQ ID NO 1113
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1113
uuuuaaacuu guucuuauug u 21

<210> SEQ ID NO 1114
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1114
auccagcugg ccuggccugg ucu 23

<210> SEQ ID NO 1115
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1115
aagccucaug gugugcccgu cca 23

<210> SEQ ID NO 1116
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1116
aaggcccagg agggucagca gcc 23

<210> SEQ ID NO 1117
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1117
agccaccgag ccacacagaa ggc 23

<210> SEQ ID NO 1118
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1118
acuucgggcc caagggggug gcc 23

<210> SEQ ID NO 1119
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 1119
agaacacagg uucaggccac uuc 23

<210> SEQ ID NO 1120
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1120
agggggaugc caggcgcccg aac 23

<210> SEQ ID NO 1121
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1121
aauacucccc uggaaagccg ggg 23

<210> SEQ ID NO 1122
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1122
accgcuccug gucauuggca uac 23

<210> SEQ ID NO 1123
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1123
augcagucag gguccagcgc cgc 23

<210> SEQ ID NO 1124
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1124
acaggcggua gccgggggu gca 23

<210> SEQ ID NO 1125
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1125 aagugggua aguagaggcg cag 23

<210> SEQ ID NO 1126
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1126
agggagagcu ccaggucgaa gug 23

<210> SEQ ID NO 1127
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1127
aagucguacu cgcagaggug gga 23

<210> SEQ ID NO 1128
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1128
accgagcuca gcuugacgaa guc 23

<210> SEQ ID NO 1129
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
auggccagca ccuuggcccc cga 23

<210> SEQ ID NO 1130
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
aucuccugcc cgcacagcgu ggc 23

<210> SEQ ID NO 1131
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1131
agcccgcucc gugucugugc ucu 23

<210> SEQ ID NO 1132
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1132 aaaaguguccc uugccagggg ccc 23

<210> SEQ ID NO 1133
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1133
acuggagccc agcgaguaga aag 23

<210> SEQ ID NO 1134
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1134
acggaaggua auguccaggc ugg 23

<210> SEQ ID NO 1135
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1135
aucguuggag uagucggagc gga 23

<210> SEQ ID NO 1136
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1136
aaaccccgug aacggcuucu cgu 23

<210> SEQ ID NO 1137
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1137
agcugcauag aaggccucga acc 23

<210> SEQ ID NO 1138
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138
agcacucguc aauguccucg gcu 23

<210> SEQ ID NO 1139
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139
acucucccgg ggccaccugg cac 23

<210> SEQ ID NO 1140
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
aguggucgca ggugggcgcc ucu 23

<210> SEQ ID NO 1141
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1141
acaggugguu guggcagugg ugg 23

<210> SEQ ID NO 1142
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1142
aggagcagua gaaaccgccc agg 23

<210> SEQ ID NO 1143
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1143
agacguagcc ugcgcggcag gag 23

<210> SEQ ID NO 1144
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1144
agcgcuuguu acggugcagg acg 23

<210> SEQ ID NO 1145
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1145
aagcacaggg cugagcaggu gcg 23

<210> SEQ ID NO 1146
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1146
agggugaaga ccuggccgga gca 23

<210> SEQ ID NO 1147
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1147
augagcuccc cagaccucug ggu 23

<210> SEQ ID NO 1148
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1148 agugguauu cagggcugcu gag 23

<210> SEQ ID NO 1149
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1149
aagaguuugg gauacggccg ugg 23

<210> SEQ ID NO 1150
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1150
augcuguaag ugcaacugga gag 23

<210> SEQ ID NO 1151
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1151
aaaccccucc uccaggcuga ugc 23

<210> SEQ ID NO 1152
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1152
aaaguccaga augacacuga acc 23

<210> SEQ ID NO 1153

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1153
aacaucgaag gacuccacaa agu 23

<210> SEQ ID NO 1154
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1154
aguuucaggg ugugucucca cau 23

<210> SEQ ID NO 1155
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1155
aaagucguag ggacacaggg uuu 23

<210> SEQ ID NO 1156
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1156
aucuguuuga aucuugagaa agu 23

<210> SEQ ID NO 1157
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1157
agggccaugu ucuucucugu cug 23

<210> SEQ ID NO 1158
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1158
acaaugucuu cccacagaau ggg 23

<210> SEQ ID NO 1159
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1159
auguuucaau ccuguggggc aau 23

<210> SEQ ID NO 1160
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1160
aggucaccgu guugcuuuuu guu 23

<210> SEQ ID NO 1161
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1161
aaucugugac aaaggugaug guc 23

<210> SEQ ID NO 1162
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1162
augugugguc uccugauuca ucu 23

<210> SEQ ID NO 1163
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1163
aguaguggau cuuccagccu gug 23

<210> SEQ ID NO 1164
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1164
aaggcugcgc ugugcucgug uag 23

<210> SEQ ID NO 1165
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1165
agcgccaucg gauaagggca agg 23

<210> SEQ ID NO 1166
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1166
aaaacguggc cauuaggugg cgc 23

<210> SEQ ID NO 1167
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1167
aauuuggcuu gcacagguga aac 23

<210> SEQ ID NO 1168
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1168
aagcugucuu ucaggaugua uuu 23

<210> SEQ ID NO 1169
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1169
aucucgcaaa agauggagaa gcu 23

<210> SEQ ID NO 1170
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1170
agcagaagcu cauagccagu cuc 23

<210> SEQ ID NO 1171
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1171
auucaggggc aagugaccuu gca 23

<210> SEQ ID NO 1172
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1172
acaaacugca guaaaggauu uca 23

<210> SEQ ID NO 1173
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1173
acaagaucca ucuuucugac aaa 23

<210> SEQ ID NO 1174
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1174
agcgggcauu ggccgguccc aag 23

<210> SEQ ID NO 1175
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1175
acagucaaca augcugcacg cgg 23

<210> SEQ ID NO 1176
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1176
aagaucauca ggagggccac agu 23

<210> SEQ ID NO 1177
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 1177
auccacucgg ccacugggua gau 23

<210> SEQ ID NO 1178
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1178
auccaggacc ugugauguac ucc 23

<210> SEQ ID NO 1179
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1179
aagcuuugua gguggucacu cca 23

<210> SEQ ID NO 1180
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1180
aacagcugua cugaaucaca gcu 23

<210> SEQ ID NO 1181
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1181
auguguagaa ggucucuuca cag 23

<210> SEQ ID NO 1182
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1182
aaccaucauu cacuuucauu gug 23

<210> SEQ ID NO 1183
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1183
aagccucaca cacauauuua cca 23

<210> SEQ ID NO 1184
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1184
agcucgucca gaauccauca gcc 23

<210> SEQ ID NO 1185
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1185
agugauuuuu cuccuuugga gcu 23

<210> SEQ ID NO 1186
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1186
acaggcucac agacugggag uga 23

<210> SEQ ID NO 1187
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1187
agggcugaua guccacaaac agg 23

<210> SEQ ID NO 1188
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1188
auacgcccuc cuguugugcg ggc 23

<210> SEQ ID NO 1189
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1189
accuuuugcc cuccauauau acg 23

<210> SEQ ID NO 1190
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1190
agaaaaucac cagguuuugc cuu 23

<210> SEQ ID NO 1191
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1191
aauaucagga cuugccaagg aaa 23

<210> SEQ ID NO 1192
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1192
agcugcugug guuccaccua aua 23

<210> SEQ ID NO 1193
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1193
aucauauaaa agugcaccug cug 23

<210> SEQ ID NO 1194
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1194
agcuguuagg acccaguugu cau 23

<210> SEQ ID NO 1195
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1195
aucauagacg gcaugagcag cug 23

<210> SEQ ID NO 1196
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1196
agaugcauca uguuuuugcu cau 23

<210> SEQ ID NO 1197
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1197
aauucgaaug uccagggcgg aug 23

<210> SEQ ID NO 1198
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1198
auagucuuuu cagggugccc auu 23

<210> SEQ ID NO 1199
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199
auuguguaua augaggugau agu 23

<210> SEQ ID NO 1200
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200
aaacagcuuc agaccaggcu ugu 23

<210> SEQ ID NO 1201
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201
aauaaccuuc auguauaaaa aca 23

<210> SEQ ID NO 1202
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1202
aaaagccagc aucaugagua uaa 23

<210> SEQ ID NO 1203
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1203
acagugcuau gucauuguca aag 23

<210> SEQ ID NO 1204
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1204
auuuguuauu caauuuaauc agu 23

<210> SEQ ID NO 1205
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1205
auguugcuau ugauuacaac uuu 23

<210> SEQ ID NO 1206
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1206
agcagacaaa uaggcgugau guu 23

<210> SEQ ID NO 1207
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1207
auuuggguua auccccaucc aga 23

<210> SEQ ID NO 1208
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1208
aauucagcuu cuuuucuugg cag 23

<210> SEQ ID NO 1209
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1209
acaucugucc ucauaaagga uuc 23

<210> SEQ ID NO 1210
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1210
acagaugcag uuccaauguc auc 23

<210> SEQ ID NO 1211
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1211
auucuagcaa gaaaaccccu uug 23

<210> SEQ ID NO 1212
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1212
aaugucgaca uacauuagau uuc 23

<210> SEQ ID NO 1213
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1213
augaugguca acaaucggua ugu 23

<210> SEQ ID NO 1214
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1214
auaugcagca guacauuuuu gau 23

<210> SEQ ID NO 1215
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1215
aggauagggu ggcuuuucau aug 23

<210> SEQ ID NO 1216
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1216
agcaguuaca cuuccccuug gau 23

<210> SEQ ID NO 1217
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1217
accagcacaa agcauguuag cag 23

<210> SEQ ID NO 1218
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1218
acuugccccc acuuucuaag cca 23

<210> SEQ ID NO 1219
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1219
agucaccucu gcagcugucc uug 23

<210> SEQ ID NO 1220
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1220
acaccagugc cccuccgcug uca 23

<210> SEQ ID NO 1221
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1221
auguuucacu aucuagaaac acc 23

<210> SEQ ID NO 1222
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1222
aucccacaaa ccaccucucu guu 23

<210> SEQ ID NO 1223
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1223
aaccccagga cacuauuccu ccc 23

<210> SEQ ID NO 1224
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1224
auuccccaca auucauggaa ccc 23

<210> SEQ ID NO 1225
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1225
aagacuccau acugaccugc uuc 23

<210> SEQ ID NO 1226
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1226
aaguuaauaa cuuuugugua gac 23

<210> SEQ ID NO 1227
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1227
aucucgaucc agggaauaua guu 23

<210> SEQ ID NO 1228
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1228
aaaaaaucac uaauuauguu cuc 23

<210> SEQ ID NO 1229
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1229
aacugcagac acgcaaguua aaa 23

<210> SEQ ID NO 1230
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1230
aaaaaaugaa gaauccuuga cug 23

<210> SEQ ID NO 1231
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1231
agucuucaca ggcauuucua aaa 23

<210> SEQ ID NO 1232

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1232
agagccacgu cgcugccaag guc 23

<210> SEQ ID NO 1233
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1233
auaaugauga augcuucucg agc 23

<210> SEQ ID NO 1234
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1234
acaacugcca uguccacagu aau 23

<210> SEQ ID NO 1235
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1235
auuuuuuugg guggagcaac aac 23

<210> SEQ ID NO 1236
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1236
aagccucacc uggagucugu uuu 23

<210> SEQ ID NO 1237
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1237
aaaguggaga aaugacagca gcc 23

<210> SEQ ID NO 1238
<211> LENGTH: 23

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
aaggcuggaa uuaaacuggc aag 23

<210> SEQ ID NO 1239
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
acccuugagu caaugguaa ggc 23

<210> SEQ ID NO 1240
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
aacucucgug guuuaugucc ccu 23

<210> SEQ ID NO 1241
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
augggcaaag augacuguca cuc 23

<210> SEQ ID NO 1242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242
acagugacau uacacugggu ggg 23

<210> SEQ ID NO 1243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1243
aaaugaaaug uaauuugagc agu 23

<210> SEQ ID NO 1244
<211> LENGTH: 23
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1244
aagacuggcu uuuuaaggua aug 23

<210> SEQ ID NO 1245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
acaacagcca guaugaaaag aga 23

<210> SEQ ID NO 1246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
aggcaguuua cagaaaugcc aac 23

<210> SEQ ID NO 1247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
aaaacaaaga gcauggacag gca 23

<210> SEQ ID NO 1248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1248
acaauaagaa caaguuuaaa aac 23

<210> SEQ ID NO 1249
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1249
agaccaggcc aggccagctg gac 23

<210> SEQ ID NO 1250
<211> LENGTH: 23
<212> TYPE: DNA
<213> ORGANISM: Unknown
<220> FEATURE:

<223> OTHER INFORMATION: Description of Unknown: Target sequence

<400> SEQUENCE: 1250
tggacgggca caccatgagg ctg 23

<210> SEQ ID NO 1251
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1251
ggctgctgac cctcctgggc ctt 23

<210> SEQ ID NO 1252
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1252
gccttctgtg tggctcggtg gcc 23

<210> SEQ ID NO 1253
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1253
ggccaccccc ttgggcccga agt 23

<210> SEQ ID NO 1254
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1254
gaagtggcct gaacctgtgt tcg 23

<210> SEQ ID NO 1255
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1255
gttcgggcgc ctggcatccc ccg 23

<210> SEQ ID NO 1256
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1256
ccccggcttt ccaggggagt atg 23

-continued

<210> SEQ ID NO 1257
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1257
gtatgccaat gaccaggagc ggc 23

<210> SEQ ID NO 1258
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1258
gcggcgctgg accctgactg cac 23

<210> SEQ ID NO 1259
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1259
tgcacccccc ggctaccgcc tgc 23

<210> SEQ ID NO 1260
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1260
ctgcgcctct acttcaccca ctt 23

<210> SEQ ID NO 1261
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1261
cacttcgacc tggagctctc cca 23

<210> SEQ ID NO 1262
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1262
tcccacctct gcgagtacga ctt 23

<210> SEQ ID NO 1263
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1263
gacttcgtca agctgagctc ggg 23

<210> SEQ ID NO 1264
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1264
tcgggggcca aggtgctggc cac 23

<210> SEQ ID NO 1265
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1265
gccacgctgt gcgggcagga gag 23

<210> SEQ ID NO 1266
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1266
agagcacaga cacggagcgg gcc 23

<210> SEQ ID NO 1267
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1267
gggcccctgg caaggacact ttc 23

<210> SEQ ID NO 1268
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1268
ctttctactc gctgggctcc agc 23

<210> SEQ ID NO 1269
<211> LENGTH: 23
<212> TYPE: DNA
<213> ORGANISM: Unknown
<220> FEATURE:
<223> OTHER INFORMATION: Target sequence

<400> SEQUENCE: 1269
ccagcctgga cattaccttc cgc 23

<210> SEQ ID NO 1270
<211> LENGTH: 23

<212> TYPE: DNA
<213> ORGANISM: Unknown
<220> FEATURE:
<223> OTHER INFORMATION: Description of Unknown: Target sequence

<400> SEQUENCE: 1270
tccgctccga ctactccaac gag 23

<210> SEQ ID NO 1271
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1271
acgagaagcc gttcacgggg ttc 23

<210> SEQ ID NO 1272
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1272
ggttcgaggc cttctatgca gcc 23

<210> SEQ ID NO 1273
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1273
agccgaggac attgacgagt gcc 23

<210> SEQ ID NO 1274
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1274
gtgccaggtg gccccgggag agg 23

<210> SEQ ID NO 1275
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1275
agaggcgccc acctgcgacc acc 23

<210> SEQ ID NO 1276
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1276

-continued ccaccactgc cacaaccacc tgg 23

<210> SEQ ID NO 1277
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1277
cctgggcggt ttctactgct cct 23

<210> SEQ ID NO 1278
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1278
ctcctgccgc gcaggctacg tcc 23

<210> SEQ ID NO 1279
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1279
cgtcctgcac cgtaacaagc gca 23

<210> SEQ ID NO 1280
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1280
cgcacctgct cagccctgtg ctc 23

<210> SEQ ID NO 1281
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1281
tgctccggcc aggtcttcac cca 23

<210> SEQ ID NO 1282
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1282
acccagaggt ctggggagct cag 23

<210> SEQ ID NO 1283
<211> LENGTH: 23
<212> TYPE: DNA
<213> ORGANISM: Unknown

<220> FEATURE:
<223> OTHER INFORMATION: Description of Unknown: Target sequence

<400> SEQUENCE: 1283
ctcagcagcc ctgaataccc acg 23

<210> SEQ ID NO 1284
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1284
ccacggccgt atcccaaact ctc 23

<210> SEQ ID NO 1285
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1285
ctctccagtt gcacttacag cat 23

<210> SEQ ID NO 1286
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1286
gcatcagcct ggaggagggg ttc 23

<210> SEQ ID NO 1287
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1287
ggttcagtgt cattctggac ttt 23

<210> SEQ ID NO 1288
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1288
actttgtgga gtccttcgat gtg 23

<210> SEQ ID NO 1289
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1289
atgtggagac acaccctgaa acc 23

<210> SEQ ID NO 1290
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1290
aaaccctgtg tccctacgac ttt 23

<210> SEQ ID NO 1291
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1291
actttctcaa gattcaaaca gac 23

<210> SEQ ID NO 1292
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1292
cagacagaga agaacatggc cca 23

<210> SEQ ID NO 1293
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1293
cccattctgt gggaagacat tgc 23

<210> SEQ ID NO 1294
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1294
attgccccac aggattgaaa caa 23

<210> SEQ ID NO 1295
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1295
aacaaaaagc aacacggtga cca 23

<210> SEQ ID NO 1296
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1296
gaccatcacc tttgtcacag atg 23

<210> SEQ ID NO 1297
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1297
agatgaatca ggagaccaca cag 23

<210> SEQ ID NO 1298
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1298
cacaggctgg aagatccact aca 23

<210> SEQ ID NO 1299
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1299
ctacacgagc acagcgcagc ctt 23

<210> SEQ ID NO 1300
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1300
ccttgccctt atccgatggc gcc 23

<210> SEQ ID NO 1301
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1301
gcgccaccta atggccacgt ttc 23

<210> SEQ ID NO 1302
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1302
gtttcacctg tgcaagccaa ata 23

<210> SEQ ID NO 1303

<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1303
aaatacatcc tgaaagacag ctt 23

<210> SEQ ID NO 1304
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1304
agcttctcca tcttttgcga gac 23

<210> SEQ ID NO 1305
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1305
gagactggct atgagcttct gca 23

<210> SEQ ID NO 1306
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1306
tgcaaggtca cttgcccctg aaa 23

<210> SEQ ID NO 1307
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1307
tgaaatcctt tactgcagtt tgt 23

<210> SEQ ID NO 1308
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1308
tttgtcagaa agatggatct tgg 23

<210> SEQ ID NO 1309
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1309
cttgggaccg gccaatgccc gcg 23

<210> SEQ ID NO 1310
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1310
ccgcgtgcag cattgttgac tgt 23

<210> SEQ ID NO 1311
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1311
actgtggccc tcctgatgat cta 23

<210> SEQ ID NO 1312
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1312
atctacccag tggccgagtg gag 23

<210> SEQ ID NO 1313
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1313
ggagtacatc acaggtcctg gag 23

<210> SEQ ID NO 1314
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1314
tggagtgacc acctacaaag ctg 23

<210> SEQ ID NO 1315
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1315
agctgtgatt cagtacagct gtg 23

<210> SEQ ID NO 1316
<211> LENGTH: 23
<212> TYPE: DNA

<213> ORGANISM: Unknown
<220> FEATURE:
<223> OTHER INFORMATION: Description of Unknown: Target sequence

<400> SEQUENCE: 1316
ctgtgaagag accttctaca caa 23

<210> SEQ ID NO 1317
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1317
cacaatgaaa gtgaatgatg gta 23

<210> SEQ ID NO 1318
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1318
tggtaaatat gtgtgtgagg ctg 23

<210> SEQ ID NO 1319
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1319
ggctgatgga ttctggacga gct 23

<210> SEQ ID NO 1320
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1320
agctccaaag gagaaaaatc act 23

<210> SEQ ID NO 1321
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1321
tcactcccag tctgtgagcc tgt 23

<210> SEQ ID NO 1322
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1322
cctgtttgtg gactatcagc ccg 23

<210> SEQ ID NO 1323
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1323
gcccgcacaa caggagggcg tat 23

<210> SEQ ID NO 1324
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1324
cgtatatatg gagggcaaaa ggc 23

<210> SEQ ID NO 1325
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1325
aaggcaaaac ctggtgattt tcc 23

<210> SEQ ID NO 1326
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1326
tttccttggc aagtcctgat att 23

<210> SEQ ID NO 1327
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1327
tattaggtgg aaccacagca gca 23

<210> SEQ ID NO 1328
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1328
cagcaggtgc acttttatat gac 23

<210> SEQ ID NO 1329
<211> LENGTH: 23
<212> TYPE: DNA
<213> ORGANISM: Unknown
<220> FEATURE:

<223> OTHER INFORMATION: Description of Unknown: Target sequence

<400> SEQUENCE: 1329
atgacaactg ggtcctaaca gct 23

<210> SEQ ID NO 1330
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1330
cagctgctca tgccgtctat gag 23

<210> SEQ ID NO 1331
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1331
atgagcaaaa acatgatgca tcc 23

<210> SEQ ID NO 1332
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1332
catccgccct ggacattcga atg 23

<210> SEQ ID NO 1333
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1333
aatgggcacc ctgaaaagac tat 23

<210> SEQ ID NO 1334
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1334
actatcacct cattatacac aag 23

<210> SEQ ID NO 1335
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1335
acaagcctgg tctgaagctg ttt 23

<210> SEQ ID NO 1336
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1336
tgtttttata catgaaggtt ata 23

<210> SEQ ID NO 1337
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1337
ttatactcat gatgctggct ttg 23

<210> SEQ ID NO 1338
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1338
ctttgacaat gacatagcac tga 23

<210> SEQ ID NO 1339
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1339
actgattaaa ttgaataaca aag 23

<210> SEQ ID NO 1340
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1340
aaagttgtaa tcaatagcaa cat 23

<210> SEQ ID NO 1341
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1341
aacatcacgc ctatttgtct gcc 23

<210> SEQ ID NO 1342
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1342
ctgccaagaa aagaagctga atc 23

<210> SEQ ID NO 1343
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1343
gaatccttta tgaggacaga tga 23

<210> SEQ ID NO 1344
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1344
gatgacattg gaactgcatc tgg 23

<210> SEQ ID NO 1345
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1345
tctggatggg gattaaccca aag 23

<210> SEQ ID NO 1346
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1346
caaaggggtt ttcttgctag aaa 23

<210> SEQ ID NO 1347
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1347
gaaatctaat gtatgtcgac ata 23

<210> SEQ ID NO 1348
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1348
acataccgat tgttgaccat caa 23

<210> SEQ ID NO 1349
<211> LENGTH: 23

<212> TYPE: DNA
<213> ORGANISM: Unknown
<220> FEATURE:
<223> OTHER INFORMATION: Description of Unknown: Target sequence

<400> SEQUENCE: 1349
atcaaaaatg tactgctgca tat 23

<210> SEQ ID NO 1350
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1350
catatgaaaa gccaccctat cca 23

<210> SEQ ID NO 1351
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1351
atccaagggg aagtgtaact gct 23

<210> SEQ ID NO 1352
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1352
ctgctaacat gctttgtgct ggc 23

<210> SEQ ID NO 1353
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1353
tggcttagaa agtgggggca agg 23

<210> SEQ ID NO 1354
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1354
caaggacagc tgcagaggtg aca 23

<210> SEQ ID NO 1355
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1355
tgacagcgga ggggcactgg tgt 23

<210> SEQ ID NO 1356
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1356
ggtgtttcta gatagtgaaa cag 23

<210> SEQ ID NO 1357
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1357
aacagagagg tggtttgtgg gag 23

<210> SEQ ID NO 1358
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1358
gggaggaata gtgtcctggg gtt 23

<210> SEQ ID NO 1359
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1359
gggttccatg aattgtgggg aag 23

<210> SEQ ID NO 1360
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1360
gaagcaggtc agtatggagt cta 23

<210> SEQ ID NO 1361
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1361
gtctacacaa aagttattaa cta 23

<210> SEQ ID NO 1362
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1362
aactatattc cctggatcga gaa 23

<210> SEQ ID NO 1363
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1363
gagaacataa ttagtgattt tta 23

<210> SEQ ID NO 1364
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1364
ttttaacttg cgtgtctgca gtc 23

<210> SEQ ID NO 1365
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1365
cagtcaagga ttcttcattt tta 23

<210> SEQ ID NO 1366
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1366
ttttagaaat gcctgtgaag acc 23

<210> SEQ ID NO 1367
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1367
gaccttggca gcgacgtggc tcg 23

<210> SEQ ID NO 1368
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1368
gctcgagaag cattcatcat tac 23

<210> SEQ ID NO 1369
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1369
attactgtgg acatggcagt tgt 23

<210> SEQ ID NO 1370
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1370
gttgttgctc cacccaaaaa aac 23

<210> SEQ ID NO 1371
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1371
aaaacagact ccaggtgagg ctg 23

<210> SEQ ID NO 1372
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1372
ggctgctgtc atttctccac ttg 23

<210> SEQ ID NO 1373
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1373
cttgccagtt taattccagc ctt 23

<210> SEQ ID NO 1374
<211> LENGTH: 23

<212> TYPE: DNA
<213> ORGANISM: Unknown
<220> FEATURE:
<223> OTHER INFORMATION: Description of Unknown: Target sequence

<400> SEQUENCE: 1374
gccttaccca ttgactcaag ggg 23

<210> SEQ ID NO 1375
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1375
aggggacata aaccacgaga gtg 23

<210> SEQ ID NO 1376
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1376
gagtgacagt catctttgcc cac 23

<210> SEQ ID NO 1377
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1377
cccacccagt gtaatgtcac tgc 23

<210> SEQ ID NO 1378
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1378
actgctcaaa ttacatttca tta 23

-continued

```
<210> SEQ ID NO 1379
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1379

cattacctta aaaagccagt ctc                                          23


<210> SEQ ID NO 1380
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1380

tctcttttca tactggctgt tgg                                          23


<210> SEQ ID NO 1381
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1381

gttggcattt ctgtaaactg cct                                          23


<210> SEQ ID NO 1382
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1382

tgcctgtcca tgctctttgt ttt                                          23


<210> SEQ ID NO 1383
<211> LENGTH: 23
<212> TYPE: DNA
<213> ORGANISM: Unknown
<220> FEATURE:
<223> OTHER INFORMATION: Description of Unknown: Target sequence

<400> SEQUENCE: 1383

gtttttaaac ttgttcttat tga                                          23
```